(12) United States Patent
Hammond et al.

(10) Patent No.: US 10,278,927 B2
(45) Date of Patent: May 7, 2019

(54) STABLE LAYER-BY-LAYER COATED PARTICLES

(71) Applicant: Massachusetts Institute of Technology, Cambridge, MA (US)

(72) Inventors: Paula T. Hammond, Newton, MA (US); Zhiyong Poon, Singapore (SG)

(73) Assignee: Massachusetts Institute of Technology, Cambridge, MA (US)

( * ) Notice: Subject to any disclaimer, the term of this patent is extended or adjusted under 35 U.S.C. 154(b) by 125 days.

(21) Appl. No.: 13/869,015

(22) Filed: Apr. 23, 2013

(65) Prior Publication Data

US 2014/0093575 A1    Apr. 3, 2014

Related U.S. Application Data

(60) Provisional application No. 61/637,265, filed on Apr. 23, 2012.

(51) Int. Cl.
| | | |
|---|---|---|
| *A61K 9/51* | (2006.01) | |
| *A61K 9/00* | (2006.01) | |
| *A61K 38/16* | (2006.01) | |
| *A61K 31/4188* | (2006.01) | |

(52) U.S. Cl.
CPC .......... *A61K 9/5161* (2013.01); *A61K 9/0019* (2013.01); *A61K 9/5146* (2013.01); *A61K 9/5169* (2013.01); *A61K 31/4188* (2013.01); *A61K 38/164* (2013.01)

(58) Field of Classification Search
CPC combination set(s) only.
See application file for complete search history.

(56) References Cited

U.S. PATENT DOCUMENTS

| | | |
|---|---|---|
| 3,266,987 A | 8/1966 | Crowley et al. |
| 3,710,795 A | 1/1973 | Higuchi et al. |
| 3,962,414 A | 6/1976 | Michaels |
| 4,191,811 A | 3/1980 | Hodgdon |
| 4,250,029 A | 2/1981 | Kiser et al. |
| 4,460,563 A | 7/1984 | Calanchi |
| 4,638,045 A | 1/1987 | Kohn |
| 4,794,000 A | 12/1988 | Ecanow |
| 4,806,621 A | 2/1989 | Kohn |
| 4,946,929 A | 8/1990 | D'amore |
| 5,010,167 A | 4/1991 | Ron |
| 5,019,379 A | 5/1991 | Domb |
| 5,114,719 A | 5/1992 | Sabel et al. |
| 5,208,111 A | 5/1993 | Decher et al. |
| 5,364,634 A | 11/1994 | Lew |
| 5,397,848 A | 3/1995 | Yang et al. |
| 5,399,665 A | 3/1995 | Barrera |
| 5,462,990 A | 10/1995 | Hubbell et al. |
| 5,512,131 A | 4/1996 | Kumar et al. |
| 5,512,600 A | 4/1996 | Mikos |
| 5,514,378 A | 5/1996 | Mikos |
| 5,518,767 A | 5/1996 | Rubner et al. |
| 5,536,573 A | 7/1996 | Rubner et al. |
| 5,630,941 A | 5/1997 | Burger et al. |
| 5,660,873 A | 8/1997 | Nikolaychik et al. |
| 5,696,175 A | 12/1997 | Mikos |
| 5,700,559 A | 12/1997 | Sheu et al. |
| 5,714,166 A | 2/1998 | Tomalia et al. |
| 5,716,303 A | 2/1998 | Scatterday |
| 5,716,404 A | 2/1998 | Vacanti |
| 5,716,709 A | 2/1998 | Ferguson et al. |
| 5,736,372 A | 4/1998 | Vacanti |
| 5,770,417 A | 6/1998 | Vacanti |
| 5,797,898 A | 8/1998 | Santini, Jr. et al. |
| 5,804,178 A | 9/1998 | Vacanti |
| 5,807,636 A | 9/1998 | Sheu et al. |
| 5,837,377 A | 11/1998 | Sheu et al. |
| 5,837,752 A | 11/1998 | Shastri |
| 5,858,746 A | 1/1999 | Hubbell et al. |
| 5,902,599 A | 5/1999 | Anseth |
| 5,904,927 A | 5/1999 | Amiji |
| 5,962,520 A | 10/1999 | Smith et al. |
| 6,022,590 A | 2/2000 | Ferguson et al. |
| 6,060,582 A | 5/2000 | Hubbell et al. |
| 6,089,853 A | 7/2000 | Biebuyck et al. |
| 6,095,148 A | 8/2000 | Shastri |
| 6,103,266 A | 8/2000 | Tapolsky et al. |
| 6,114,099 A | 9/2000 | Liu et al. |
| 6,123,681 A | 9/2000 | Brown, III |
| 6,123,727 A | 9/2000 | Vacanti |
| 6,131,211 A | 10/2000 | Hennessey |
| 6,180,239 B1 | 1/2001 | Whitesides et al. |
| 6,180,329 B1 | 1/2001 | Paris |
| 6,235,224 B1 | 5/2001 | Mathiowitz et al. |
| 6,235,334 B1 | 5/2001 | Donovan |

(Continued)

FOREIGN PATENT DOCUMENTS

| | | |
|---|---|---|
| CN | 1679518 A | 10/2005 |
| DE | 19812083 | 9/1999 |

(Continued)

OTHER PUBLICATIONS

Abeloff, M.D. et al., Chapter 95: Cancer of the Breast, in Abeloff's Clinical Oncology, Fourth Edition, pp. 1875-1943, Churchill Livingstone Elsevier (2008).
Abramoff et al., "Image Processing with ImageJ" Biophotonics International 2004, 11, 36-42.
Absolom et al., "Protein adsorption to polymer particles: role of surface properties" J Biomed Mater Res. Feb. 1987;21(2):161-71.
Ai et al., Biomedical applications of electrostatic layer-by-layer nano-assembly of polymers, enzymes, and nanoparticles Cell Biochem Biophys. 2003;39(1):23-43.
Akinc et al., "Synthesis of poly(beta-amino ester)s optimized for highly effective gene delivery" Bioconjugate Chem. 2003, 14:979-988.

(Continued)

*Primary Examiner* — Hasan S Ahmed
(74) *Attorney, Agent, or Firm* — Foley Hoag LLP

(57) ABSTRACT

Systems and methods for coating a particle core with a layer-by-layer film are disclosed.

8 Claims, 72 Drawing Sheets

(56) References Cited

U.S. PATENT DOCUMENTS

| | | |
|---|---|---|
| 6,267,784 B1 | 7/2001 | Benz et al. |
| 6,312,727 B1 | 11/2001 | Schacht et al. |
| 6,402,918 B1 | 6/2002 | Schlenoff et al. |
| 6,447,887 B1 | 9/2002 | Claus et al. |
| 6,451,871 B1 | 9/2002 | Winterton et al. |
| 6,479,146 B1 | 11/2002 | Caruso et al. |
| 6,492,096 B1 | 12/2002 | Liu et al. |
| 6,497,729 B1 | 12/2002 | Moussy et al. |
| 6,699,501 B1 | 3/2004 | Neu et al. |
| 6,716,813 B2 | 4/2004 | Lim et al. |
| 6,740,643 B2 | 5/2004 | Wolff et al. |
| 6,743,521 B2 | 6/2004 | Hubbell et al. |
| 6,833,192 B1 | 12/2004 | Caruso et al. |
| 6,860,980 B2 | 3/2005 | Locascio et al. |
| 6,896,926 B2 | 5/2005 | Qiu et al. |
| 6,919,373 B1 | 7/2005 | Lam et al. |
| 6,998,115 B2 | 2/2006 | Langer |
| 7,045,087 B2 | 5/2006 | Kotov |
| 7,045,146 B2 | 5/2006 | Caruso et al. |
| 7,101,575 B2 | 9/2006 | Donath et al. |
| 7,101,947 B2 | 9/2006 | Schlenoff et al. |
| 7,112,361 B2 | 9/2006 | Lynn et al. |
| 7,223,327 B2 | 5/2007 | Schlenoff et al. |
| 7,303,814 B2 | 12/2007 | Lamberti et al. |
| 7,348,399 B2 | 3/2008 | Haynie |
| 7,364,585 B2 | 4/2008 | Weber |
| 7,365,142 B2 | 4/2008 | Schlenoff et al. |
| 7,427,354 B2 | 9/2008 | Eto |
| 7,427,394 B2 | 9/2008 | Anderson |
| 7,491,263 B2 | 2/2009 | Wang et al. |
| 7,879,575 B2 | 2/2011 | Kricka et al. |
| 8,105,652 B2 | 1/2012 | Wood et al. |
| 9,737,557 B2 | 8/2017 | Hammond et al. |
| 2002/0053514 A1 | 5/2002 | Locascio et al. |
| 2002/0131933 A1 | 9/2002 | Delmotte |
| 2002/0131951 A1 | 9/2002 | Langer et al. |
| 2002/0187197 A1 | 12/2002 | Caruso et al. |
| 2003/0059398 A1 | 3/2003 | Ranger et al. |
| 2003/0113368 A1 | 6/2003 | Nomoto et al. |
| 2003/0124368 A1 | 7/2003 | Lynn et al. |
| 2003/0236573 A1 | 12/2003 | Evans et al. |
| 2004/0013721 A1 | 1/2004 | Antipov |
| 2004/0020423 A1 | 2/2004 | Lewis et al. |
| 2004/0044100 A1 | 3/2004 | Schlenoff et al. |
| 2004/0052865 A1 | 3/2004 | Gower et al. |
| 2004/0149572 A1 | 8/2004 | Schlenoff et al. |
| 2004/0258753 A1 | 12/2004 | Demeester et al. |
| 2005/0019404 A1 | 1/2005 | Sung et al. |
| 2005/0089890 A1 | 4/2005 | Cubicciotti |
| 2005/0152955 A1 | 7/2005 | Akhave et al. |
| 2005/0208100 A1 | 9/2005 | Weber et al. |
| 2005/0265961 A1 | 12/2005 | Langer et al. |
| 2005/0276841 A1 | 12/2005 | Davis et al. |
| 2006/0118754 A1 | 6/2006 | Lapen |
| 2006/0127437 A1 | 6/2006 | Kennedy et al. |
| 2006/0198897 A1 | 9/2006 | Pacetti |
| 2006/0216494 A1 | 9/2006 | Furedi-Milhofer et al. |
| 2006/0246112 A1 | 11/2006 | Snyder et al. |
| 2007/0020469 A1 | 1/2007 | Wood et al. |
| 2007/0077276 A1 | 4/2007 | Haynie |
| 2007/0083186 A1 | 4/2007 | Carter et al. |
| 2007/0129792 A1 | 6/2007 | Picart et al. |
| 2007/0141100 A1 | 6/2007 | Sung et al. |
| 2007/0197568 A1 | 8/2007 | Bunn et al. |
| 2007/0276330 A1 | 11/2007 | Beck et al. |
| 2008/0139450 A1 | 6/2008 | Madhyastha et al. |
| 2008/0200982 A1 | 8/2008 | Your |
| 2008/0228280 A1 | 9/2008 | Cohen et al. |
| 2008/0248108 A1 | 10/2008 | Krotz et al. |
| 2008/0286345 A1 | 11/2008 | Lynn et al. |
| 2008/0311177 A1 | 12/2008 | Hammond et al. |
| 2009/0018029 A1 | 1/2009 | Miao et al. |
| 2009/0047517 A1 | 2/2009 | Caruso et al. |
| 2009/0053139 A1 | 2/2009 | Shi et al. |
| 2009/0061006 A1 | 3/2009 | Leuschner et al. |
| 2009/0088479 A1 | 4/2009 | Allmendinger et al. |
| 2009/0088679 A1 | 4/2009 | Wood et al. |
| 2009/0155326 A1 | 6/2009 | Mack et al. |
| 2009/0170179 A1 | 7/2009 | Lynn et al. |
| 2009/0214615 A1 | 8/2009 | Zhao |
| 2009/0246142 A1 | 10/2009 | Bhatia et al. |
| 2009/0258045 A1 | 10/2009 | Chuang et al. |
| 2009/0263468 A1 | 10/2009 | McAnulty et al. |
| 2009/0275906 A1 | 11/2009 | Berland et al. |
| 2010/0003499 A1 | 1/2010 | Krogman et al. |
| 2010/0016439 A1 | 1/2010 | Thomes et al. |
| 2010/0040674 A1 | 2/2010 | Smith et al. |
| 2010/0189683 A1 | 7/2010 | Holmlund et al. |
| 2011/0038939 A1* | 2/2011 | Lvov et al. .................. 424/490 |
| 2011/0114244 A1 | 5/2011 | Yoo et al. |
| 2011/0143127 A1 | 6/2011 | Gupta et al. |
| 2011/0244048 A1* | 10/2011 | Amiji .................. A61K 9/1273 |
| | | 424/493 |
| 2011/0301209 A1 | 12/2011 | Zaknocn et al. |
| 2012/0015146 A1 | 1/2012 | Advincula et al. |
| 2012/0027837 A1 | 2/2012 | DeMuth et al. |
| 2012/0058355 A1 | 3/2012 | Lee et al. |
| 2012/0156389 A1 | 6/2012 | Kotov |
| 2012/0207795 A1* | 8/2012 | Zink .................. A61K 9/0019 |
| | | 424/400 |
| 2012/0277719 A1 | 11/2012 | Shukla et al. |
| 2012/0277852 A1 | 11/2012 | Shukla et al. |
| 2013/0190890 A1 | 7/2013 | Shah et al. |
| 2013/0273137 A1 | 10/2013 | Mandell et al. |
| 2014/0011759 A1 | 1/2014 | Yaffe et al. |
| 2014/0039575 A1 | 2/2014 | Bradley |
| 2014/0302116 A1 | 10/2014 | Castleberry et al. |
| 2014/0328931 A1 | 11/2014 | Hammond et al. |
| 2015/0086599 A1 | 3/2015 | Hammond et al. |
| 2015/0125879 A1 | 5/2015 | Li et al. |

FOREIGN PATENT DOCUMENTS

| | | |
|---|---|---|
| DE | 29907804 | 10/1999 |
| EP | 0 443 809 | 8/1991 |
| EP | 1 116 516 | 7/2001 |
| EP | 2 162 283 | 9/2010 |
| EP | 2 566 468 | 3/2013 |
| EP | 2 701 908 | 3/2014 |
| GB | 1213803 | 11/1970 |
| GB | 1213805 | 11/1970 |
| WO | WO 1995/11748 | 5/1995 |
| WO | WO 1995/34595 | 12/1995 |
| WO | WO 1996/03147 | 2/1996 |
| WO | WO 1998/03573 | 1/1998 |
| WO | WO 9817330 A1 | 4/1998 |
| WO | WO 1998/47948 | 10/1998 |
| WO | WO 1999/47253 | 9/1999 |
| WO | WO 99/59647 A1 | 11/1999 |
| WO | WO-1999/56878 A1 | 11/1999 |
| WO | WO 2000/77281 | 12/2000 |
| WO | WO 2001/57118 | 8/2001 |
| WO | WO 2001/94441 | 12/2001 |
| WO | WO 2002/12888 A2 | 2/2002 |
| WO | WO 2002/085500 | 10/2002 |
| WO | WO 2003/035716 | 5/2003 |
| WO | WO 2006/051227 | 5/2006 |
| WO | WO-2006/079928 A2 | 8/2006 |
| WO | WO 2006/086391 | 8/2006 |
| WO | WO 2007/140391 | 12/2007 |
| WO | WO 2007/140402 | 12/2007 |
| WO | WO 2008/057127 A2 | 5/2008 |
| WO | WO 2008/157372 | 12/2008 |
| WO | WO 2008157372 | 12/2008 |
| WO | WO-2009/051734 A1 | 4/2009 |
| WO | WO-2009/117473 A2 | 9/2009 |
| WO | WO 2010/021973 | 2/2010 |
| WO | WO-2010/097814 A2 | 9/2010 |
| WO | WO 2010/120531 | 10/2010 |
| WO | WO 2011/140136 | 11/2011 |
| WO | WO 2012/149492 | 11/2012 |
| WO | WO 2012/149494 | 11/2012 |
| WO | WO 2013/110047 | 7/2013 |
| WO | WO 2013/163234 | 10/2013 |

(56) References Cited

FOREIGN PATENT DOCUMENTS

| WO | WO 2014/059269 | 4/2014 |
| WO | WO 2014/066862 | 5/2014 |
| WO | WO-2014/134029 A1 | 9/2014 |
| WO | WO 2014/150074 | 9/2014 |

OTHER PUBLICATIONS

Albeck, J.G. et al., Modeling a Snap-Action, Variable-Delay Switch Controlling Extrinsic Cell Death, PLoS Biology, 6(12):2831-2852 (2008).

Albrektsson et al., "Osteoinduction, osteoconduction and osseointegration" Eur Spine J. Oct. 2001;10 Suppl 2:S96-101.

Alves et al., "Self assembling and crosslinking of polyelectrolyte multilayer films of chitosan and alginate studied by QCM and IR spectroscopy" Macromol Biosci. Aug. 11, 2009;9(8):776-85.

Anderson et al., "Semi-Automated Synthesis and Screening of a Large Library of Degradable Cationic Polymers for Gene Delivery," Angew. Chem. Int. Ed. 42:3151-3158 (2003).

Anderson, "Human Gene Therapy" Nature, 392: 25-30 (1996).

Anderson, et al., "Biodegradation and Biocompatibility ofPLA and PLGA Microspheres" Adv. Drug Delivery Rev. 28: 5-24, 1997.

Ando, et al., "PLGA Micospheres Containing Plasmid DNA: Preservation of Supercoiled DNA via Cryopreparation and Carbohydrate Stabilization" J. Pharm. Sci. 88: 126-130, 1999.

Antipov, et al., "Sustained Release Properties of Polyelectrolyte Multilayer Capsules" J. Phys. Chem., 105:2281-2284 (2001).

Ariga et al., "Layer-by-layer assembly as a versatile bottom-up nanofabrication technique for exploratory research and realistic application" Phys Chem Chem Phys. May 21, 2007;9(19):2319-40.

Balabushevich et al., "Protein-loaded microspheres prepared by sequential adsorption of dextran sulphate and protamine on melamine formaldehyde core" J Microencapsul. Nov. 2009;26(7):571-9.

Balko, J.M. et al., Gene expression patterns that predict sensitivity to epidermal growth factor receptor tyrosine kinase inhibitors in lung cancer cell lines and human lung tumors, BMC Genomics, 7:289-302 (2006).

Barrera et al., "Synthesis and RGD peptide modification of a new biodegradable copolymer: poly(lactic acid-co-lysine)" J. Am. Chem. Soc. 115:11010-11011, 1993.

Bass, Brenda L., "RNA Interference the Short Answer", Nature 411, 428-429, 2001.

Behr, "Synthetic Gene-Transfer Vectors" Ace. Chem. Res. 26: 274-278, 1993.

Behr, "The Proton Sponge: a Trick to Enter Cells the Viruses Did Not Expoit" Chimia, 51: 34-36, 1997.

Benkiranc-Jessel et al., "Build-up if Polypeptide Multilayer Coatings with Anti-Inflammatory Properties Based on the Embedding of Piroxicam-Cyclodextrin Complexes," Advanced Functional Materials. 14:2, 2004.

Berg et al., "Controlling mammalian cell interactions on patterned polyelectrolyte multilayer surfaces" Langmuir. Feb. 17, 2004;20(4):1362-8.

Bershteyn et al., "Polymer-supported lipid shells, onions, and flowers" Soft Matter 2008, 4, 1787.

Biggs et al., "The use of nanoscale topography to modulate the dynamics of adhesion formation in primary osteoblasts and ERK/MAPK signalling in STRO-1+ enriched skeletal stem cells" Biomaterials Oct. 2009;30(28):5094-103.

Blacklock et al., "Cross-linked bioreducible layer-by-layer films for increased cell adhesion and transgene expression" J Phys Chem B. Apr. 29;114(16):5283-91.

Boes et al., "T-cell engagement of dendritic cells rapidly rearranges MHC class II transport" Nature 2002, 418, 983-988.

Bonewald et al., "von Kossa staining alone is not sufficient to confirm that mineralization in vitro represents bone formation" Calcif Tissue Int. May 2003;72(5):537-47.

Bott "Applications of "Wired" Enzyme Electrodes," Current Separations, 21(1):3-6 (2004).

Boudou et al., "Internal composition versus the mechanical properties of polyelectrolyte multilayer films: the influence of chemical cross-linking" Langmuir. Dec. 15, 2009;25(24):13809-19.

Boudou et al., "Multiple functionalities of polyelectrolyte multilayer films: new biomedical applications" Adv. Mater., 22(4):441-467 (2010).

Boussif, et al., "A Versatile Vector for Gene and Oligonucleotide Transfer into Cells in Culture and in Vivo: Polyethylenimine" Proc. Nat/. Acad. Sci, USA, 92: 7297-7301, 1995.

Brama et al., "Effect of titanium carbide coating on the osseointegration response in vitro and in vivo" Biomaterials. Feb. 2007;28(4):595-608.

Brange et al., "Insulin formulation and delivery" Pharm Biotechnol. 1997;10:343-409 (need to locate electronic ref.).

Brazeau, et al., "In Vitro Myotoxicity of Selected Cationic Macromolecules Used in Non-1tb1 Gene Delivery" Pharm. Res. 15: 680-684, 1998.

Brewer et al., "Condensation of DNA by spermatid basic nuclear proteins" J Biol Chem. Oct. 11, 2002;277(41):38895-900.

Brewster et al. 2007, "Cyclodextrins as Pharmaceutical Solubilizers," Advanced Drug Delivery. 59: 645-666).

Buser et al., "The Crystal Structure of Prussian Blue: Fe4[Fe(CN)5]3XH20," Inorganic D Chemistry, 16(11):2704-2710 (1977).

Calvo et al. "Donnan Permselectivity in Layer-by-Layer Self-Assembled Redox Polyelectrolyte thin film", J. Am. Soc. 124: 8490-8497(2002).

Carey, L.A. et al., "EGFR inhibition with cetuximab added to carboplatin in metastatic triple-negative (basal-like) breast cancer," Supplement to Journal of Clinical Oncology, ASCO Annual Meeting Proceedings, TBCRC 001: Clinical Science Symposium, 43S (2009).

Carpenter et al., "A Single-Film Electrochromic Device," J. Electrochem. Soc., 137(8):2464-2467 (1990).

Carpenter, A. E. et al., CellProfiler: image analysis software for identifying and quantifying cell phenotypes, Genome Biology, 7(10):R100-R100.11 (2006).

Carrell et al., "The aetiology of sperm protamine abnormalities and their potential impact on the sperm epigenome" Int J Androl. Dec. 2008;31(6):537-45.

Caruso, F., "COLL 34-Polymer Design and Assembly for Next-Generation Particle Delivery", Abastracts of Papers American Chemical Society, 237th National Meeting of American Chemical Society, Salt Lake City Utah, Mar. 22, 2009.

Castleberry, S., et al., "Nanolayered siRNA Dressing for Sustained Localized Knockdown," ACS NANO, 7(6): 5251-5261 (2013).

Castleberry, S., et al., "Surface Mediated Delivery of siRNA from Layer-by-Layer Assembled Polyelectrolyte Films for the Acceleration of Wound Healing," Abstracts of Papers, 244th National Mtg & Exposition, Aug. 19-23, 2012.

Cavalieri et al., "Assembly and functionalization of DNA-polymer microcapsules" ACS Nano 2009, 3, 234.

Chen, "Preparation, characterization, and electrocatalytic oxidation properties of iron, cobalt, nickel, and indium hexacyanoferrate," Journal of Electroanalytical Chemistry, 521:29-52 (2002).

Choksakulnimitr et al., "In Vitro Cytotoxicity of Macromolecules in Different Cell Culture Systems" Controlled Release, 34: 233-241 (1995).

Chou, T-C. et al., Quantitative Analysis of Dose-Effect Relationshiios: The Combined Effects of Mutiple Drugs or Enzyme Inhibitors, Advances in Enzyme Regulation, 22:27-55 (1984).

Christensen et al., "Heparin coating of the stent graft—effects on platelets, coagulation and complement activation," Biomaterials, 22:349-355 (2001).

Cini et al., "Step-by-step assembly of self-patterning polyelectrolyte films violating (almost) all rules of layer-by-layer deposition" J Am Chem Soc. Jun. 23;132(24):8264-5.

Clark et al., "Selective Deposition in Multilayer Assembly: SAMs as molecular templates," Supramolecular Science 4:141, 1997.

Corkery, B. et al., Epidermal growth factor receptor as a potential therapeutic target in triple-negative breast cancer, Annals of Oncology, 20:862-867 (2009).

(56) References Cited

OTHER PUBLICATIONS

Cotten, et al., "Receptor-Mediated Transport of DNA into Eukaryotic Cells" Methods Enzym. 217:618, 1993.
Crane et al., "Cyclodextrin Inclusion Complexes with a Solvatochromic Flurorescent Probe," Journal of Chemical Education. 79(10):1261-1263 (2002).
Crouzier et al., "Ion pairing and hydration in polyelectrolyte multilayer films containing polysaccharides" Biomacromolecules. Feb. 9, 2009;10(2):433-42.
Crystal, "Transfer of Genes to Humans: Early Lessons and Obstacles to Success" Science, 270: 404-410 (1995).
Dalby et al., "The control of human mesenchymal cell differentiation using nanoscale symmetry and disorder" Nat Mater. Dec. 2007;6(12):997-1003.
Danusso, et al., "Synthesis of Tertiary Amine Polymers" Polymer, 11:88-113 (1970).
Davis et al., "Cyclodextrin-Based Pharmaceutics: Past, Present and Future," Nature Reviews (3), 1023-1035 (2004).
Davis et al., "Challenges and potential for RNA nanoparticles (RNPs)" J Biomed Nanotechnol, 5(1):36-44 (2009). (need to locate electronic ref.).
De Jonge et al., "The osteogenic effect of electrosprayed nanoscale collagen/calcium phosphate coatings on titanium" Biomaterials. Mar;31(9):2461-9.
Decher et al., "Buildup of Ultrathin Multilayer Films by a Self-Assembly Process, 1 Consecutive Adsorption of Anionic and Cationic Bipolar Amphiphiles on Charged Surfaces," Makromol. Chem., Macro mol. Symp., 46:321-327 (1991).
Decher et al., ""Layer-by-layer assembled multicomposite films,"" Curr. Opinion Coli. & Interf. Sci. 3:32-39 (1998).
Decher et al., ""New nanocomposite films for biosensors: layer-by-layer adsorbed films of polyelectrolytes, proteins or DNA,"" Biosensors & Bioelectronics, 9:677-684 (1994).
Decher, "Fuzzy Nanoassemblies: Toward Layered Polymeric Multicomposites" Science, 277: 1232-1237 (1997).
Decher, et al., "Buildup of Ultrathin Multilayer Films by a Self-Assembly Process: II. Consecutive Adsorption of Anionic and Cationic Bipolar Amphiphiles and Polyelectrolytes on Charged Surfaces," Ber. Bunsenges. Phys. Chem., 95(11 ):1430-1434 (1991).
Delongchamp "High-Contrast Electrochromism from Layer-by-Layer Polymer Films," Chem. Mater, 15: 1575-1586 (2003).
"Delongchamp et al., ""Fast Ion Conduction in Layer-by-Layer Polymer Films,"" Chem. Mater., 15:1165-1173 (2003)."
"Delongchamp et al., ""High-Contrast Electrochromism and Controllable Dissolution of Assembled Prussian Blue/Polymer Nanocomposites,"" Adv. Funct. Mater., 14(3):224-231 (2004)."
Demeneix, et al., "The Proton Sponge: A Trick the Viruses Did Not Exploit," American Chemical Socicty,146-151 (1996).
DeMuth et al., "Nano-layered microneedles for transcutaneous delivery of polymer nanoparticles and plasmid DNA" Adv Mater. Nov. 16;22(43):4851-6.
Dent, R. et al., "Triple-Negative Breast Cancer: Clinical Features and Patterns of Recurrence," Clinical Cancer Research, 13: 4429-4434 (2007).
Deshmukh, et al., "Liposome and Polylysine Mediated Gene Transfer" New J. Chem. 21: 113-124 (1997).
Diaz, R. et al., "Antitumor and anti angiogenic effect of the dual EGFR and HER-2 tyrosine kinase inhibitor lapatinib in a lung cancer model," BMC Cancer, 10:188 (2010).
Dimitrova et al., "Sustained delivery of siRNAs targeting viral infection by cell-degradable multilayered polyelectrolyte films" Proc. Natl. Acad. Sci. U. S. A. 2008, 105, 16320.
Dixon, "Quartz crystal microbalance with dissipation monitoring: enabling real-time characterization of biological materials and their interactions" J Biomol Tech. Jul. 2008;19(3):151-8.
Donatus et al., "Model-based estimates of risks of disease transmission and economic costs of seven injection devices in sub-Saharan Africa" Bull World Health Organ 2002, 80, 859-870.

Dowben, R.M., "General Physiology: A Molecular Approach," Division of Biological and Medical Sciences, pp. 142-143, Harper & Row Publishers (1969).
Dubas, et al., "Multiple Membranes from 'True' Polyelectrolyte Multilayers", J. Am. Chem. Soc., 123:5368-5369 (2001).
Dubas, et al., Polyelectrolyte Multilayers Containing a Weak Polyacid: Construction and Deconstruction, Macromolecules, 34: 3736-3740 (2001).
Duek et al., "A Solid-State Electrochromic Device Based on Polyaniline, Prussian Blue and an Elastomeric Electrolyte," Advanced Materials, 5(9):650-652 (1993).
Ekins, S. et al., Pathway Mapping Tools for Analysis of High Content Data, Methods in Molecular Biology, 356:319-350 (2007).
Elbert et al., "Self-assembly and steric stabilization at heterogeneous, biological surfaces using absorbing block copolymers" Chemistry & Biology 5(3): 177-183 (1998).
El-Ghannam et al., "Model surfaces engineered with nanoscale roughness and RGD tripeptides promote osteoblast activity" J Biomed Mater Res A. Mar. 15, 2004;68(4):615-27.
Ellis et al., "Eietrochromism in the Mixed-Valence Hexacyanides. 1. Voltammetric and Spectral Studies of the Oxidation and Reduction of Thin Films of Prussian Blue," J. Phys. Chem., 85:1225-1231 (1981).
Feiler et al., "Adsorption and viscoelastic properties of fractionated mucin (BSM) and bovine serum albumin (BSA) studied with quartz crystal microbalance (QCM-D)" J Colloid Interface Sci. Nov. 15, 2007;315(2):475-81.
Ferruti, e.t al., "Synthesis, Characterisation and Anti tumour Activity of Platinum (II) Complexes of Novel Functionalised Poly (Arnido Amine)s" Macromol. Chem. Phys., 200:1644-1654 (1999).
Ferruti, et al., "Amphoteric Linear Poly(amido-amine)s as Endosomolytic Polymers: Correlation between Physicochemical and Biological Properties", Macromolecules, 2000.
Ferruti, et al., "Linear Amino Polymers: Synthesis, Protonation and Complex Formation" Advances in Polymer Science, 58: 55-92, 1984.
Ferruti, et al., "Recent Results on Functional Polymers and Macromonomers offiuterest as Biomaterials or for Biomaterial Modifcation" Biomaterials, 15: 1235-1241 (1994).
Ferruti, et al., "Synthesis, Physico-Chemical Properties and Biomedical Applications of Poly(amino-amine)s" Polymer, 26: 1336 (1985).
Fire, et al., "Potent and Specific Genetic Interference by Double-Stranded RNA in Caenorhabditis Elegans" Nature, 391: 806-811 (1998).
Fitzgerald, J.B. et al., Systems biology and combination therapy in the quest for clinical efficacy, Nature Chemical Biology, 2(9):458-466 (2006).
Flessner, R.M., et al., "Degradable Polyelectrolyte Multilayers That Promote the Release of siRNA," Langmuir, 27(12): 7868-7876 (2011).
Freiberg et al., "Polymer microspheres for controlled drug release," Int. J. Pharm. 282:1-18 (2004).
Friedman, "Human Gene Therapy—An Immature Genie, but Certainly out of the Bottle" Nature Med, 2: 144-147 (1996).
Gao et al., "Layer-by-layer electrodeposition of redox polymers and enzymes on screenprinted carbon electrodes for the preparatioin of reagentess biosensors," ChemComm, (2003).
Gaudet, S. et al., A Compendium of Signals and Responses Triggered by Pro-death and Prosurvival Cytokines, Molecular & Cellular Proteomics, 4:1569-1590 (2005).
Gemici et al., "Hydrothermal treatment of nanoparticle thin films for enhanced mechanical durability" Langmuir. Mar. 4, 2008;24(5):2168-77.
Gerasimov, et al., "Cytosolic Drug Delivery Using pH- and Light~Sensitive Liposomes" Adv. Drug Delivery Rev. 38: 317-338, 1999.
Gill et al., "Coated microneedles for transdermal delivery" J. Controlled Release 2007, 117, 227-237.
Gill et al., "Cutaneous vaccination using microneedles coated with hepatitis C DNA vaccine" Gene Ther. 2010,.
Giudice et al., "Needle-free vaccine delivery" Adv. Drug Delivery Rev. 2006, 58, 68.

(56) References Cited

OTHER PUBLICATIONS

Glenn et al., "Transcutaneous immunization and immunostimulant strategies: capitalizing on the immunocompetence of the skin" Expert Rev. Vaccines, 2: 253 (2003). (need to locate electronic ref.).
Gonzalez, et al., "New Class ofPolymers for the Delivery ofMacromolecularTherapeutics" Bioconjugate Chem. 10: 1068-1074, 1999.
Grabow, W. W., et al., "siRNA delivery: Loaded-up Microsponges," Nature Materials, 11(4): 268-269 (2012).
Graham, P.D., et al., "Phase inversion dynamics of PLGA solutions related to drug delivery," J Control Release 58(2): 233-245 (1999).
Grayson et al., "Electronic MEMS for triggered drug delivery," Advanced Drug Delivery Reviews, 56:173-184 (2004).
Greenland et al., "Beta-amino ester polymers facilitate in vivo DNA transfection and adjuvant plasmid DNA immunization" Mol. Ther. 2005, 12, 164.
Guo, P., "Rolling Circle Transcription of Tandem siRNA to Generate Spherulitic RNA Nanoparticles for Cell Entry," Molecular Therapy, Nucleic Acids, 1:3162-2531 (2012).
Habib et al., "A tungsten-trioxide/prussian blue complementary eletrochromic cell with a polymer electrolyte," Journal of Applied Electrochemistry, 21:203-207 (1991).
Habib et al., "Effect of Temperature on a Complementary W03—Prussian Blue Electrochromic System," J. Electrochem. Soc., 139(8):2155-2157 (1992).
Haensler, et al., "Polyamidoamine Cascade Polymers Mediate Efficient Transfection of Cells in Culture" Bioconjugate Chem. 4:372-379, 1993.
Hammond et al., "Fromation of Polymer Microstructures by Selective Deposition of Polyion Multilayers Using Patterned Self-Assembled Monolayers as a Template," Macromolecules 28:7569-7571 (1995).
Hammond, "Form and Function in Multilayer Assembly: New Applications at the Nanoscale," Adv. Mater. 16:1271-1293 (2004).
Hanahan, D. et al., The Hallmarks of Cancer, Cell, 100 57-70 (2000).
Hanes, et al., "New Advances in Microsphere-Based Single-Dose Vaccines" Adv. Drug Delivery Rev. 28:97-119,1997.
Hansen, et al., "Re-Examination and Further Development of a Precise and Rapid Dye Method for Measuring Cell Growth/Cell Kill" Immunol. Methods, 119:203-210, 1989.
Haq et al., "Clinical administration of microneedles: Skin puncture, pain and sensation" Biomed Microdevices 2009, 11, 35.
Harper, J.W. et al., The DNA Damage Response: Ten Years After, Molecular Cell, 28(5):739-745 (2007).
Haynic et al., "Protein-inspired multilayer nanofilms: science, technology and medicine" Nanomedicine. Sep. 2006;2(3):150-7.
Hehrlein et al., "Drug-eluting stent: the "magic bullet" for prevention of restenosis?" Basic Res Cardiel, 97:417-423 (200:2).
Helfrich, B.A. et al., Antitumor Activity of the Epidermal Growth Factor Receptor (EGFR) Tyrosine Kinase Inhibitor Gefitinib (ZD1839, 1ressa) in Non-Small Cell Lung Cancer Cell Lines Correlates with Gene Copy Number and EGFR Mutations but not EGFR Protein Levels, Clinical Cancer Research, 12:7117-7125 (2006).
Heller "Redox hydrogel-based electrochemical biosensore," Biosensors, Second Edition, pp. 1-18 (2004).
Hill, et al., "Tn Vitro Cytotoxicity ofPoly(amidoamine)s: Relevance to DNA Delivery" Biochim. Biophys. Acta, 1427: 161q 74, 1999.
Hillberg et al., "Effect of genipin cross-linking on the cellular adhesion properties of layer-by-layer assembled polyelectrolyte films" Biomaterials Sep. 2009;30(27):4463-70.
Hope, et al., "Cationic Lipids, Phosphatidylethanolamine and the Intracellular Delivery of Polymeric, Nucleic Acid-Based Drugs (Review), Molecular Membrane Technology, 15: 1-14, 1998.
Hossfeld, S., et al., "Bioactive Coronary Stent Coating Based on Layer-by-Layer Technology for SiRNA release," Acta Biomaterialia, 9(5): 6741-6752 (2013).
Itaya et al., "Prussian-blue-modified electrodes: An application for a stable eletrochromic display device," J. Appl. Phys., 53:804-805 (1982).

Janes, K.A. et al., A Systems Model of Signaling Identifies a Molecular Basis Set for Cytokine-Induced Apoptosis, Science, 310:1646-1653 (2005).
Janes, K.A. et al., Cytokine-Induced Signaling Networks Prioritize Dynamic Range over Signal Strength, Cell, 135:343-354 (2008).
Jelle et al., "Transmission Spectra of an Electrochromic Window Consisting of Polyaniline, Prussian Blue and Tungsten Oxide," Electrochimica Acta, 38(11 ):1497-1500 (1993).
Jessel et al. Multiple and time-scheduled in situ DNA delivery mediated by B-cyclodextrin embedded in a polyelectrolyte multilayer, Jun. 6, 2006, PNAS, vol. 103, No. 23, pp. 8618-8621.
Jewell et al., "Multilayered polyelectrolyte assemblies as platforms for the delivery of DNA and other nucleic acid-based therapeutics" Adv. Drug Delivery Rev. 2008, 60, 979.
Jiang et al., "Selective Deposition in Layer-by-Layer Assembly: Functional Graft," Langmuir, 16:8501-8509, (2000).
Johannsmann et al., "Effect of sample heterogeneity on the interpretation of QCM(-D) data: comparison of combined quartz crystal microbalance/atomic force microscopy measurements with finite element method modeling" Anal Chem. Dec. 1, 2008;80(23):8891-9.
Kabanov, et al., "DNA Complexes with Polycations for the Delivery of Genetic Material inot Cells" Bioconjugate Chem. 6:7-20 (1995).
Kang, N. et al., Inhibition of EGFR signaling augments oridonin-induced apoptosis in human laryngeal cancer cells via enhancing oxidative stress conicident with activiation of both the intrinsic and extrinsic apoptotic pathways, Cancer Letters, 294:147-158 (2010).
Каргина, , О.В. СимораещEшляющиЕСя ВОДОРАСТВОРИМЫЕ ИОНОГЕННЫЕ полимеры (English Abstract).
Katsuhiko, Sato, et al., (cited as: Sato, K. et al.,) "Layered Assemblies Composed of Sulfonated Cyclodextrin and Poly(allyamine)," Colloid & Polymer Science, 282:287-290 (2003).
Keselowsky et al., "Integrin alpha(5) controls osteoblastic proliferation and differentiation responses to titanium substrates presenting different roughness characteristics in a roughness independent manner" J Biomed Mater Res A. Mar. 1, 2007;80(3):700-10.
Khopade et al., "Electrostatically Assembled Polyelectrolyte/ Dendrimer Multilayer Films as Ultrathin Nanoreservoirs," Nano Letters. 2:415, (2002).
Kim et al., "Enhanced memory responses to seasonal H1N1 influenza vaccination of the skin with the use of vaccine-coated microneedles" J Infect Dis 2010, 201, 190.
Kim et al., "Hydrogen-Bonding Layer-by-Layer-Assembled Biodegradable Polymeric Micelles as Drug Delivery Vehicles from Surfaces" ACS Nano 2008, 2, 386.
Kim et al., "MAD (multiagent delivery) nanolayer: delivering multiple therapeutics from hierarchically assembled surface coatings" Langmuir 2009, 25, 14086.
Kim, R., Recent Advances in Understanding the Cell Death Pathways Activated by Anticancer Therapy, Cancer, 1 03(8):1551-1560 (2005).
Klopman et al., "Recent Methodologies for the Estimation of N-Octanol/Water Partition Coefficents and their Use in the Prediction of Membrane Transport Properties of Drugs," Mini-Reviews in Medicinal Chemistry. 5:127-133, (2005).
Krogman et al., Spraying asymmetry into functional membranes layer-by-layer Nat. Mater. 2009, 8, 512-518.
Kukowska-Latallo, et al., "Efficient Transfer of Genetic Material into Manunalian Cells Using Starburst Polyamidoamine Dendrimers" Proc. Nat/. Acad. Sci. USA, 93: 4897-4902, 1996.
Kumar et al., "Patterning Self-Assembled Monolayers: Applications in Materials Science," Langmuir, 10:1498-1511 (1994).
Kwon et al., "Pseudopoly(amino acids): A Study of the Synthesis and Characterization of Poly(trans-4-hydroxy-N-acyi-L-proline esters)," Macromolecules, 22:3250-3255 (1989).
Langer, "Biomaterials in Drug Delivery and Tissue Engineering: One Laboratory's Experience," Ace. Chem. Res. 33:94-101, (2000).
Langer, "Selected Advances in Drug Delivery and Tissue Engineering," J. Control Release 62:7-11 (1999).
Lavan et al., "Small-scale systems for in vivo drug delivery," Nature Biotechnology 21 (10):1184-1191 (2003).

(56) References Cited

OTHER PUBLICATIONS

Lavos-Valereto et al., "In vitro and in vivo biocompatibility testing of Ti—6A1—7Nb alloy with and without plasma-sprayed hydroxyapatite coating" J Biomed Mater Res. 2001;58(6):727-33.
Lee, J.B., et al., "Self-assembled RNA interference microsponges for efficient siRNA delivery," Nature Materials, 11(4): 316-322 (2012).
Leguen et al., "Bioactive coatings based on polyelectrolyte multilayer architectures functionalized by embedded proteins, peptides or drugs" Biomol Eng., 24(1):33-41 (2007). (need to locate electronic ref.).
Liang, et al., "The minimal functional sequence of protamine" Biochem. and Biophys. Res. Commun., 336: 653-659 (2005).
Liao, et al., "Response of rat osteoblast-like cells to microstructured model surfaces in vitro" Biomaterials, (4):649-654 (2003).
Lichter, A.S., et al., "Recent Advances in Radiation Oncology.," New England Journal of Medicine, 332(6):371-379 (1995).
Lim, et al., "A Self-Destroying Polycationic Polymer: Biodegradable Poly(4-Hydroxy-LProline Ester)" Jam. Chem. Soc. 121: 5633-5639 (1999).
Lim, et al., "Cationic Hyperbranched Poly(amino ester): A Novel Class of DNA Condensing Molecule with Cationic Surface, Biodegradable Three-Dimensional Structure, and Tertiary Amine Groups in the Interior," J. Am. Chem. Soc., 123: 2460-2461 (2001).
Lim, et al., "Development of a Safe Gene Delivery System Using Biodegradable Polymer, Poly [a-(4-Aminobutyl-L-Glycolic Acid]" Jam. Chem. Soc., 122: 6524-6525 (2000).
Linhardt, et al., "Free-Radical Synthesis of Poly(2-Ethylacrylic Acid) Fractions of Low Polydispersity: Effects of Molecular Weight and Polydispersity on the pH-Dependent Conformational Transition in Aqueous Solution," Macromolecules, 32: 4457-4459 (1999).
Linhardt, et al., "pH-Induced Fusion and Lysis of Phosphatidylcholine Vesicles by Hydrophobic Polyelectrolyte Poly(2-ethylacrylic Acid)" Langmuir, 16:122-127 (2000).
Livingstone et al., "Theoretical Property Predictions," Current Topics in Medicinal Chemistry 3:1171-1192 (2003).
Liu, "Ultrathin Multilayered Films that Promote the Release of Two DNA Constructs with Separate and Distinct Release Profiles" Adv. Mater. 2008, 20 (pp. 4148-4153).
Lo, H., et al., "Fabrication of controlled release biodegradable foams by phase separation," Tissue Eng. 1(1), 15-28 (1995).
Lopez, J.P. et al., Gefitinib Inhibition of Drug Resistance to Doxorubicin by Inactivating ABCG2 in Thyroid Cancer Cell Lines, Archives of Otolaryngology—Head & Neck Surgery, 133(10):1022-1027 (2007).
Luo, et al., "Synthetic DNA Delivery Systems" Nat. Biotechnol. 18: 33-37, 2000.
Lynn et al., "Degradable Poly(β-amino esters): Synthesis, Characterization, and Self-Assembly with Plasmid DNA," J. Am. Chem. Soc., 122:10761-10768 (2000).
Lynn et al., "pH-Responsive Polymer Microspheres: Rapid Release of Encapsulated Material Within the Range of Intracellular pH" Angewandte Chemie International Edition, 40: 1707-1710 (2001).
Lynn, "Peeling Back the Layers: Controlled Erosion and Triggered Disassembly of Multilayered Polyelectrolyte Thin Films," Adv. Mater., 19: 4118-4130 (2007).
Lynn, et al., "Accelerated Discovery of Synthetic Transfection Vectors: Parallel Synthesis and Screening of a Degradable Polymer Library" Journal of the American Chemical Society, 123: 8155-8156 (2001).
Lynn, et al., Construction of Degradable Thin Films via Layber-by-Layer Deposition of Polyelectrolytes: Fabrication, Characterization, and Application to Controlled Release, MIT Proposal 2001.
MacBeath, G., Protein microarrays and proteomics, Nature Genetics Supplement, 32:526-532 (2002).
Macdonald, et al., "Release of a model protein from biodegradable self assembled films for surface delivery applications," J. Control Release., 131(3):228-234 (2008).
MacDonald, et al., "Tissue Integration of Growth Factor-Eluting Layer-by-Layer Polyelectrolyte Multilayer Coated Implants," Biomaterials, 32(5): 1446-1453 (2010).

Mansouri et al., "Modulating the release kinetics through the control of the permeability of the layer-by-layer assembly: a review" Expert Opin Drug Deliv. Jun. 2009;6(6):585-97.
Martin et al., "Solubility and Kinetic Release Studies of Naproxen and Ibuprofen in Soluble Epichlorohydrinβ-cyclodextrin Polymer," Supramolecular Chemistry, 18(8): 627-631, (2006).
Mathiowitz, et al., "Polyanhydride Microspheres as Drug Carriers I. Hot-Melt Microencapsulation" J. Controlled Release, 5:13-22 (1987).
Mathiowitz, et al., "Polyanhydride Microspheres as Drug Carriers. II. Microencapsulation" J. Appl. Polymer Sci., 35: 755-774 (1988).
Mehrotra et al., "Time Controlled Protein Release from Layer-by-Layer Assembled Multilayer Functionalized Agarose Hydrogels" Adv Funct Mater. Jan. 22;20(2):247-58.
Mendelsohn et al., "Rational design of cytophilic and cytophobic polyelectrolyte multilayer thin films" Biomacromolecules. Jan.-Feb. 2003;4(1):96-106.
Michel, et al., "Printing meets lithography: Soft approaches to high-resolution patterning" IBM Journal of Research and Development, 45(5): 697-719 (2001).
Mikos A.G., et al., "Preparation and Characterization of Poly(L-Lactic Acid) Foams," Polymer 35(5): 1068-1077 (1994).
Mikszta et al., "Improved genetic immunization via micromechanical disruption of skin-barrier function and targeted epidermal delivery" Nat. Med. 2002, 8, 415.
Milano, G. et al., EGFR-targeting drugs in combination with cytotoxic agents: from bench to bedside, a contrasted reality, British Journal of Cancer, 99:1-5 (2008).
Miller, "Cationic Liposomes for Gene Therapy" Angew. Chem. Int. Ed. 37: 1769-1785, 1998.
Mizushima, N. et al., Methods in Mammalian Autophagy Research, Cell, 140:313-326 (2010).
Montesano, R. et al., Test for Malignant Transformation of Rat Liver Cells in Culture: Cytology, Growth in Soft Agar, and Production of Plasminogen Activator, Journal of the National Cancer Institute, 59(6):1651-1658 (1977).
Moor, A., et al., "Proteolytic Activity in Wound Fluids and Tissues Derived from Chronic Venous Leg Ulcers," Wound Repair and Regeneration, 17(6): 1067-1927 (2009).
Moran et al., Mixed protein carriers for modulating DNA release. Langmuir. Sep. 1, 2009;25(17):10263-70.
Morgillo, F. et al., Antitumor activity of bortezomib in human cancer cells with acquired resistance to anti-epidermal growth factor receptor tyrosine kinase inhibitors, Lung Cancer, 71:283-290 (2011 ).
Moriguchi et al., "Synthesis of Ultrathin Films of Prussian Blue by Successive Ion Adsorption Technique," Chemistry Letters, 31 (3):31 0-311 (2002).
Moskowitz et al., "The effectiveness of the controlled release of gentamicin from polyelectrolyte multilayers in the treatment of Staphylococcus aureus infection in a rabbit bone model" Biomaterials. Aug;31(23):6019-30.
Mulligan, "The Basic Science of Gene Therapy" Science, 260: 926-932 (1993).
Murphy, et al., "A Combinatorial Approach to the Delivery of Efficient Cationic Peptoid Reagents for Gene Delivery", Proc. Natl. Acad. Sci. USA, 95: 1517-1522 (1998).
Neve, R.M. et al., A collection of breast cancer cell lines or the study of functionally distinct cancer subtypes, Cancer Cell, 10:515-527 (2006).
Newman et al., "Natural Products as Sources of New Drugs over the Period 1981-2002," Journal of Natural Products. 66:1022-1037 (2003).
Nguyen et al., "Extended Release Antibacterial Layer-by-Layer Films Incorporating Linear-Dendritic Block Copolymer Micelles," Chemistry of Materials. 19:5524-5530 (2007).
Niemiec et al., Nanoheterogeneous multilayer films with perfluorinated domains fabricated using the layer-by-layer method. Langmuir. Jul. 20;26(14):11915-20.
O'Donnell, et al., "Preparation of Microspheres by the Solvent Evaporation Technique" Adv. Drug Delivery Rev., 28:25-42, 1997.
Oh et al., "Stem cell fate dictated solely by altered nanotube dimension" Proc Natl Acad Sci U S A. Feb. 17, 2009;106(7):2130-5.

(56) References Cited

OTHER PUBLICATIONS

Okada, "One-and Three-Month Release Injectable Microspheres of the LH-RH Superagonist Leuprorelin Acetate" Adv. Drug Delivery Rev. 28: 43-70, 1997.
Oliva et al., "Antiproliferative Drug-Eluting Stents: Systematic Review of the Benefits and Estimate of Economic Impact," Rev Esp Cardiel, 57(7):617-628 (2004).
Pareta et al., "An understanding of enhanced osteoblast adhesion on various nanostructured polymeric and metallic materials prepared by ionic plasma deposition" J Biomed Mater Res A. Mar. 1;92(3):1190-201.
Park et al., "Biodegradable polymer microneedles: fabrication, mechanics and transdermal drug delivery" J. Controlled Release 2005, 104, 51.
Park et al., "Osteoconductivity of hydrophilic microstructured titanium implants with phosphate ion chemistry" Acta Biomater. Jul. 2009;5(6):2311-21.
Pasco et al., "Characterization of a thermophilic L-glutamate dehydrogenase biosenor for amperometric determination of L-glutamate by flow injection analysis," Biosensors & Bioelectronics, 14:171-178 (1999).
Pawson, T. et al., Network medicine., FEBS Letters, 582:1266-1270 (2008).
Pearton et al., "Gene delivery to the epidermal cells of human skin explants using microfabricated microneedles and hydrogel formulations" Pharm. Res. 2008, 25, 407.
Peer, D., P. Zhu, C. V. Carman, J. Lieberman, and M. Shimaoka, Selective gene silencing in activated leukocytes by targeting siRNAs to the integrin lymphocyte function-associated antigen-1. Proc Natl Acad Sci USA, 2007. 104(10): p. 4095-100.
Peerce et al., "Polymer Films on Electrodes, Part III. Digital Simulation Model for Cyclic Voltammetry of Electroactive Polymer Film and Electrochemistry of Poly(vinylferrocene) on Platinum," J. Electroanal. Chem, 114:89-115 (1980).
Perou, C.M. et al., Molecular portraits of human breast tumours, Nature, 406:747-752 (2000).
Petrie et al., "The effect of integrin-specific bioactive coatings on tissue healing and implant osseointegration" Biomaterials. Jul. 2008;29(19):2849-57.
Pfeifer et al., "Formulation and surface modification of poly(ester-anhydride) micro- and nanoshperes," Biomaterials, 26:117-124 (2005).
Picart et al., ""Molecular basis for the explanation of the expotential growth of polyelectrolyte multilayers"" PNAS 99(20):12531-12535 (2002).
Poerner et al., "Drug-coated stents," Minimally Invasive Therapy & Allied Technologies 11(4):185-192 (2002).
Porcel et al., "From exponential to linear growth in polyelectrolyte multilayers" Langmuir. Apr. 25, 2006;22(9):4376-83.
Porcel et al., "Influence of the polyelectrolyte molecular weight on exponentially growing multilayer films in the linear regime" Langmuir. Feb. 13, 2007;23(4):1898-904.
Prausnitz, "Microneedles for transdermal drug delivery" Adv. Drug Delivery Rev. 2004, 56, 581.
Prausnitz, et al., "Transdermal drug delivery" Nat. Biotechnol., 26: 1261 (2008).
Pruss-Ustun et al., WHO Environmental Burden of Disease Series, World Health Organization, 2003.
Putnam et al., "Poly(4-hydroxy-L-proline ester): Low-Temperature Polycondensation and Plasmid DNA Complcxation," Macromolecules, 32:3658-3662 (1999).
Qiu, et al., "Studies on the Drug Release Properties of Polysaccharide Multi layers Encapsulated Ibuprofen Microparticles" Langmuir 17: 5375-5380 (2001).
Quan et al., "Stabilization of influenza vaccine enhances protection by microneedle delivery in the mouse skin" PLoS One 2009, 4, e7152.
Quarles et al., "Distinct proliferative and differentiated stages of murine MC3T3-E1 cells in culture: an in vitro model of osteoblast development" J Bone Miner Res. Jun. 1992;7(6):683-92.

Rajan et al., "Eiectrochromism in the Mixed-Valence Hexacyanides. 2. Kinetics of the Reduction of Ruthenium Purple and Prussian Blue," J. Phys. Chem., 86:4361-4368 (1982).
Ramaswamy et al., "Sphene ceramics for orthopedic coating applications: an in vitro and in vivo study" Acta Biomater. Oct. 2009;5(8):3192-204.
Rao, et al., "Poly (Butaneodiol Spermate): A Hydrolytically Labile Polyester-Based Nitric Oxide Carrier" J. Bioactive and Compatible Polymers 14: 54-63, 1999.
Rausch-fan et al., "Differentiation and cytokine synthesis of human alveolar osteoblasts compared to osteoblast-like cells (MG63) in response to titanium surfaces" Dent Mater. Jan. 2008;24(1):102-10.
Razzackt et al., "Integrated microsystems for controlled drug delivery," Advanced Drug Delivery Reviews, 56:185-198 (2004).
Richert et al., "Cell interactions with polyelectrolyte multilayer films" Biomacromolecules. Nov.-Dec. 2002;3(6):1170-8.
Roach et al., "Interpretation of protein adsorption: surface-induced conformational changes" J Am Chem Soc. Jun. 8, 2005;127(22):8168-73.
Roach et al., "Modern biomaterials: a review—bulk properties and implications of surface modifications" J Mater Sci Mater Med. Jul. 2007;18(7):1263-77.
Roberts, et al., "Preliminary Biological Evaluation ofPolyamidoamine (P AMAM) Starburst TM Dendrimers" J. Biomed. Mater. Res. 30: 53-65, 1996.
Robin et al., "The Color and Electronic Configurations of Prussian Blue," Electronic Configurations of Prussian Blue, 1( 2):337-342 (1962).
Rohanizadeh, R., et al., "Gelatin Sponges (Gelfoam®) as a scaffold for Osteoblasts", J. Mater Sci. Mater Med., 19:1173-1182 (2008).
Rusnak, D.W. et al., Assessment of epidermal growth factor receptor (EGFR, ErbB1) and HER2 (ErbB2) protein expression levels and response to lapatinib (Tykerb®, GW572016) in an expanded panel of human normal and tumour cell lines, Cell Proliferation, 40: 580-594 (2007).
Sachs, K. et al., Casual Protein-Signaling Networks Derived from Multiparameter Single-Cell Data, Science, 308:523-529 (2005).
Saha et al., "Designing synthetic materials to control stem cell phenotype" Curr Opin Chem Biol. Aug. 2007;11(4):381-7.
Sanford, "The Biolistic Process" Trends Biotechnol. 6:288-302, 1988.
Santini et al., "Microchips as Controlled Drug-Delivery Devices," Angew. Chem. Int. Ed., 39:2396-2407 (2000).
Santini et al., "Microchips for drug delivery," Abstracts of Papers of the American Chemical Society, 219(174):U34-U34 (2000).
Sapi, E. et al., Ets-2 Transdominant Mutant Abolishes Anchorage-independent Growth and Macrophage Colony-stimulating Factor-stimulated Invasion by BT20 Breast Carcinoma Cells, Cancer Research, 58:1027-1033 (1998).
Schaffer, et al., "Vector Unpacking as a Potential Banier for Receptor-Mediated Polyplex Gene Delivery" Biotechnol. Bioeng., 61: 598-606 (000).
Schechter, A.L. et al., The neu oncogene: an erb-8-related gene encoding a 185,000-Mr tumour antiQen, Nature, 312:513-516 (1984).
Schlenoff, "Retrospective on the future of polyelectrolyte multilayers" Langmuir. Dec. 15, 2009;25(24):14007-10.
Schmidt et al., "Electrochemically controlled swelling and mechanical properties of a polymer nanocomposite" ACS Nano. Aug. 25, 2009;3(8):2207-16.
Schuler "Decomposable Hollow Biopolymer-Based Capsules" Biomacromolecules, vol. 2, 2001 921-26.
Schwarz et al., "Potential of chemically modified hydrophilic surface characteristics to support tissue integration of titanium dental implants" J Biomed Mater Res B Appl Biomater. Feb. 2009;88(2):544-57.
Schweikl, et al., "Triethylene Glycol Dimethacrylate Induces Large Deletions in the Hprt Gene of V79 Cells" Mutat. Rcs. 438: 71-78 (1999).
Sengupta, S. et al., Temporal targeting of tumor cells and neovasculature with a nanoscale delivery system, Nature, 436:568-572 (2005).

(56) References Cited

OTHER PUBLICATIONS

Seo et al., "Effect of the layer-by-layer (LbL) deposition method on the surface morphology and wetting behavior of hydrophobically modified PEO and PAA LbL films" Langmuir. Aug. 5, 2008;24(15):7995-8000.
Sevecka, M. et al., State-based discovery: a multidimensional screen for small-molecule modulators of EGF signaling, Nature Methods, 3(1 0):825-831 (2006).
Seyhan, A. A., et al., "RNA interference from Multimeric shRNSs generated by rolling circle transcripotion," Oligonucleotides, 16(4): 353-363 (2006).
Shiratori et al., "pH-Dependent Thickness Behavior of Sequentially Adsorbed Layers of Weak Polyelectrolytes," Macormolecules, 33:4213-4219 (2000).
Shkula et al., "Tunable Vancomycin Releasing Surfaces for Biomedical Applications", Small Nano Mirco, 2010, 21 (6), 2392-2404.
Shukla et al., "Controlling the release of peptide antimicrobial agents from surfaces" Biomatcrials. Mar. 2010;31(8):2348-2357.
Shutava et al., "Layer-by-Layer-Coated Gelatin Nanoparticles as a Vehicle for Delivery of Natural Polyphenols" ACS Nano. Jul. 28, 2009;3(7):1877-85.
Singh, et al., "Cationic Microparticles: A Potent Delivery System for DNA Vaccines" Proc. Nat/. Acad. Sci. USA, 97: 811-816,2000.
Slamon, D.J. et al., Human Breast Cancer: Correlation of Relapse and Survival with Amplification of the HER-2/neu Oncogene, Science, 235:177-182 ( 1987).
Smith et al., "Layer-by-Layer Platform Technology for Small-Molecule Delivery", Anqew.Chem.Int.Ed., 2009, 48, 8974-8977, with English Abtract.
Song, Jie, et al., "Growth of endothelial cell on the surface of intravascular sent material: Bionic construction of bioactive extracellular matrix", Journal of Clinical Rehabilitative Tissue Enqineerinq Research, Oct. 22, 2009, 13(43), 8425-8431.
Sordella, R. et al., Gefitinib-Sensitizing EGFR Mutations in Lung Cancer Activate Anti-Apoptotic Pathways, Science, 305:1163-1167 (2004).
Su et al., "Layer-by-layer-assembled multilayer films for transcutaneous drug and vaccine delivery" ACS Nano 2009, 3, 3719-3729.
Subramanian, A. et al., Gene set enrichment analysis: A knowledge-based approach for interpreting genome-wide expression profiles, Proceedings of the National Academy of Sciences of the USA, 102(43):15545-15550 (2005).
Sun, T. et al., Activation of Multiple Proto-oncogenic Tyrosine Kinases in Breast Cancer via Loss of the PTPN12 Phosphatase, Cell, 144:703-718 (2011).
Tang, et al., "Adhesion and endothelialization of endothelial cells on the surface of endovascular stents by the novel rotational culture of cells," Applied Surface Science, 255:315-319 (2008).
Tang, et al., "In Vitro Gene Delivery by Degraded Polyamidoamine Dendrimers" Bioconjugate Chem. 7:703-714, 1996.
Tetko et al., "Virtual Computational Chemistry Laboratory-design and description," Computer-Aided Mol. Des. 19: 453-463, (2005).
Thompson et al., "Biochemical functionalization of polymeric cell substrata can alter mechanical compliance" Biomacromolecules. Jun. 2006;7(6):1990-5.
Thompson et al., "Tuning compliance of nanoscale polyelectrolyte multilayers to modulate cell adhesion" Biomaterials. Dec. 2005;26(34):6836-45.
Toniolo et al., "II. Circular dichroism study of the three main components of clupcinc" Biochim Biophys Acta. Feb. 26, 1979;576(2):429-39.
Turner, J.G. et al., ABCG2 expression, function, and promoter methylation in human multiple myeloma, Blood, 108(12):3881-3889 (2006).
Uhrich et al., "Polymeric Systems for Controlled Drug Release," Chem. Rev. 99:3181-3198 (1999).
Uhrich, K., "Hyperbranched Polymers for Drug Delivery" Trends Polym. Sci. 5: 388-393 (1997).

Van de Wetering, et al., "Structure-Activity Relationships of Water-Soluble Cationic Methacrylate/Methacrylamide Polymers for Non viral Gene Delivery" Bioconjugatc Chem. 10: 589-597, 1999.
Vazquez et al., "Variation of polyelectrolyte film stiffness by photo-cross-linking: a new way to control cell adhesion" Langmuir. Apr. 9, 2009;25(6):3556-63.
Vittal et al., "Surfactant Promoted Enhancement on Electrochemical and Electrochromic Properties of Films of Prussian Blue and Its Analogs," Journal of the Electrochmical Socitey, 146(2):786-793 (1999).
Wang et al., "A Novel Biodegradable Gene Carrier Based on Polyphoophoester," J. Am. Chem. Soc. 123:9480-9481 (2001).
Wang D., et al., "Synthesis and evaluation of water-soluble polymeric bone-targeted drug delivery systems," Bioconjugate Chemistry 14(5): 853-859 (2003).
Warner, T.D., et al., "Nonsteroid Drug Selectives for Cyclo-Oxygenase-1 Rather Than Cyclo-Oxygenase-2 are associated with Human Gastrointestinal Toxicity: A full in vitro Analysis," Proceedings of the National Academy of Sciences of the United States of America, 96: 9966 (1999).
Winer, E.P. et al., Optimizing Treatment of "Triple-Negative" Breast Cancer. SABCS 2007: Improving Outcomes in Advanced and Meta-static Breast Cancer, http://www.medscape.org/viewarticle/569483 (2007).
Woeblecke, H. et al., Reversal of breast cancer resistance protein-mediated drug resistance by tryprostatin A, International Journal of Cancer, 107:721-728 (2003).
Wood et al., "Controlling Interlayer Diffusion to Achieve Sustained, Multiagent Delivery from Layer-by-Layer Thin Films," Proceedings of the National Academy of Sciences of the United States of America, 103(27):10207-10212 (2006).
Wood et al., "Tunable drug release from hydrolytically degradable layer-by-layer thin films" Langmuir. Feb. 15, 2005;21(4):1603-9.
Wood, E.R. et al., A Unique Structure for Epidermal Growth Factor Receptor Bound to GW572016 (Lapatinib): Relationships among Protein Conformation, Inhibitor Off-Rate, and Receptor Activity in Tumor Cells, Cancer Research, 64:6652-6659 (2004).
Yang, et al., "A New Approach to Identifying Genotoxic Carcinogens: p53 Induction as an Indicator ofGenotoxic Damage" Carcinogenesis, 19: P1117-P1125, 1998.
Yoon, C-H. et al., Activation of p38 Mitogen-Activated Protein Kinase Is Required for Death Receptor—Independent Caspase-8 Activation and Cell Death in Response to Sphingosine, Molecular Cancer Research, 7(3):361-370 (2009).
Zauner, et al., "Polylysine-Based Transfection Systems Utilizing Receptor-Mediated Delivery" Adv. Drug. Del. Rev. 30: 97-113, 1998.
Zang, Y., et al., "In Vitro Observations of Self-Assembled ECM-Mimetic Bioceramic Nanoreservoir Delivering rFN/CDH to Modulate Osteogenesis", Biomaterials, 33(30): 7468-7477 (2012).
Zhang, J., et al., "Multilayered Thin Films that Sustain the Release of Functional DNA under Physiological Conditions," Langmuir, 20(19): 8015-8021 (2004).
Zheng et al., "Controlling cell attachment selectively onto biological polymer-colloid templates using polymer-on-polymer stamping" Langmuir. Aug. 17, 2004;20(17):7215-22.
Zhou, et al., "Preparation ofPoly(L-serine ester): A Structural Analogue of Conventional Poly(L-serine)" Macromolecules, 23: 3399-3406, 1990.
Wikipedia, Heparin, accessed Oct. 15, 2014, pp. 1-18.
John Wiley and Sons, Lysozyme: Substrate Structure, accessed Oct. 15, 2014, p. 1.
Stubbs, Milton T., et al, Eur. J. Biochem. 2006 (1992), pp. 187-195.
Place ES, Evans ND, Stevens MM. Complexity in biomaterials for tissue engineering. Nat Mater 2009, 8(6): 457-470.
Woodruff MA, Lange C, Reichert J, Berner A, Chen F, Fratzl P, et al. Bone tissue engineering: from bench to bedside. Materials Today 2012, 15(10): 430-435.
Grabowski G, Cornett CA. Bone graft and bone graft substitutes in spine surgery: current concepts and controversies. The Journal of the American Academy of Orthopaedic Surgeons 2013, 21(1): 51-60.

(56) References Cited

OTHER PUBLICATIONS

Neovius E, Engstrand T. Craniofacial reconstruction with bone and biomaterials: review over the last 11 years. Journal of plastic, reconstructive & aesthetic surgery : JPRAS 2010, 63(10): 1615-1623.
Dimitriou R, Jones E, McGonagle D, Giannoudis PV. Bone regeneration: current concepts and future directions. BMC medicine 2011, 9: 66.
Alsberg E, Hill EE, Mooney DJ. Craniofacial tissue engineering. Critical reviews in oral biology and medicine : an official publication of the American Association of Oral Biologists 2001, 12(1): 64-75.
Vo TN, Kasper FK, Mikos AG. Strategies for controlled delivery of growth factors and cells for bone regeneration. Adv Drug Deliv Rev 2012, 64(12): 1292-1309.
Martino MM, Tortelli F, Mochizuki M, Traub S, Ben-David D, Kuhn GA, et al. Engineering the growth factor microenvironment with fibronectin domains to promote wound and bone tissue healing. Sci Transl Med 2011, 3(100): 100ra189.
Lin C-C, Anseth KS. PEG hydrogels for the controlled release of biomolecules in regenerative medicine. Pharmaceutical research 2009, 26(3): 631-643.
Pashuck ET, Stevens MM. Designing Regenerative Biomaterial Therapies for the Clinic. Science translational medicine 2012, 4(160): 160sr164-160sr164.
Carragee EJ, Hurwitz EL, Weiner BK. A critical review of recombinant human bone morphogenetic protein-2 trials in spinal surgery: emerging safety concerns and lessons learned. Spine J 2011, 11(6): 471-491.
Smiell JM, Wieman TJ, Steed DL, Perry BH, Sampson AR, Schwab BH. Efficacy and safety of becaplermin (recombinant human platelet-derived growth factor-BB) in patients with nonhealing, lower extremity diabetic ulcers: a combined analysis of four randomized studies. Wound repair and regeneration : official publication of the Wound Healing Society [and] the European Tissue Repair Society 1999, 7(5): 335-346.
Nevins M, Giannobile WV, McGuire MK, Kao RT, Mellonig JT, Hinrichs JE, et al. Platelet-derived growth factor stimulates bone fill and rate of attachment level gain: results of a large multicenter randomized controlled trial. J Periodontol 2005, 76(12): 2205-2215.
Papanas N, Maltezos E. Benefit-risk assessment of becaplermin in the treatment of diabetic foot ulcers. Drug safety : an international journal of medical toxicology and drug experience 2010, 33(6): 455-461.
Watts NB, Diab DL. Long-Term Use of Bisphosphonates in Osteoporosis. J Clin Endocr Metab 2010, 95(4): 1555-1565.
Schmitz JP, Hollinger JO. The Critical Size Defect as an Experimental-Model for Craniomandibulofacial Nonunions. Clinical Orthopaedics and Related Research 1986(205): 299-308.
Spicer PP, Kretlow JD, Young S, Jansen JA, Kasper FK, Mikos AG. Evaluation of bone regeneration using the rat critical size calvarial defect. Nature protocols 2012, 7(10): 1918-1929.
Alsberg E, Kong HJ, Hirano Y, Smith MK, Albeiruti A, Mooney DJ. Regulating bone formation via controlled scaffold degradation. J Dent Res 2003, 82(11): 903-908.
Kearney CJ, Mooney DJ. Macroscale delivery systems for molecular and cellular payloads. Nat Mater 2013, 12(11): 1004-1017.
Lee K, Silva EA, Mooney DJ. Growth factor delivery-based tissue engineering: general approaches and a review of recent developments. Journal of the Royal Society Interface 2011, 8(55): 153-170.
Porter JR, Ruckh TT, Popat KC. Bone tissue engineering: a review in bone biomimetics and drug delivery strategies. Biotechnology Progress 2009, 25(6): 1539-1560.
Mistry AS, Mikos AG. Tissue engineering strategies for bane regeneration. Regenerative Medicine II. Springer, 2005, pp. 1-22.
Will J, Melcher R, Treul C, Travitzky N, Kneser U, Polykandriotis E, et al. Porous ceramic bone scaffolds for vascularized bone tissue regeneration. Journal of Materials Science: Materials in Medicine 2008, 19(8): 2781-2790.

Kinsella CR, Jr., Bykowski Mr, Lin AY, Cray JJ, Durham EL, Smith DM, et al. BMP-2-mediated regeneration of large-scale cranial defects in the canine: an examination of different carriers. Plast Reconstr Surg 2011, 127(5): 1865-1873.
Khan Y, Yaszemski MJ, Mikos AG, Laurencin CT. Tissue engineering of bone: material and matrix considerations. J Bone Joint Surg Am 2008, 90 Suppl 1: 36-42.
Krogman K, Cohen R, Hammond P, Rubner M, Wang B. Industrial-scale spray layer-by-layer assembly for production of biomimetic photonic systems. Bioinspiration & biomimetics 2013, 8(4): 045005.
Strathmann H. Membrane separation processes: current relevance and future opportunities. AIChE Journal 2001, 47(5): 1077-1087.
Crouzier T, Sailhan F, Becquart P, Guillot R, Logeart-Avramoglou D, Picart C. The performance of BMP-2 loaded TCP/HAP porous ceramics with a polyelectrolyte multilayer film coating. Biomaterials 2011, 32(30): 7543-7554.
Facca S, Cortez C, Mendoza-Palomares C, Messadeq N, Dierich A, Johnston AP, et al. Active multilayered capsules for in vivo bone formation. Proc Natl Acad Sci U S A 2010, 107(8): 3406-3411.
Shah NJ, Hyder MN, Moskowitz JS, Quadir MA, Morton SW, Seeherman HJ, et al. Surface-Mediated Bone Tissue Morphogenesis from Tunable Nanolayered Implant Coatings. Science Translational Medicine 2013, 5(191).
Stevens MM. Biomaterials for bone tissue engineering. Materials Today 2008, 11(5): 18-25.
Danhier F, Ansorena E, Silva JM, Coco R, Le Breton A, Preat V. PLGA-based nanoparticles: an overview of biomedical applications. J Control Release 2012, 161(2): 505-522.
Landes CA, Ballon A, Roth C. Maxillary and mandibular osteosyntheses with PLGA and P(L/DL)LA implants: A 5-year inpatient biocompatibility and degradation experience. Plastic and Reconstructive Surgery 2006, 117(7): 2347-2360.
DeMuth PC, Min YJ, Huang B, Kramer JA, Miller AD, Barouch DH, et al. Polymer multilayer tattooing for enhanced DNA vaccination. Nature Materials 2013, 12(4): 367-376.
Elbashir, S.M. et al. Duplexes of 21-nucleotics RNAs mediate RNA interference in cultured mammalian cells. Nature 411, 494-498 (20011).
Martinez, J., Patkaniowska, A., Urlaub, H., Luhrmann, R. & Tuschi, T. Single-stranded antisense siRNAs guide target RNA cleavage n RNAi. Cell 110, 563-574 (2002).
Morris, K.V., Chan, S.W., Jacobsen, S.E. & Looney, D.J. Small interfering RNA-induced transcriptional gene silencing in human cells. Science 305, 1289-1202 (2004).
Patil, m.L., et al., Surface-modified and internally Cationic polyamidoamine dendrimers for efficient siRNA delivery. Bioconjug Chem 19, 1396-1403 (2008).
Beyer, S., Nickels, P. & Simmel, F.C. Periodic DNA nanotemplates synthesized by rolling circle amplification, Nano Lett 5, 719-722 (2005).
Krebs, M.R. et al. The formation of spherulites by6 amyloid fibrils of bovine insulin. Proc Natl Acad Sci USA 101, 14420-14424 (2004).
Semple, S. C. et al. Rational design of cationic lipids for siRNA delivery. Nature Biotechnol. 28, 172-176 (2010).
Peer, D., Park, E. J., Morishita, Y., Carman, C. V. & Shimaoka, M. Systemic leukocyte-directed siRNA delivery revealing cyclin D1 as an anti-inflammatory target. Science 319, 627-630 (2008).
Mok, H., Lee, S. H., Park, J. W. & Park, T. G. Multimeric small interfering ribonucleic acid for highly efficient sequence-specific gene silencing. Nature Mater. 9, 272-278 (2010).
Lee, J. S. et al. Gold, poly(_-amino ester) nanoparticles for small interfering RNA delivery. Nano Lett. 9, 2402-2406 (2009).
Elbakry, A. et al. Layer-by-layer assembled gold nanoparticles for siRNA delivery. Nano Lett. 9, 2059-2064 (2009).
Giljohann, D. A., Scfcros, D. S., Prigodich, A. E., Patel, P. C. & Mirkin, C. A. Gene regulation with polyvalent siRNA-nanoparticle conjugates. J. Am. Chem. Soc. 131, 2072-2073 (2009).
Taratula, O. et al. Surface-engineered targeted PPI dendrimer for efficient intracellular and intratumoral siRNA delivery. J. Control. Release 140, 284-293 (2009).
Grewal, S. I. & Moazed, D. Heterochromatin and epigenetic control of gene expression. Science 301, 798-802 (2003).

(56) References Cited

OTHER PUBLICATIONS

Davis, M. E. et al. Evidence of RNAi in humans from systemically administered siRNA via targeted nanoparticles. Nature 464, 1067-1070 (2010).
Akinc, A. et al. A combinatorial library of lipid-like materials for delivery of RNAi therapeutics. Nature Biotechnol. 26, 561-569 (2008).
Seeman, N. C. Nanomaterials based on DNA. Annu. Rev. Biochem. 79, 65-87 (2010).
Guo, P. The emerging field of RNA nanotechnology. Nature Nanotechnol. 5, 833-842 (2010).
Guo, P. RNA nanotechnology: Engineering, assembly and applications in detection, gene delivery and therapy. J. Nanosci. Nanotechnol. 5, 1964-1982 (2005).
Afonin, K. A. et al. In vitro assembly of cubic RNA-based scaffolds designed in silico. Nature Nanotechnol. 5, 676-682 (2010).
Daubendiek, S. L., Ryan, K. & Kool, E. T. Rolling-circle RNA-synthesis—circular oligonucleotides as efficient substrates for T7 RNA-polymerase. J. Am. Chem. Soc. 117, 7818-7819 (1995).
Richards, K. E., Williams, R. C. & Calendar, R. Mode of DNA packing within bacteriophage heads. J. Mol. Biol. 78, 255-259 (1973).
Hendrix, R. W. Bacteriophage DNA packaging: RNA gears in a DNA transport machine. Cell 94, 147-150 (1998).
Trubetskoy, V. S., Loomis, A., Hagstrom, J. E., Budker, V. G. & Wolff, J. A. Layer-by-layer deposition of oppositely charged polyelectrolytes on the surface of condensed DNA particles. Nucleic Acids Res. 27, 3090-3095 (1999).
Tijsterman, M., Ketting, R. F. & Plasterk, R. H. The genetics of RNA silencing. Annu. Rev. Genet. 36, 489-519 (2002).
Diegelman, A. M. & Kool, E. T. Generation of circular RNAs and trans-cleaving catalytic RNAs by rolling transcription of circular DNA oligonucleotides encoding hairpin ribozymes. Nucleic Acids Res. 26, 3235-3241 (1998).
Sullivan Sean, P. et al. Dissolving polymer microneedle patches for influenza vaccination. Nat Med 16, 915-920.
Sullivan, S. P.,Murthy, N. & Prausnitz ,M. R. Minimally invasive protein delivery with rapidly dissolving polymer microneedles. Adv. Mater. 20, 933-938 (2008).
Bins,A. D. et al. A rapid and potent DNA vaccination strategy defined by in vivo monitoring of antigen expression. Nat. Med. (N. Y.,NY,U.5.) 11,899-904,doi:10.1038/nm1264 (2005).
Johansen, P. et al. Antigen kinetics determines immune reactivity. Proc. Natl. Acad. Sci. U. S. A. 105,5189-5194,doi:10.1073/pnas. 0706296105 (2008).
Smith, K. A. et al. Multivalent immunity targeting tumor-associated antigens by intra-lymph node DNA-prime ,peptide-boost vaccination. Cancer Gene Ther. 18, 63-76,doi:10.1038/cgt.2010.45 (2011).
Smith, K. A. et al. Enhancing ONA vaccination by sequential injection of lymph nodes with plasmid vectors and peptides. Vaccine 27,2603-2615,doi:10.1016/j.vaccine.2009.02.038 (2009).
Wick, D. A., Martin, S. D., Nelson, B. H. & Webb ,J. R. Profound CD8+ T cell immunity elicited by sequential daily immunization with exogenous antigen plus the TLR3 agonist poly(I:C) Vaccine 29, 984-993, doi:10.1016/j.vaccine.2010.11.036 (2011).
Alvarez-Roman, R., Naik, A., Kalia ,Y. N., Guy, R. H. & Fessi ,H. Skin penetration and distribution of polymeric nanoparticles. J. Controlled ReJease 99 ,53-62,doi:10.1016/j.jconrel.2004.06.015 (2004).
Wang, P. M., Cornwell, M., HiII, J. & Prausnitz ,M. R. Precise Microinjection into Skin Using Hollow Microneedles. J. Invest. Dermatol. 126,1080-1087,doi:10.1038/sj jid.5700150 (2006).
Park, J.-H., Allen, M. G. & Prausnitz ,M. R. Polymer microneedles for controlled-release drug delivery. Pharm. Res. 23, 1008-1019 (2006).
Doh, J. & Irvine ,D. J. Photogenerated polyelectrolyte bilayers from an aqueous-processible photoresist for multicomponent protein patterning. J. Am. Chem. Soc. 126, 9110-9171 (2004).
Doh, J. & Irvine, D. J. Aqueous-processible photoresist polymer for multiple protein patterning: Synthesis, characterization and application to T cell activation. PMSE Prepr. 93, 327-328 (2005).

Jewell, C. M., Zhang, J., Fredin, N. J. & Lynn ,D. M. Multilayered polyelectrolyte films promote the direct and localized delivery of DNA to cells. J. Controlled Release 106, 214-223 (2005).
Samuel, R. E. et al. Osteoconductive protamine-based polyelectrolyte multilayer functionalized surfaces. Biomoteriols 32,1491-1502,do1:10. 1016/j.biomaterials.2011.06.032 (2011).
Jewell, C. M. et al. Release of Plasmid DNA from Intravascular Stents Coated with Ultrathin Multilayered Polyelectrolyte Films. Biomacromolecules 7, 2483-2491(2006).
Zhang,J., Fredin, N. J., Janz, J. F. , Sun, B. & Lynn, D. M. Structure/property relationships in erodible multilayered films: influence of polycation structure on erosion profiles and the release of anionic polyelectrolytes. Langmuir 22, 239-245, doi:10.1021/1a052360b (2006).
Sallusto, F., Geginat, J. & Lanzavecchia, A. Central memory and effector memory T cell subsets: Function, generation, and maintenance. Annu. Rev. Immunol. 22 ,145-163, doi:10.1146/annurev. immunol.22.012103.104102 (2004).
European Search Report of 08771046.3, entitled "Self Assembled Films for Protein and Drug Delivery Applications," dated Oct. 22, 2012, 4 pages.
International Preliminary Report on Patentability for PCT/US08/66948, entitled: Self Assembled Films for Protein and Drug Delivery Applications: dated Dec. 17, 2009.
International Search Report for PCT/US08/66948: entitled: Self Assembled Films for Protein and Drug Delivery Applications: dated Aug. 29, 2008. (incorrectly cited as Aug. 23, 2008).
International Preliminary Examination Report for PCT/US2002/34191, entitled: Methods of Making Decomposable Thin Films of Polyelectrolytes and Uses Thereof, Date of completion of report: Sep. 11, 2003.
International Search Report for PCT/US2002/34191, entitled: Methods of Making Decomposable Thin Films of Polyelectrolytes and Uses Thereof, dated Jan. 17, 2003.
International Search Report for PCT/US2006/004295, entitled: Electrochemically Degradable Layer-by-Layer Thin Films, dated Oct. 2, 2006.
International Preliminary Report on Patentability for PCT/US2006/004295, entitled: Electrochemically Degradable Layer-by-Layer Thin Films, dated Aug. 7, 2007.
International Search Report for PCT/US2007/069937, entitled: Methods of Making Decomposable Thin Films of Polyelectrolytes and Uses Thereof, dated Aug. 13, 2008.
International Preliminary Report on Patentability for PCT/US2007/069937, entitled: Methods of Making Decomposable Thin Films of Polyelectrolytes and Uses Thereof, dated Dec. 3, 2008.
International Preliminary Report on Patentability for PCT/US2007/69964, entitled: Methods of Making Decomposable Thin Films of Polyelectrolytes and Uses Thereof, dated Dec. 3, 2008.
International Search Report and Written Opinion for PCT/US2007/69964, entitled: Methods of Making Decomposable Thin Films of Polyelectrolytes and Uses Thereof, dated Oct. 29, 2007.
International Preliminary Report on Patentability and Written Opinion for PCT/US2009/054011, entitled: Controlled Delivery of Bioactive Agents From Decomposable Films: dated Feb. 22, 2011.
International Search Report for PCT/US2009/054011, entitled: Controlled Delivery of Bioactive Agents From Decomposable Films: dated Nov. 24, 2010.
International Preliminary Report on Patentability for PCT/US2011/035057, entitled: Drug Deliver Coating and Devices, dated Nov. 6, 2012.
International Search Report for PCT/US2011/035057, entitled: Drug Deliver Coating and Devices, dated Feb. 8, 2012.
International Preliminary Report on Patentability and Written Opinion for PCT/US2012/035689, entitled: Coating Compositions, Methods and Coated Devices, dated Oct. 29, 2013.
International Search Report for PCT/US2012/035689, entitled: Coating Compositions, Methods and Coated Devices, dated Jul. 31, 2012.
International Preliminary Report on Patentability for PCT/US2012/035692, entitled: Coating Compositions, Methods and Coated Devices, dated Oct. 29, 2013.

(56) References Cited

OTHER PUBLICATIONS

International Search Report for PCT/US2012/35692, entitled: Coating Compositions, Methods and Coated Devices, dated Oct. 5, 2012.
International Search Report for PCT/US2013/066980, entitled: Devices and Methods for Layer-by-Layer Assembly, dated Apr. 30, 2014.
International Search Report for PCT/US2013137868, entitled: Compositions and Methods of Treatment of Drug Resistant Cancers, dated Sep. 6, 2013.
International Search Report for PCT/US2013/37869, entitled: Stable Layer-by-Layer Coated Particles, dated Sep. 13, 2013.
International Search Report for PCT/US2014/018284, entitled:Nucleic Acid Particles, Methods and Use Thereof, dated Jul. 30, 2014.
Written Opinion PCT/US2014/018284, entitled:Nucleic Acid Particles, Methods and Use Thereof, dated Jul. 30, 2014.
International Search Report for PCT/US2014/022107, entitled: Compositions and Methods for Nucleic Acid Delivery, dated Jun. 5, 2014.
Written Opinion for PCT/US2014/022107, entitled: Compositions and Methods for Nucleic Acid Delivery, dated Jun. 5, 2014.
International Preliminary Report on Patentability for PCT/US2013/37869, entitled: Stable Layer-by-Layer Coated Particles, dated Nov. 6, 2014.
International Preliminary Report on Patentability for PCT/US2013/037868, entitled: Compositions and Methods of Treatment of Drug Resistant Cancers, dated Nov. 20, 2014.
International Search Report for PCT/US2013/022430, entitled: Compositions and Methods for Coating, dated May 15, 2013.
International Preliminary Report on patentability for PCT/US2013/022430, entitled: Compositions and Methods for Coating, dated Jul. 22, 2014.
International Search Report for PCT/US2014/057496, entitled: Biodegradable Layer-by-Layer (LbL) Films for Cell Capture and Release, dated Jan. 8, 2015.
Office Action for U.S. Appl. No. 13/115,107, entitled: "Multilayer Coating Compositions, Coated Substrates and Methods Thereof", dated Apr. 17, 2014.
Office Action for U.S. Appl. No. 12/542,267, entitled: "Controlled Delivery of Bioactive Agents From Decomposable Films", dated Mar. 31, 2014.
Office Action for U.S. Appl. No. 12/542,267, entitled: "Controlled Delivery of Bioactive Agents From Decomposable Films", dated Jun. 7, 2013.
Office Action for U.S. Appl. No. 12/542,267, entitled: "Controlled Delivery of Bioactive Agents From Decomposable Films", dated Aug. 17, 2012.
Office Action for U.S. Appl. No. 12/139,151, entitled: "Self Assembled Films for Protein and Drug Delivery Applications", dated Jun. 11, 2014.
Office Action for U.S. Appl. No. 12/139,151, entitled: "Self Assembled Films for Protein and Drug Delivery Applications", dated Jun. 20, 2012.
Office Action for U.S. Appl. No. 12/139,151, entitled: "Self Assembled Films for Protein and Drug Delivery Applications", dated Sep. 22, 2011.
Office Action for U.S. Appl. No. 11/459,979, entitled: "Methods of Making Decomposable Thin Films of Polyelectrolytes and Uses Thereof", dated Jul. 23, 2010.
Office Action for U.S. Appl. No. 11/459,979, entitled: "Methods of Making Decomposable Thin Films of Polyelectrolytes and Uses Thereof", dated Oct. 29, 2009.
Office Action for U.S. Appl. No. 11/815,718, entitled: "Electrochemically Degradable Layer-by-Layer Thin Films", dated Mar. 27, 2014.
Office Action for U.S. Appl. No. 11/815,718, entitled: "Electrochemically Degradable Layer-by-Layer Thin Films", dated Nov. 27, 2012.
Office Action for U.S. Appl. No. 11/815,718, entitled: "Electrochemically Degradable Layer-by-Layer Thin Films", dated Mar. 26, 2012.
Office Action for U.S. Appl. No. 10/280,268, entitled: "Methods of Making Decomposable Thin Films of Polyelectrolytes and Uses Thereofs", dated Nov. 2, 2004.
Office Action for U.S. Appl. No. 10/280,268, entitled: "Methods of Making Decomposable Thin Films of Polyelectrolytes and Uses Thereofs", dated Jul. 6, 2005.
Office Action for U.S. Appl. No. 10/280,268, entitled: "Methods of Making Decomposable Thin Films of Polyelectrolytes and Uses Thereofs", dated Jun. 29, 2006.
Office Action for U.S. Appl. No. 13/459,066, entitled: "Coating Compositions, Methods and Coated Devices", dated Oct. 15, 2014.
Office Action for U.S. Appl. No. 13/459,069 entitled: "Coating Compositions, Methods and Coated Devices", dated Oct. 23, 2014.
Office Action for U.S. Appl. No. 13/695,836 entitled: "Drug Delivery Coating and Devices", dated Nov. 28, 2014.
Office Action for U.S. Appl. No. 13/746,902 entitled: "Compositions and Methods for Coating," dated Jan. 2, 2015.
Office Action for U.S. Appl. No. 14/190,983, "Nucleic Acid Particles, Methods and Use Thereof", dated Jan. 29, 2015.
Ekwueme, D.U., et al., "Model-Based Estimates of Risks of Disease Transmission and Economic Costs of Seven Injection Devices in Sub-Saharan Africa" Bull World Health Organ, 80:859-870 (2002).
Final Office Action for U.S. Appl. No. 13/115,107, entitled: "Multilayer Coating Compositions, Coated Substrates and Methods Thereof", dated Apr. 17, 2014.
Final Office Action for U.S. Appl. No. 12/542,267, entitled: "Controlled Delivery of Bioactive Agents From Decomposable Films", dated Mar. 11, 2015.
Office Action for U.S. Appl. No. 12/542,267, entitled "Controlled Delivery of Bioactive Agents from Decompostable Films", dated Mar. 27, 2014.
Office Action for U.S. Appl. No. 13/115,107, entitled "Multilayer Coating Compositions, Coated Substrates and Methods Thereof", dated Jan. 28, 2015.
Final Office Action for U.S. Appl. No. 12/542,267, entitled: "Controlled Delivery of Bioactive Agents From Decomposable Film," dated: Mar. 11, 2015.
Office Action for U.S. Appl. No. 13/869,012, "Compositions and Methods of Treatment of Drug Resistant Cancers," dated Apr. 7, 2015.
Office Action for U.S. Appl. No. 13/869,015 entitled: "Stable Layer-by-Layer Coated Particles", dated Nov. 21, 2014.
Barker et al., "Fabrication, Derivatization and Applications of Plastic Microfluidic Devices," Proceedings of SPIE—The International Society for Optical Engineering, 112-118 (2001).
Baselga et al., "Phase II Multicenter Study of the Antiepidermal Growth Factor Receptor Monoclonal Antibody Cetuximab in Combination with Platinum-Based Chemotherapy in Patients with Platinum-Refractory Metastatic and/or Recurrent Squamous Cell Carcinoma of the Head and Neck," J. of Clinical Oncology, 23(25): 5568-5577 (2005).
Bernards et al., "Nanotemplating of Biodegradable Polymer Membranes for Constant-Rate Drug Delivery," Adv Mater, 22: 2358-2362 (2010).
Hammond, "Building biomedical materials layer-by-layer," Mater Today, 15(5):196-206 (2012).
International Preliminary Report on Patenability for PCT/US2013/064530, entitled "Multilayer Compositions, Coated Devices and Use Thereof", dated Apr. 8, 2014.
International Preliminary Report on Patentability for PCT/US2013/066980, dated May 7, 2015.
International Search Report and Written Opinion for International Application No. PCT/US2016/068823 dated Mar. 10, 2017.
International Search Report for International Application No. PCT/US11/35057, dated Feb. 8, 2012.
Isakoff et al., "Triple Negative Breast Cancer: Role of Specific Chemotherapy Agents," Cancer Journal, 16(1): 53-61 (2010).
Jewell et al., "Multilayered polyelectrolyte films promote the direct and localized delivery of DNA to cells," J Controlled Release, 106: 214-223 (2005).
Johnston et al., "Targeting Cancer Cells: Controlling the Binding and Internalization of Antibody-Functionalized Capsules," ACS Nano, 6(8): 6667-6674 (2012).

(56) References Cited

OTHER PUBLICATIONS

Kang et al., "Inhibition of EGFR Signaling Augments Oridonin-induced Apoptosis in Human Laryngeal Cancer Cells via Enhancing Oxidative Stress Conicident with Activiation of Both the Intrinsic and Extrinsic Apoptotic Pathways," Cancer Letters, 294: 147-158 (2010).
Kargina, O.V., "Samorasscheplyayuschiyesya Vodorastvorimye Ionogennye Polymery," (English Abstract).
Kuchler-Bopp et al., "Nanostructured hybrid materials for bone-tooth unit regeneration," Open Journal of Regenerative Medicine, 2(1): 47-52 (2013).
Ma et al., "Collagen/chitosan porous scaffolds with improved biostability for skin tissue engineering," Biomaterials, 24: 4833-4841 (2003).
Machine Translation of CN1679518A, 8 pages, publication date of CN1679518A is Oct. 2005. Translation was performed on Jul. 24, 2015.
Nagashima et al., "BCRP/ABCG2 levels account for the resistance to topoisomerase I inhibitors and reversal effects by gefitinib in non-small cell lung cancer," Cancer Chemotherapy and Pharmacology, 58: 594-600 (2006).
Nam et al., "Porous biodegradable polymeric scaffolds prepared by thermally induced phase separation," J Biomed Mater Res, 47(1): 8-17 (1999).
Notice of Allowance and Fees Due for U.S. Appl. No. 14/811,263 dated Apr. 10, 2017.
Portin., "Layer-by-Layer Assembly of the Polyelectrolytes on Mesoporous Silicon Nanoparticles", Unpublished Master's Thesis, University of Eastern Finland, Joensuu, Finland (2012).
Shi et al., "The epidermal growth factor tyrosine kinase inhibitor AG1478 and erlotinib reverse ABCG2-meditated drug resistance," Oncology Reports, 21: 483-489 (2008).
Written Opinion for PCT/US06/04295, dated Oct. 2, 2006.
Written Opinion for PCT/US08/66948 dated Aug. 23, 2008.
Written Opinion for PCT/US11/35057, dated Feb. 8, 2012, 5 pages.
Written Opinion for PCT/US2002/34191 dated Jun. 17, 2003.
Written Opinion for PCTUS2007/69937 dated Aug. 13, 2008.
Written Opinion for PCTUS2007/69964 dated Oct. 29, 2007.

\* cited by examiner

US 10,278,927 B2

STABLE LAYER-BY-LAYER COATED PARTICLES

CROSS-REFERENCE TO RELATED APPLICATION

This application claims priority to and the benefit of, and incorporates herein by reference in its entirety, U.S. Provisional Patent Application No. 61/637,265, filed Apr. 23, 2012.

BACKGROUND

Great efforts have been made to develop nanoparticle delivery systems for decades. The majority of the research on nanoparticle delivery systems highlights their use as platforms for release of therapeutics after on-site administration, but it is still desired to use stable systems via systemic administration.

SUMMARY

Layer-by-layer (LbL) assembly of layers (e.g., polyelectrolyte layers) on solid surfaces is a well-established technique for generating functional thin films for applications in biosensing, drug and gene delivery, regenerative medicine, tissue engineering and biomimetics research. The present application encompasses the recognition that LbL films are particularly useful to coat particle cores for their systemic delivery based on the versatility in manipulating properties including film architecture, film materials, film thickness and surface chemistry, when combined with the rich diversity of therapeutic or other agents which are adaptable to the LbL films.

The present disclosure provides certain particle or a collection of particle, each comprising a particle core coated with an LbL film. In some embodiments, an LbL film includes one or more therapeutic or other agents in at least one of its layers. In some embodiments, the LbL film releases such agent(s) over time.

In one aspect, the disclosure provides particle systems each comprising a particle coated with one or more LbL films that govern in vivo stability, biodistribution, tissue interaction and/or other vital pharmacokinetic behaviors. Various combinations of different dimensions, location, and compositions of one or more LbL films can be used to coat a particle in accordance with the present disclosure.

In many embodiments, provided particle systems comprise a particle core of any shape or size. In some embodiments, a particle core is made of or comprises one or more inorganic materials.

In some embodiments, provided particle systems comprise an LbL film comprising at least 3, 4, 6, 8, 10, 12, 14, 16, 18, 20, 30, 40, 50, 60, 70, 80, 90 or even 100 layers. In some embodiments, an LbL film comprises or is consist of polyelectrolyte layers of alternating charges.

In certain embodiments, an LbL film comprises a layer comprising or consisting of a positively charged polyelectrolyte. For example, poly-lysine or other amino-containing polypeptide can be used.

In certain embodiments, an LbL film comprises an outer layer comprising or consisting of a negative charged polyelectrolyte. For example, hyaluronic acid (HA) or carboxylated polysaccharides can be used. In certain embodiments, an outer layer is or comprises polyether such as PEG.

In some embodiments, an LbL film comprises layers associated to each other via non-covalent interactions. In certain embodiments, a non-covalent interaction is electrostatic interaction. In certain embodiments, a non-covalent interaction is specific binding interaction.

In some embodiments, provided particle systems comprise one or more agents, which are associated with or serve as at least one layer of an LbL film. In certain embodiments, an agent comprises or is a therapeutic agent. For example, an agent comprises or is an anti-infective agent or an anti-inflammatory agent. In certain embodiments, an agent comprises or is a nucleic acid or a protein.

Other features, objects, and advantages of the present disclosure are apparent in the detailed description, drawings and claims that follow. It should be understood, however, that the detailed description, the drawings, and the claims, while indicating embodiments of the present disclosure, are given by way of illustration only, not limitation. Various changes and modifications within the scope of the disclosure will become apparent to those skilled in the art.

DEFINITIONS

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "associated" typically refers to two or more moieties connected with one another, either directly or indirectly (e.g., via one or more additional moieties that serve as a linking agent), to form a structure that is sufficiently stable so that the moieties remain connected under the conditions in which the structure is used, e.g., physiological conditions. In some embodiments, associated moieties are attached to one another by one or more covalent bonds. In some embodiments, associated moieties are attached to one another by a mechanism that involves specific (but non-covalent) binding (e.g. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

The term "nucleic acid" as used herein, refers to a polymer of nucleotides. Deoxyribonucleic acids (DNA) or ribonucleic acids (RNA) and polymers thereof in either single- or double-stranded form are exemplary polynucleotides. Unless specifically limited, the term encompasses nucleic acid molecules containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. In some embodiments, a polynucleotide sequence of relatively shorter length (e.g., no more than 50 nucleotides, preferably no more than 30 nucleotides, and more preferably no more than 15-20 nucleotides) is typically referred to as an "oligonucleotide."

The term "particles" as used herein, refers to discrete solid phases. Such solid phases can be of any shape or size. In some embodiments, some or all particles are substantially spherical. In some embodiments, utilized particles have sized within a defined range and/or showing a defined distribution. In some embodiments, particles having a diameter of less than 1000 nanometers (nm) are also referred to as nanoparticles. Any of a variety of materials can be used to form or provide particles, as will be understood by those of skill in the art. In some embodiments, particular materials and/or shapes may be preferred based on chemistries or other features utilized in relevant embodiments; those of ordinary skill will be well familiar with various options and parameters guiding selection. In many embodiments, suitable materials include, but are not limited to, plastics, ceramics, glass, polystyrene, methylstyrene, acrylic polymers, metal, paramagnetic materials, thoria sol, graphitic carbon, titanium dioxide, latex or cross-linked dextrans such as Sepharose, cellulose, nylon, cross-linked micelles and teflon. In some embodiments, particles can be optically or magnetically detectable. In some embodiments, particles contain fluorescent or luminescent moieties, or other detectable moieties.

The term "protein" as used herein, refers to a string of at least three amino acids linked together by peptide bonds. Proteins may contain only natural amino acids, although non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in a protein may be modified, for example, by the addition of a chemical entity such as a carbohydrate group, a phosphate group, a farnesyl group, an isofarnesyl group, a fatty acid group, a linker for conjugation, functionalization, or other modification, etc.

BRIEF DESCRIPTION OF THE SEVERAL VIEWS OF THE DRAWING

FIG. 2 Characterization of LbL nanoparticles.

FIG. 3C shows the biodistribution monitored on the 700 nm channel. FIG. 3D shows the biodistribution monitored on the 800 nm channel. Data shown is normalized by tissue weight and presented as the percentage recovered fluorescence per gram of tissue (% rf/g) and given in mean±SEM (n=3-5). The results show that a single terminal layer of antifouling polysaccharide is sufficient for preventing cellular interaction with the PLL layer to shift the biodistribution pattern in favor of only the liver and spleen. Li=Liver, Sp=spleen, Ki=kidneys, H=heart, Lu=lungs and LN=lymph node.

FIG. 5 The effect of the terminal layer on LbL nanoparticle biodistribution.

FIG. 13 Examination of RES involvement in liver uptake of DXS and HA terminated LbL nanoparticles.

DETAILED DESCRIPTION OF CERTAIN EMBODIMENTS

Figure 1:
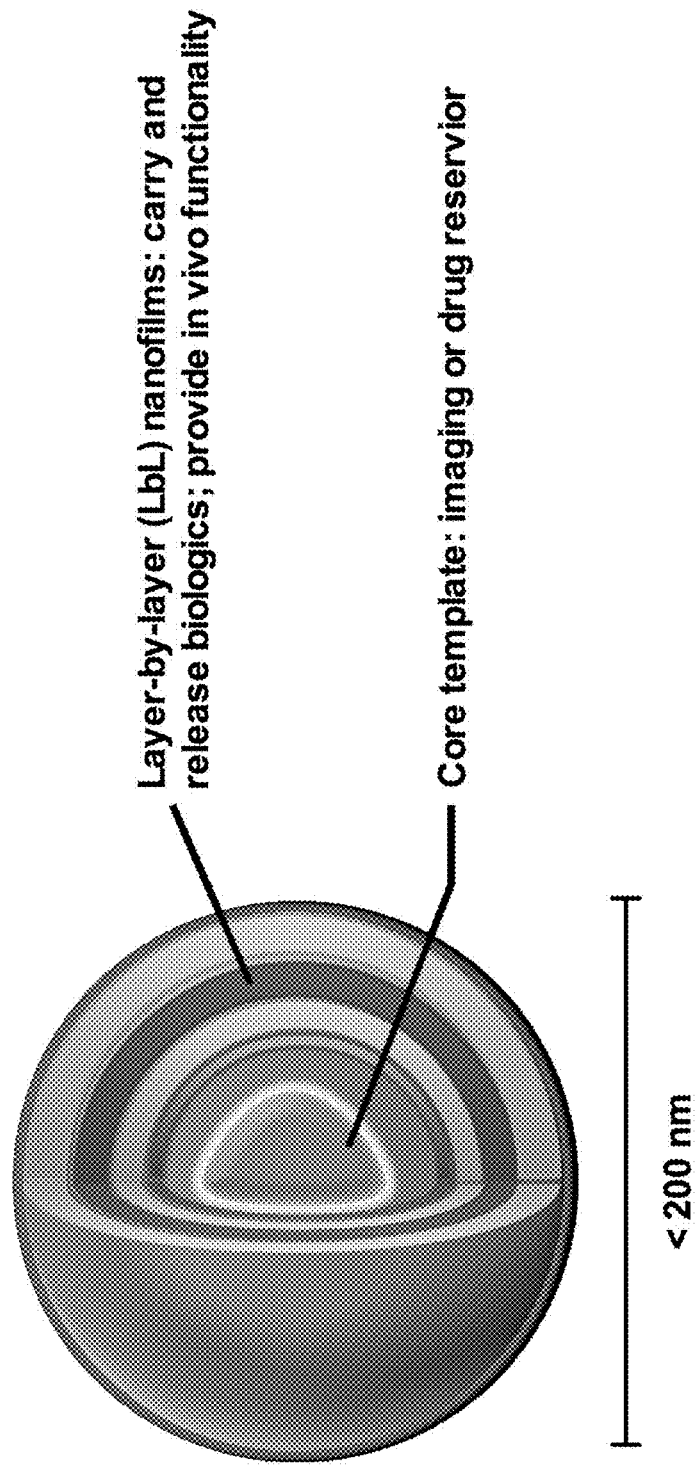
FIG. 1 Schematic for an exemplary LbL-based nanoparticle system capable of delivering multiple classes of therapeutics and releasing them in a programmable manner.

In various embodiments, systems and methods for coating an LbL film onto a particle core are disclosed. Provided systems and methods can be used to manipulate in vivo stability, biodistribution, targeting and/or controlled release of one or more agents from a stable particle.

Particle Cores

A variety of particle cores with different shapes, sizes and/or materials can be coated with an LbL film in accordance with the present disclosure. Suitable particles can be biocompatible or non-biocompatible. Suitable particles can also be biodegradable or non-biodegradable.

Materials

The present disclosure provides nanoparticles with organic or inorganic cores. Those skilled in the art appreciate that different challenges may be presented by inorganic as compared with organic cores, and also that other characteristics of the core (e.g., ability and/or requirement to be detected or detectable) may impact appropriate or acceptable coating properties as described herein.

Particular examples of inorganic cores include, but are not limited to, plastics; ceramics; silicon; glasses; mica; graphite; metals (e.g., gold, silver, platinum, steel or other alloys); metal-coated materials; metal oxides; and combinations thereof.

In some embodiments, particle cores are made of or comprise inorganic polymers such as silica ($SiO_2$). In some embodiments, particle cores according to the disclosure are silica-based. For example, silicate materials may be useful for the present applications due to their biocompatibility, ease of production and functionalization, and large surface-to-volume ratio. Silica-based particle cores such as porous silica particle cores, and any modified or hybrid particle cores can be of use in accordance with the present disclosure.

As well known in the art, silica-based particle cores may be made by a variety of methods. Some methods utilize the Stöber synthesis which involves hydrolysis of tetraethoxyorthosilicate (TEOS) catalyzed by ammonia in water/ethanol mixtures, or variations thereof. In some embodiments, silica-based particle cores are synthesized using known sol-gel chemistry, e.g., by hydrolysis of a silica precursor or precursors. Silica precursors can be provided as a solution of a silica precursor and/or a silica precursor derivative. Hydrolysis can be carried out under alkaline (basic) or acidic conditions. For example, hydrolysis can be carried out by addition of ammonium hydroxide to a solution comprising one or more silica precursor and/or derivatives. Silica precursors are compounds which under hydrolysis conditions can form silica. Examples of silica precursors include, but are not limited to, organosilanes such as, for example, tetraethoxysilane (TEOS), tetramethoxysilane (TMOS) and the like. In some embodiments, silica precursor has a functional group. Examples of such silica precursors includes, but is not limited to, isocyanatopropyltriethoxysilane (ICPTS), aminopropyltrimethoxysilane (APTS), mercaptopropyltrimethoxysilane (MPTS), and the like. In some embodiments, microemulsion procedures can be used to synthesize particle cores suitable for use in the present disclosure. For example, a water-in-oil emulsion in which water droplets are dispersed as nanosized liquid entities in a continuous domain of oil and surfactants and serve as nanoreactors for particle core synthesis offer a convenient approach.

In some embodiments, particle cores may contain detectable moieties that generate fluorescent, luminescent and/or scatter signal.

In some embodiments, particle cores contain quantum dots (QDs). QDs are bright, fluorescent nanocrystals with physical dimensions small enough such that the effect of quantum confinement gives rise to unique optical and electronic properties. Semiconductor QDs are often composed of atoms from groups II-VI or III-V in the periodic table, but other compositions are possible. By varying their size and composition, the emission wavelength can be tuned (i.e., adjusted in a predictable and controllable manner) from the blue to the near infrared. QDs generally have a broad absorption spectrum and a narrow emission spectrum. Thus different QDs having distinguishable optical properties (e.g., peak emission wavelength) can be excited using a single source. In general, QDs are brighter and photostable than most conventional fluorescent dyes. QDs and methods for their synthesis are well known in the art (see, e.g., U.S. Pat. Nos. 6,322,901; 6,576,291; and 6,815,064; all of which are incorporated herein by reference). Exemplary QDs suitable for use in accordance with the present disclosure in some embodiments, includes ones with a wide variety of absorption and emission spectra and they are commercially available, e.g., from Quantum Dot Corp. (Hayward Calif.; now owned by Invitrogen) or from Evident Technologies (Troy, N.Y.).

In certain embodiments, optically detectable particle cores are or comprise metal particle cores. Metals of use include, but are not limited to, gold, silver, iron, cobalt, zinc, cadmium, nickel, gadolinium, chromium, copper, manganese, palladium, tin, and alloys thereof. Oxides of any of these metals can be used.

Certain metal particle cores, referred to as plasmon resonant particle cores, exhibit the well known phenomenon of plasmon resonance. The features of the spectrum of a plasmon resonant particle core (e.g., peak wavelength) depend on a number of factors, including the particle core's material composition, the shape and size of the particle core, the refractive index or dielectric properties of the surrounding medium, and the presence of other particles in the vicinity. Selection of particular shapes, sizes, and compositions of particle cores makes it possible to produce particle cores with a wide range of distinguishable optically detectable properties thus allowing for concurrent detection of multiple analytes by using particle cores with different properties such as peak scattering wavelength.

Magnetic properties of particle cores can be used in accordance with the present disclosure. Particle cores in some embodiments are or comprise magnetic particle cores, that is, magnetically responsive particle cores that contain one or more metals or oxides or hydroxides thereof. Magnetic particle cores may comprise one or more ferrimagnetic, ferromagnetic, paramagnetic, and/or superparamagnetic materials. Useful particle cores may be made entirely or in part of one or more materials selected from the group consisting of: iron, cobalt, nickel, niobium, magnetic iron oxides, hydroxides such as maghemite ($\gamma$-$Fe_2O_3$), magnetite ($Fe_3O_4$), feroxyhyte (FeO(OH)), double oxides or hydroxides of two- or three-valent iron with two- or three-valent other metal ions such as those from the first row of transition metals such as Co(II), Mn(II), Cu(II), Ni(II), Cr(III), Gd(III), Dy(III), Sm(III), mixtures of the afore-mentioned oxides or hydroxides, and mixtures of any of the foregoing. Additional materials that may be used in magnetic particle cores include yttrium, europium, and vanadium.

Those skilled in the art will appreciate that teachings of the present disclosure are also applicable to particles having organic and/or polymeric cores. In some embodiments, polymeric cores are made of or comprise natural polymers (e.g., polypeptides, nucleic acids, and/or polysaccharides); in some embodiments, polymeric cores are made of or comprise synthetic polymers. In some embodiments, polymeric cores are made of or comprise synthetic derivatives of natural polymers.

To give but a few examples, in some embodiments, polymeric cores may comprise one or more of poly(arylates), poly(anhydrides), poly(hydroxy acids), polyesters, poly(ortho esters), poly(alkylene oxides), polycarbonates, poly(propylene fumerates), poly(caprolactones), polyamides, polyamino acids, polyacetals, polylactides, polyglycolides, poly(dioxanones), polyhydroxybutyrate, polyhydroxyvalyrate, poly(vinyl pyrrolidone), polycyanoacrylates, polyurethanes and polysaccharides. In some embodiments, polymeric cores may comprise polyethylene glycol (PEG).

In some embodiments, polymers of particle cores may be formed by step or chain polymerization. The amount and kind of radical initiator, e.g., photo-active initiator (e.g., UV or infrared), thermally-active initiator, or chemical initiator, or the amount of heat or light employed, may be used to control the rate of reaction or modify the molecular weight. Where desired, a catalyst may be used to increase the rate of reaction or modify the molecular weight. For example, a strong acid may be used as a catalyst for step polymerization. Trifunctional and other multifunctional monomers or cross-linking agents may also be used to increase the cross-link density. For chain polymerizations, the concentration of a chemical initiator in a mixture of one or more monomers may be adjusted to manipulate final molecular weight.

In some embodiments, particle cores are or comprise hydrogels. In general, hydrogels comprise a substantially dilute crosslinked network. Water or other fluids can penetrate in the network forming such a hydrogel. In some embodiments, hydrogels suitable for use in the present disclosure are made of or comprise a hydrophilic polymer. For example, hydrophilic polymers may comprise anionic groups (e.g. phosphate group, sulphate group, carboxylate group); cationic groups (e.g. quaternary amine group); or polar groups (e.g. hydroxyl group, thiol group, amine group). In some embodiments, hydrogels are superabsorbent (e.g. they can contain over 99% water) and possess a degree of flexibility very similar to natural tissue, due to their significant water content. Both of weight and volume, hydrogels are fluid in composition and thus exhibit densities to those of their constituent liquids (e.g., water). The present disclosure encompasses the recognition that hydrogels are particularly useful in some embodiments of the present disclosure. Due to their bio-friendly nature, hydrogels have been used extensively in the fields of tissue engineering, drug delivery, and biomolecule separation.

Various additional materials and methods can be used to synthesize particle cores. In some embodiments, particle cores may be made of or comprise one or more polymers. Polymers used in particle cores may be natural polymers or unnatural (e.g. synthetic) polymers. In some embodiments, polymers can be linear or branched polymers. In some embodiments, polymers can be dendrimers. Polymers may be homopolymers or copolymers comprising two or more monomers. In terms of sequence, copolymers may be block copolymers, graft copolymers, random copolymers, blends, mixtures, and/or adducts of any of the foregoing and other polymers.

In some embodiments, particle cores of the present disclosure may be made of or comprise a natural polymer, such as a carbohydrate, protein, nucleic acid, lipid, etc. In some embodiments, natural polymers may be synthetically manufactured. Many natural polymers, such as collagen, hyaluronic acid (HA), and fibrin, which derived from various components of the mammalian extracellular matrix can be used in particle cores of the present disclosure. Collagen is one of the main proteins of the mammalian extracellular matrix, while HA is a polysaccharide that is found in nearly all animal tissues. Alginate and agarose are polysaccharides that are derived from marine algae sources. Some advantages of natural polymers include low toxicity and high biocompatibility.

In some embodiments, particle cores of the present disclosure may be made of or comprise synthetic polymers, including, but not limited to, poly(arylates), poly(anhydrides), poly(hydroxy acids), poly(alkylene oxides), poly (propylene fumerates), polymethacrylates polyacetals, polyethylenes, polycarbonates (e.g. poly(1,3-dioxan-2-one)), polyanhydrides (e.g. poly(sebacic anhydride)), polyhydroxyacids (e.g. poly(β-hydroxyalkanoate)), polypropylfumarates, polycaprolactones, polyamides (e.g. polycaprolactam), polyacetals, polyethers, polyesters (e.g. polylactide, polyglycolide, poly(dioxanones), polyhydroxybutyrate,), poly(orthoesters), polycyanoacrylates, polyvinyl alcohols, polyurethanes, polyphosphazenes, polyacrylates, polymethacrylates, polyureas, polyamines and copolymers thereof. Exemplary polymers also include polyvalerolactone, poly (sebacic anhydride), polyethylene glycol, polystyrenes, polyhydroxyvalyrate, poly(vinyl pyrrolidone) poly(hydroxyethyl methacrylate) (PHEMA), poly(vinyl alcohol) (PVA), and derivatives and copolymers thereof.

Size and Shape

In general, particle cores suitable for the present disclosure can be of any size. In some embodiments, a collection of particle cores have an average greatest dimension (e.g. diameter) of less than 1000 micrometers (μm). In some embodiments, a collection of particle cores have a greatest dimension (e.g. diameter) of about 100 um, about 10 um, about 5 um, about 2 um, about 1.5 um, about 1000 nm, about 500 nm, about 200 nm, about 150 nm, about 100 nm, about 90 nm, about 80 nm, about 70 nm, about 60 nm, about 50 nm, about 40 nm, about 30 nm, about 20 nm, about 10 nm, 5 nm or 1 nm. In some embodiments, a collection of particle cores have a greatest dimension of less than 1000 nm. In some embodiments, a collection of particle cores have a greatest dimension of less than or more than 500 nm. In some embodiments, a collection of particle cores have a greatest dimension of less than or more than about 250 nm. In some embodiments, a collection of particle cores have a greatest dimension of less than or more than about 200 nm. In some embodiments, a collection of particle cores have a greatest dimension of less than or more than about 150 nm. In some embodiments, a collection of particle cores have a greatest dimension of less than or more than about 100 nm. In some embodiments, a collection of particle cores have a greatest dimension of less than or more than about 50 nm. In some embodiments, a collection of particle cores have a greatest dimension of less than or more than about 20 nm. In some embodiments, a collection of particle cores have a greatest dimension of less than about or more than 10 nm. In some embodiments, a collection of particle cores have a greatest dimension in between of 1-1000 nm, 10-500 nm, or 20-100 nm. In some embodiments, a collection of particle cores have a greatest dimension in between of any two values above. In some embodiments, a greatest dimension is a hydrodynamic diameter.

Suitable particle cores can have a variety of different shapes including, but not limited to, spheres, oblate spheroids, cylinders, ovals, ellipses, shells, cubes, cuboids, cones, pyramids, rods (e.g., cylinders or elongated structures having a square or rectangular cross-section), tetrapods (particle cores having four leg-like appendages), triangles, prisms, etc. In some embodiments, particle cores are rod-shaped. In some embodiments, particle cores are bar-shaped. In some embodiments, particle cores are bead-shaped. In some embodiments, particle cores are column-shaped. In some embodiments, particle cores are ribbon or chain-like. In some embodiments, particle cores can be of any geometry or symmetry. For example, planar, circular, rounded, tubular, ring-shaped, tetrahedral, hexagonal, octagonal particle cores, particle cores of other regular geometries, and/or particle cores of irregular geometries can also be used in the present disclosure.

It is often desirable to use a population of particle cores that is relatively uniform in terms of size, shape, and/or composition so that each particle core has similar properties. In some embodiments, a population of particle cores with homogeneity with diameters (e.g., hydrodynamic diameters) are used. As used herein, a population of particle cores with homogeneity with diameters (e.g., hydrodynamic diameters) refers to a population of particle cores with at least about 80%, at least about 90%, or at least about 95% of particle cores with a diameter (e.g., hydrodynamic diameter) that falls within 5%, 10%, or 20% of the average diameter (e.g., hydrodynamic diameter). In some embodiments, the average diameter (e.g., hydrodynamic diameter) of a population of particle cores with homogeneity with diameters (e.g., hydrodynamic diameters) ranges as discussed above. In some embodiments, a population of particle cores with homogeneity with diameters (e.g., hydrodynamic diameters) refers to a population of particle cores that has a polydispersity index less than 0.2, 0.1, 0.05, 0.01, or 0.005. For example, polydispersity index of particle cores used in accordance with the present disclosure is in a range of about 0.005 to about 0.1. Without wishing to be bound by any theory, it is contemplated that particle cores with homogeneity (e.g., with respect to particle core size) may have higher repeatability and can produce more accuracy in the present application. In some embodiments, a population of particle cores may be heterogeneous with respect to size, shape, and/or composition.

Particle cores can be solid or hollow and can comprise one or more layers (e.g., nanoshells, nanorings, etc.). Particle cores may have a core/shell structure, wherein the core(s) and shell(s) can be made of different materials. Particle cores may comprise gradient or homogeneous alloys. Particle cores may be composite particle cores made of two or more materials, of which one, more than one, or all of the materials possesses magnetic properties, electrically detectable properties, and/or optically detectable properties.

LbL Films

LbL films may have various film architecture, film materials, film thickness, surface chemistry, and/or incorporation of agents according to the design and application of particles/particle delivery systems.

In general, LbL films comprise multiple layers. In accordance with the present disclosure, individual layers in an LbL film interact with one another. In particular, each layer in an LbL film comprises an interacting moiety that interacts with each adjacent layer, so that the first layer, which coats the core, and the outer layer, which forms the particle surface (and is exposed to its environment), each contain at least one interacting moiety; each intermediate layer contains at least two interacting moieties (one to interact with the immediately preceding layer and one to interact with the immediately subsequent layer), except that in some embodiments the same chemical moiety can mediate interaction with both the immediately preceding and immediately subsequent layer. That is, in some embodiments, an intermediate layer contains first and second interacting moieties that are the same.

In some embodiments, an LbL film is or comprises at least 3, 4, 6, 8, 10, 12, 14, 16, 18, 20, 30, 40, 50, 60, 70, 80, 90 or even 100 layers. In some embodiments, an LbL film comprises fewer than 3, 4, 6, 8, 10, 12, 14, 16, 18, 20, 30, 40, 50, 60, 70, 80, 90 or even 100 layers. In certain embodiments, an LbL film has 3 layers. In certain embodiments, an LbL film has 6 layers. In some embodiments, an LbL film comprises at least 3 layers. In some embodiments, and LbL film comprises at least 6 layers. In some embodiments, an LbL film comprises an even number of layers. In some embodiments, an LbL film comprises a first layer, and outer layer, and an even number of intermediate layers. In some embodiments, an LbL film comprises a first layer, an outer layer, and a number of intermediate layers that is a multiple of 3. In some embodiments, an LbL film comprises a first layer, an outer layer, and a number of intermediate layers that is a multiple of 4. In some embodiments, an LbL film comprises a first layer, an outer layer, and a number of intermediate layers that is a multiple of 6.

In some embodiments LbL film comprises one or more distinct units or sets of layers. Exemplary units include, but are not limited to, bilayer, a trilayer, and a tetralayer. In addition or alternatively, an LbL film can comprise a base and/or an outer layer.

In some embodiments, an adjacent layer interacting moiety is a charge. For example, LbL films can include alternating layers of opposite charge, that is, anionic and cationic layers. Typically, anionic polyelectrolytes may be polymers with anionic groups distributed along the polymer backbone. Anionic groups, which may include carboxylate, sulfonate, sulphate, phosphate, nitrate, or other negatively charged or ionizable groupings, may be disposed upon groups pendant from the backbone or may be incorporated in the backbone itself. Cationic polyelectrolytes may be polymers with cationic groups distributed along the polymer backbone. Cationic groups, which may include protonated amine, quaternary ammonium or phosphonium-derived functions or other positively charged or ionizable groups, may be disposed in side groups pendant from the backbone, may be attached to the backbone directly, or can be incorporated in the backbone itself.

In some embodiments, an LbL film comprises a layer comprising or consisting of a positively charged polyelectrolyte. Positively charged polyelectrolytes can comprise cationic groups including primary or secondary amines. They may be derived from natural or unnatural poly-amino acids wherein one or more monomer possesses a cationic moiety such as amino or guanidinium groups. Exemplary monomers of natural polyaminoacids include lysine, ornithine, guanidine or any combination thereof. Examples of positively charged polyelectrolytes include, but are not limited to, poly(lysine) (PLL), poly(arginine), polyethyleneimine and poly(allyl amine).

In some embodiments, an LbL film comprises an outer layer comprising or consisting of a negative charged polyelectrolyte. Negative charged polyelectrolytes can comprise carboxyl groups such as carboxylic acid groups and carboxylate salt groups. For example, carboxylated polyelectrolytes can be a carboxyalkyl cellulose, such as a carboxymethyl cellulose or carboxyethyl cellulose. Other carboxylated polyelectrolytes include polysaccharides that are natural, synthetic, or semi-synthetic in origin. Exemplary negative charged polysaccharides include, but are not limited to, hyaluronic acids, carboxymethyldextran, carboxyalkyl starches, alginic acids, carboxymethyl or butyl glucans or chitosans. In certain embodiments, carboxylated polyelectrolytes can comprise polyacrylic acid, polymaleic acid, polyaspartic acid, any combination or co-polymer thereof.

Polyethylene glycol (PEG) may be useful, in some embodiments, in accordance with the present application since they are nontoxic, non-immunogenic, inert to most biological molecules (e.g. proteins), and approved by the FDA for various clinical uses. In some embodiments, PEG can be used an outer layer. For examples, an outer layer may include PEG chains that are crosslinked through photopolymerization using acrylate-terminated PEG monomers. To give another example, block copolymers of PEG, such as triblock copolymers of PEO and poly(propylene oxide)

(henceforth designated as PEO-b-PPO-b-PEO), degradable PEO, poly(lactic acid) (PLA), and other similar materials, can be used. In addition, PEG or a layer comprising PEG can be physically or chemically modified for multi-functionality.

Additionally or alternatively, LbL films can comprise layers associated with one another via non-electrostatic interaction. A layer in an LbL film may be physically or chemically modified to generate an adjacent layer interacting moiety for an electrostatic or other interactions with an adjacent layer. In certain embodiments, an adjacent layer interacting moiety is biotin or avidin. For example, polylysine can be functionalized to have iminobiotin for associate with a linker layer of neutravidin, as demonstrated in Example 2.

In some embodiments, a protein can be included or serves as a layer of an LbL film. Such a protein can be used to design a linker layer. In addition or alternatively, a protein can be used as an agent that can be released by breaking down of its association with layers in LbL films.

In some embodiments, a layer in an LbL film includes a degradable polyelectrolyte. LbL films may be exposed to a liquid medium (e.g., intracellular fluid, interstitial fluid, blood, intravitreal fluid, intraocular fluid, gastric fluids, etc.). In some embodiments, an LbL film comprises at least one polycationic layer that degrades and at least one polyanionic layer that delaminates sequentially. Releasable agents can thus be gradually and controllably released from the LbL film. It will be appreciated that the roles of the layers of an LbL film can be reversed. In some embodiments, an LbL film comprises at least one polyanionic layer that degrades and at least one polycationic layer that delaminates sequentially. Alternatively, polycationic and polyanionic layers may both include degradable polyelectrolytes.

Degradable polyelectrolytes and their degradation byproducts may be biocompatible so as to make LbL films amenable to use in vivo. Any degradable polyelectrolyte can be used in the thin film disclosed herein, including, but not limited to, hydrolytically degradable, biodegradable, thermally degradable, and photolytically degradable polyelectrolytes. Hydrolytically degradable polymers known in the art include for example, certain polyesters, polyanhydrides, polyorthoesters, polyphosphazenes, and polyphosphoesters. Biodegradable polymers known in the art, include, for example, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly(glycolic acid) (PGA), poly(caprolactone) (PCL), poly (lactide-co-glycolide) (PLG), poly(lactide-co-caprolactone) (PLC), and poly(glycolide-co-caprolactone) (PGC). Those skilled in the art will recognize that this is an exemplary, not comprehensive, list of biodegradable polymers. Co-polymers, mixtures, and adducts of these polymers may also be employed.

Releasable Agents

According to the present disclosure, LbL films can include one or more releasable agents for delivery. In some embodiments, an agent can be associated with individual layers of an LbL film for incorporation, affording the opportunity for exquisite control of loading and release from the film. In certain embodiments, an agent is incorporated into an LbL film by serving as a layer.

In theory, any agents including, for example, therapeutic agents (e.g. antibiotics, NSAIDs, glaucoma medications, angiogenesis inhibitors, neuroprotective agents), cytotoxic agents, diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be associated with the LbL film disclosed herein to be released.

In some embodiments, compositions and methods in accordance with the present disclosure are particularly useful for release of one or more therapeutic agents. Exemplary agents include, but are not limited to, small molecules (e.g. cytotoxic agents), nucleic acids (e.g., siRNA, RNAi, and microRNA agents), proteins (e.g. antibodies), peptides, lipids, carbohydrates, hormones, metals, radioactive elements and compounds, drugs, vaccines, immunological agents, etc., and/or combinations thereof. In some embodiments, a therapeutic agent to be delivered is an agent useful in combating inflammation and/or infection.

In some embodiments, a therapeutic agent is a small molecule and/or organic compound with pharmaceutical activity. In some embodiments, a therapeutic agent is a clinically-used drug. In some embodiments, a therapeutic agent is or comprises an antibiotic, anti-viral agent, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, etc.

In some embodiments, a therapeutic agent may be a mixture of pharmaceutically active agents. For example, a local anesthetic may be delivered in combination with an anti-inflammatory agent such as a steroid. Local anesthetics may also be administered with vasoactive agents such as epinephrine. To give but another example, an antibiotic may be combined with an inhibitor of the enzyme commonly produced by bacteria to inactivate the antibiotic (e.g., penicillin and clavulanic acid).

In some embodiments, a therapeutic agent may be an antibiotic. Exemplary antibiotics include, but are not limited to, β-lactam antibiotics, macrolides, monobactams, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, bacitracin, erythromycin, nalidixic acid, vancomycin, and trimethoprim. For example, β-lactam antibiotics can be ampicillin, aziocillin, aztreonam, carbenicillin, cefoperazone, ceftriaxone, cephaloridine, cephalothin, cloxacillin, moxalactam, penicillin G, piperacillin, ticarcillin and any combination thereof.

An antibiotic may be bacteriocidial or bacteriostatic. Other anti-microbial agents may also be used in accordance with the present disclosure. For example, anti-viral agents, anti-protazoal agents, anti-parasitic agents, etc. may be of use.

In some embodiments, a therapeutic agent may be an anti-inflammatory agent. Anti-inflammatory agents may include corticosteroids (e.g., glucocorticoids), cycloplegics, non-steroidal anti-inflammatory drusg (NSAIDs), immune selective anti-inflammatory derivatives (ImSAIDs), and any combination thereof. Exemplary NSAIDs include, but not limited to, celecoxib (Celebrex®); rofecoxib (Vioxx®), etoricoxib (Arcoxia®), meloxicam (Mobic®), valdecoxib, diclofenac (Voltaren®, Cataflam®), etodolac (Lodine®), sulindac (Clinori®), aspirin, alclofenac, fenclofenac, diflunisal (Dolobid®), benorylate, fosfosal, salicylic acid including acetylsalicylic acid, sodium acetylsalicylic acid, calcium acetylsalicylic acid, and sodium salicylate; ibuprofen (Motrin), ketoprofen, carprofen, fenbufen, flurbiprofen, oxaprozin, suprofen, tiaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene®), indomethacin (Indocin®), nabumetone (Relafen®), naproxen (Naprosyn®), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

Those skilled in the art will recognize that this is an exemplary, not comprehensive, list of agents that can be released using compositions and methods in accordance with the present disclosure. In addition to a therapeutic agent or alternatively, various other agents may be associated with an LbL film in accordance with the present disclosure.

Methods and Uses

There are several advantages to LbL assembly techniques used in accordance with the present disclosure, including mild aqueous processing conditions (which may allow preservation of biomolecule function); nanometer-scale conformal coating of surfaces; and the flexibility to coat objects of any size, shape or surface chemistry, leading to versatility in design options. According to the present disclosure, one or more LbL films can be assembled and/or deposited on a particle core using an LbL technique.

It will be appreciated that various physical or chemical modifications of particle cores and/or LbL films can be used before coating. For example, particle cores can be primed with specific polyelectrolyte bilayers.

In some embodiments, LbL assembly of an LbL film may involve a series of dip coating steps in which a substrate is dipped in alternating polycationic and polyanionic solutions. In some embodiments, LbL assembly of a film may involve mixing, washing or incubation steps to facilitate interactions of layers, in particular, for non-electrostatic interactions. Additionally or alternatively, it will be appreciated that deposition of alternating polycationic and polyanionic layers may also be achieved by spray coating, dip coating, brush coating, roll coating, spin casting, or combinations of any of these techniques.

Certain characteristics of an LbL film-coated particle may be modulated to achieve desired functionalities for different applications.

In some embodiments, a collection of particles comprising a particle core coated by an LbL film has an average greatest dimension (e.g. diameter) of less than 1000 micrometers (μm). In some embodiments, a collection of particles have a greatest dimension (e.g. diameter) of about 100 um, about 10 um, about 5 um, about 2 um, about 1.5 um, about 1000 nm, about 500 nm, about 200 nm, about 150 nm, about 100 nm, about 90 nm, about 80 nm, about 70 nm, about 60 nm, about 50 nm, about 40 nm, about 30 nm, about 20 nm, about 10 nm, 5 nm or 1 nm. In some embodiments, a collection of particles have a greatest dimension of less than 1000 nm. In some embodiments, a collection of particles have a greatest dimension of less than or more than 500 nm. In some embodiments, a collection of particles have a greatest dimension of less than or more than about 250 nm. In some embodiments, a collection of particles have a greatest dimension of less than or more than about 200 nm. In some embodiments, a collection of particles have a greatest dimension of less than or more than about 150 nm. In some embodiments, a collection of particles have a greatest dimension of less than or more than about 100 nm. In some embodiments, a collection of particles have a greatest dimension of less than or more than about 50 nm. In some embodiments, a collection of particles have a greatest dimension of less than or more than about 20 nm. In some embodiments, a collection of particles have a greatest dimension of less than about or more than 10 nm. In some embodiments, a collection of particles have a greatest dimension in between of 1-1000 nm, 10-500 nm, or 20-100 nm. In some embodiments, a collection of particles have a greatest dimension in between of any two values above. In some embodiments, an average greatest dimension is an average hydrodynamic diameter.

In some embodiments, a collection of particles has a zeta potential of less than 200 mV. In some embodiments, a collection of particles has a zeta potential of about 150 mV, about 100 mV, about 90 mV, about 80 mV, about 70 mV, about 60 mV, about 50 mV, about 40 mV, about 30 mV, about 20 mV, about 10 mV, 5 mV or 1 mV. In some embodiments, a collection of particles have a zeta potential of less than or more than 100 mV. In some embodiments, a collection of particles have a zeta potential of less than or more than 80 mV. In some embodiments, a collection of particles have a zeta potential of less than or more than about 50 mV. In some embodiments, a collection of particles have a zeta potential of less than or more than about 40 mV. In some embodiments, a collection of particles have a zeta potential of less than or more than about 30 mV. In some embodiments, a collection of particles have a zeta potential of less than or more than about 20 mV. In some embodiments, a collection of particles have a zeta potential of less than or more than about 10 mV. In some embodiments, a collection of particles have a zeta potential of less than or more than about 5 mV. In some embodiments, a collection of particles have a zeta potential in between of 1-200 mV, 10-100 mV, or 20-50 mV. In some embodiments, a collection of particles have a zeta potential in between of any two values above.

Particles comprising particle cores coated with LbL films can have improved in vivo stability as compared to particle cores without coating of LbL films in accordance with the present disclosure. In some embodiments, particles are about 10 times, about 9 times, about 8 times, about 7 times, about 6 times, about 5 times, about 4 times, about 3 times, about 2 times more stable than particle cores.

As compared to particle cores, particles comprising the particle cores coated with LbL films typically have improved pharmacokinetic behaviors including biodistribution, tissue interaction and targeting.

Releasing of an agent associated with LbL films in accordance with present disclosure can be fine tuned. For example, the mechanism, dose or kinetics of releasing agents may vary depending on film design and construction.

EXAMPLES

Example 1: Layer-by-Layer Coated Particles for Systemic Delivery

Characteristics of particles comprising particle cores coated by layer-by-layer (LbL) films (such as, particle stability, biodistribution, tissue interaction, and other important pharmacokinetic behavior) vary depending on materials and methods used to assembly the films on particles. Exemplary systems were developed here to demonstrate how changes in film properties affect their in vivo pharmacokinetics.

The present Example describes a particular embodiment of a particle system as described herein. In this particular embodiment, a particle core is coated with an LbL film comprising at least six layers, wherein each layer is comprised of a polyelectrolyte, such that each adjacent layer interacting moiety comprises a charge, wherein each layer has opposite charge from its adjacent layers, such that a non-covalent interaction between adjacent layers comprise electrostatic interactions, and wherein a first layer that cores the particle core is positively charged. In particular, particle cores exemplified herein are gold particles and quantum dots, coated with a first layer of $PLL_{800}$, a number of intermediate layers consisting of DXS/PLL, and an outer layer of DXS or HA.

Materials and Reagents

All chemicals and biological material were purchased from Sigma-Aldrich or Invitrogen unless otherwise noted.

Mice.

Female BALB/c and NCr nude mice (4-6 weeks old) were purchased from Taconic and the AIN-76A purified diet was from PharmaServ/Testdiets. Mice were kept on the AIN-76A diet for at least a week before experimentation to reduce levels of body phosphorescent alfalfa. All in vivo experimentation was carried out under the supervision of the Division of Comparative Medicine (DCM), Massachusetts Institute of Technology, and in compliance with the Principles of Laboratory Animal Care of the National Institutes of Health. Cell lines were purchased from ATCC and were tested routinely for pathogens before use in animals via DCM.

Cell Culture.

KB nasopharyngeal carcinoma cells (ATCC) and J774A.1 macrophages were used in our experiments and grown in MEM alpha media supplemented with 10% fetal bovine serum, 50 units/mL penicillin and 50 units/mL streptomycin.

Fabrication and Characterization of Layer-by-Layer (LbL) Nanoparticles.

LbL nanoparticles with functional shells were prepared using a commonly used assembly technique for nanoparticle coating. The negatively charged fluorescent cores used were either carboxyl functionalized gold nanoparticles (AuNPs) (~20 nm; -25 mV; see section below for synthesis) or carboxyl functionalized quantum dots ($QD_{705}$) (8 µM; em: 705 nm; ~20 nm; -25 mV; Invitrogen). Pol-L-lysine (15 kDa) was labeled with a near IR dye (VivoTag 800, Visen medical) following the manufacturer's instructions on ~5% of the primary amine side groups (based on reaction feed ratio) under aqueous conditions and at a pH of 7.4. After reaction, the labeled polymers were purified by dialysis (3.5 kDa cut-of dialysis bag) before use. For LbL assembly, nanoparticles were mixed vigorously with polyelectrolytes that were prepared at concentrations of 500 µM at pH 7.4. The mixing ratios of polyelectrolyte (PLL: poly-L-lysine (10 kDa), DXS: dextran sulfate (10 kDa), HA: hyaluronic acid (10 kDa, Lifecore Biomedical Inc.) to nanoparticle were approximately 400-500 µM:0.05-0.1 µM. After addition of the nanoparticle to polyelectrolyte, the mixture was left stirring vigorously at pH 7-7.4 for 4 h. No salt was added to the mixture. The particles were purified by three centrifugation (13000 rpm; 1.5 h) and resuspension (millipore water, pH 7.4) cycles. No salt was added in the process.

All size and zeta potential measurements were made using a Zeta PALS (Brookhaven) analyzer. Tapping mode AFM characterization was performed on a Dimension 3100 instrument with Nanoscope III controller (Digital Instruments) For TEM imaging, micelle solutions were drop-cast onto carbon coated copper grids without any staining Particle concentrations were estimated using standard calibration graphs made from native particles. To attain equal particle concentrations, LbL nanoparticle solutions were adjusted with water based on $QD_{705}$ fluorescence measured. For in vivo experiments, the concentration of $QD_{705}$ particles used was ~0.5 µM given in 0.1 mL injections.

Synthesis of MUA Capped Gold Nanoparticles.

Gold nanoparticles (AuNPs) were synthesized using a known method. Briefly, 100 mg of hydrogen tetra-chloroaurate(III) (HAuCl4) in water was transferred to toluene with tetraoctylammonium bromide (10 mM). The gold particles in toluene were washed three times with deionized water and transferred to a flask. Sodium borohydride (100 mg in 10 mL deionized water) was then added and the orange-colored HAuCl4 solution turned wine-red. The reaction was left stirring for 2 h. The two phases were then separated and the toluene phase was subsequently washed with 0.1 M sulfuric acid, 0.1 M sodium hydroxide, and three times with deionized water. The gold nanoparticle solution in toluene was heated to 60° C., and 5 g of 11-mercaptoundecanoic acid (MUA) in 10 mL of toluene (at 60° C.) was then added to the gold nanoparticles. The gold nanoparticles settled to the bottom of the flask upon addition of MUA and the black precipitate obtained was separated and washed three times with toluene to remove any uncoordinated MUA. The precipitate was dried and redispersed in basic buffer. A wine red solution was obtained with a plasmon absorption maximum at 525 nm. The concentration of AuNPs was estimated using mass conservation considerations.

In Vivo Experimentation.

BALB/c mice were used for blood circulation experiments and the NCr nudes were used for all other experiments. Mice fed on AIN-76A diet for at least a week were given single injections of the different LbL particles via the tail vein. The concentration of particles ($QD_{705}$ and LbL nanoparticles) administered was ~0.5 µM given in 0.1 mL injection. Free $PLL_{800}$ was administered at doses of 5 mg/kg. At various time points after injection, they were imaged ventrally using the IVIS system (Caliper Lifescience). Living Image software Version 3.0 (Xenogen) was used to acquire and quantitate the fluorescence. The images showing $QD_{705}$ fluorescence was captured using Ex: 640 nm and Em: 720 nm. The images showing $PLL_{800}$ fluorescence was captured using Ex: 710 nm and Em: 800 nm. Spectrally unmixed images were captured using a sequence of Ex: 640 nm and Em: 700 nm/720 nm/740 nm/760 nm for $QD_{705}$; and Ex: 745 nm and Em: 800 nm/820 nm/840 nm for $PLL_{800}$.

Subcutaneous tumors were induced in either the left or right hind flank of NCr nudes after injection of ~1-2 million cells (KB) in 0.1 mL media. Tumors were allowed to grow to ~100 mm³ before experimentation. Where applicable, tissue samples were extracted for further imaging using the Licor Odyssey system. For biodistribution, tissue samples were harvested, washed, weighed, and macerated before imaging with the IVIS system for their respective fluorescence. The fluorescent data was normalized by tissue weight. Blood circulation analysis was performed by measuring the remaining QD signal from blood taken after injection with the Licor Odyssey system.

In Vitro Experimentation.

As the first examination of the stealth properties of these LbL particles, we tried opsonising them with human IgG-488. 0.2 µM LbL particles were subjected to incubation with 0.25 mg/mL of aqueous IgG-488 at pH 7.4, 37° C. for 30 min. After incubation, the particles were centrifuged down and washed with DI water three times. The amount of IgG-488 adsorbed onto the LbL particle surface was determined by the ratio of IgG-488 fluorescence to the $QD_{705}$ fluorescence, measured using a spectrofluorometer. Subsequently, we measured their degree of uptake into J774A.1 macrophages using confocal microscopy and flow cytometry. For uptake studies, non-labeled mouse IgG was used to opsonize the particles (30 min, pH 7.4 and at 37° C.) and the fluorescent $QD_{705}$ signal was used to quantitate nanoparticle uptake. A Cy5 filter was used to detect quantum dot (em: 705 nm) fluorescence on both a DeltaVision confocal microscope (Applied Precision) and FACS LSRII flow cytometer (BD Biosciences). For confocal microscopy, cells were grown until 50% confluent on chamber slides and treated with various nanoparticles. The cells were then washed repeatedly with PBS and fixed with 4% paraformaldehyde. Fluoromount-G was used to prepare the cells for confocal analysis. For FACS analysis, cells after treatment were trypsinized and washed three times with PBS to remove unbound particles before analysis. Nanoparticle aggregation was investigated by taking time dependent size measurements of different LbL nanoparticles in a solution of 20 mg/ml bovine serum albumin in PBS.

Statistical Analysis.

All values shown are in mean±SEM unless otherwise specified. Analyses were done by unpaired Student's t-test and considered significant at P<0.05.

LbL Film Construction on Nanoparticles.

The schematic for an LbL-based nanoparticle system capable of delivering multiple classes of therapeutics and releasing them in a programmable manner is shown in FIG. 1. The multi-component nanofilm built around a core template forms a crucial structural component of the LbL nanoparticle, and is responsible for transporting and controlling the release of therapeutics as well as imparting in vivo functionality. LbL nanoparticle cores can be made hollow to allow compartmentalization of biologics or left as a solid template structure. Several material options are available for use as the solid core template, from metal or metal oxides to commercial degradable polymers, either to provide further multi-functionality or to compartmentalize another reservoir of drugs; but this aspect of LbL nanoparticle design will not be explored in this paper.

We built LbL nanofilms on two types of core templates (gold nanoparticles (AuNPs) and quantum dots (QD)), both with sizes of ~20 nm and carboxyl functional groups presented on their surfaces (see, Table 1 below). The zeta potentials of both core nanoparticle templates are ~-25 mV above pH 4.5. AuNPs serve as a convenient model system from which we can obtain precise information on their state of aggregation by measuring their plasmon shift. This feature makes the gold nanoparticle core a useful tool for determining optimal LbL assembly conditions, which are especially critical for the deposition of LbL films on nanoscopic objects due to the high potential for particle aggregation and loss of yield during assembly. The plasmon shift can originate from two different phenomena: 1) the deposition of polyelectrolyte layers onto the particle surface, which typically results in a dielectric environment that shifts frequencies by less than 10 nm; and 2) the aggregation of multiple particles which causes a much more pronounced shift of more than 150 nm.

TABLE 1

The sizes, zeta potentials and PDI the main LbL nanoparticles used for in vivo experimentation. Data is given in mean ± SEM, n = 10.

| | Effective Diameter (nm) | Zeta Potential (mV) | PDI |
|---|---|---|---|
| $QD_{705}$ | ~ 18 ± 5.2 | ~ −25 ± 3.6 | 1.13 |
| $QD_{705}/PLL_{800}/[DXS/PLL]_3/DXS$ | ~ 47 ± 6.1 | ~ −30 ± 5.8 | 1.21 |
| $QD_{705}/PLL_{800}/[DXS/PLL]_3/HA$ | ~ 50 ± 7.9 | ~ −20 ± 6.2 | 1.27 |
| $QD_{705}/PLL_{800}/[DXS/PLL]_4$ | ~ 48 ± 6.6 | ~ +20 ± 4.5 | 1.22 |

Figure 2A:
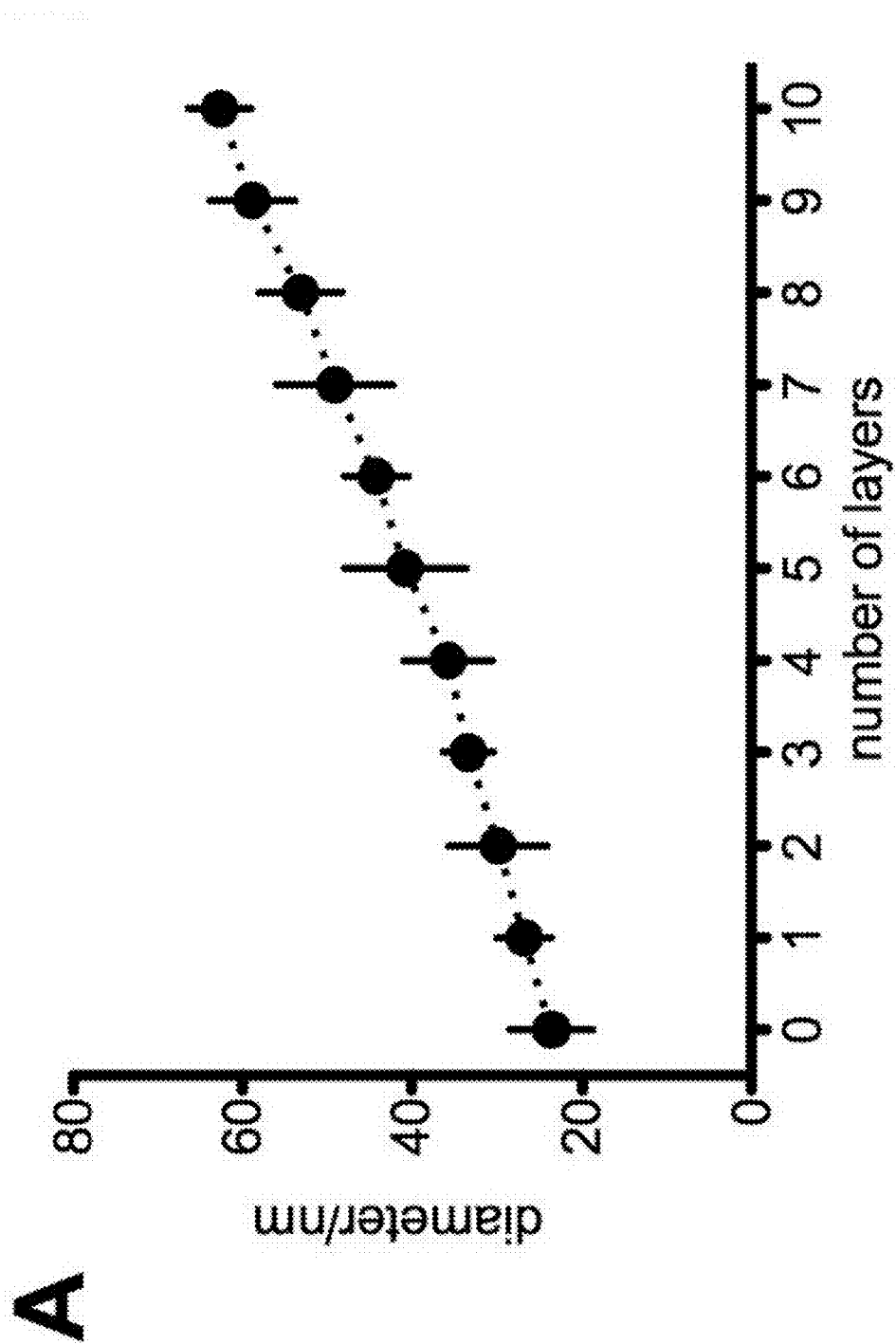
FIG. 2A shows the growth curve of PLL/DXS (poly-L-lysine/dextran sulfate) nanofilms deposited on AuNPs (gold nanoparticles) particles. Each layer is ~2 nm thick.
Figure 2B:
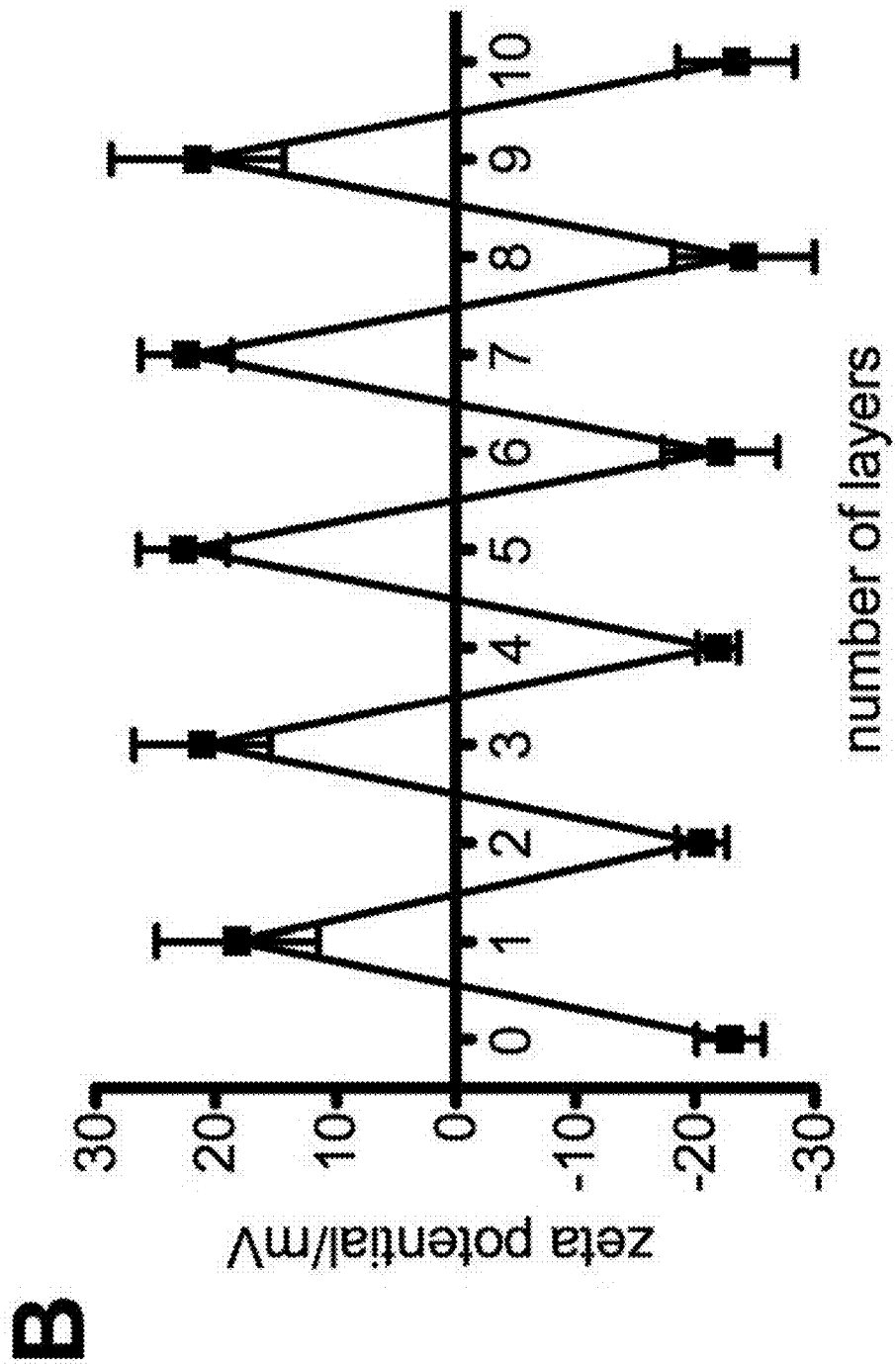
FIG. 2B shows the zeta potential of LbL particle after deposition of each PLL or DXS layer show complete reversal of charge.
Figure 2C:
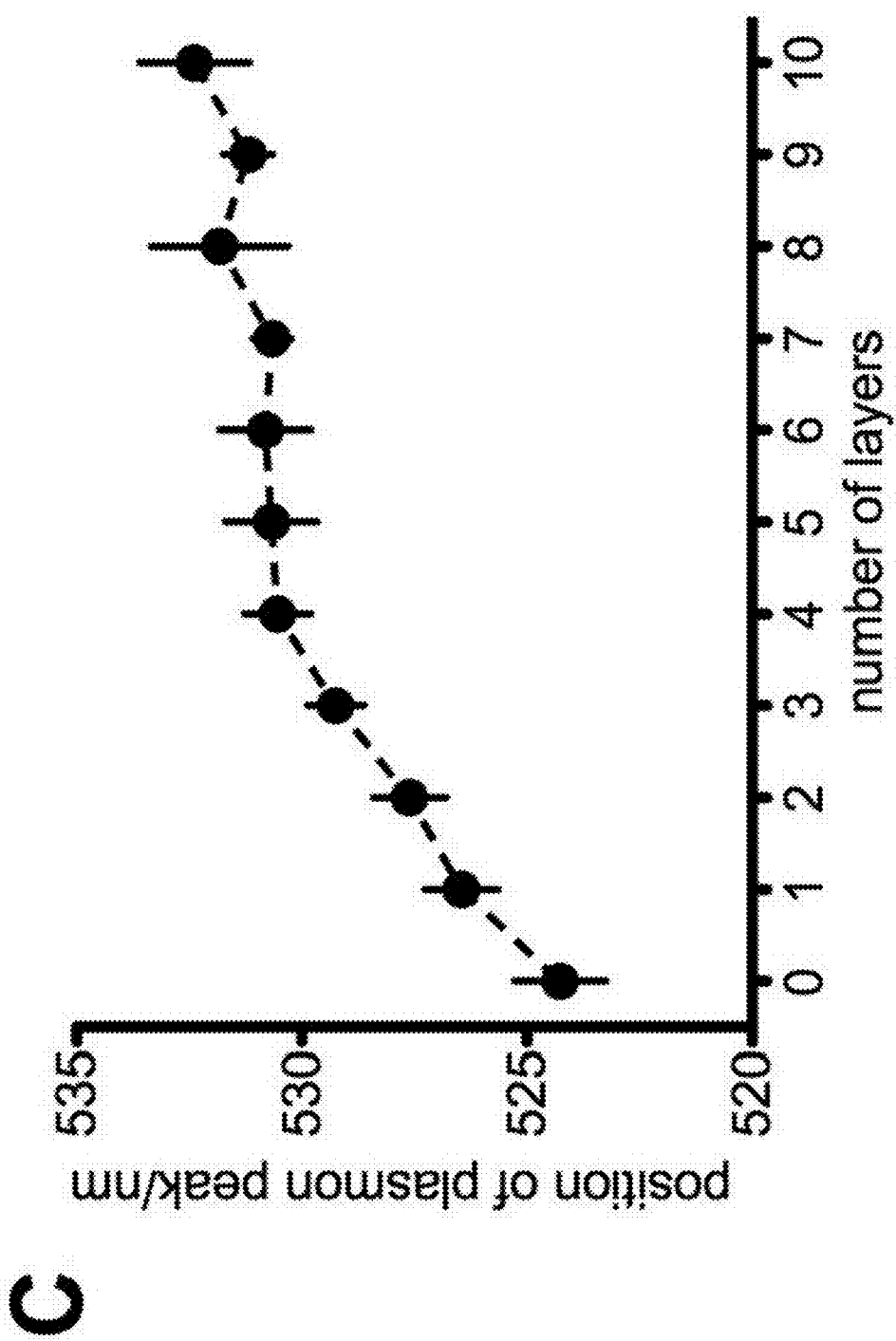
FIG. 2C shows the position of plasmon peak of AuNPs after each step of the LbL deposition process. A small red shift of 1-2 nm per layer corresponds to the deposition of a nanofilm and not the aggregation of AuNPs.
Figure 2D:
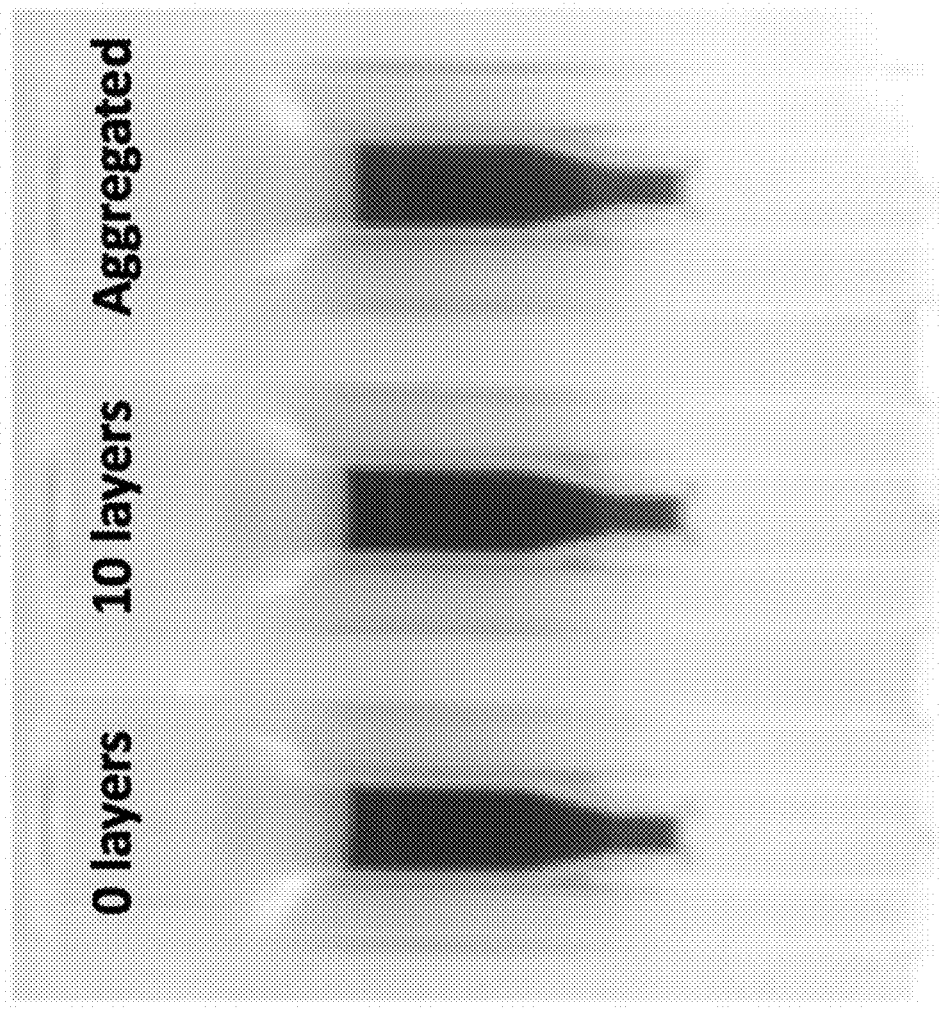
FIG. 2D is a photograph showing the color of dispersions of AuNPs before and after 10 layers of LbL film deposition confirming the non-aggregated state of AuNPs even after 10 layers of polyelectrolyte deposition. Assembly conditions are described in the experimental section.
Figure 2E:
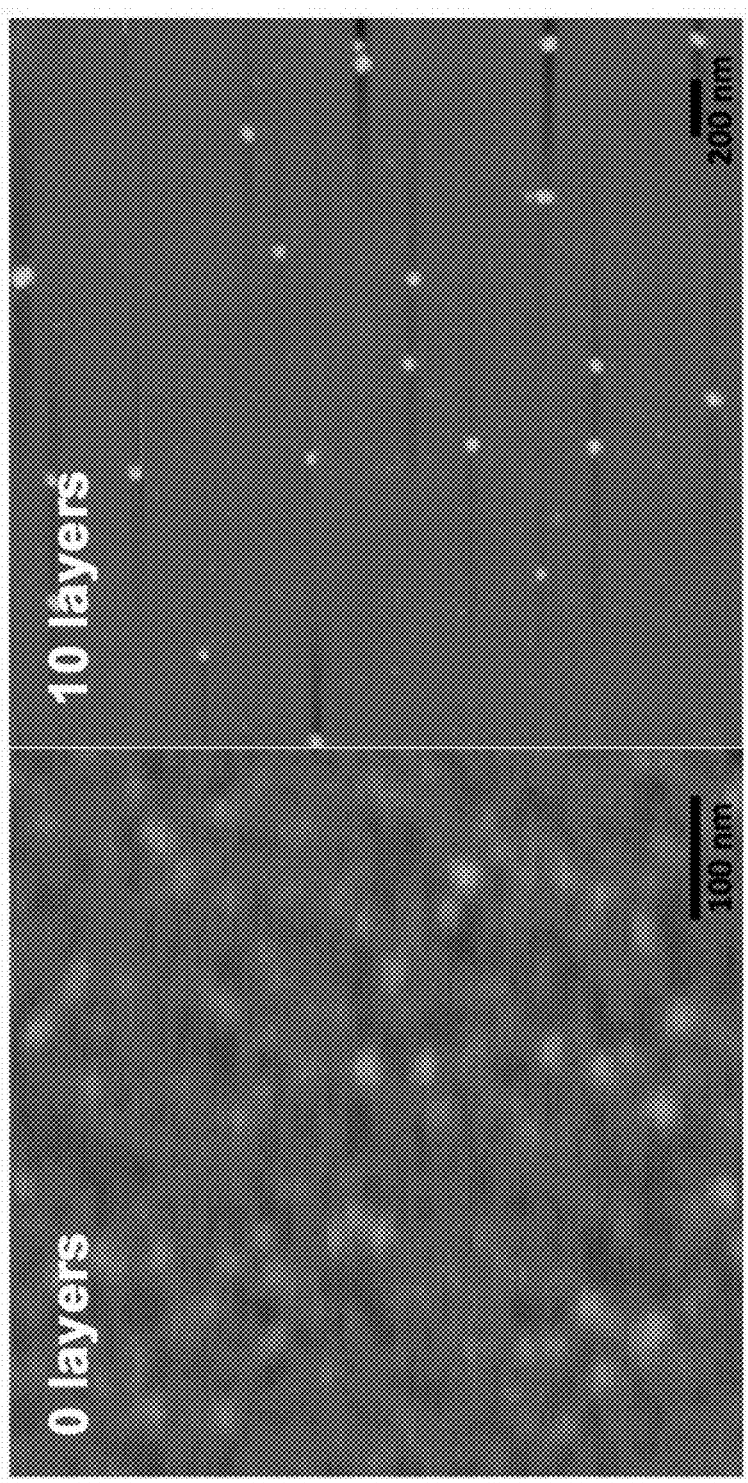
FIG. 2E is shows AFM images of LbL AuNPs before and after deposition of 10 polyelectrolyte layers. The resultant particles preserved a spherical shape and are uniform in size.
Figure 2F:
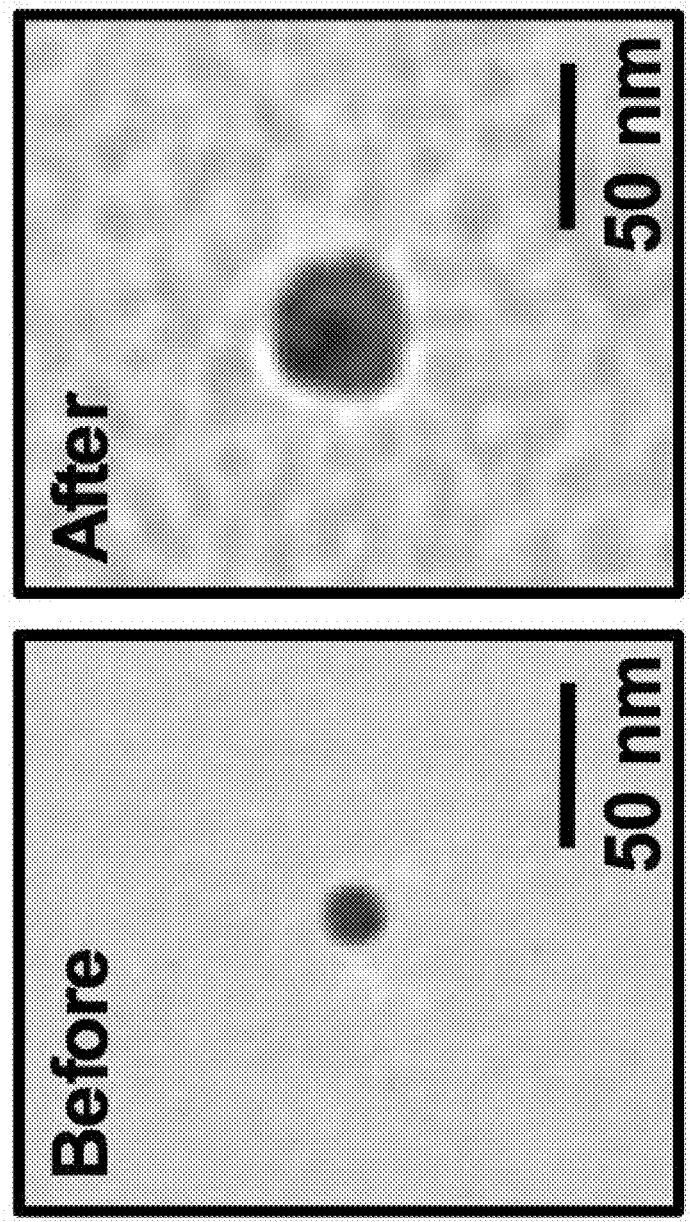
FIG. 2F shows the before and after TEM images showing an LbL coating of 4 bilayers around a AuNP core (AuNP/(PLL/DXS)$_4$). All data in FIG. 2 is given in mean±SEM, n=5-10.
Figure 6:
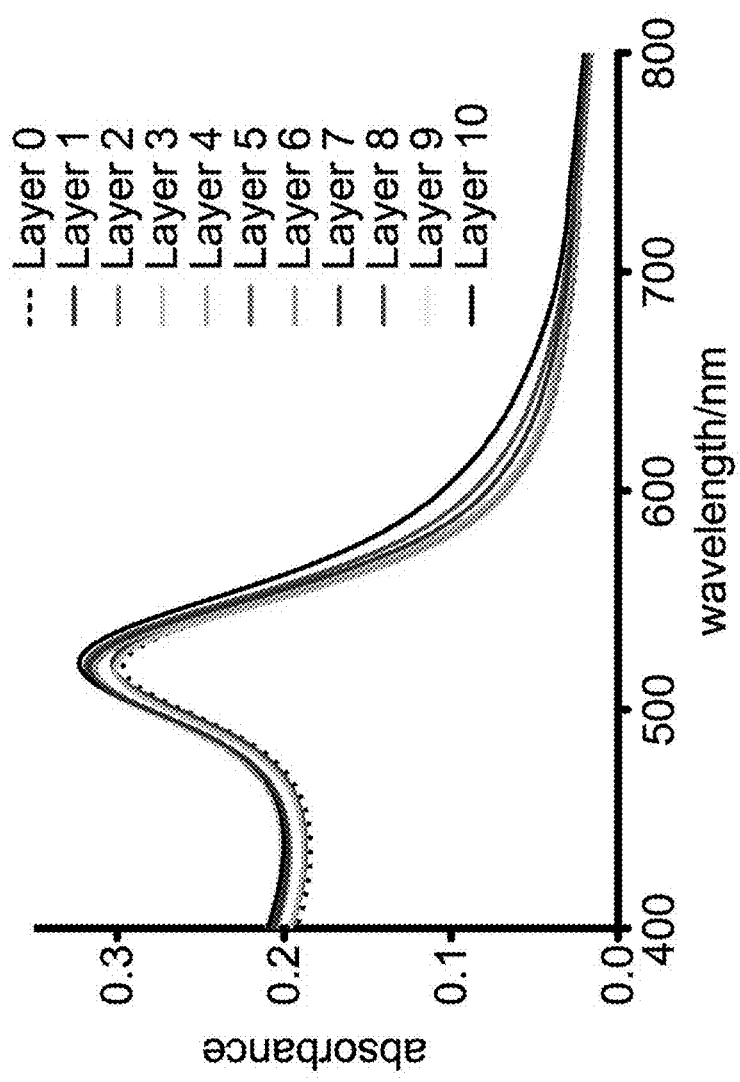
FIG. 6 UV/vis spectra of the layer-by-layer (LbL) gold nanoparticles (AuNPs) after the deposition of each layer of polyelectrolyte. (poly-L-lysine or dextran sulfate).

In order to bring these systems closer to biomedical translation, it is necessary to construct films composed entirely of biocompatible or biodegradable elements; we chose to use known biopolymers to create LbL nanoparticle systems. Using a dextran sulfate (DXS, 10 kDa) and poly-L-lysine (PLL, 10 kDa) polyelectrolyte pair, up to 10 polyelectrolyte layers were deposited on AuNPs. Based on zeta potential and light scattering analysis, an increase in the effective diameter and reversal of the zeta potential of the nanoparticles after each layering step confirmed the construction of LbL nanofilms around the AuNPs (FIG. 2A and FIG. 2B). The UV-vis spectra and peak shift for the particles are shown in FIG. 6 and FIG. 2C respectively. The plasmon bands have a peak that is increasing between ~525 nm to ~532 nm, corresponding to a red shift of about 1-2 nm per layer; this indicates polymer deposition on the nanoparticle with low levels of aggregation. The state of aggregation of AuNPs can also be followed visibly by a change in color of the solution from wine red to a purple-blue (FIG. 2D). The resultant color of the LbL particle colloidal solution (AuNP/(PLL/DXS)$_5$) maintained a wine red color, further evidence that the majority of the particles remain non aggregated under the chosen assembly conditions for up to 10 layers. The assembly of LbL films on AuNPs was attempted for a total of 20 layers, but significant aggregation of nanoparticles was observed during layers 15-20. In the future, more effective means of producing multi-layered LbL nanoparticles are necessary to expand the capabilities of these systems. The morphology of the particles was examined with AFM (FIG. 2E) and TEM (FIG. 2F). AFM images of the particles before and after 10 layers show a uniform increase in particle size, with the particles preserving their spherical shape after layering. TEM analysis of a single LbL particle shows the presence of a thin LbL shell constructed around a gold nanoparticle, confirming the creation of LbL nanofilms on AuNPs.

Stability of LbL-Based Nanoparticle Systems In Vivo.

Figure 7:
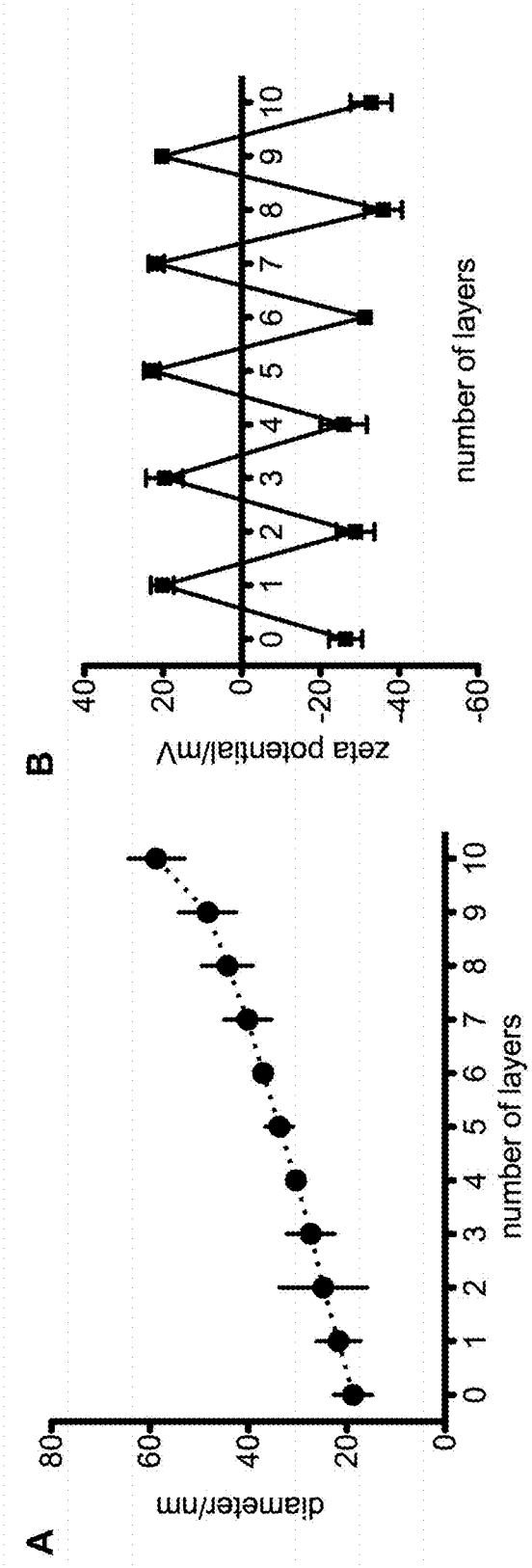
FIG. 7 A) The growth curve of PLL/DXS (poly-L-lysine/dextran sulfate) nanofilms deposited carboxyl functionalized quantum dots ($QD_{705}$). Each layer is ~2 nm thick. B) The zeta potential of LbL particle after deposition of each PLL or DXS layer show complete reversal of charge.

The reticuloendothelial system and related components, circulating macrophages, renal and biliary clearance as well as the overall shear and dilution effects of blood represent the first important barrier posed to any systemically administered nanoparticle based therapy. Conventional nanoparticles capable of passively targeting solid tumors via the enhanced permeation and retention (EPR) effect are typically designed to be structurally stable in blood, between 10 nm to 200 nm in size and with an anti-fouling surface that is hydrophilic and either neutral or slightly negative in charge. When combined, these features allow nanoparticles to circulate for longer periods of time so that the accumulated nanoparticles can reach therapeutic levels. To replicate these design features on LbL-based nanoparticles, an appropriate number of layers (PLL/DXS) are deposited to manipulate particle size, which are terminally capped with a layer of polyelectrolyte that is negatively charged and antifouling. For in vivo experimentation, this simple film architecture was built around carboxyl functionalized $QD_{705}$, which have similar sizes and zeta potentials to AuNPs. Unlike AuNPs, $QD_{705}$ can be tracked in vivo, and this feature, together with the incorporation of a layer of PLL labeled with a near IR dye ($PLL_{800}$, ex/em: 785/800 nm), allows insight into the stability of the nanofilms as well as the LbL nanoparticle by real-time fluorescent tracking of their in vivo fate. The model systems described here are thus abbreviated as $QD_{705}/PLL_{800}/[DXS/PLL]_n/[DXS$ or HA (hyaluronic acid)]. Both DXS and HA are negatively charged linear polysaccharides at physiological pH with reported anti-fouling properties, and are being investigated as biomimetic alternatives to poly(ethylene glycol) as hydrated 'stealth' coatings that prevent protein adsorption and opsonization. The growth curves and zeta potentials of these particles are given in the FIG. 7. The doses given are similar and based on a calibration of $QD_{705}$ fluorescence (see experimental section).

Figure 8:
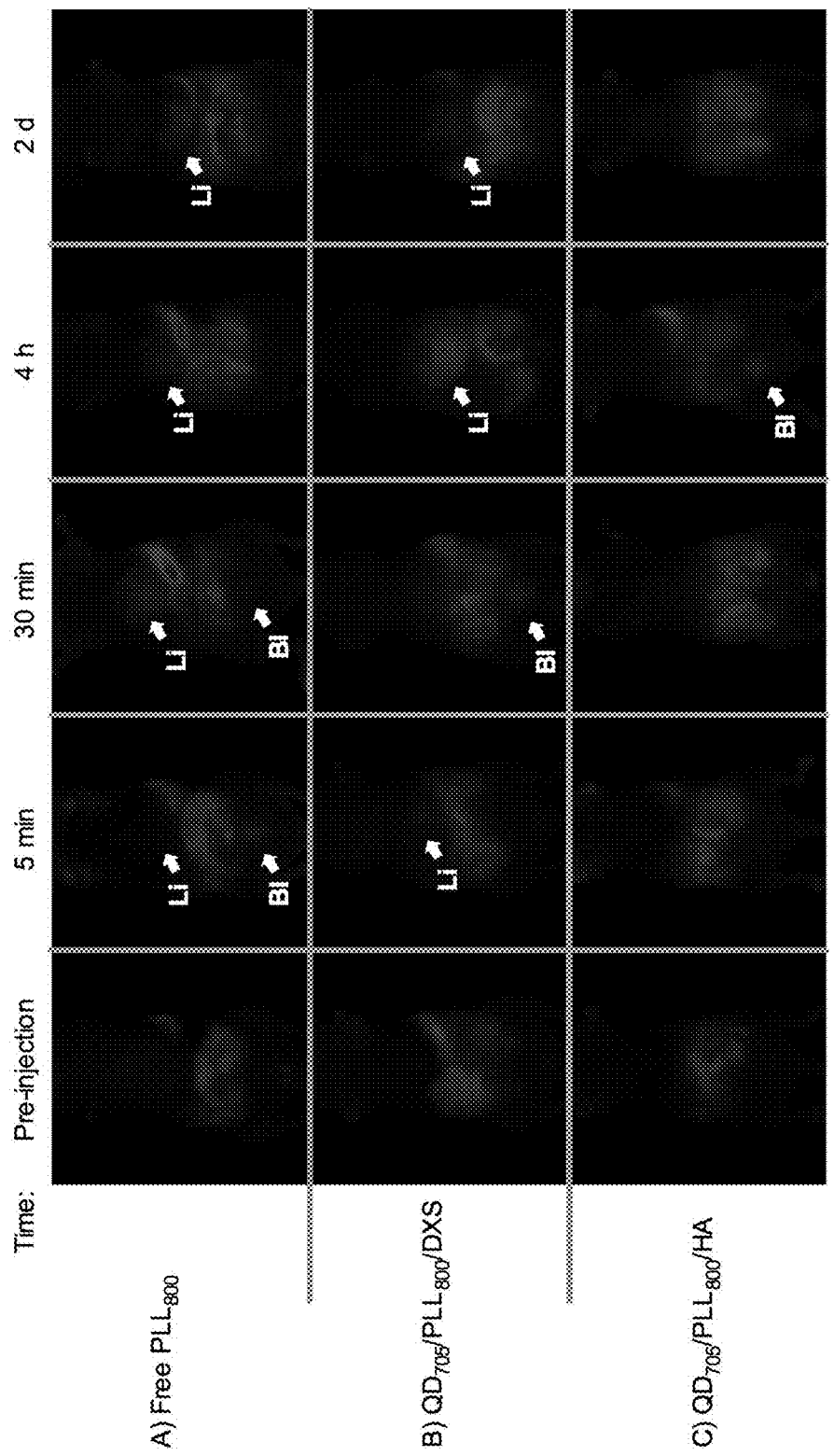
FIG. 8 Spectrally unmixed images of mice representative of the in vivo events that occur to near-IR labeled poly-L-lysine (PLL, 15 kDa) after injection. PLL$_{800}$ is injected in free form in (A) and as part of a single bilayer LbL nanoparticle in (A) and (C). Images show PLL$_{800}$ fluorescence in blue and tissue auto fluorescence in red. A PLL$_{800}$ signal detected in the bladder (Bl) indicates destabilization of LbL nanoparticles. Li=liver; Bl=bladder. Note: these mice were not maintained on the alfalfa free AIN-76A die.

If the LbL films on our model systems are unstable in vivo, they fall apart and low molecular weight polymers like $PLL_{800}$ (15 kDa) will be filtered from the blood by the kidneys, which can then be rapidly detected in the bladder (for example, see FIG. 8A); therefore, early detection of high concentrations of $PLL_{800}$ in the bladder after injection of the LbL particles is an indication of their instability in vivo. We hypothesize that a gradual decomplexation process would eventually be responsible for the breakdown of these particles, which may lead to the accumulation of $PLL_{800}$ in the bladder at much later time points. The results of an in vivo stability study are shown in FIG. 3. After single bilayer nanoparticles (n=0) terminated with either dextran sulfate ($QD_{705}/PLL_{800}/DXS$) or hyaluronic acid ($QD_{705}/PLL_{800}/HA$) were injected, a strong $PLL_{800}$ bladder signal can be seen after ~30 min and ~4 h for $QD_{705}/PLL_{800}/DXS$ and $QD_{705}/PLL_{800}/HA$ particles respectively, indicating the destabilization of the layers over these time periods. Near-IR mouse images depicting these events are given in FIG. 3A(i) and FIG. 8. Although the single bilayer films eventually destabilized, there was a significant delay in time taken to observe bladder accumulation in contrast to injections of free $PLL_{800}$, signifying that some degree of stability is afforded by incorporating $PLL_{800}$ into films. Additionally, the difference in times taken for $QD_{705}/PLL_{800}/HA$ and $QD_{705}/PLL_{800}/DXS$ particles to destabilize shows that the choice of the terminal polyelectrolyte layer is another factor that contributes to the stability of LbL films. When the number of bilayers was increased (n=3), a marked improvement in the stability of the nanofilms was observed in general. This can be clearly seen in FIG. 3A, where compared to the single bilayer films (FIG. 3A(i)), only a weak $PLL_{800}$ bladder signal was detected from a portion of the mice injected with $QD_{705}/PLL_{800}/[DXS/PLL]_3/DXS$ after 30 min and no bladder signal was found in mice injected with $QD_{705}/PLL_{800}/[DXS/PLL]_3/HA$. Changing the order of the $PLL_{800}$ layer to a position adjacent to the HA terminal layer (FIG. 3A(iv)) yielded similar results, demonstrating the structural stability of the entire HA terminated tri-bilayer film. Overall, these findings show that the number of layers, and to a degree, the terminal layer, are key variables in promoting LbL film stability. The observation that systemic stability of LbL films increases with the number of deposited layers is not surprising; electrostatically assembled LbL films are held together by ionic interactions between interpenetrated polymer layers. An increase in the number of deposited layers would increase the number of inter-layer ionic crosslinks, and would enhance the cohesion and mechanical stability of the film. This distinguishing trait of LbL systems therefore provides a convenient approach for tuning the stability of LbL assembled nano- and microparticles for applications in vivo. Similar observations have been made after assessment of LbL microcapsules in a subcutaneous environment; and this study further demonstrates that tuning film stability with increased layer deposition is also a viable approach for generating stable particles in harsher systemic environments.

Biodistribution of Nanoparticles.

Figure 3A:
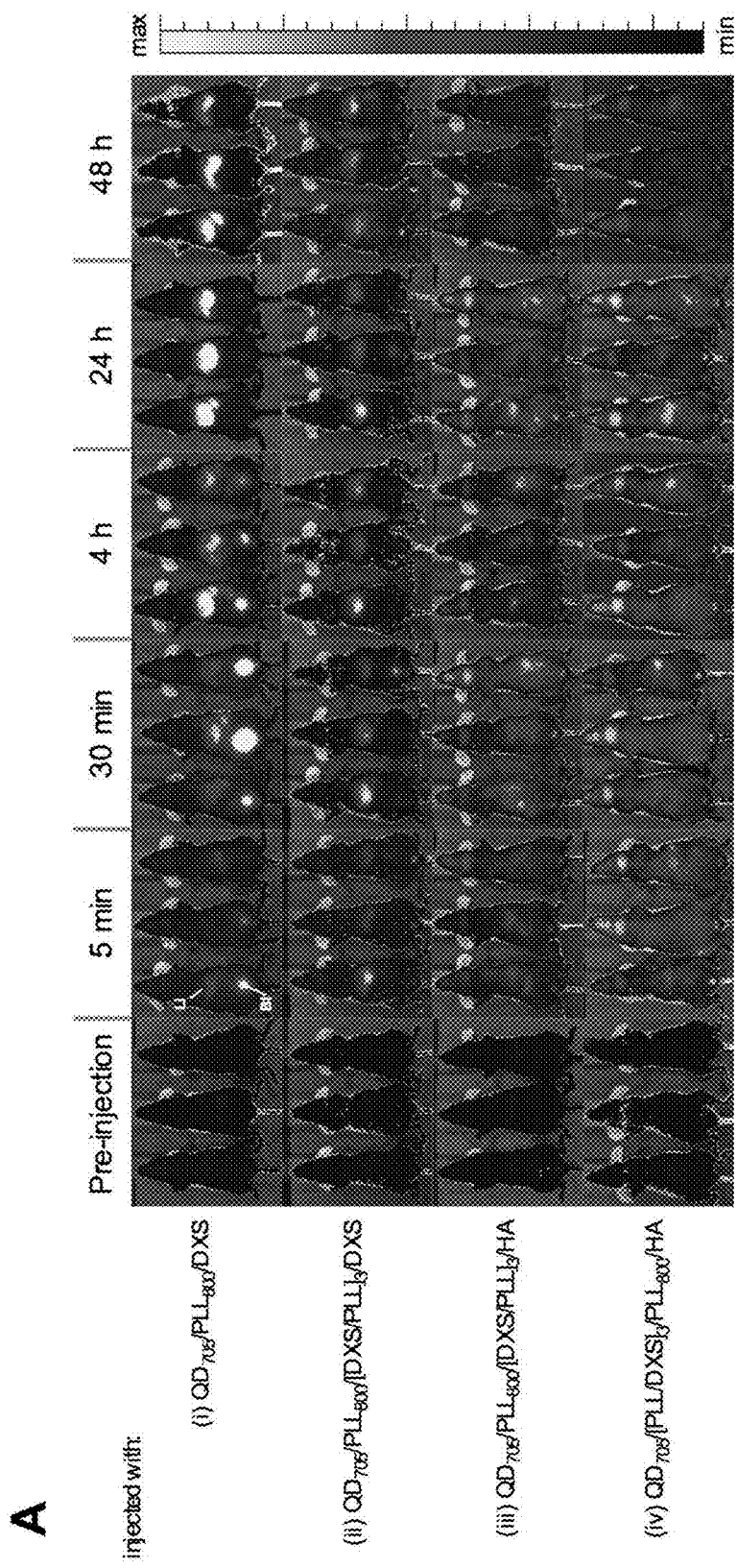
FIG. 3A shows the in vivo fate of LbL nanofilms with different architectures: (i) QD$_{705}$/PLL$_{800}$/DXS, (ii) QD$_{705}$/PLL$_{800}$/[DXS/PLL]$_3$/DXS, (iii) QD$_{705}$/PLL$_{800}$/[DXS/PLL]$_3$/HA, and (iv) QD$_{705}$/[PLL/DXS]$_3$/PLL$_{800}$/HA are examined by tracking PLL$_{800}$. Only images from the 800 nm channels are shown. Single bilayer architectures (i) are unstable and the disassembled PLL$_{800}$ localizes in the bladder and liver within 30 min. Multi-layered films grant more stability (ii, iii, iv); for these film architectures, the bladder PLL$_{800}$ signal was either weakly or not detected. Stable DXS terminated LbL nanoparticles (ii) also preferentially accumulated in the liver and the liver PLL$_{800}$ signal is due to the accumulation of the whole LbL nanoparticle, which is confirmed in FIG. 3B and shows the co-localization of both nanoparticle film (PLL$_{800}$) and core (QD$_{705}$) in the livers of mice for the stable multi-layered LbL nanoparticles.
Figure 3B:
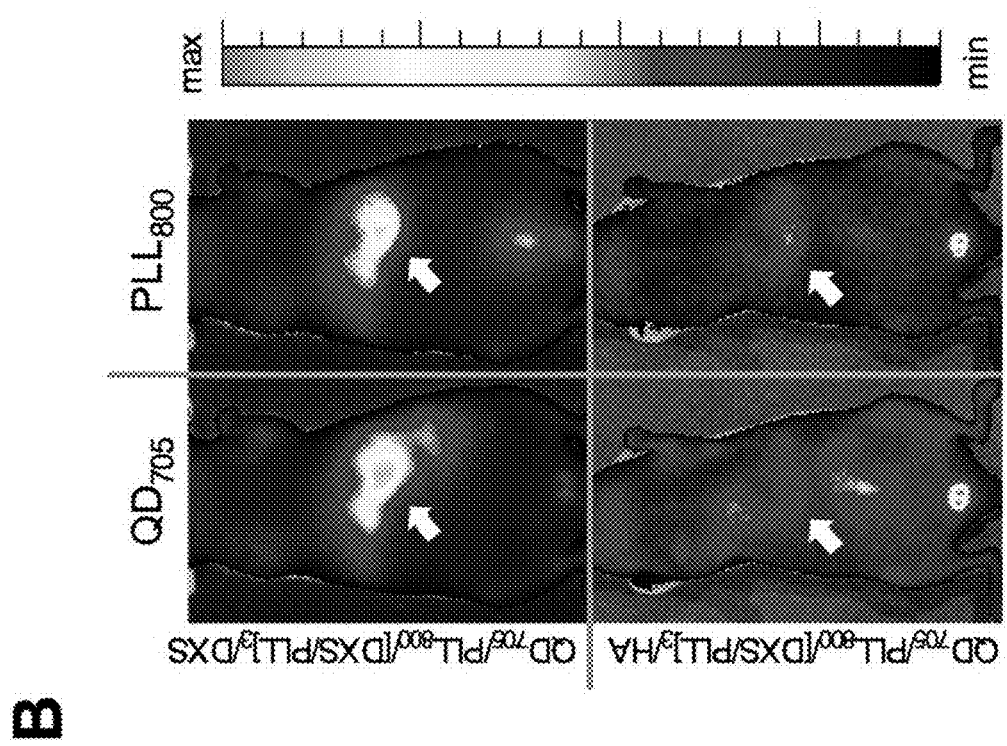
FIG. 3 Systematic examination of the pharmacokinetics and biodistribution profile of LbL nanoparticles with different film architectures. A carboxyl functionalized quantum dot (QD$_{705}$) template was used to build the LbL nanoparticles to allow tracking of both the film (using PLL$_{800}$, a near-IR labeled poly-L-lysine layer (15 kDa, ex: 800 nm)) and core (using QD$_{705}$, ex: 705 nm), which would allow more information on these systems to be obtained in vivo. FIG. S3 gives the close up images showing the anatomical positions of the liver and bladder of a mice from a ventral position to help with the analysis of these sets of data.
FIG. 3C and FIG. 3D show the biodistribution of QD$_{705}$/PLL$_{800}$/[DXS/PLL]$_3$/DXS, QD$_{705}$/PLL$_{800}$/[DXS/PLL]$_3$/HA and QD$_{705}$/PLL$_{800}$/[DXS/PLL]$_4$ particles, with QD$_{705}$ and PLL$_{800}$ controls.
Figure 3C:
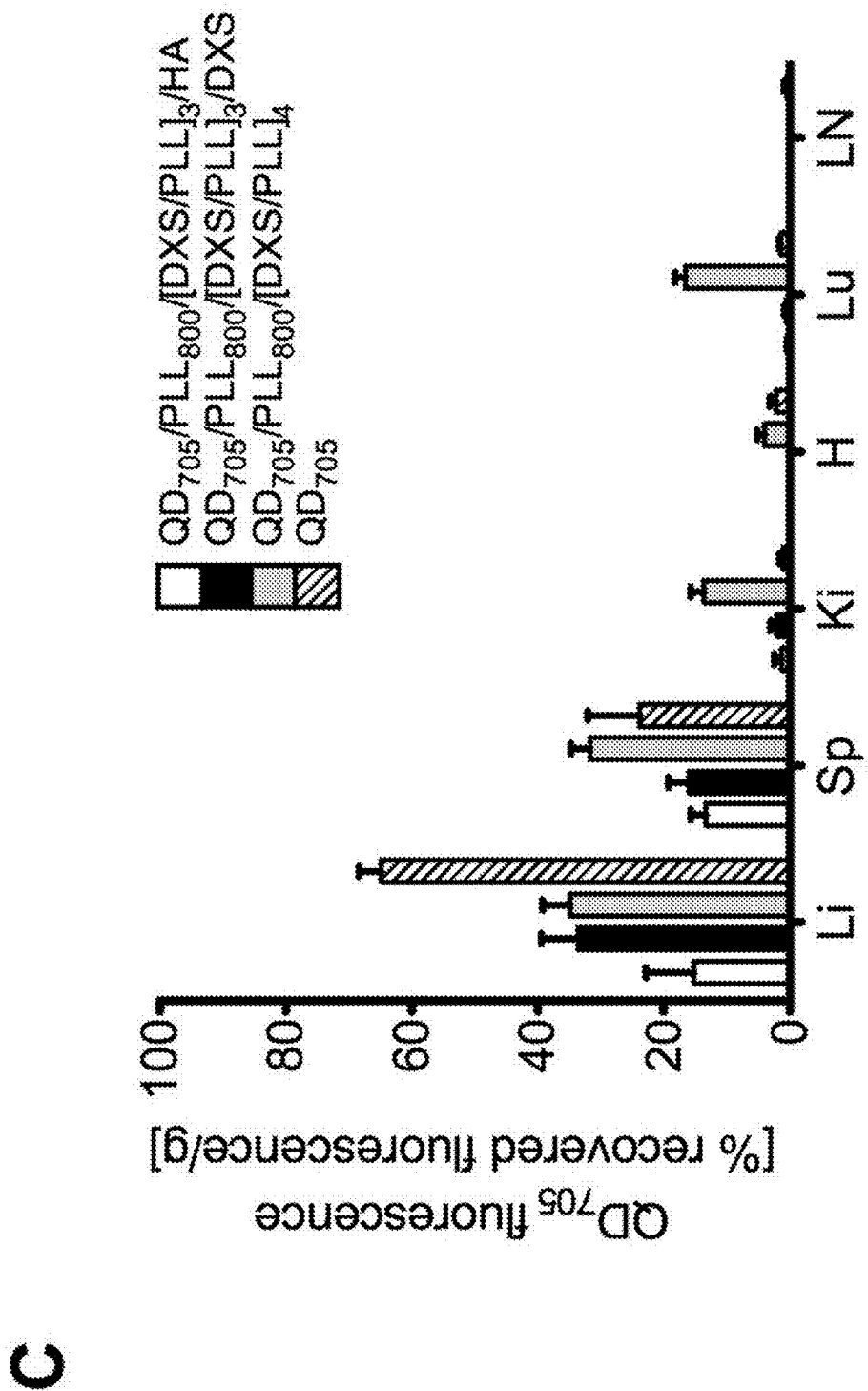
Figure 3D:
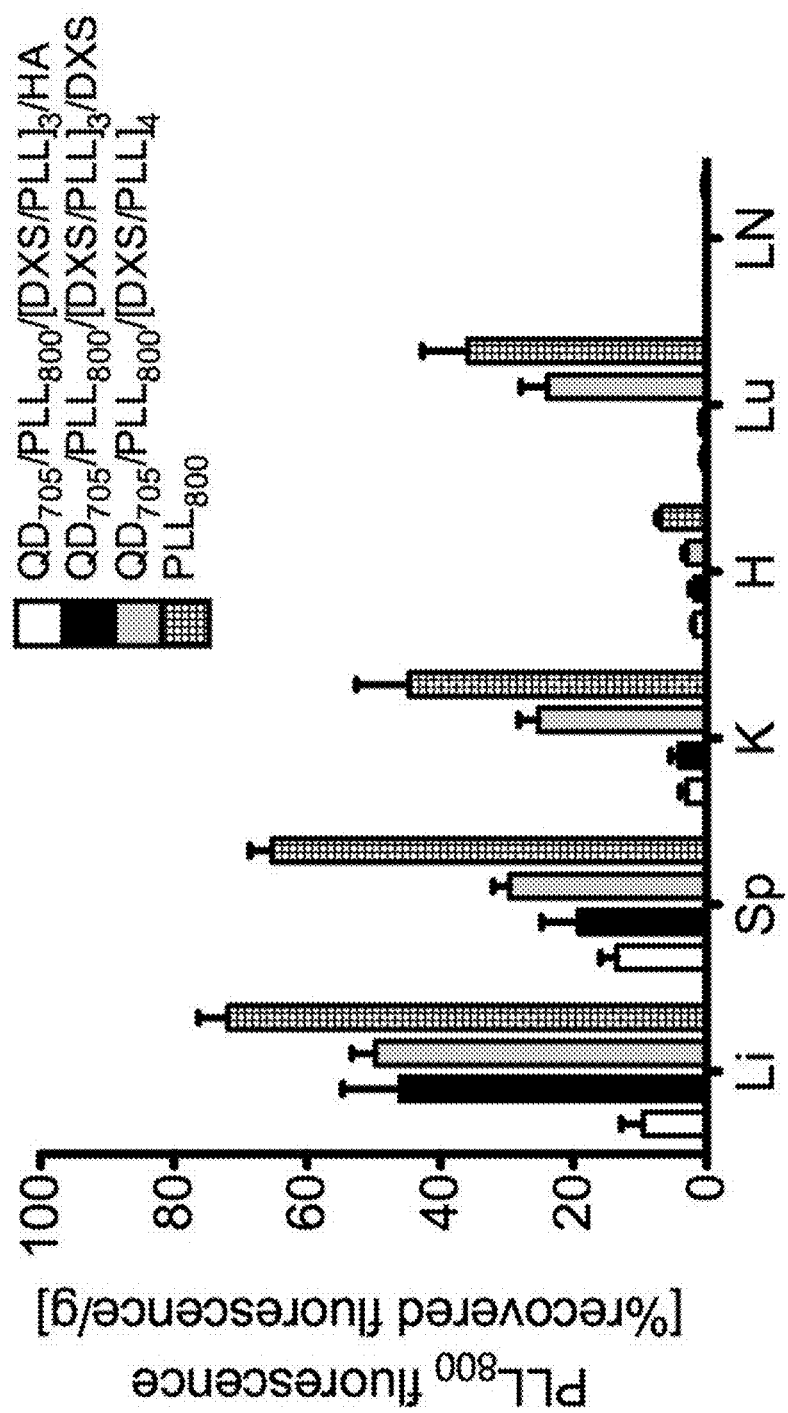
Figure 9:
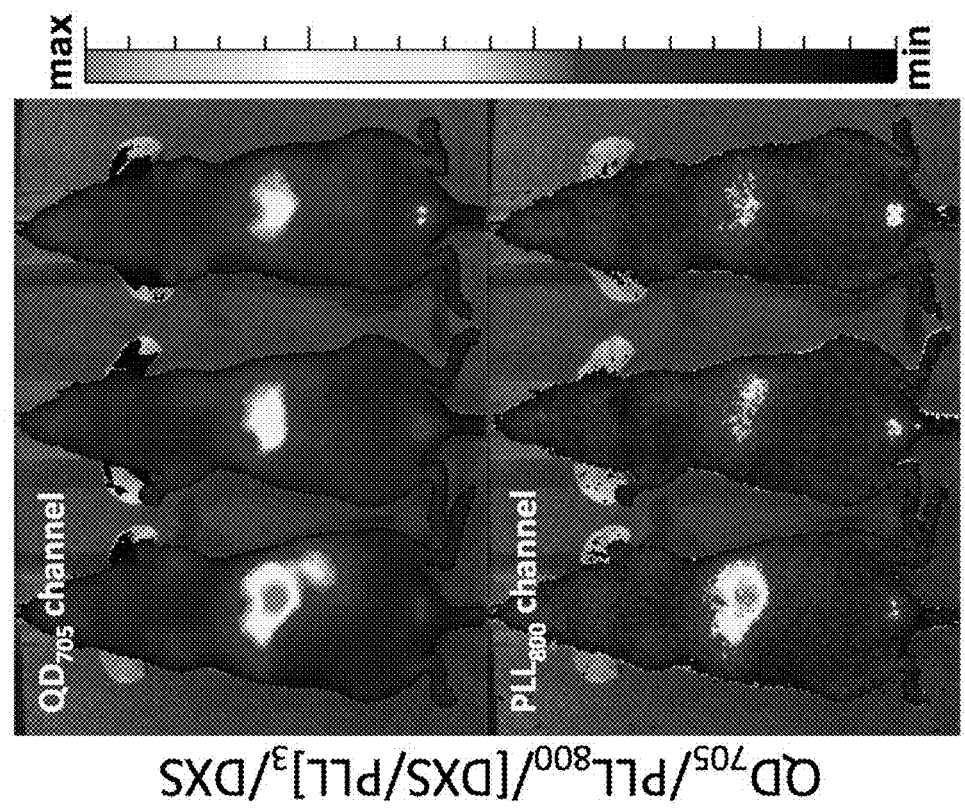
FIG. 9 Co-localization of both nanoparticle film (PLL$_{800}$) and core ($QD_{705}$) in the livers of a set of 3 mice after injection with $QD_{705}$/PLL$_{800}$/[DXS/PLL]$_3$/DXS shows stability and liver uptake of entire LbL nanoparticle.
Figure 10:
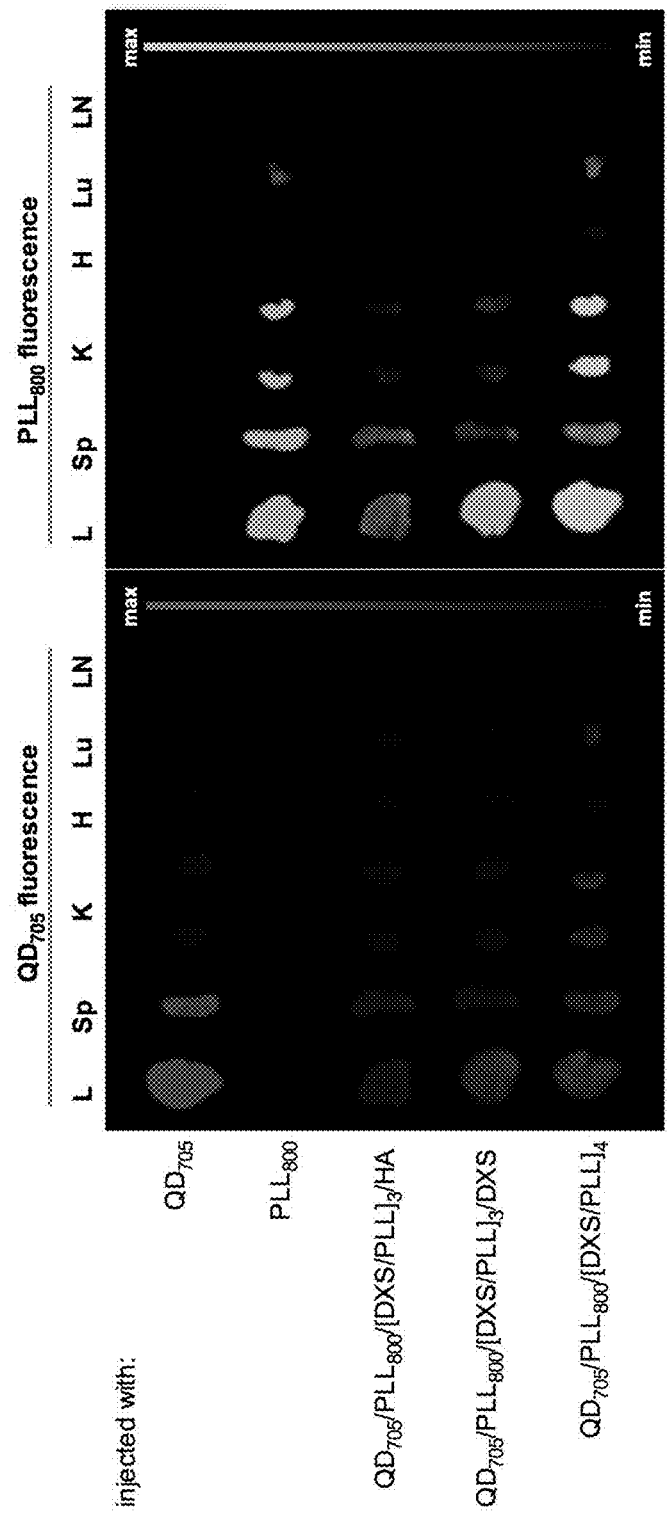
FIG. 10 Tissue harvested from mice at 4 h after different agents were administered. $QD_{705}$ and PLL$_{800}$ fluorescence were detected from the same set of tissue. This image gives a visual representation of the biodistribution of each system, tracked on both fluorescent channels. Li=Liver, Sp=spleen, Ki=kidneys, H=heart, Lu=lungs and LN=lymph node.

Based on data obtained from real time intravital imaging, a key observation made was that the terminal layer of the LbL nanoparticles played a vital role in their biodistribution. Clear differences were found in the levels of liver accumulation between the two differently terminated LbL particles. Strong $QD_{705}$ and $PLL_{800}$ signals were always detected in the livers of all mice that received $QD_{705}/PLL_{800}/[DXS/PLL]_3/DXS$ but were weak in mice injected with $QD_{705}/PLL_{800}/[DXS/PLL]_3/HA$ (FIG. 3B). The images of mice showing colocalization of $QD_{705}$ and $PLL_{800}$ signals for both particles shown in FIG. 3B and FIG. 9, together with the lack of a $PLL_{800}$ bladder signal during the experimental period (FIG. 3A(ii-iv)), confirm that these particles are truly stable and are retained by cells in the liver. To further examine the contribution of the terminal layer to particle trafficking in vivo, biodistribution studies were performed. The distribution of a single dose of injected LbL particles with different terminal layers as well as free $QD_{705}$ and $PLL_{800}$ at the 4 h time point after injection was determined with ex vivo fluorescence imaging of macerated tissue (3-5 mice per treatment) on both the $QD_{705}$ and $PLL_{800}$ channel; these fluorescence values were normalized by tissue weight and presented as the percentage injected per gram of tissue. From FIG. 3C and FIG. 3D, the similar biodistribution trends for both LbL nanoparticles determined on the two fluorescent channels reaffirm the stability of these systems. Both $QD_{705}/PLL_{800}/[DXS/PLL]_3/DXS$ and $QD_{705}/PLL_{800}/[DXS/PLL]_3/HA$ particles were mainly found in the liver (~35-45% rf/g and ~10-15% rf/g respectively) and spleen (~15-20% rf/g and ~15% rf/g respectively); the weak signals detected in the kidneys, heart and lungs are attributed to nanoparticles in blood that remained in these organs after their extraction. The increased liver accumulation of $QD_{705}/PLL_{800}/[DXS/PLL]_3/DXS$ particles over $QD_{705}/PLL_{800}/[DXS/PLL]_3/HA$ particles is consistent with our observations using near IR intravital imaging. As expected, the biodistribution of free $QD_{705}$, $PLL_{800}$ and PLL terminated $QD_{705}/PLL_{800}/[DXS/PLL]_4$ were markedly different from the negatively charged HA and DXS terminated LbL nanoparticles. Importantly, significant levels of $PLL_{800}$ and $QD_{705}/PLL_{800}/[DXS/PLL]_4$ were detected in the kidneys and lungs; and in general, higher biodistribution levels were noted in both the liver and spleen. As any circulating low molecular weight polymer is expected to be cleared rapidly by renal filtration, the retention of positively charged $PLL_{800}$ in the kidneys and lungs is likely due to its non-specific interactions with cells in these highly vascularized organs. Positively charged $QD_{705}/PLL_{800}/[DXS/PLL]_4$ particles, which have a layer of exposed PLL on the surface also interact directly with cells in the same manner as $PLL_{800}$, causing their uptake and accumulation in these organs. Positively charged species in vivo also readily adsorb to opsonins, leading to pronounced RES uptake in the liver and spleen. A single terminal layer of antifouling polysaccharide prevented cellular and protein interaction with the nanoparticles, and the biodistribution pattern changes to favor only the liver and spleen. The presence of this terminal layer actively reduces RES involvement, as evidenced by the significantly higher levels of free $QD_{705}$, in the liver and spleen. Representative fluorescent images of whole tissue showing the distribution of $QD_{705}$ and $PLL_{800}$ are provided in FIG. 10 to help understand the different biodistribution patterns more visually.

We have achieved, via optimizing the architecture of LbL nanofilms, stable nanoparticles with biodistribution profiles comparable to the most promising block copolymer delivery systems; and this is particularly evident in their low degrees of uptake (~10-15% rf/g) by the liver and spleen, which are among the lowest numbers observed for any nanoparticle delivery system. Due to the presence of scavenging cells, the liver typically accounts for a significant portion of the biodistribution of systemically administered nanoparticles. For applications that aim to target tumors, the undesirable level of nanoparticle accumulation in the liver and spleen, which can be as high as ~40% rf/g, can result in reduced delivery to tumors. Further modulation of liver accumulation of LbL particles, achieved via the selection of the appropriate terminal layer, would likely improve EPR-based targeting to solid tumors as well as reduce the potential toxicity to the liver and other important organs. Knowledge gained from this study would not only facilitate future development of LbL particle systems, but should also be relevant to other electrostatically assembled nucleic acid delivery systems, which are formed from complexing nucleic acids and polyelectrolytes that mediate transfection (PEI). As the underlying mechanisms influencing complex formation and transfection efficacy are similar to LbL, the same rules may apply toward improved stability and biodistribution of the complexes in vivo.

Passive Tumor Targeting of Long Circulating LbL Nanoparticles.

Figure 4:
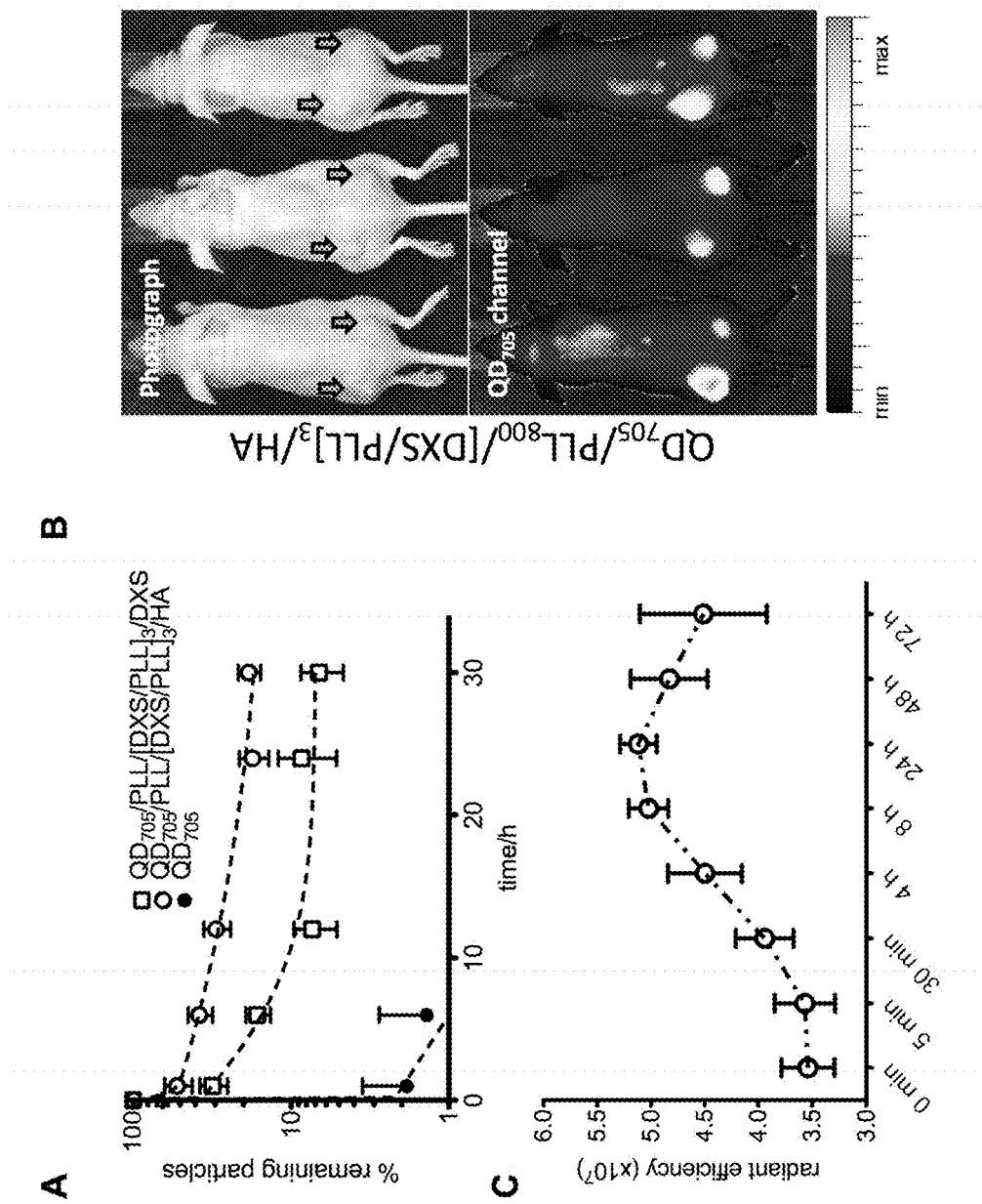
FIG. 4 Blood circulation and tumor targeting of optimized LbL nanoparticles. A) Blood circulation profiles of QD$_{705}$, QD$_{705}$/PLL/[DXS/PLL]$_3$/HA and QD$_{705}$/PLL/[DXS/PLL]$_3$/DXS. The longer persistence of QD$_{705}$/PLL/[DXS/PLL]$_3$/HA in the blood stream corroborates their superior stability and biodistribution profile. B) Enhanced permeation and retention (EPR) based targeting of solid KB tumors induced subcutaneously on both hind flanks using QD$_{705}$/PLL/[DXS/PLL]$_3$/HA. Image is taken at the 24 h time point. C) Time dependant accumulation of QD$_{705}$/PLL/[DXS/PLL]$_3$/HA in KB tumors. Accumulation of the nanoparticles in tumors is transient and typical of EPR dominated targeting. Data is given in mean±SEM, n=6.

To assess the use of optimized LbL nanoparticles for cancer delivery, we tested their ability to target solid tumors via EPR. The stability and biodistribution profile of multi-layered, HA terminated films in vivo indicate that they might be able to extend the circulation times of LbL nanoparticles to levels sufficient for passive targeting to solid tumors via EPR. Three particles were tested for their blood circulation profile: 1) free $QD_{705}$, 2) $QD_{705}/PLL/[DXS/PLL]_3/DXS$ particles and 3) $(QD_{705}/PLL/[DXS/PLL]_3/HA)$ particles. After systemic intravenous injection in mice (via tail vein), the blood concentrations of the nanoparticles decreased in a two-phase manner (FIG. 4A). All particles were observed to undergo a rapid distribution phase within 1 h of injection. After 10 h, $QD_{705}$ were no longer detected in the blood, while blood concentrations of $QD_{705}/PLL/[DXS/PLL]_3/DXS$ and $QD_{705}/PLL/[DXS/PLL]_3/HA$ particles dropped to ~7% and ~29% respectively. Using a two compartment model, we estimate that the distribution and elimination half-lives for $QD_{705}/PLL/[DXS/PLL]_3/DXS$ particles are 0.16 h and 3.2 h respectively, while the half-lives for $QD_{705}/PLL/[DXS/PLL]_3/HA$ particles are 0.21 h and 8.4 h respectively. The longer persistence of $QD_{705}/PLL/[DXS/PLL]_3/HA$ in the blood stream corroborates their superior stability and biodistribution profile. The whole body fluorescence intensity of mice given $QD_{705}/PLL/[DXS/PLL]_3/HA$ particles (FIG. 3A) were also observed to be higher when compared to other systems for up to 24 h. We next monitored the accumulation of the $QD_{705}/PLL/[DXS/PLL]_3/HA$ particles in subcutaneously induced KB tumors with intravital fluorescence imaging over a period of 72 h. At 24 h post injection, $QD_{705}/PLL/[DXS/PLL]_3/HA$ particles were detectable in tumors (FIG. 4B) and the time dependent nanoparticle signal from the tumors is given in FIG. 4C. KB tumors are not know to express significant levels of CD44, the receptor for hyaluronic acid and therefore, the nanoparticle accumulation and clearance profile in the tumor is typical of EPR based targeting, which is short-lived as there are no active mechanisms in place to promote cell uptake or extend their residence time in the tumor interstitials.

Examining Reasons for the Different Biodistribution of HA and DXS Terminated LbL Nanoparticles.

Figure 5A:
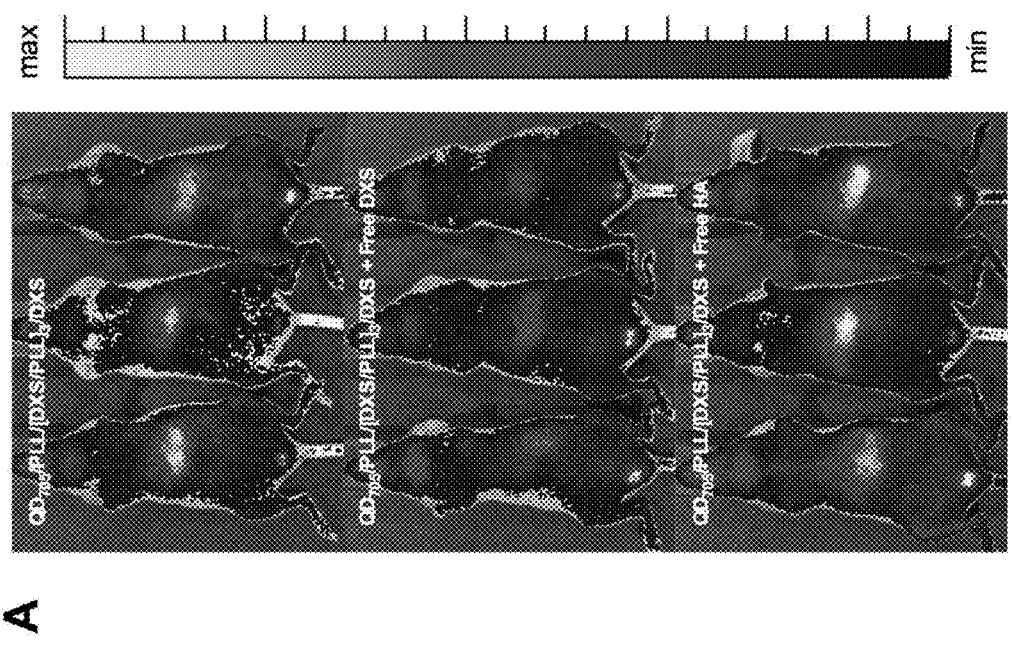
FIG. 5A shows images of mice receiving $QD_{705}$/PLL/[DXS/PLL]$_3$/DXS with co-injections of free DXS and HA (10 mg/kg) taken at the 4 h time point. Accumulation of $QD_{705}$/PLL$_{800}$/[DXS/PLL]$_3$/DXS particles in the liver is reduced with free DXS competition, suggesting a receptor mediated mechanism for the uptake of DXS terminated particles by the liver.
Figure 11:
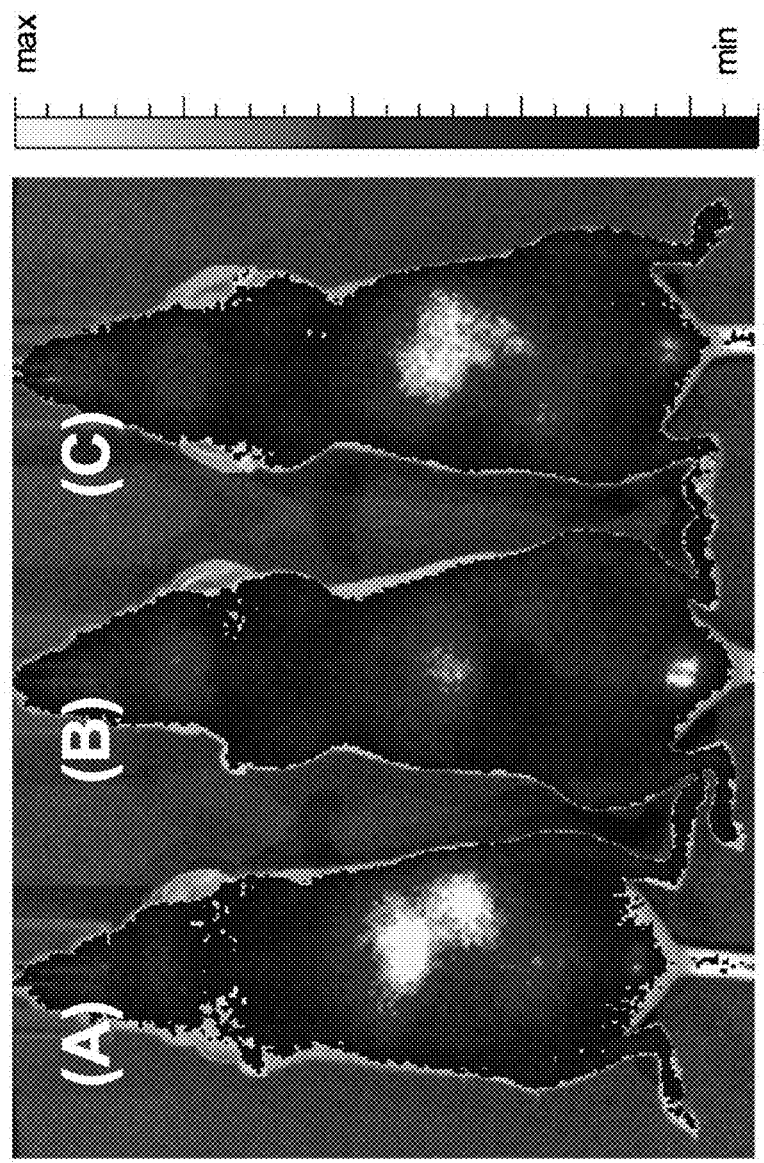
FIG. 11 Competition of liver uptake of $QD_{705}$/PLL/[DXS/PLL]$_3$/DXS (A) with free DXS and HA (10 mg/kg each). B=(A)+DXS, C=(A)+HA. A representative mouse from each treatment is imaged on a single viewing field.
Figure 12:
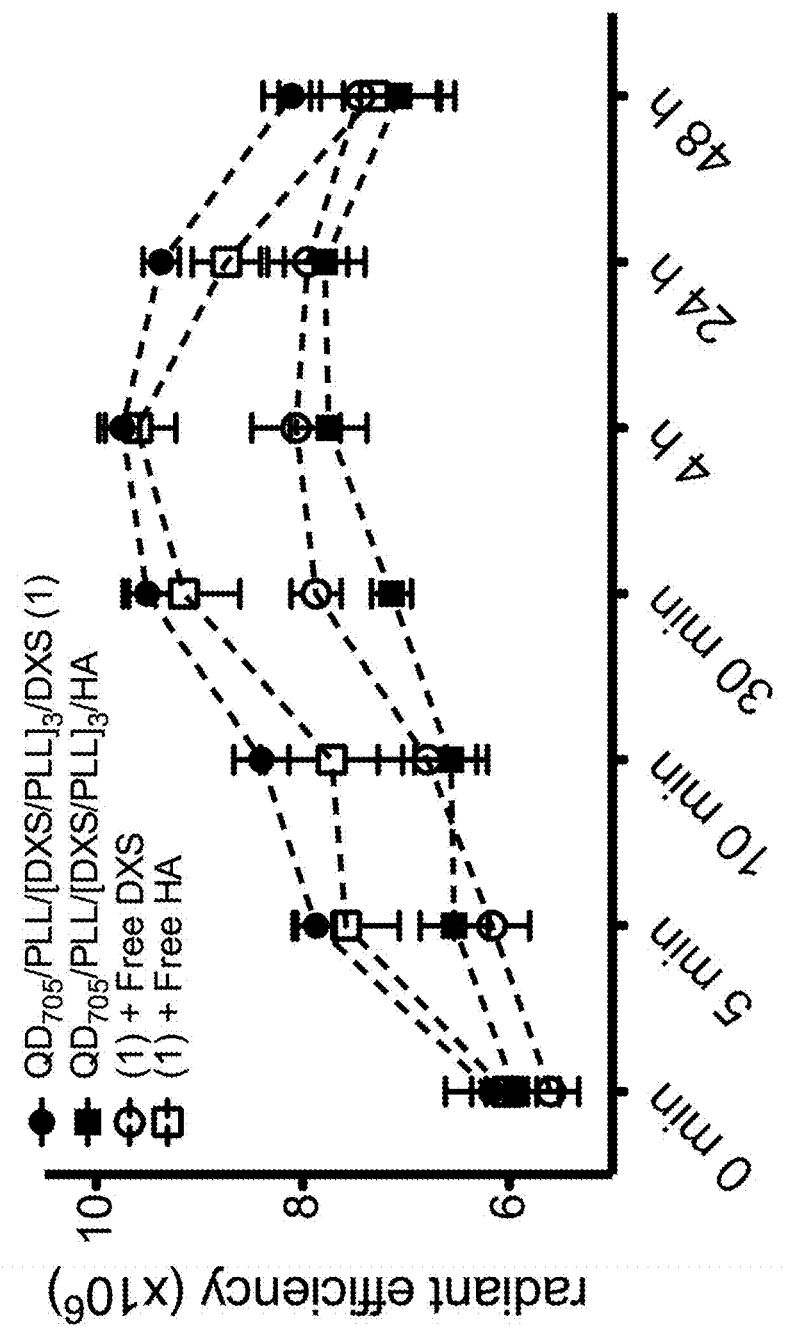
FIG. 12 The time dependant accumulation of HA and DXS terminated particles in the liver, with co-injections of free DXS and HA (10 mg/kg). Data is given in mean±SEM, n=3.

In an attempt to understand the different liver retention of HA and DXS terminated particles, we examined the involvement of liver receptors in taking up the differently coated LbL nanoparticles, as well as the degree of particle phagocytosis by macrophages to account for RES involvement. The liver sinusoidal endothelial cells (LSEC) present a variety of different receptors that scavenge blood for soluble macromolecules. Biological polysaccharides like HA bind to some of these receptors, but this can be inhibited by sulfated polysaccharides like DXS and chondroitin sulfate (CS), which show greater specificity to these liver receptors. Our observations that DXS terminated LbL nanoparticles accumulate in the liver more significantly than those that are HA terminated suggest that this receptor-mediated mechanism is also relevant when HA or DXS is used as the terminal layer on LbL nanoparticles. To investigate this, $QD_{705}/PLL/[DXS/PLL]_3/DXS$ particle injections were competed with co-injections of free (~10 kDa) DXS and HA (10 mg/kg each). FIG. 5A shows the degree of liver accumulation of $QD_{705}/PLL_{800}/[DXS/PLL]_3/DXS$ with and without free DXS or HA competition in the liver 4 h after injection. An image of a representative mouse for each treatment taken in a single viewing field is shown in FIG. 11 and plots of the time dependent accumulation of particles in the liver are given in FIG. 12. When free dextran sulfate was co-injected with $QD_{705}/PLL/[DXS/PLL]_3/DXS$, the levels of its liver accumulation were significantly lower. This effect was not observed with co-injections of HA at the same dose. These observations suggest that the stronger liver accumulation of dextran sulfate terminated LbL particles could be due to uptake mechanisms in the liver that are specific to dextran sulfate. In addition to their different surface chemistry, recent studies also suggest that the stronger negative surface charge of DXS terminated systems could have contributed to their higher liver accumulation.

Figure 5B:
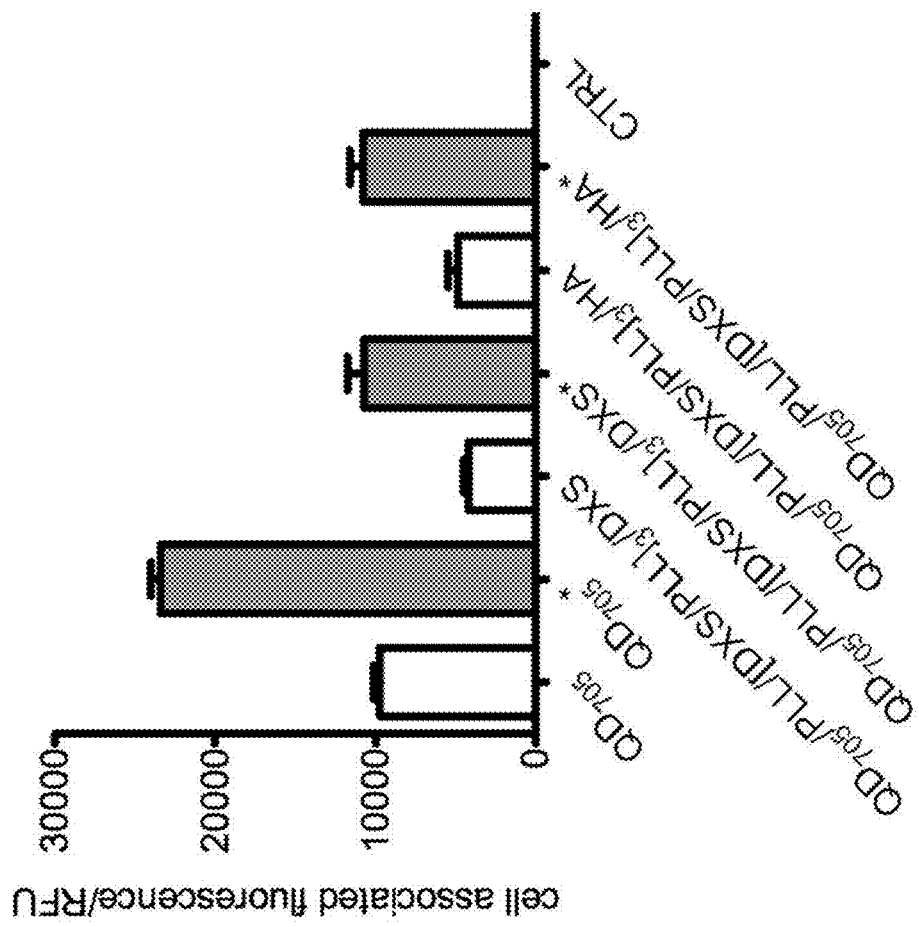
FIG. 5B shows phagocytosis of nanoparticles determined by flow cytometry analysis of mouse macrophage J774A.1 cells after incubation with different nanoparticles. Opsonized nanoparticles are indicated with (*). Opsonized LbL nanoparticles terminated with HA or DXS show reduced uptake compared to opsonized $QD_{705}$ but phagocytosis of both opsonized and non-opsonized LbL nanoparticles did not exhibit a strong dependence on their terminal layer. Data is given in mean±SEM for n=5 with >5000 events each. Representative raw flow cytometry histograms and confocal images showing phagocytosis are given in FIGS. 13B and 13C.
Figure 13A:
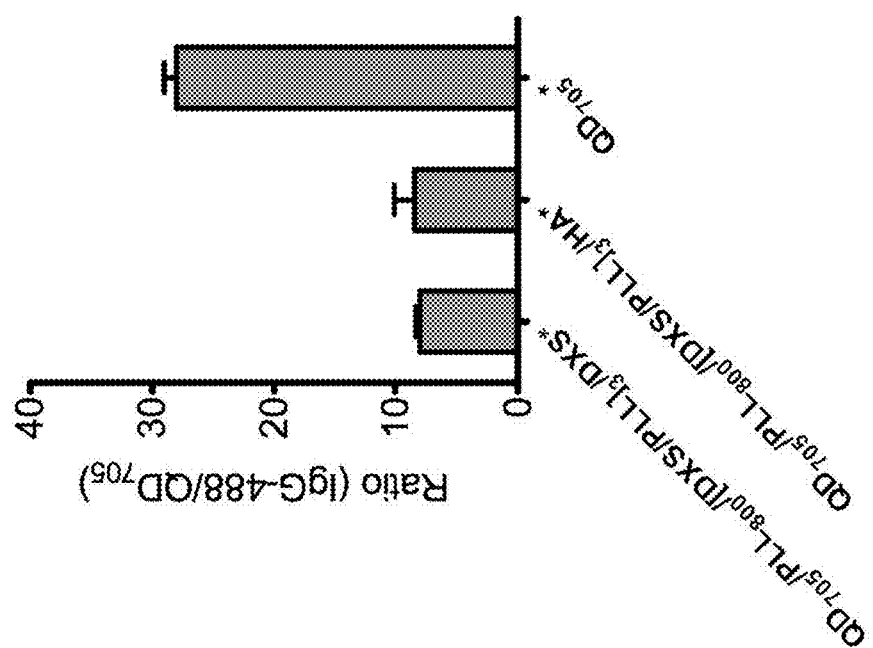
FIG. 13A shows the degree of opsonization with IgG-AF488 measured by taking the ratio of AF488/$QD_{705}$. Free $QD_{705}$ bound to more IgG without an antifouling terminal layer while there were no differences in the degree of opsonization of HA and DXS terminated films.
Figure 13B:
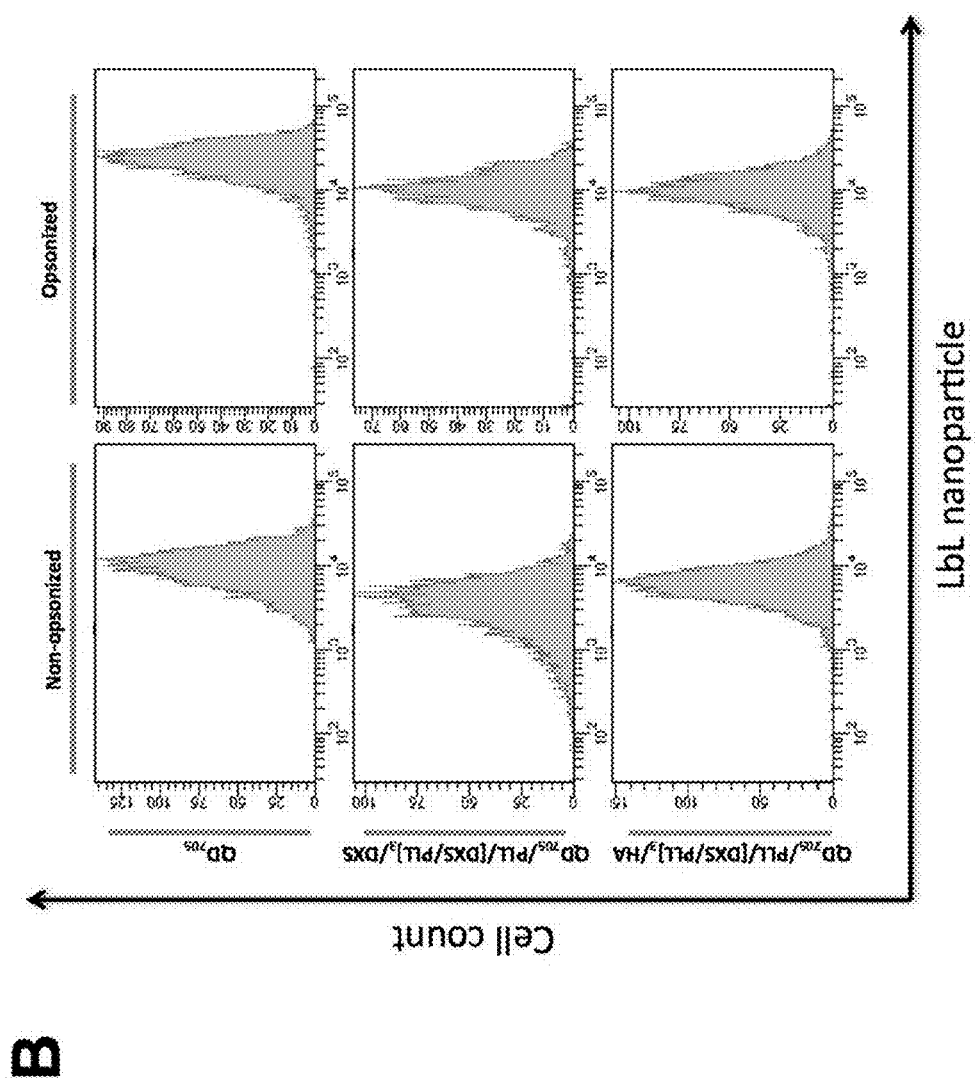
FIG. 13B depicts raw histograms showing the cell associated fluorescence after treatment of each of each condition in FIG. 4C.
Figure 13C:
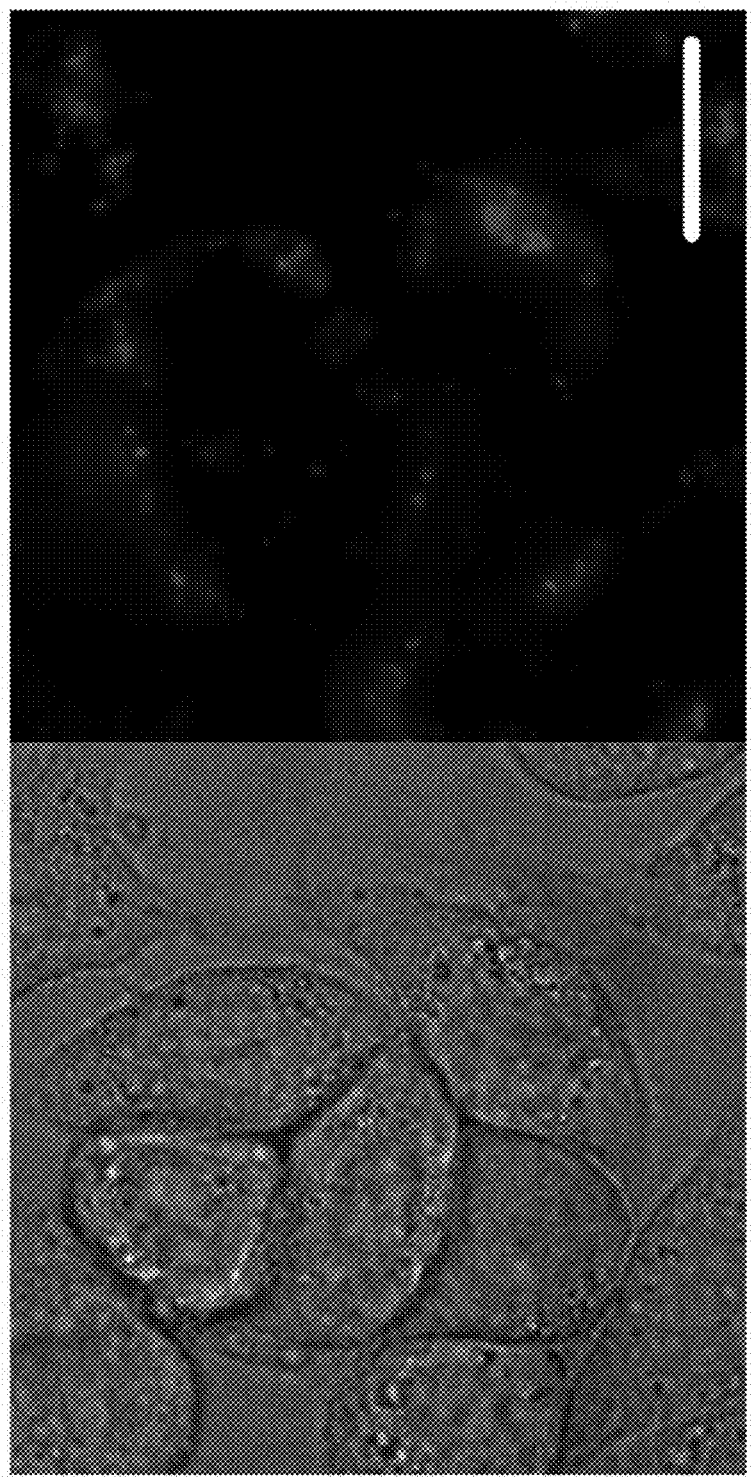
FIG. 13C is of a representative confocal image showing the uptake of LbL nanoparticles after opsonization into mouse macrophage J774A.1 cells. Scale bar=10 μm.
Figure 13D:
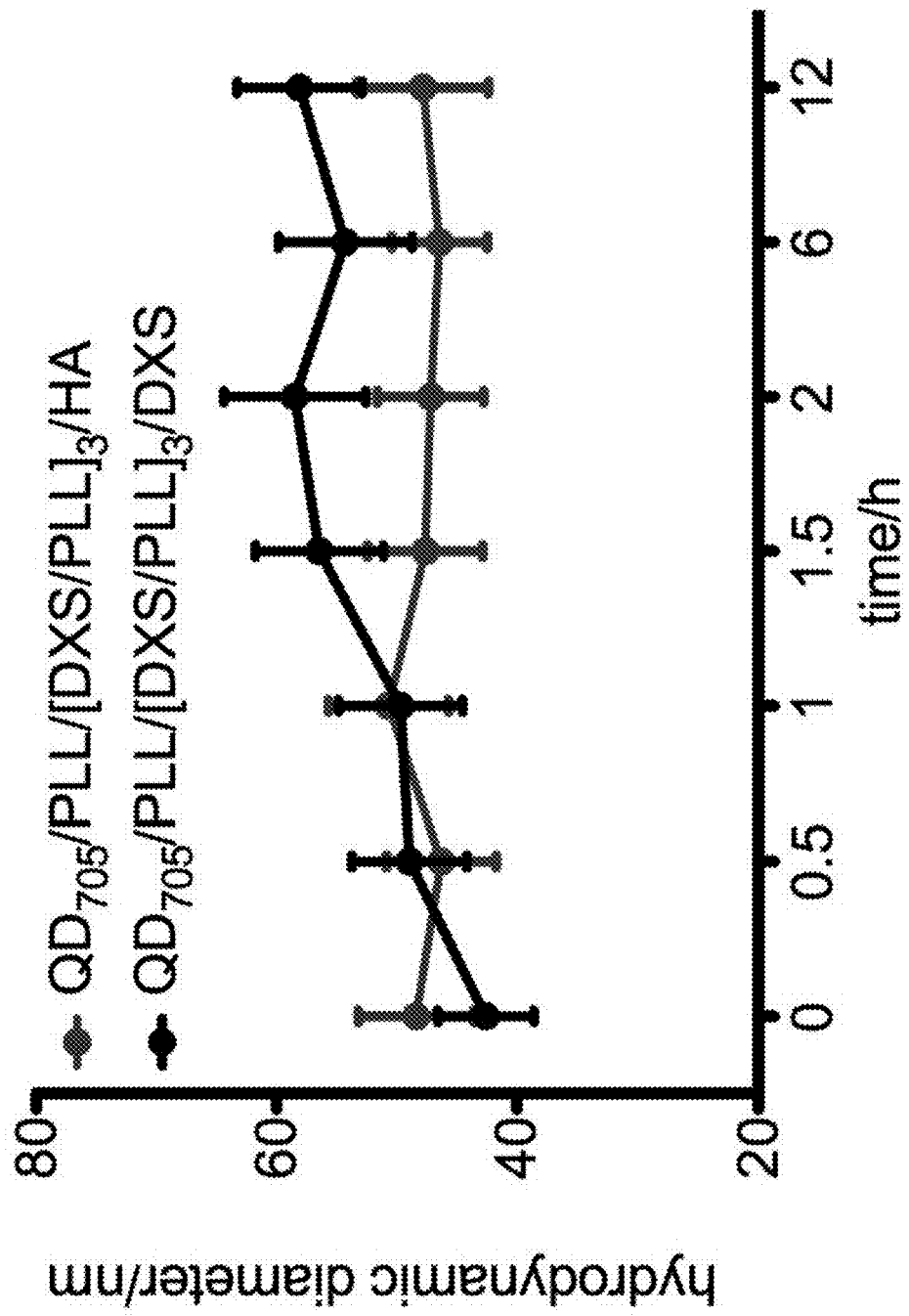
FIG. 13D shows a time dependent increase of the hydrodynamic diameter of LbL nanoparticles in a solution of 20 mg/ml bovine serum albumin in PBS.

Phagocytosis of both opsonized and non-opsonized LbL nanoparticles was examined in vitro using mouse macrophages to give insight into the role that the RES (kupffer cells) plays in influencing LbL nanoparticle accumulation in the liver. We found that these processes did not exhibit a strong dependence on HA or DXS terminated nanoparticles (FIG. 5B). Compared to free $QD_{705}$, LbL nanoparticles terminated with either HA or DXS bound to IgG, a major class of opsonins, to a lesser extent than free $QD_{705}$, owing to the formation of an anti-fouling layer around the nanoparticle (FIG. 13A, FIG. 13B and FIG. 13C); this subsequently led to lower levels of phagocytosis when compared to opsonized $QD_{705}$. As no significant differences were found for both the opsonization and the phagocytosis of HA and DXS terminated LbL nanoparticles, RES uptake does not appear to play an important role in the different liver accumulations for these two negatively charged exterior layered systems. The biodistribution data in FIG. 3C and FIG. 3D support this conclusion, as only liver uptake of the LbL nanoparticles were notably different, even though splenic cells are known to constitute part of the RES system. Finally, an in vitro examination of the aggregation behavior of these particles was also performed to help account for their biodistribution. Although DXS terminated particles exhibited a slight degree of aggregation over a 12 h period (FIG. 13D), we do not expect this behavior to have affected its biodistribution in vivo, in light of our observation that free DXS competes with DXS terminated nanoparticles in the liver and the lack of their accumulation in the lungs (FIG. 3C and FIG. 3D), where the capillary beds are a typical accumulation point for large aggregates. Looking forward, work examining the influence of the terminal polyelectrolyte layer on tissue or cell receptor interactions is crucial to these systems and is on going in our laboratory.

We have elucidated the important nature of the LbL film composition and its effects on the pharmacokinetics of LbL-based nanoparticle systems. Our findings highlight unique aspects of this stable nanoparticle system: the electrostatically assembled nanoparticles gain increased stability in vivo with increased numbers of adsorbed film layers, and the final layer deposited is an important surface layer, which dictates the surface and biological properties of the nanoparticle, and is therefore an important variable to control to affect the biodistribution of the LbL nanoparticle. In addition, LbL-based nanoparticles can entrap a diverse range of therapeutics and allow further control over dosage and regimen from a single nanoscopic platform for drug delivery.

Example 2: Nanoparticles with a pH-Sheddable Layer for Targeting of Tumor Hypoxia An exemplary trilayer architecture was constructed layer-by-layer on model nanoparticle core, quantum dots (QD). An LbL film coats the core, which film comprises at least three layers, wherein the first layer is a positively-charged polyelectrolyte comprising a first adjacent layer interacting moiety; a second layer comprising a second adjacent layer; and an outer layer. In this Example, an LbL film used a first layer of PLL modified with iminobiotin, followed by a second layer of the linker protein, neutravidin, and the outer layer of biotin end-functionalized PEG.

This example illustrates an approach for systemic tumor targeting using LbL-coated nanoparticles. We demonstrate that the electrostatic assembly nature of LbL allows the use of charge to aid or inhibit their cellular uptake and extend this idea to enable tumor targeting in vivo by incorporating a pH responsive layer that exposes the underlying charged surface when localized in an acidic tumor microenvironment. As EPR based targeting is transient, strategies to extend the persistence of accumulated particles can greatly impact nanoparticle therapy. The stronger persistence of QD/PLLib/PEG particles in two different tumor models highlights an important advantage of this system: as hypoxia is ubiquitous in tumors, this form of targeting with LbL nanoparticles can be employed to broadly target all cancers, even those that do not express distinctive surface markers.

Materials and Reagents

Materials.

All chemicals and biological material were purchased from Sigma-Aldrich or Invitrogen unless otherwise noted.

Mice.

Female Nu/Nu mice (4-6 weeks old) were from Taconic. All in vivo experimentation was carried out under the supervision of the Division of Comparative Medicine (DCM), Massachusetts Institute of Technology, and in compliance with the Principles of Laboratory Animal Care of the National Institutes of Health. Cell lines were purchased from ATCC and were tested routinely for pathogens before use in animals via DCM.

Fabrication of Layer-by-Layer (LbL) Nanoparticles.

LbL nanoparticles with functional shells were prepared using a commonly used assembly technique for LbL on nanoparticles. The negatively charged fluorescent cores used were either sulfonated polystyrene beads (LB) ($\sim 5 \times 10^{13}$ particles/mL; ex/em: 575 nm/610 nm; ~130 nm; −35 mV; Sigma-Aldrich) or carboxylated quantum dots (QD) (8 µM; em: 705 nm; ~20 nm; −25 mV; Invitrogen). Pol-L-lysine was functionalized to NHS-activated iminobiotin (Thermo Scientific) or NHS-activated biotin (Sigma Aldrich) on ~20% of the primary amine side groups (based on reaction feed ratio) under aqueous conditions and at a pH of 8.0. After reacting for 2 h at room temperature, the functionalized peptides were then dialyzed in a 5 kDa dialysis bag before use. For LbL assembly, nanoparticles were mixed with a saturating amount of layering material with continuous agitation. Mixing was carried out for 2 h, followed by particle purification with three centrifugation (30000 rcf; 2 h) and resuspension (millipore water, pH 7.4) cycles. Layering conditions are as follows: for aqueous polymer solutions (poly-L-lysine (15 kDa), dextran sulfate (15 kDa); Sigma Aldrich), a final concentration of ~500 µM for 2 h; for neutravidin (Thermo Scientific), a saturating ratio of 1 mg neutravidin to 0.05 moles nanoparticle for 2 h; for mPEG-biotin (20 kDa; Laysan Bio), 100 mg mPEG-biotin in aqueous conditions for 2 h. A pH of 7.4 was used in all cases but for situations involving iminobiotin, a pH of 8.0 was used instead. No salt was added in the process.

Characterization of Particles.

All size and zeta potential measurements were made using a Zeta PALS (Brookhaven) and scanning electron microscopy was performed on particles spin-cast on silicon. Particle concentrations were estimated using standard calibration graphs made from unmodified particles. These graphs were linear in the range of concentrations used for all experiments. For in vitro experiments, the concentration of particles used was fixed for any one set of experiments and ranged from 1E+8 to 1E+10 particles/mL. For in vivo experiments, the concentration of particles used was ~0.1 µM given in 0.1 mL injections.

Examination of Neutravidin-Iminobiotin Bond.

The pH dependence of this bond was investigated by conjugating iminobiotin to high molecular weight polyethyleneimine (500 kDa) via NHS chemistry followed by suspending the polyethyleneimide and avidin-FITC (Sigma Aldrich) complex inside a 100 kDa float-a-lyzer (Spectrum Laboratories) in buffer sinks at different pH conditions. The content of the float-a-lyzer was tested regularly for FITC fluorescence with a spectrofluorometer.

In Vitro Experimentation.

HeLa, MDA-MB-435, KB and A549 cells were cultured with Alpha MEM (Invitrogen) supplemented with heat inactivated bovine serum (10%; Invitrogen) and penicillin/streptomycin (1%). For flow cytometry measurements, cells were plated on 96 well plates at 70% confluence a day before use. Treated cells were trypsinized, washed and resuspended in PBS before analysis. Transferrin-FITC, wortmannin and heparinase III (Sigma-Aldrich) were used at concentrations of 100 nM, 200 nM and 0.1 U/mL. All measurements were made with 10000 events and at least in triplicate. For confocal microscopy analysis, cells were washed, fixed in 10% formalin and permeabilized with 70% ethanol before staining. For analysis of hypoxia, HIF-1α and the appropriate FITC-labeled secondary antibody (Santa Cruz Biotechnology) were used. Images were captured using an Applied Precision DeltaVision confocal. A Cy5 filter was used to detect quantum dot (em: 705 nm) fluorescence.

In Vivo Experimentation.

Subcutaneous tumors were induced in either the left or right hind flank after injection of ~1-2 million cells (MDA-MB-435 or KB, n=3 each) in 0.1 mL media. Tumors were allowed to grow to ~100 mm³ before experimentation. The concentration of particles administered was ~0.1 µM given in 0.1 mL injections via the tail vein. All nanoparticle solutions were filtered with a 0.2 µm filter before injection. LbL nanoparticle accumulation in vivo was tracked and quantified using intravital imaging (Caliper LifeSciences). The images showing $QD_{705}$ fluorescence was captured using Ex: 640 nm and Em: 720 nm. Spectrally unmixed images were captured using a sequence of Ex: 640 nm and Em: 700 nm/720 nm/740 nm/760 nm for $QD_{705}$. For histology, tumors were frozen in OCT (−80° C.) and cut into 5 µm sections for analysis. Blood circulation analysis was performed by measuring the remaining QD signal from blood taken after injection (tail vein) with a spectrofluorometer.

Statistical Analysis.

All data in figures and text are given in mean±sem. Flow cytometry measurements were made with n=10000 events and performed in triplicates at the minimum.

pH-Dependent Erosion of LbL Film

Figure 14:
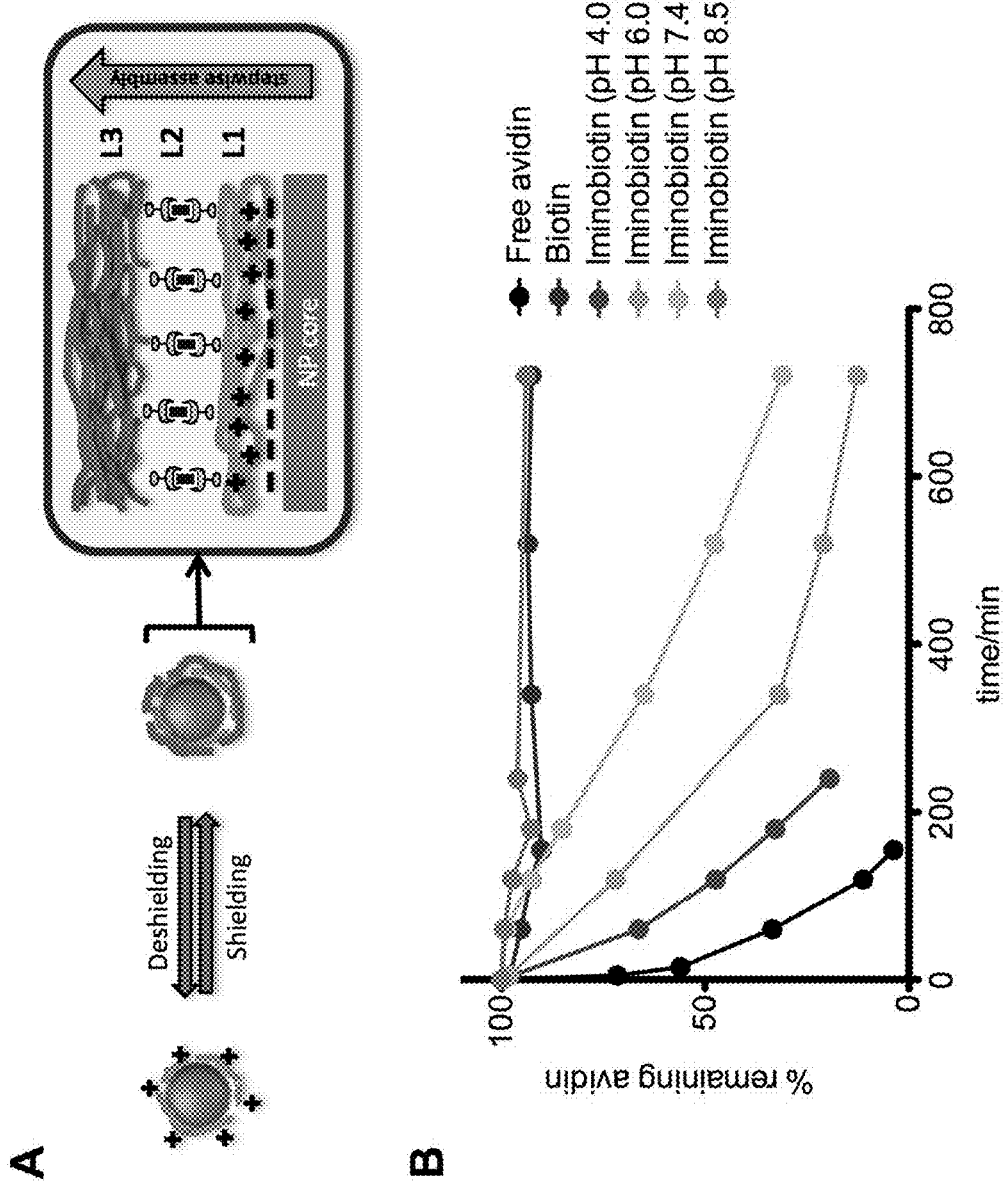
FIG. 14 A) Schematic illustration of the design and concept for achieving tumor specificity with layer-by-layer (LbL) nanoparticles. This design takes advantage of a lowered pH in hypoxic tissues to deshield the terminal poly(ethylene glycol) (PEG) layer, exposing the underlying positively charged poly-L-lysine (PLL) layer for cell targeting. L1: PLL modified with iminobiotin; L2: neutravidin; L3: biotin end-functionalized PEG. B) The rate of loss of avidin-FITC from iminobiotin conjugated to polyethyleneimine (500 kDa). The pH dependence of the iminobiotin-avidin bond used to predict behavior of iminobiotin-neutravidin bond. This bond is stable above pH 8.0 but gradually dissociates at pH 7.4. In acidic conditions (pH<6), the bond rapidly breaks down.

To demonstrate a concept for gaining tumor cell selectivity via the erosion of LbL layers, we utilize a trilayer architecture of poly-L-lysine (PLL) modified with iminobiotin, followed by the linker protein, neutravidin, and biotin end-functionalized poly(ethylene glycol) (PEG). This schematic illustration is shown in FIG. 14A. The first PLL layer improves cellular uptake of nanoparticles. The second neutravidin (nav) layer bridges PLL and PEG via neutravidin-iminobiotin bonds. Iminobiotin and neutravidin are modified versions of biotin and avidin respectively, and the iminobiotin-neutravidin interaction is a pH dependent non-chemical bond akin to the biotin-avidin bond. Iminobiotin-neutravidin bonds are stable at pH 8-12 but are easily decomposed at pH 4-6 as a result of the lower affinity of the protonated iminobiotin to neutravidin (FIG. 14B). Lastly, the terminal PEG layer is a commonly used antifouling polymer that would enable the layered nanoparticles to avoid rapid reticuloendothelial system (RES) clearance, allowing their accumulation in tumor interstitials due to the enhanced permeation and retention effect (EPR). When these nanoparticles accumulate in the acidic tumor environment, we hypothesized that they would gradually lose their PEG shells as the iminobiotin-neutravidin interactions decreased, allowing the exposed PLL layer to facilitate cellular uptake; thus shifting the biodistribution of the layered nanoparticles to favor tumor retention.

Cellular Uptake of PLL Coated Nanoparticles.

Figure 15A:
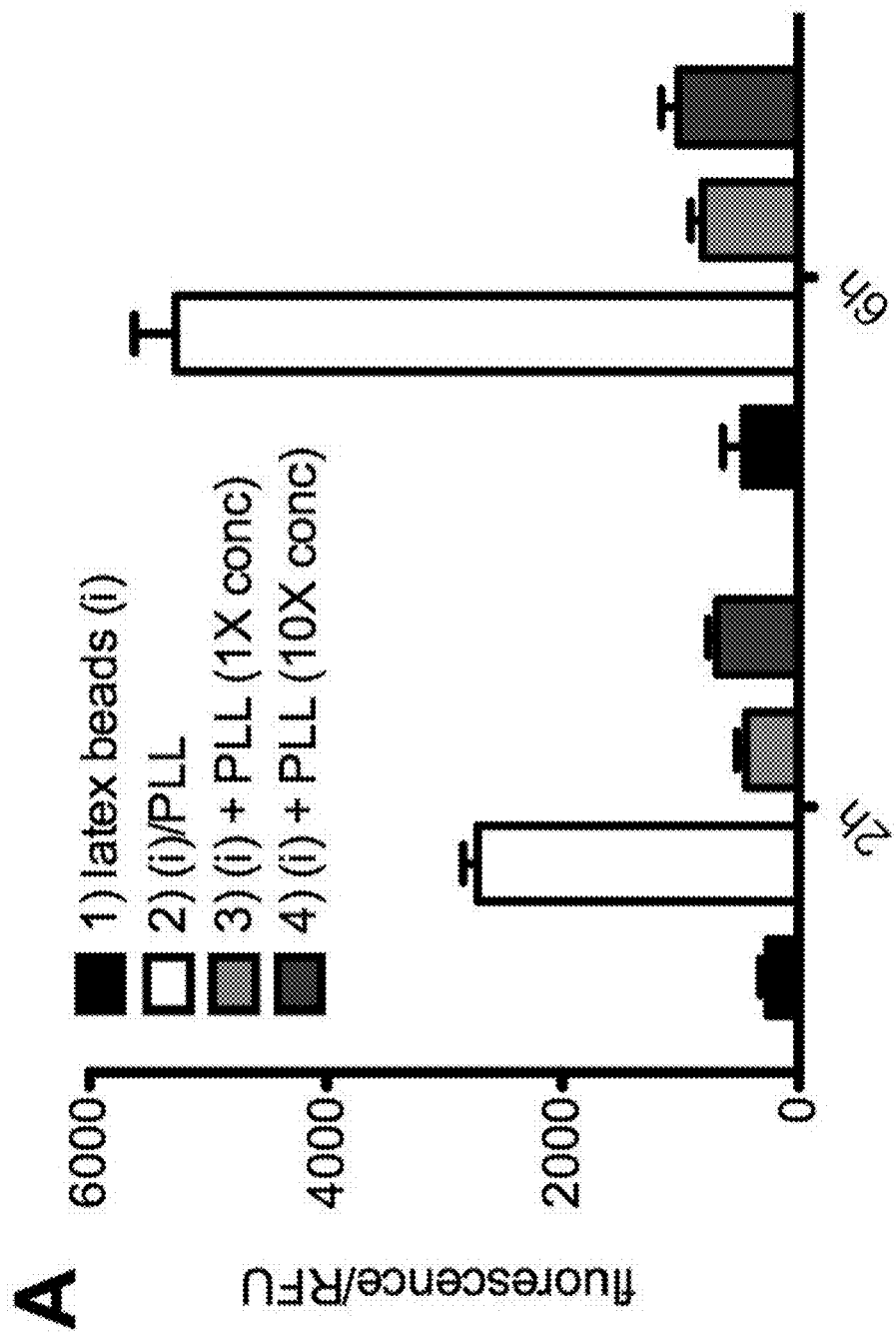
FIG. 15A shows a flow cytometry analysis of HeLa cells incubated with 1) fluorescent sulfonated latex beads (i), 2) (i) with a PLL layer, 3)/4) (i) co-incubated with PLL at different concentrations. In comparison to uncoated fluorescent latex beads co-incubated with cells using an estimated amount of PLL equivalent to one layer (HPLC estimates based on mass conservation calculations), as well as a second control with 10 times this estimated amount, PLL coated latex beads induced a significantly greater amount (~4-10× increase) of cell uptake.
Figure 15B:
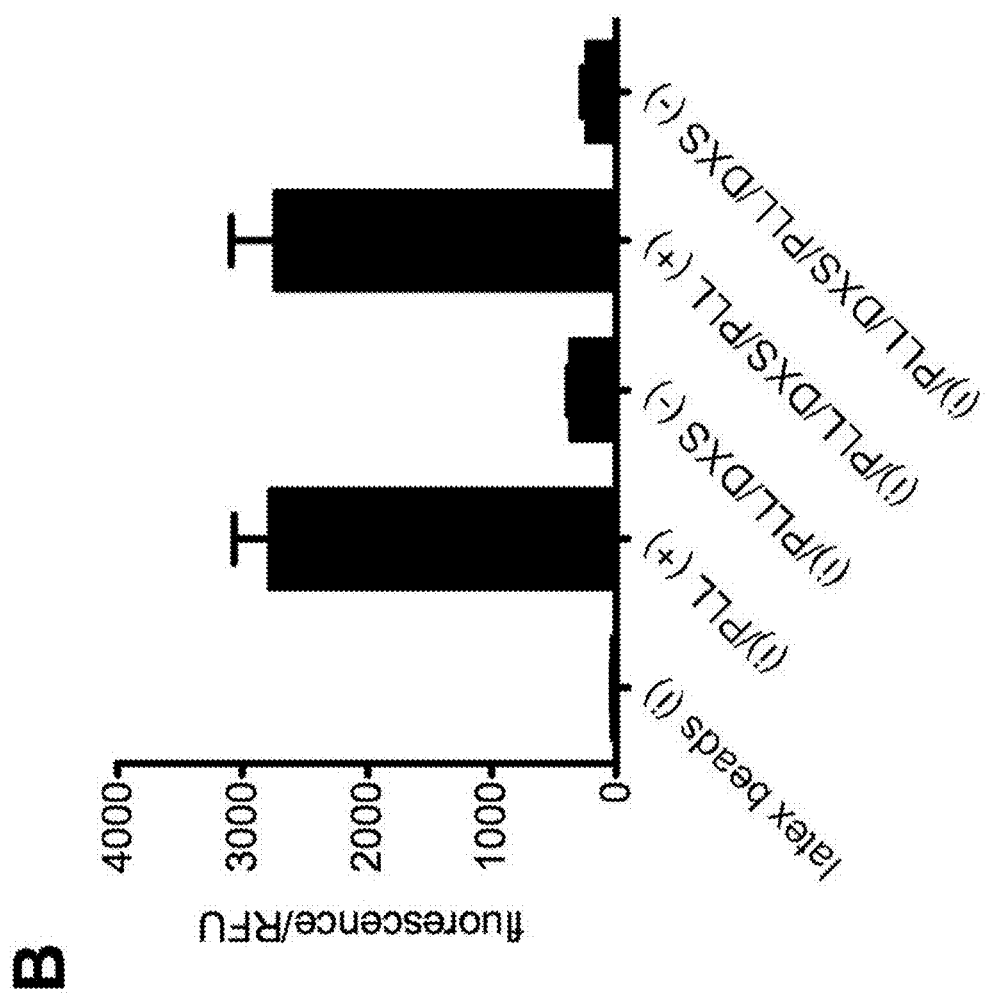
FIG. 15B shows the uptake of LbL nanoparticles can be enhanced or diminished by the terminal layer charge. LbL nanoparticles with positive zeta potentials (PLL terminated) are taken up by cells more readily than nanoparticles with negative zeta potentials (DXS terminated). This trend is consistent as the film thickness increases.
Figure 19A:
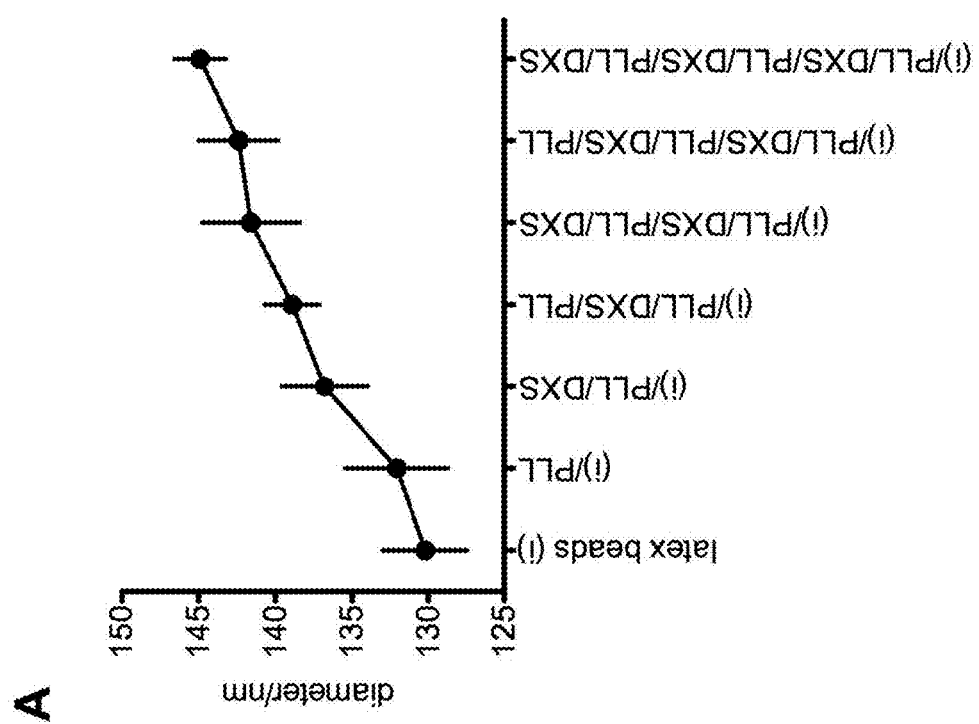
FIG. 19A is of a growth curve of PLL/DXS (poly-L-lysine/dextran sulfate) nanofilms deposited on sulfonated latex beads (130 nm). PLL and DXS layers are ~3 nm and ~5 nm thick respectively.
Figure 19B:
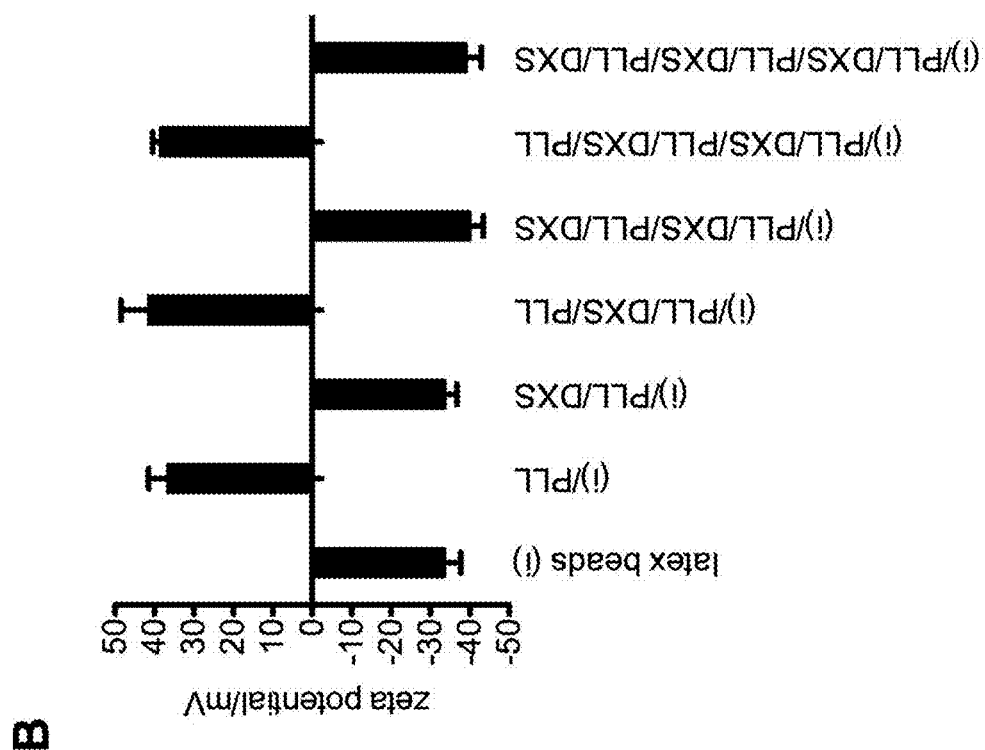
FIG. 19B shows a zeta potential of LbL particle after deposition of each PLL or DXS layer show complete reversal of charge.

As this strategy for gaining tumor selectivity relies on exposing a positively charged PLL layer to cancer cells for uptake, it is firstly important to examine the cellular uptake of positively charged PLL coated nanoparticles to understand the mechanism for charge-mediated uptake. Flow cytometry measurements in FIG. 15A show that even a single terminal layer of PLL was able to bring about notably increased levels (at least 5× increase) of nanoparticle uptake with HeLa cells. Cellular internalization of PLL coated fluorescent latex beads was confirmed with confocal microscopy (FIG. 15C(ii)). In comparison to uncoated fluorescent latex beads co-incubated with cells using an estimated amount of PLL equivalent to one layer (HPLC estimates based on mass conservation calculations), as well as a second control with 10 times this estimated amount, PLL coated latex beads induced a significantly greater amount (~4-10× increase) of cell uptake (FIG. 15A). When the topmost layer of the LbL film was DXS, yielding a negatively charged surface, cellular uptake decreased. This alternating trend of cellular uptake for positively (PLL) or negatively (DXS) charged terminal layers was consistent even as the LbL films were built thicker (FIG. 15B). The procedure for LbL deposition of PLL/DXS on sulfonated latex beads is given in the experimental section and FIG. 19 shows the average hydrodynamic diameter and zeta potential of these particles during LbL film construction.

Figure 15C:
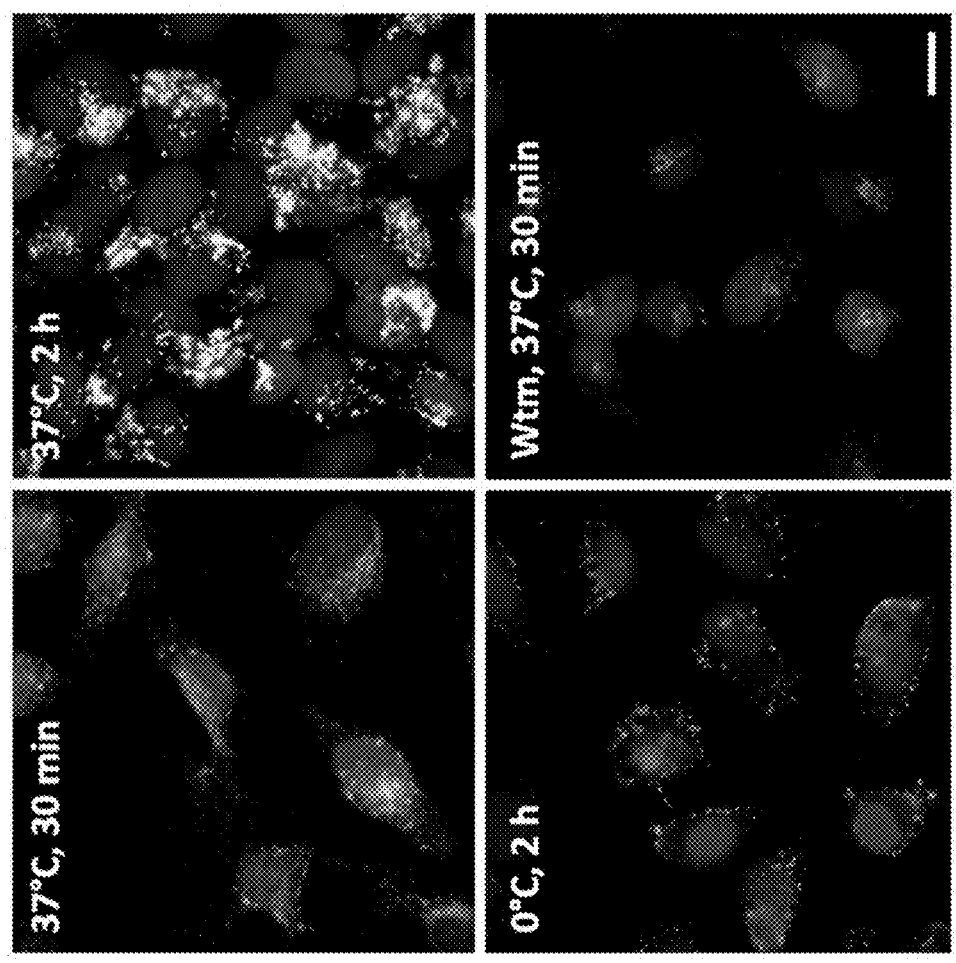
FIG. 15C shows a confocal microscopy analysis of HeLa cells given different PLL coated LbL nanoparticles under different conditions described in the image (Wtm: wortmannin treatment, 0° C. indicate treatment of cells on ice). The cell fluorescence measured by flow cytometry was due to internalized nanoparticles. Internalized particles co-localized with transferrin downstream of the internalization pathway but not at early times, indicating that the nanoparticles are taken into the cell in a manner that is separate from and slower than transferrin endocytosis. Co-localization of both signals downstream indicate similar means of trafficking past 2 h. Additional control experiments with cells treated on ice and wortmannin show that the uptake of these particles is energy driven. Confocal images from each fluorescent channel is shown in FIG. 20. Red=LbL nanoparticle; Green=transferrin; Blue=nuclei; Yellow=colocalization of LbL nanoparticle and transferrin. Scale bar=10 μm.
Figure 15D:
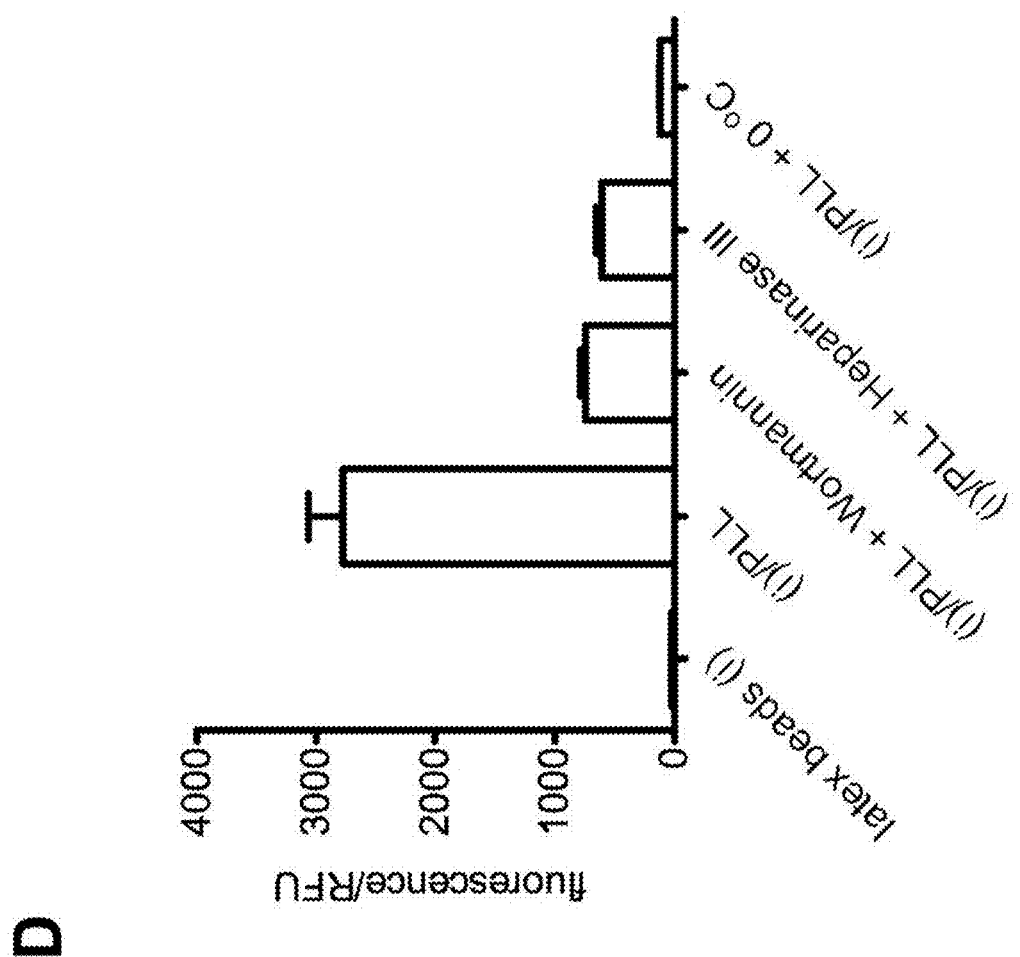
FIG. 15D is of a flow cytometry analysis of HeLa cells under different conditions described in FIG. 15C. Additionally, treatment of cells with heparinase III, an enzyme that breaks down the negatively charged heparan sulfate found bound on cell surfaces, also significantly reduced positively charged nanoparticle uptake, showing that interaction of positive nanoparticles with negatively charged heparan sulfate on the cell surface play an important role for uptake. All flow cytometry analyses represent fluorescence from the entire single cell population (10000 events) and are presented as mean±sem. Analyses in FIGS. 15C and 15D are taken at the 2 h time point.
Figure 20:
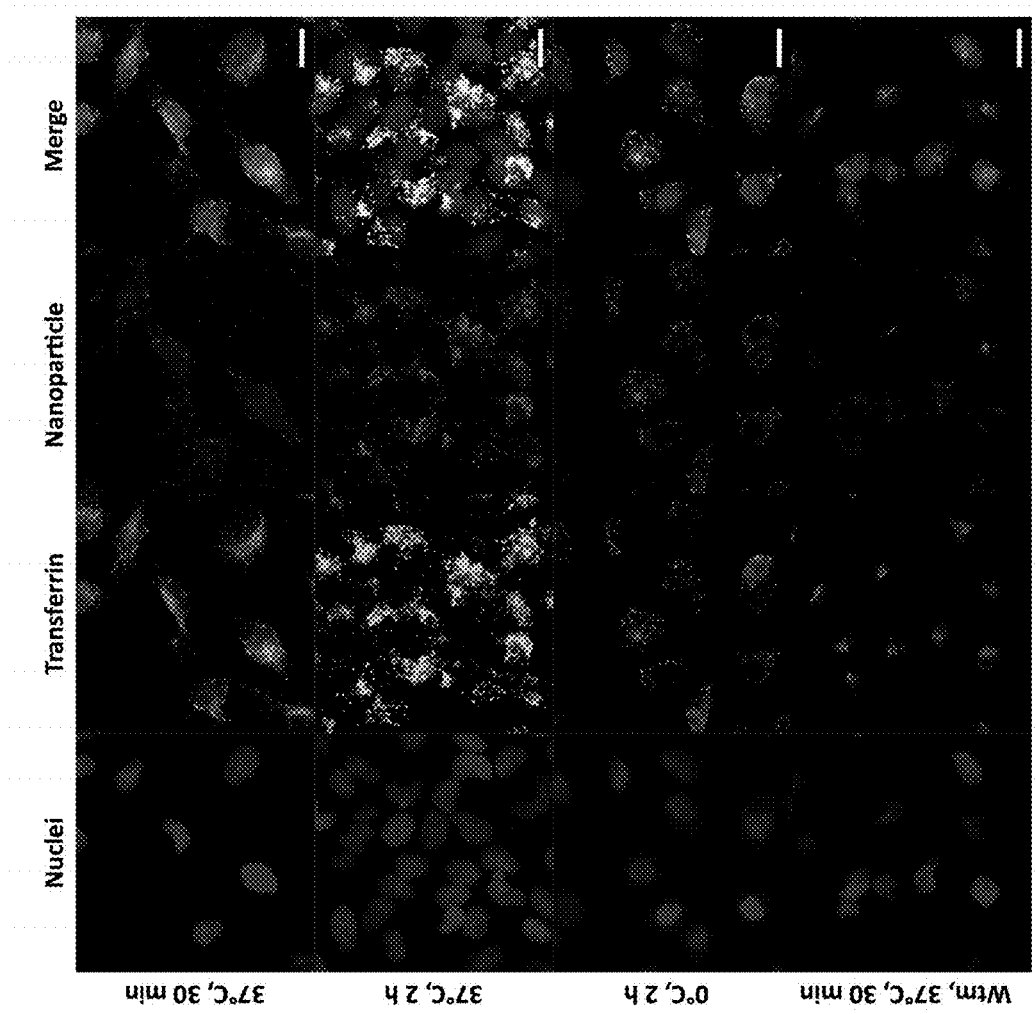
FIG. 20 The fluorescence image for each individual channel of the confocal images in FIG. 15C. Scale bar=10 μm.
Figure 21:
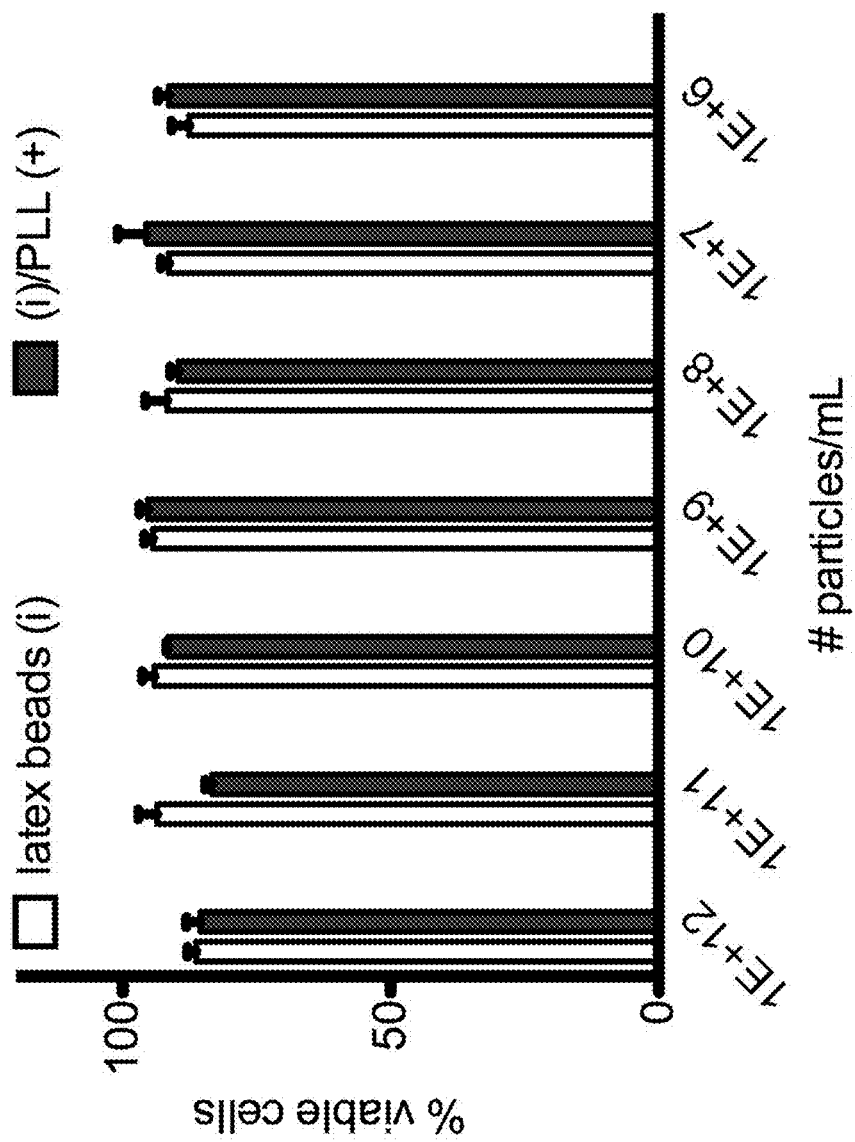
FIG. 21A MTT assay measuring the percentage of viable cells after a 48 h incubation period with positively charged PLL coated latex beads.

The mechanism of cell uptake of positively charged LbL nanoparticles was studied with confocal microscopy and flow cytometry analysis (FIG. 15C and FIG. 15D). Images from each individual fluorescence channel for FIG. 15C are shown in FIG. 20. From confocal analysis (FIG. 15C), incubation times between 30 min to 2 h was found to be necessary for inducing nanoparticle uptake by HeLa cells. Once taken up by HeLa cells, the layered nanoparticles were observed to internalize with transferrin, a well-studied molecule that undergoes clathrin-mediated endocytosis. Colocalization of transferrin and nanoparticle occurred downstream of the internalization pathway (2 h) but not at early times (30 min), indicating that the nanoparticles are taken into the cell in a manner that is separate from and slower than transferrin endocytosis. Experiments with cells treated on ice (0° C.) and wortmannin, an inhibitor of clathrin-mediated processes, indicate that the mechanism of uptake for positively charged nanoparticles is energy driven. Quantitative results for these experiments were measured with flow cytometry analysis and given in FIG. 15D. Additionally, treatment of cells with heparinase III, an enzyme that breaks down the negatively charged heparan sulfate found bound on cell surfaces, also significantly reduced positively charged nanoparticle uptake, showing that interaction of positive nanoparticles with negatively charged heparan sulfate on the cell surface play an important role for uptake (FIG. 15D). Finally, the cytotoxicity of these positively charged LbL nanoparticles was found to be negligible when tested with an MTT assay with HeLa cells (FIG. 21). Polypeptides containing a high percentage of cationic amino acids, such as PLL, are used routinely used to facilitate cellular uptake of a variety of biopolymers and small molecules. The use of such polymers to significantly enhance cellular uptake of nanoparticles via their LbL deposition provides a convenient approach for LbL-based nanoparticles to gain cellular entry into well-studied pathways for the delivery of therapeutics.

LbL Nanoparticle Assembly and In Vitro Examination

After verifying that the charge shielding of PLL coated LbL nanoparticles makes a significant difference in their cellular uptake, we sought to evaluate if the use of the trilayer architecture depicted in FIG. 1A would allow LbL nanoparticles to gain tumor selectivity after their systemic injection. Assembly of the trilayers for was carried out with carboxyl functionalized near-infrared quantum dots (QD, em: 705 nm) as the charged core material that would allow building of polymer films and tracking of the particles in vivo. Before depositing the PLL layer, the side chain primary amines on PLL were modified with iminobiotin (~20% of available side groups; PLLib) using NHS chemistry. Neutravidin and mPEG-biotin (~20 KDa) were subsequently layered onto the nanoparticle in a stepwise fashion (see experimental section for full details). The deposition of each layer was followed by dynamic light scattering and zeta potential measurements (Table 1). Addition of the trilayer architecture (PLLib/nav/PEG) increased the hydrodynamic diameter of the original particles from ~20 nm to ~80 nm, with most of the increase attributed to the terminal PEG layer. The zeta potential of the nanoparticle shifted from ~−25 mV to ~+30 mV with the deposition of PLLib and finally, to ~0 mV when terminated with PEG. An SEM image of the QD/PLLib/nav/PEG particles is shown in FIG. 3A. These particles are generally spherical and uniform in size after the LbL coating process.

TABLE 1

Figure 19C:
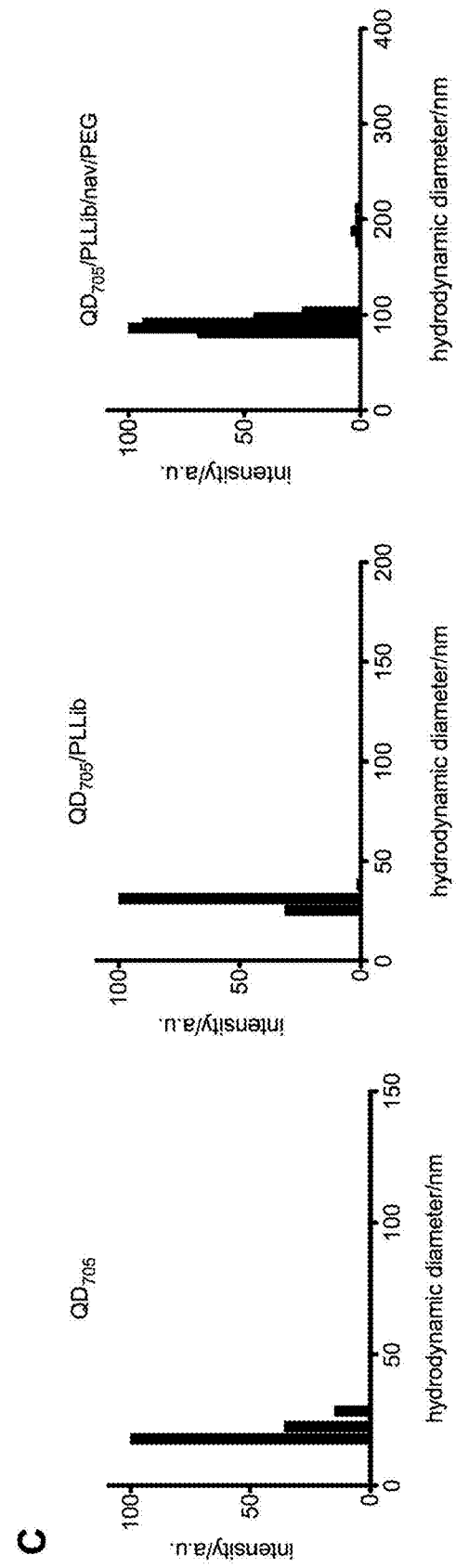
FIG. 19C shows a raw number average size distribution data for DLS experiments on QD, QD/PLLib and QD/PLLib/nav/PEG particles.

The average hydrodynamic diameter and zeta potentials of LbL NPs. QD = quantum dot; PLL = poly-L-lysine; PLLib = PLL functionalized with iminobiotin; PLLb = PLL functionalized with biotin; nav = neutravidin; PEG = biotin end-functionalized poly(ethylene glycol). The values shown are in mean ± sem, where n = 10. The raw data for the number average diameters of QD, QD/PLLib and QD/PLLib/nav/PEG is shown in FIG. 19C.

| LbL Nanoparticle | Effective Diameter (nm) | PDI | Zeta Potential (mV) |
|---|---|---|---|
| QD | 20 ± 5 | 1.09 | −26 ± 4 |
| QD/PLL | 24 ± 6 | 1.21 | +30 ± 5 |
| QD/PLLib | 24 ± 8 | 1.23 | +33 ± 2 |
| QD/PLLib/nav/PEG (pH 7.4) | 76 ± 7 | 1.25 | +1.3 ± 3 |
| QD/PLLib/nav/PEG (pH 5.5) | 38 ± 11 | 1.21 | +25 ± 7 |
| QD/PLLb/nav/PEG | 82 ± 8 | 1.23 | +0.7 ± 2 |

Figure 16A:
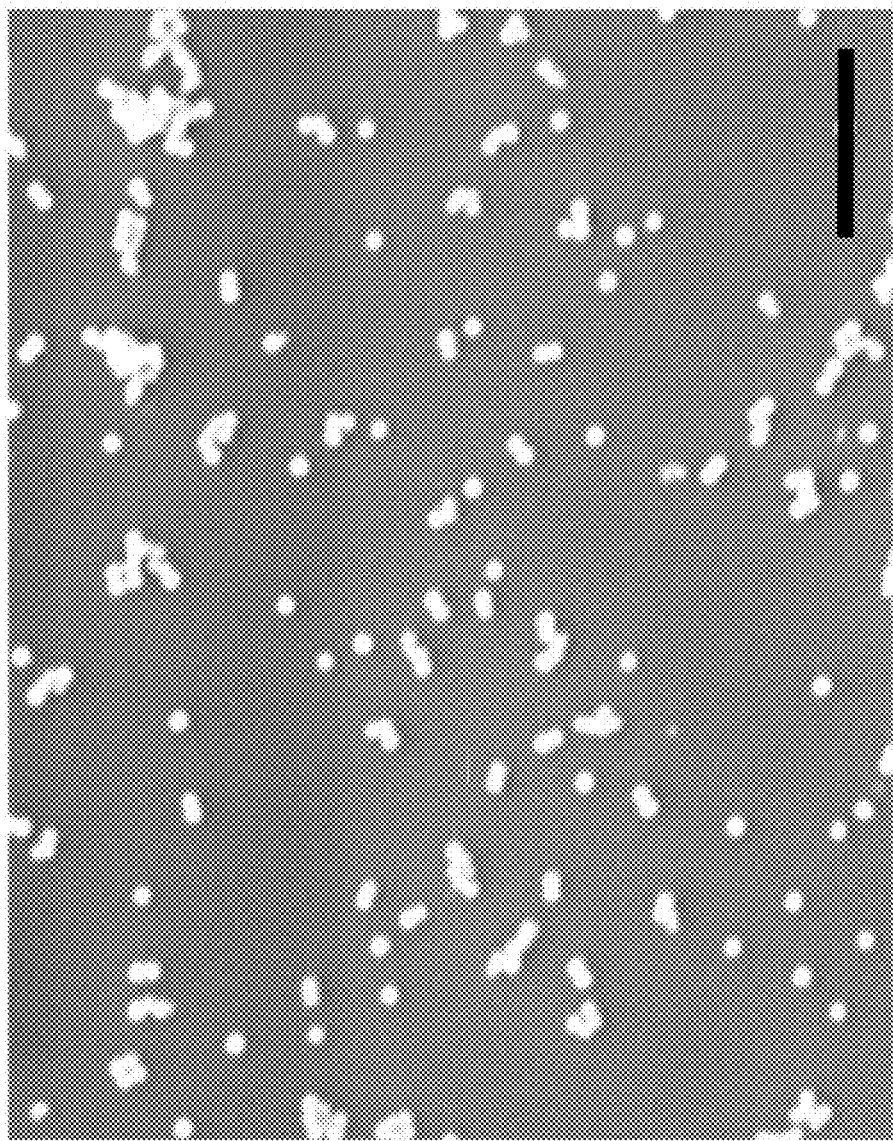
FIG. 16A shows an SEM image of QD/PLLib/nav/PEG particles. These particles are generally spherical and uniform in size after the LbL coating process. Scale bar=1 μm.
Figure 16B:
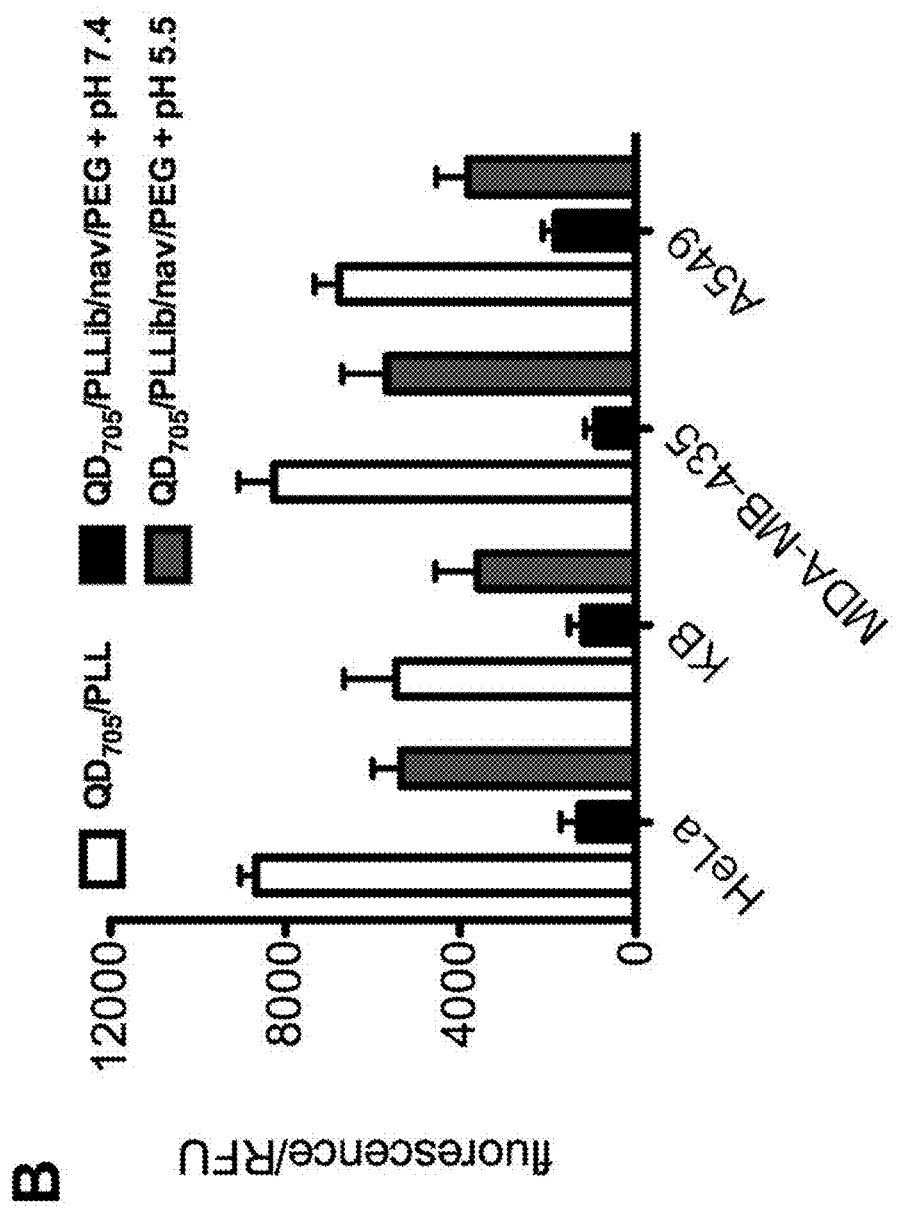
FIG. 16B shows cellular uptake of QD/PLLib/nav/PEG particles across a panel of cancer cell lines is restored after acidic pretreatment (pH 5.5 for 4 h), suggesting the potential to target a broad range of cancers with hypoxic microenvironments, as the LbL particles lose their PEG shells in the lowered pH environments of hypoxic tissue.

To confirm that cellular uptake of the LbL particles can be restored after deshielding the terminal layer of PEG, we incubated different cancer cells with LbL nanoparticles subjected to pretreatments at pH 7.4 and 5.5 for 4 h. After acidic treatment (pH 5.5) QD/PLLib/nav/PEG particles decreased in average size and increased in charge (Table 1), indicating removal of the charge shielding terminal PEG layer (zeta potential shifted from ~0 mV to ~25 mV), while LbL particles incubated at pH 7.4 remained the same in size and charge. Deshielding the external PEG layer restored cellular uptake (FIG. 16B); compared to LbL particles incubated at pH 7.4, those that were deshielded (pH 5.5 treatment) caused a greater amount of uptake in all tested cancer cell lines, suggesting that this strategy could be used as a generic way of targeting tumors, as an acidic microenvironment is a hallmark of all tumors.

Targeting of Tumors In Vivo

Figure 17A:
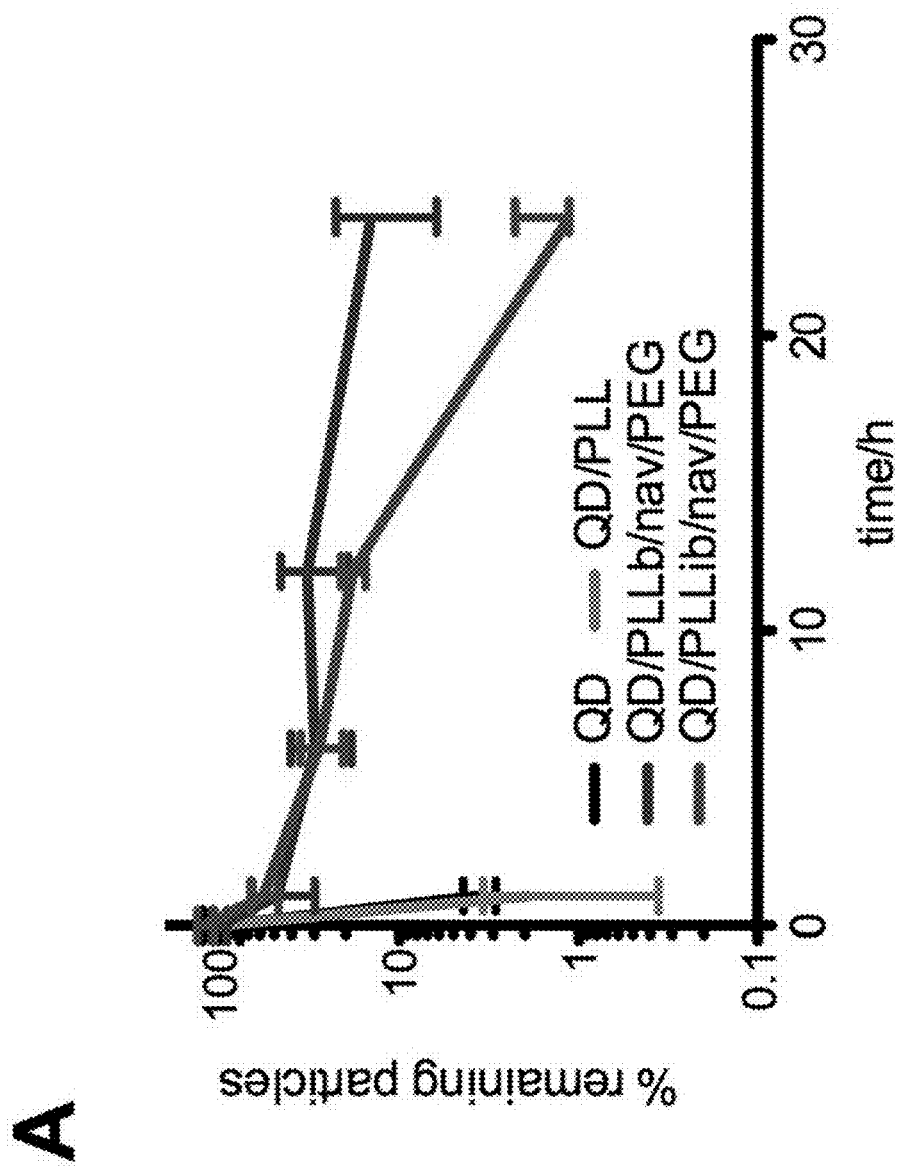
FIG. 17A shows a log-linear blood circulation profiles of QD, QD/PLL, QD/PLLib/nav/PEG and QD/PLLb/nav/PEG. Changing the surface properties of QDs with LbL improves nanoparticle circulation. QD/PLLib/nav/PEG and QD/PLLb/nav/PEG have similar profiles up to 12 h post administration QD/PLLib/nav/PEG clears faster after 12 h.

Next, the utility of this tumor targeting strategy was tested in vivo with subcutaneous tumor models. Control nanoparticles were constructed by substituting iminobiotin (PLLib) for biotin (PLLb), which does not have a pH dependent bond with neutravidin. The resulting particles (QD/PLLib/nav/PEG and QD/PLLb/nav/PEG) are less than 100 nm in size and have a near neutral zeta potential (Table 1). Their sub-100 nm sizes would facilitate their diffusion within the tumor tissue to more readily encounter hypoxic pockets. After systemic intravenous injection in mice of the nanoparticles, the blood concentrations of the nanoparticles decreased in a two-phase manner (FIG. 17A). The significantly longer circulation profiles of the administered LbL particles compared to free QD due to the presence of the PEG nanolayer indicate a certain level of nanofilm stability while in systemic circulation. Initially, both QD/PLLib/nav/PEG and QD/PLLb/nav/PEG were observed to have a relatively similar circulation profile, with more than 25% of the particles still in the blood by 6 h; however, the blood level of QD/PLLib/nav/PEG was detected to be significantly lower than QD/PLLb/nav/PEG after 12 h. Blood concentrations of QD/PLLib/nav/PEG and QD/PLLb/nav/PEG had dropped to 1% and 14% respectively of the original amount by 24 h. The faster elimination of QD/PLLib/nav/PEG is likely due to the gradual removal of the terminal PEG layer while at physiological pH, as the iminobiotin-neutravidin bond is most stable above pH 8.0. This is supported by examinations of the iminobiotin-avidin bond (FIG. 13B), which show a slow degradation of the bond at pH 7.4. The resulting exposure of the PLL layer leads to rapid elimination of the particles, presumably by processes of opsonization of the complement system.

We monitored the accumulation of the particles in subcutaneously induced MDA-MB-435 (FIG. 17B) and KB (FIG. 54, see supplemental information online) tumors with intravital fluorescence imaging over a period of 48 h. For both tumor models (n=3), accumulation of particles within the tumor reached a peak at the 8 h time point and steadily decreased thereafter, as particle elimination from the blood reservoir diminishes the effect of EPR based tumor-targeting. The mechanisms of EPR are not expected to discriminate between the two sets of nanoparticles, which have similar sizes, charges, surface properties and blood circulation (in the initial period after injection), and equal levels of accumulation were observed 7 in both tumor models at the 8 h point (FIG. 17C, two tailed student's t test shows no significant difference 95%; CI $P_{KB}$=0.92, $P_{MDA-MD-435}$=0.56); this is evidence of the dominance of the EPR based targeting during this initial period.

Figure 17B:
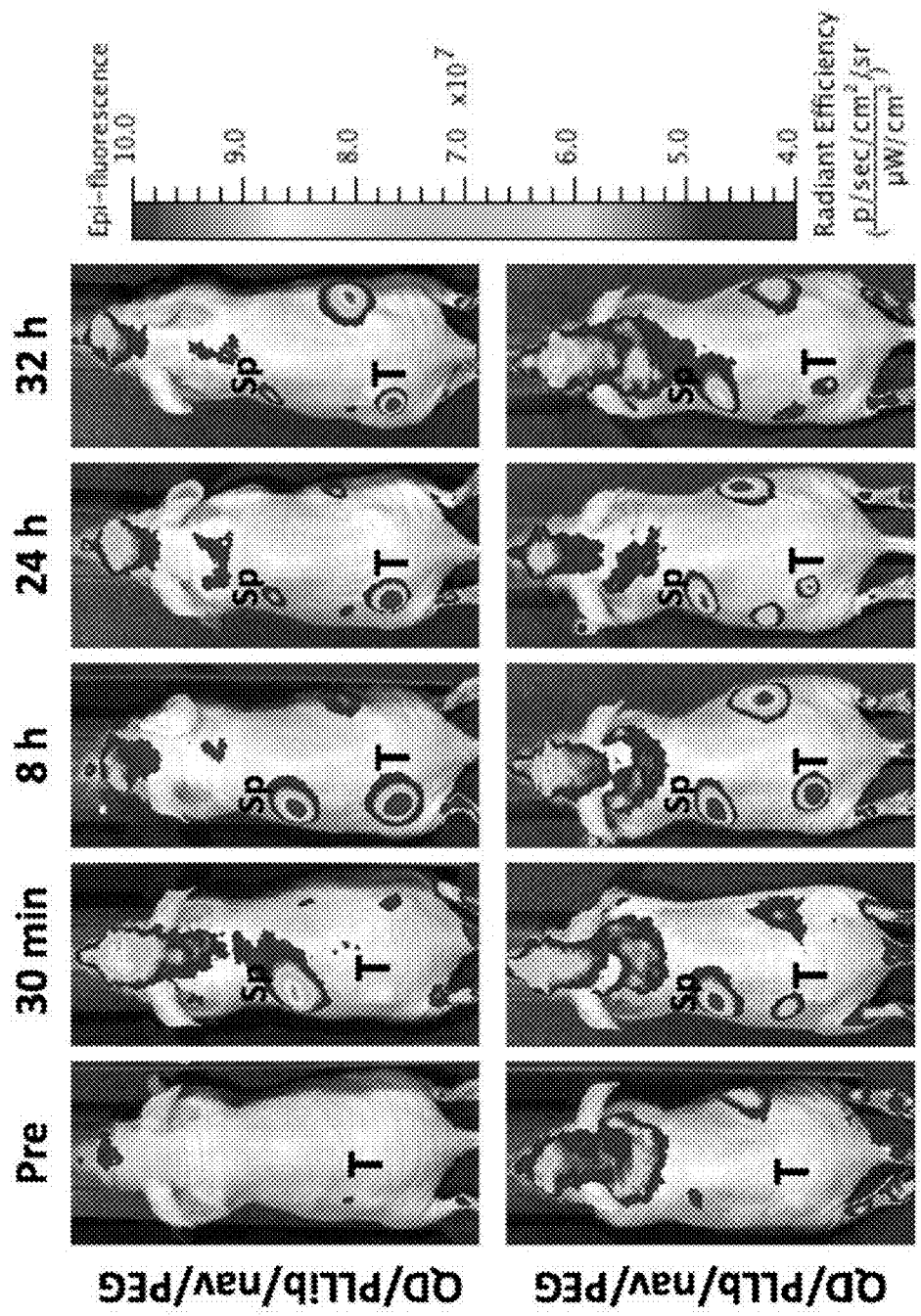
FIG. 17B is of dorsal scans of representative mice showing the accumulation and clearance of LbL nanoparticles in MDA-MB-435 tumors (left hind flank). T=tumor; Sp=spleen. Similar images of mice with KB xenografts are shown in FIG. 22A.
Figure 17C:
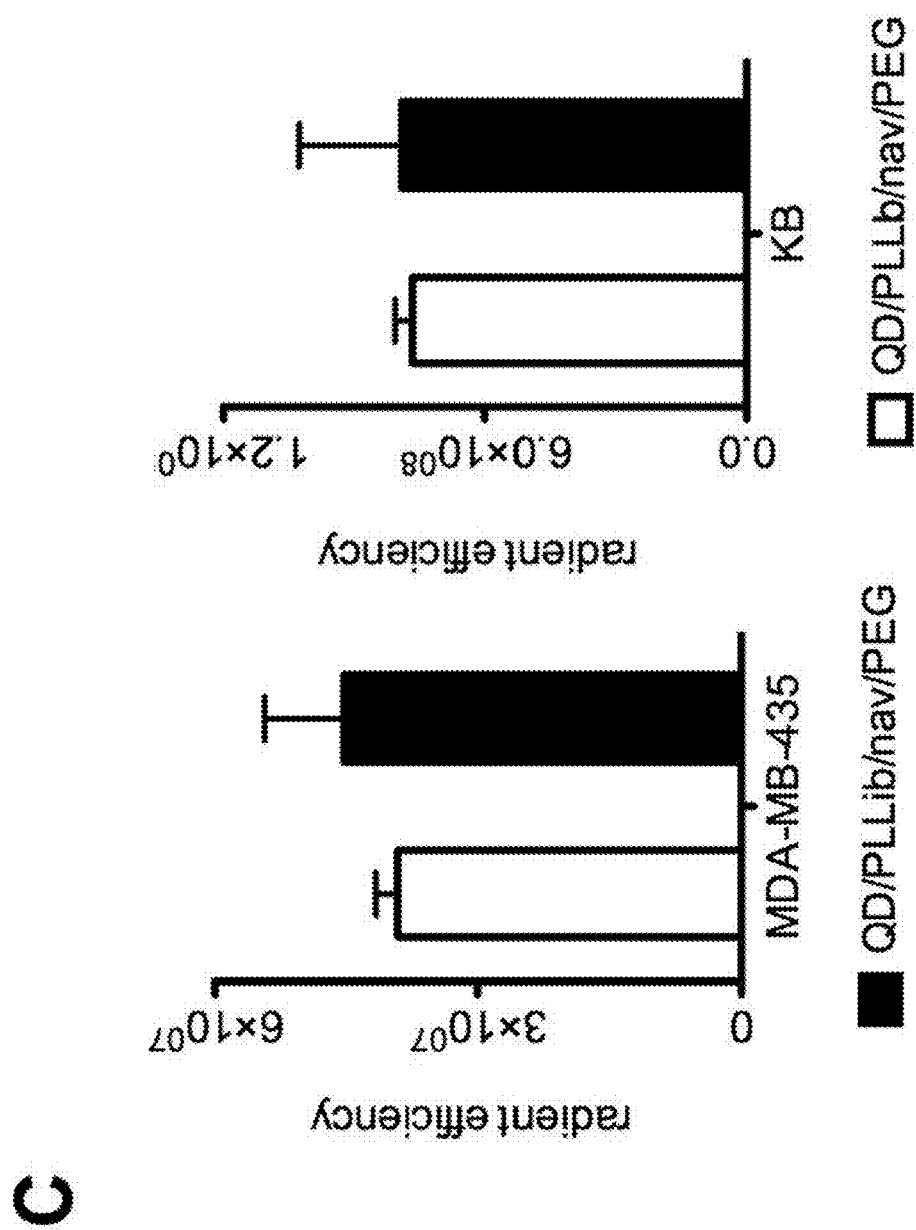
FIG. 17C shows LbL nanoparticle accumulation levels in tumors at 8 h. There was no statistical difference between fluorescence from both particle type for each tumor model (95%; CI $P_{KB}$=0.92, $P_{MDA-MD-435}$=0.56).
Figure 17D:
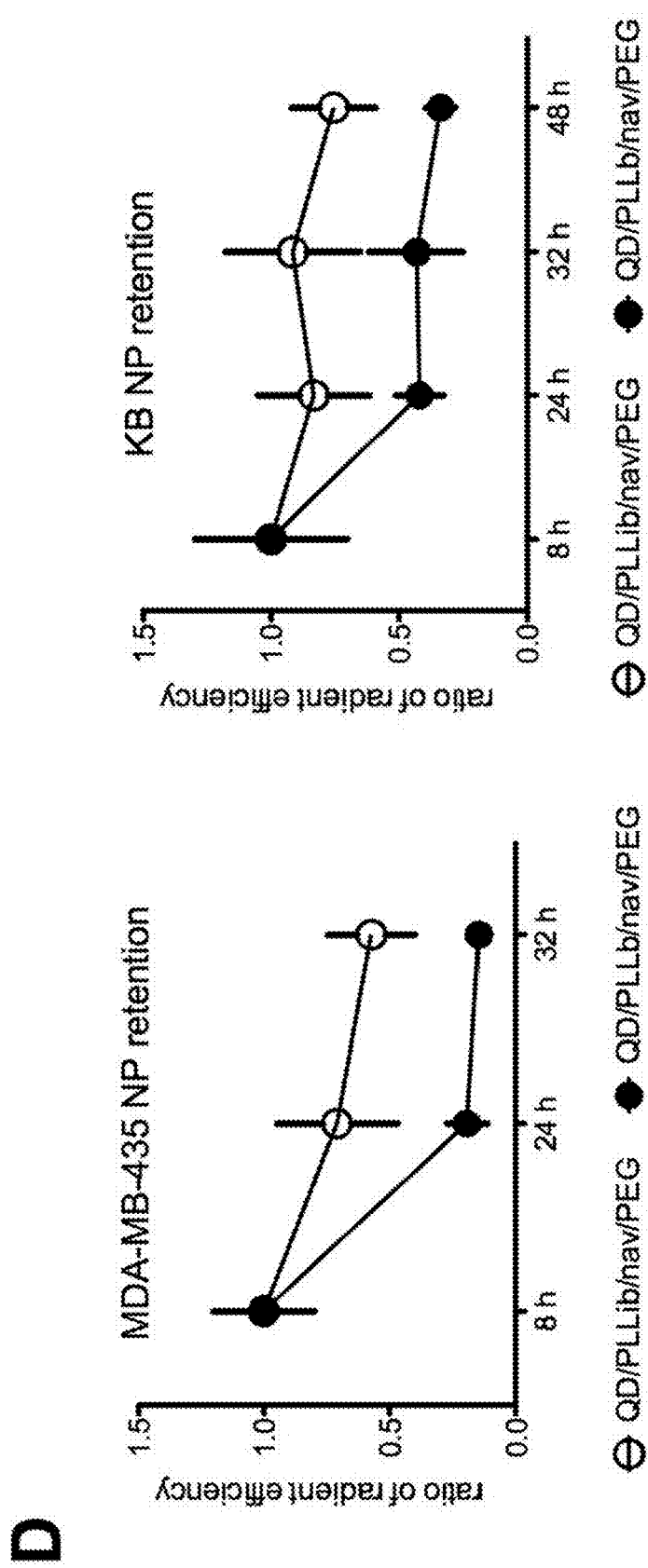
FIG. 17D shows the rate of clearance of nanoparticles from tumors relative to the 8 h time point. QD/PLLib/nav/PEG is cleared slower, demonstrating the deshielding of PEG and subsequent tumor cell targeting. The absolute levels of nanoparticle fluorescence are given in FIG. 54C (see supplemental information online).
Figure 18:
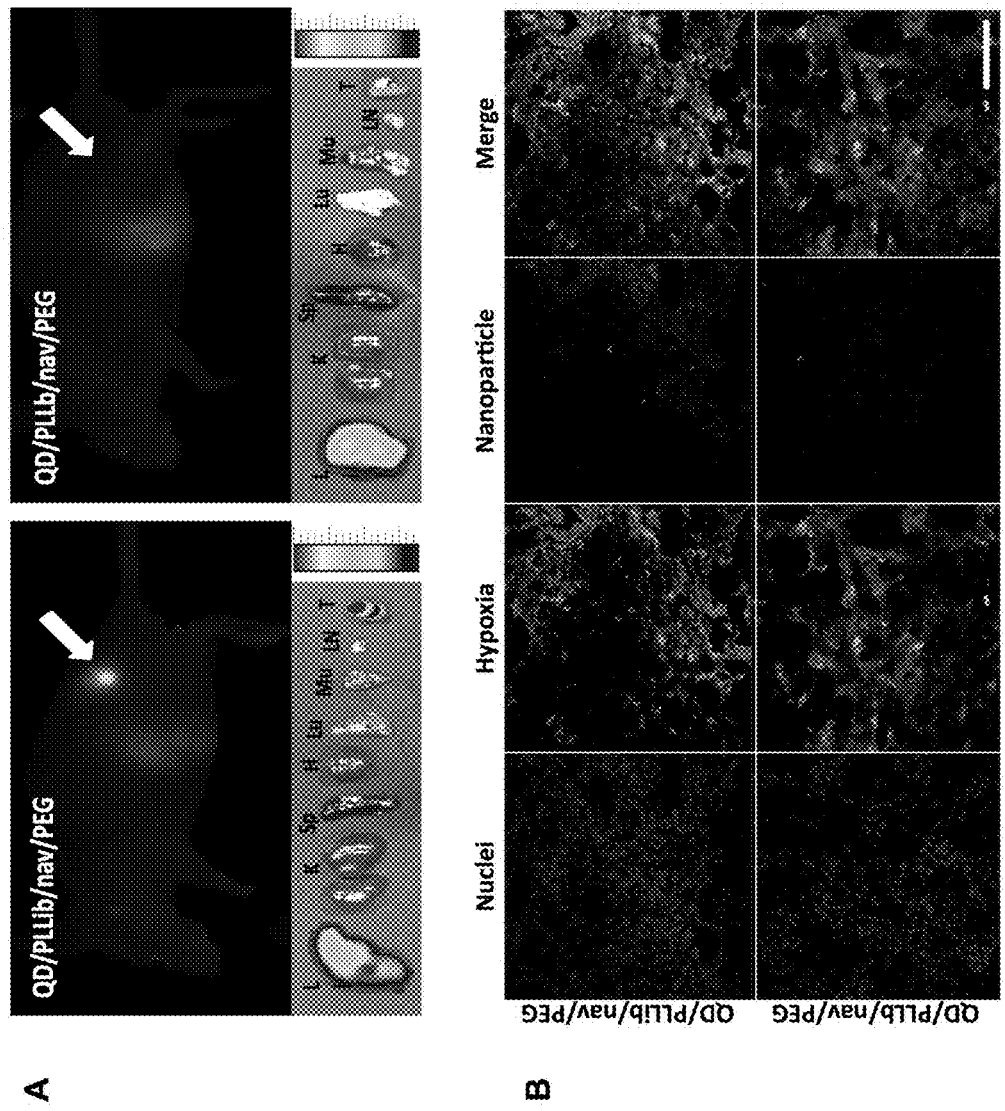
FIG. 18 A) Spectrally unmixed lateral scan of representative MDA-MB-435 mice model and biodistribution of nanoparticles in organs 48 h after administration. QD/PLLib/nav/PEG nanoparticle fluorescence was still present in tumors at 48 h, which suggests significant nanoparticle uptake by tumor cells. Red=tissue and food autofluorescence, Teal=nanoparticle fluorescence. Li=liver; K=kidney; Sp=spleen; H=heart; Lu=lungs; Mu=muscle; LN=lymph nodes; T=tumor. Image is spectrally unmixed to separate the nanoparticle fluorescence from tissue autofluorescence. B) Tumor sections (20×) from mice given QD/PLLib/nav/PEG or QD/PLL/nav/PEG. In tumors given QD/PLLib/nav/PEG treatments, a colocalization between nanoparticle and HIF-1α positive regions was found. Nanoparticle presence was not significant in tumors given QD/PLL/nav/PEG. Red=LbL nanoparticle; Green=hypoxia; Blue=nuclei. Scale bar=50 μm.
Figure 22A:
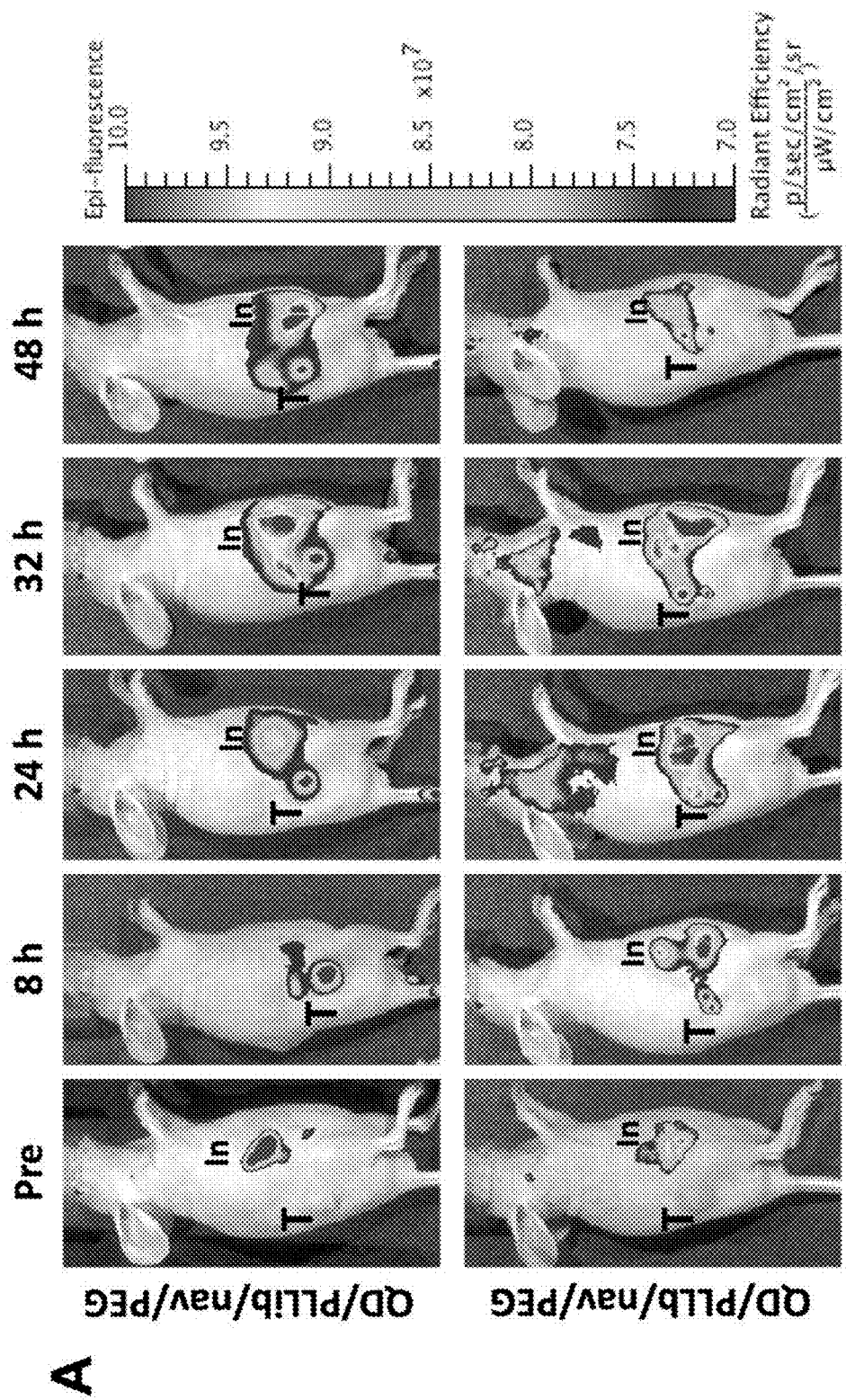
FIG. 22A shows the right lateral scans of a representative mouse showing the accumulation and clearance of LbL nanoparticles in KB tumors. T=tumor; In=intestines (food autofluorescence); Absolute values of nanoparticle accumulation in MDA-MB-435 tumors are show in FIG. 22B and KB tumors are show in FIG. 22C over the experimental period.
Figure 22B:
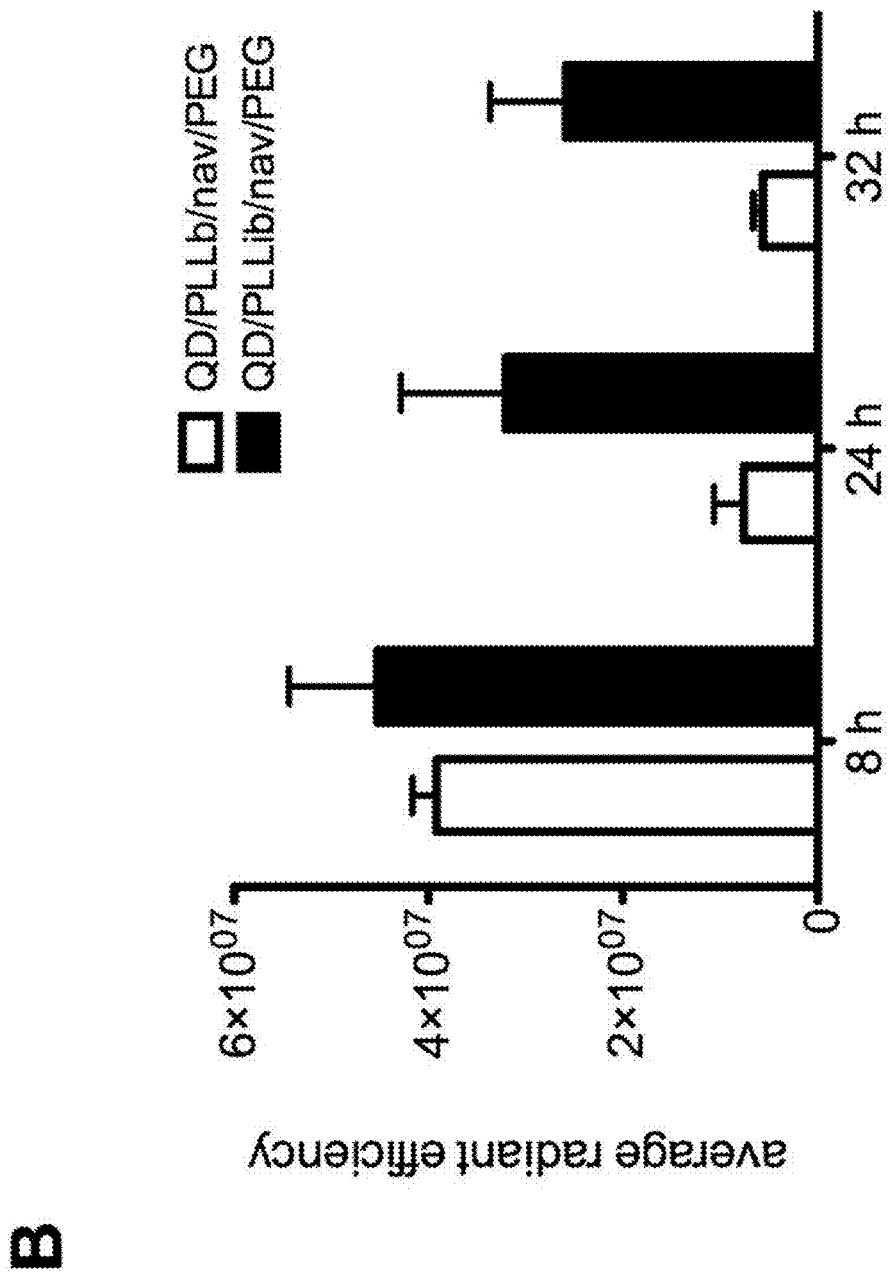
Figure 22C:
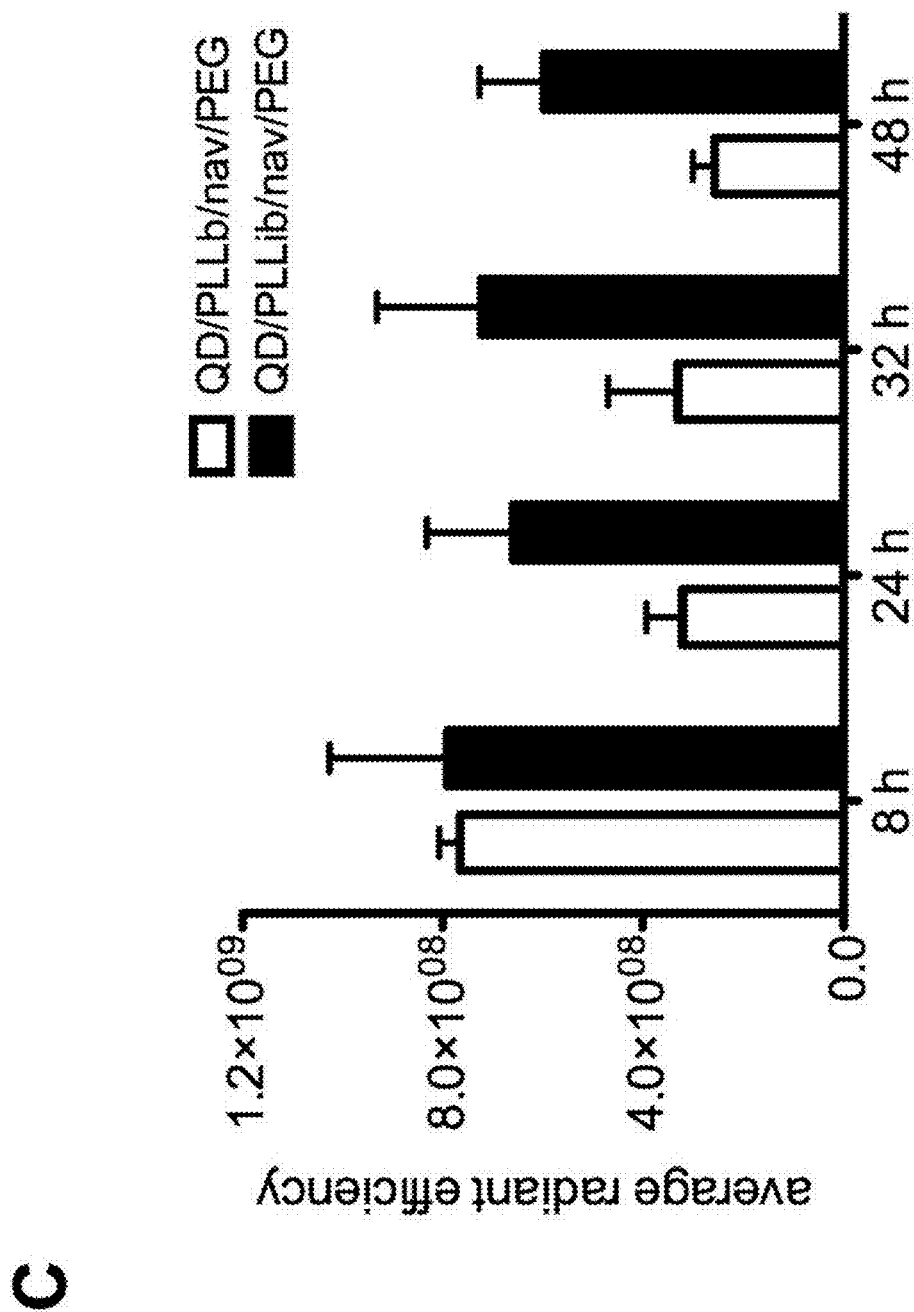
Figure 23:
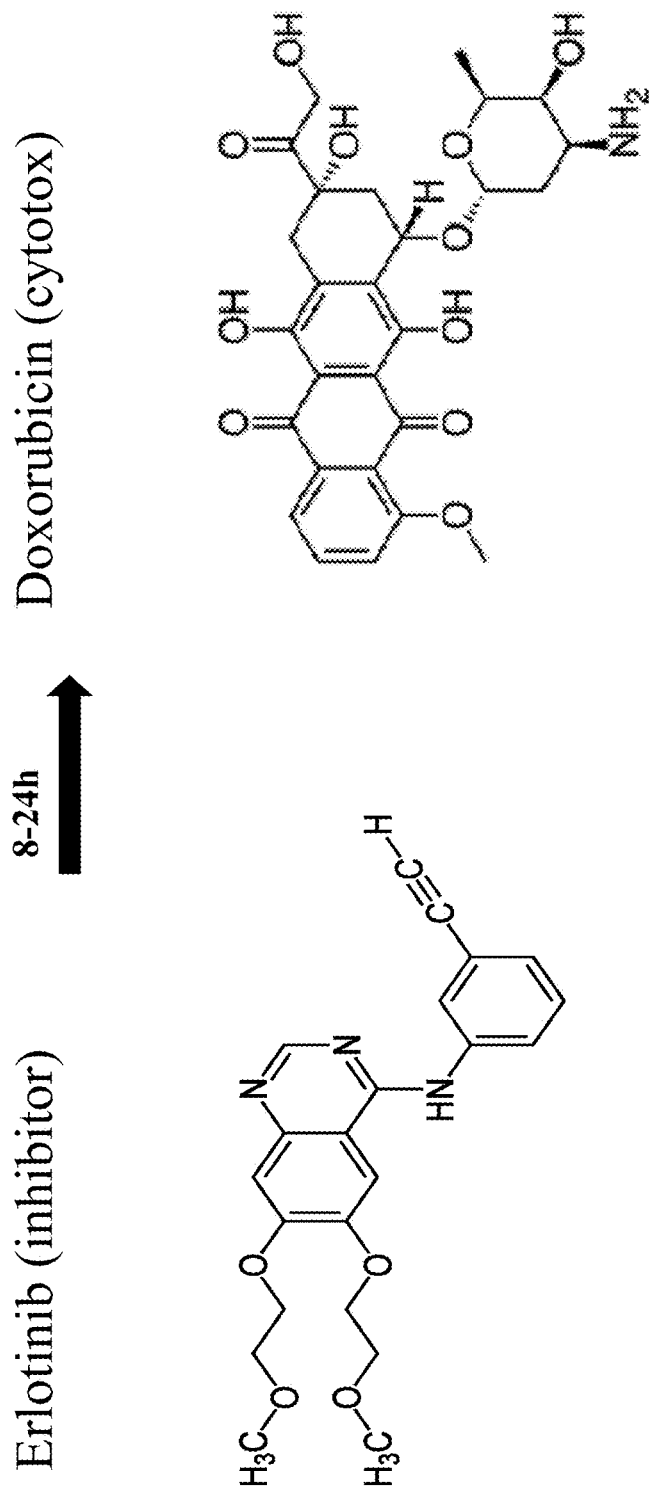
FIG. 23 Structures of two exemplary drugs, Erlotinib and Doxorubicin.
Figure 24A:
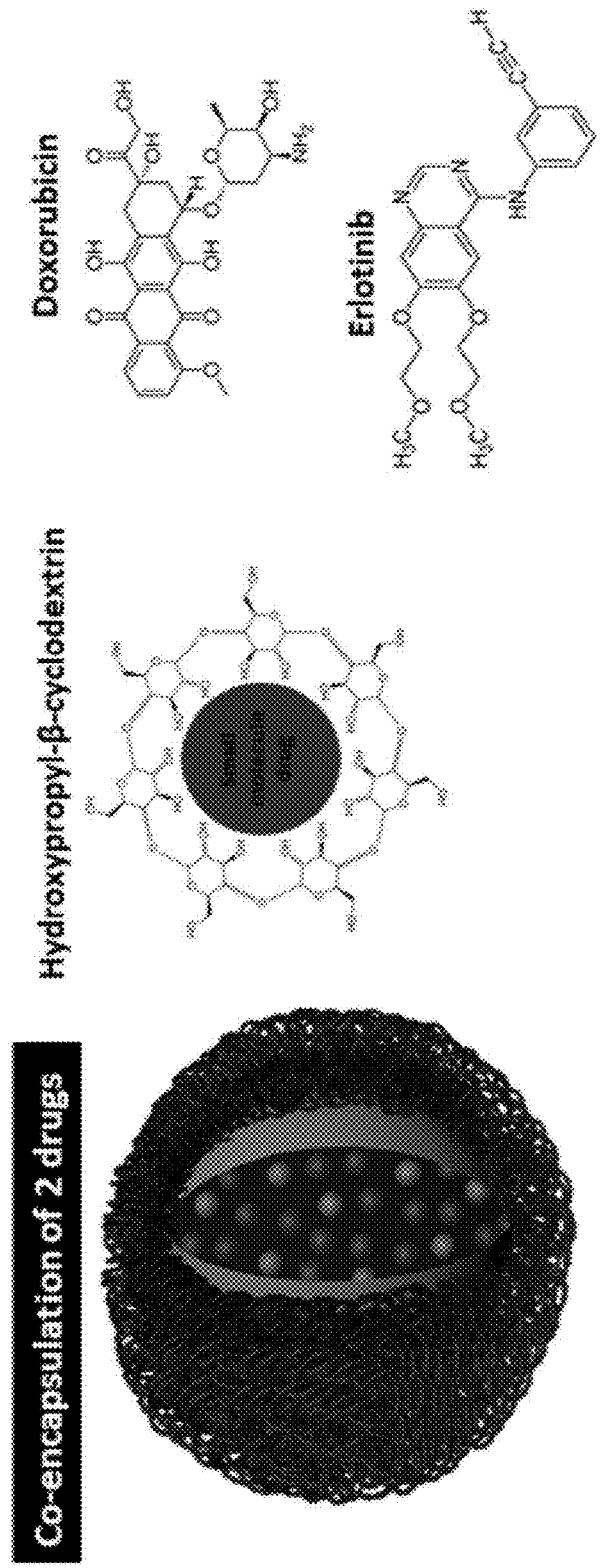
FIG. 24A illustrates co-encapsulation of two drugs.
Figure 24B:
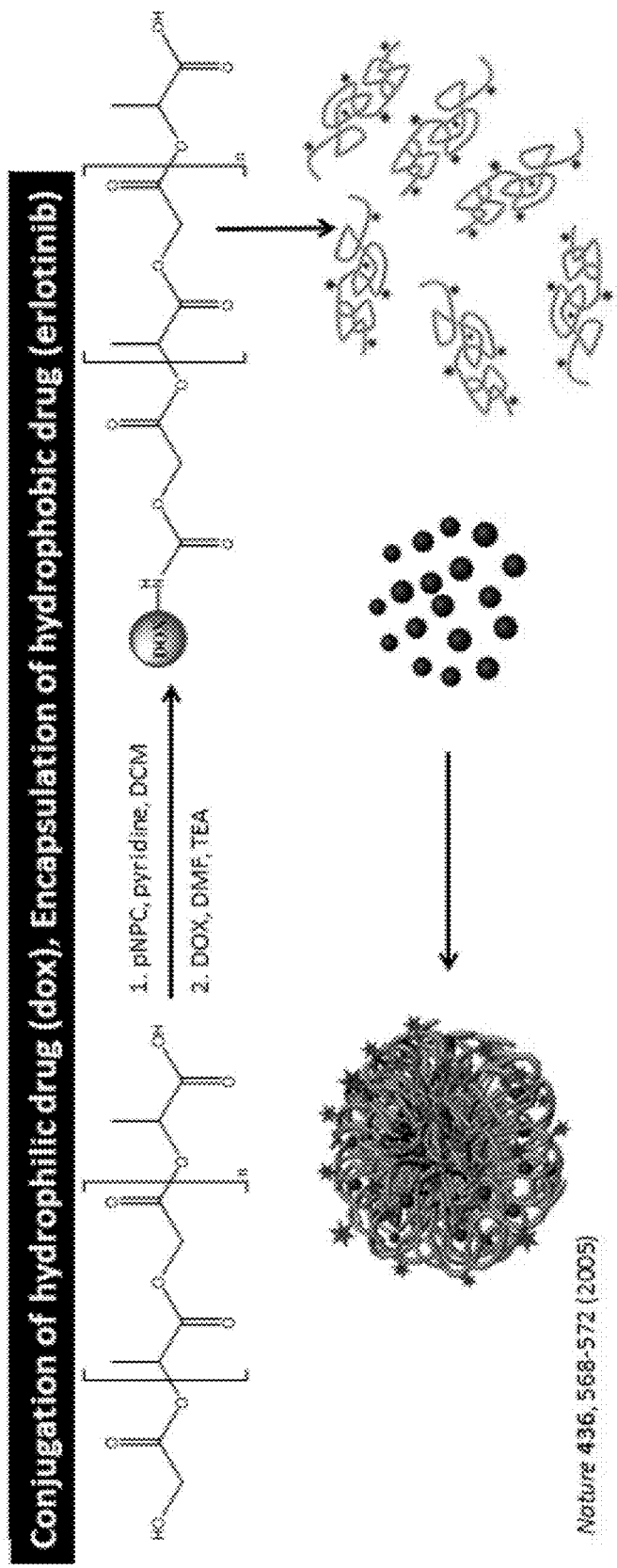
FIG. 24B shows conjugation of hydrophilic (Dox) and encapsulation of hydrophobic drug (erlotinib) (bottom). See details in "Temporal targeting of tumor cells and neovasculature with a nanoscale delivery system" by Sengupta et al., Nature 436, 568-572 (2005), the contents of which are incorporated here by reference.
Figure 25:
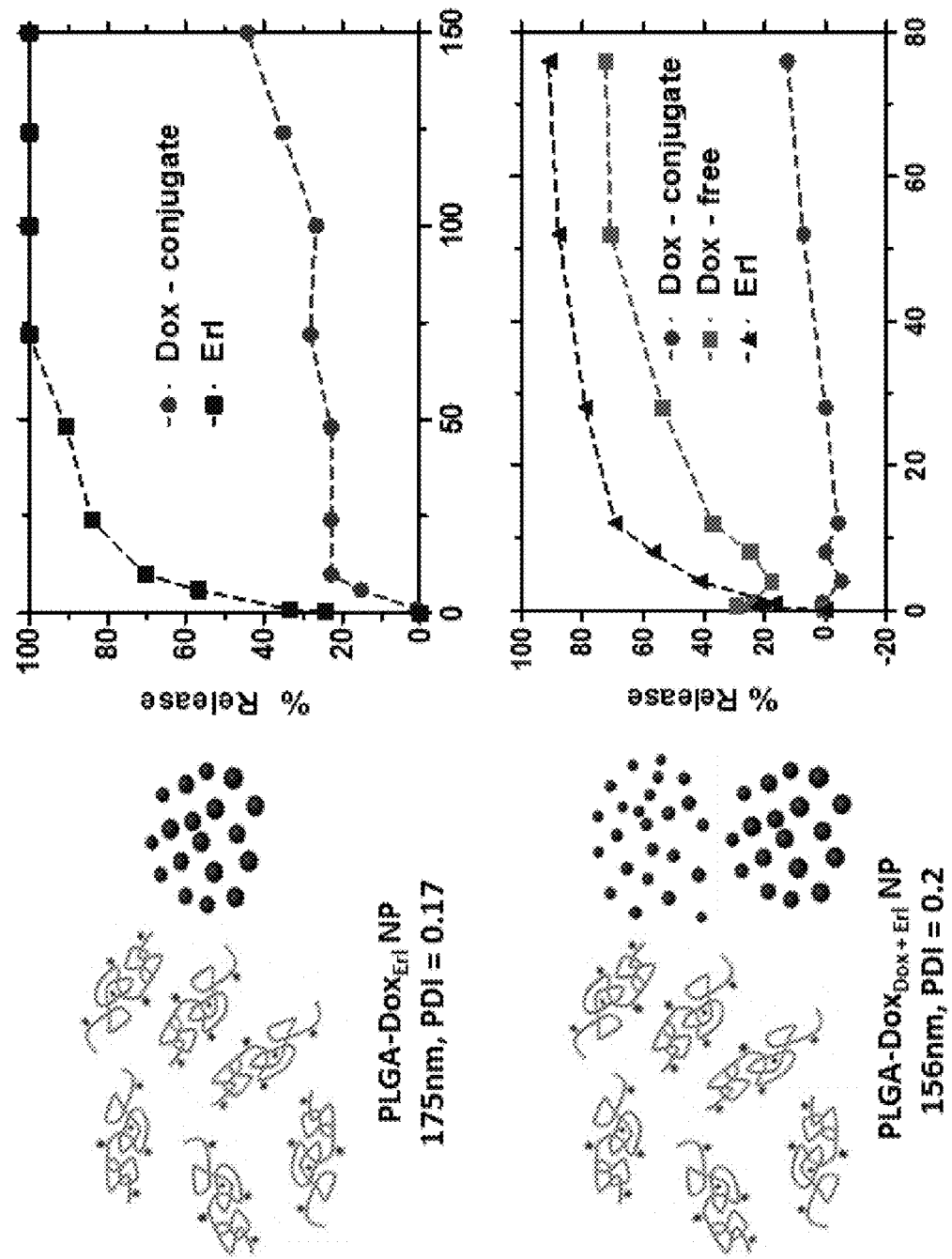
FIG. 25 Drug release characteristics of two exemplary particles.
Figure 26:
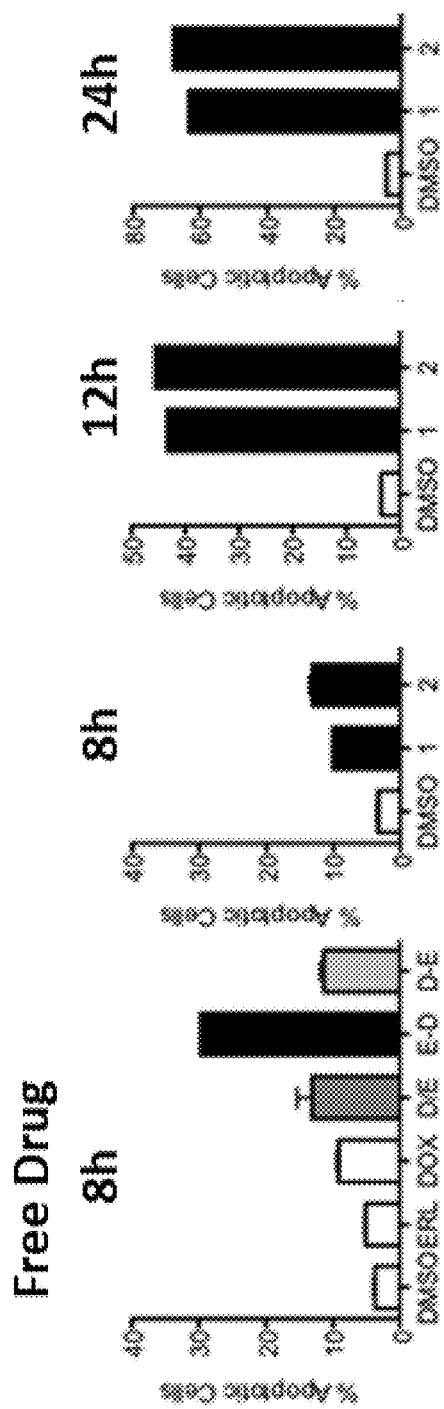
FIG. 26 Cell apoptotic response showing 1) loading issue with erlotinib (consistent theme with PLGA); 2) variability in loading efficiency; and 3) size of particles.
Figure 26:
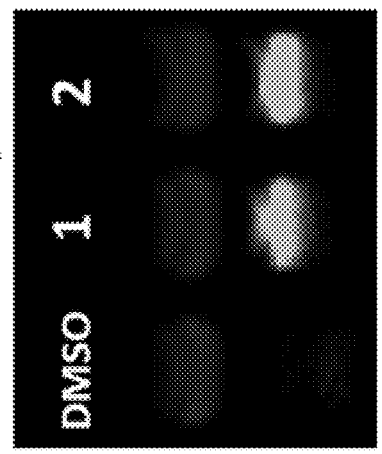
Figure 26:
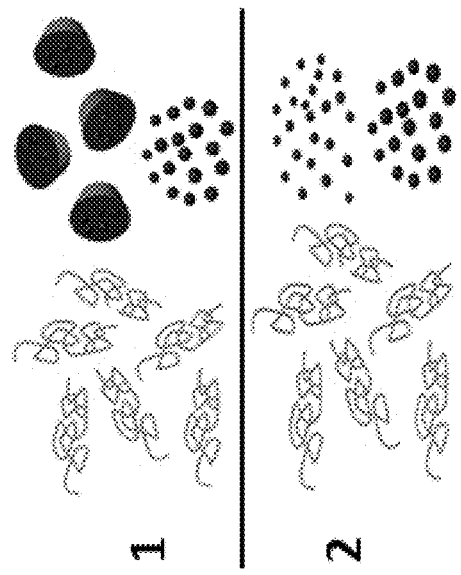
Figure 27:
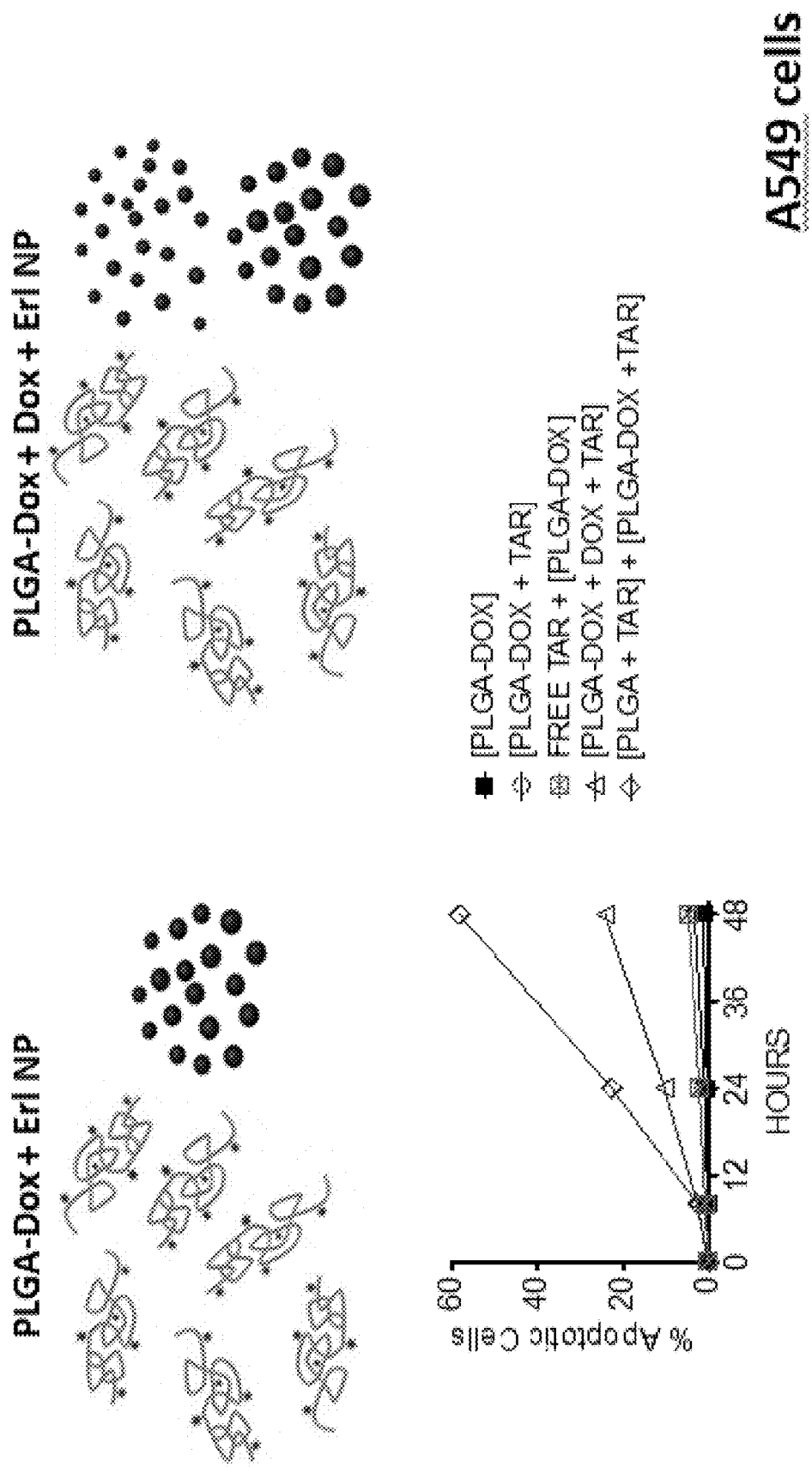
FIG. 27 Cell apoptotic response showing 1) Dox-conjugate release being too slow to be therapeutic alone; 2) one vs. two particles; and 3) inhibitor loading issue (1:5-10 ratio of Erl:Dox).
Figure 28:
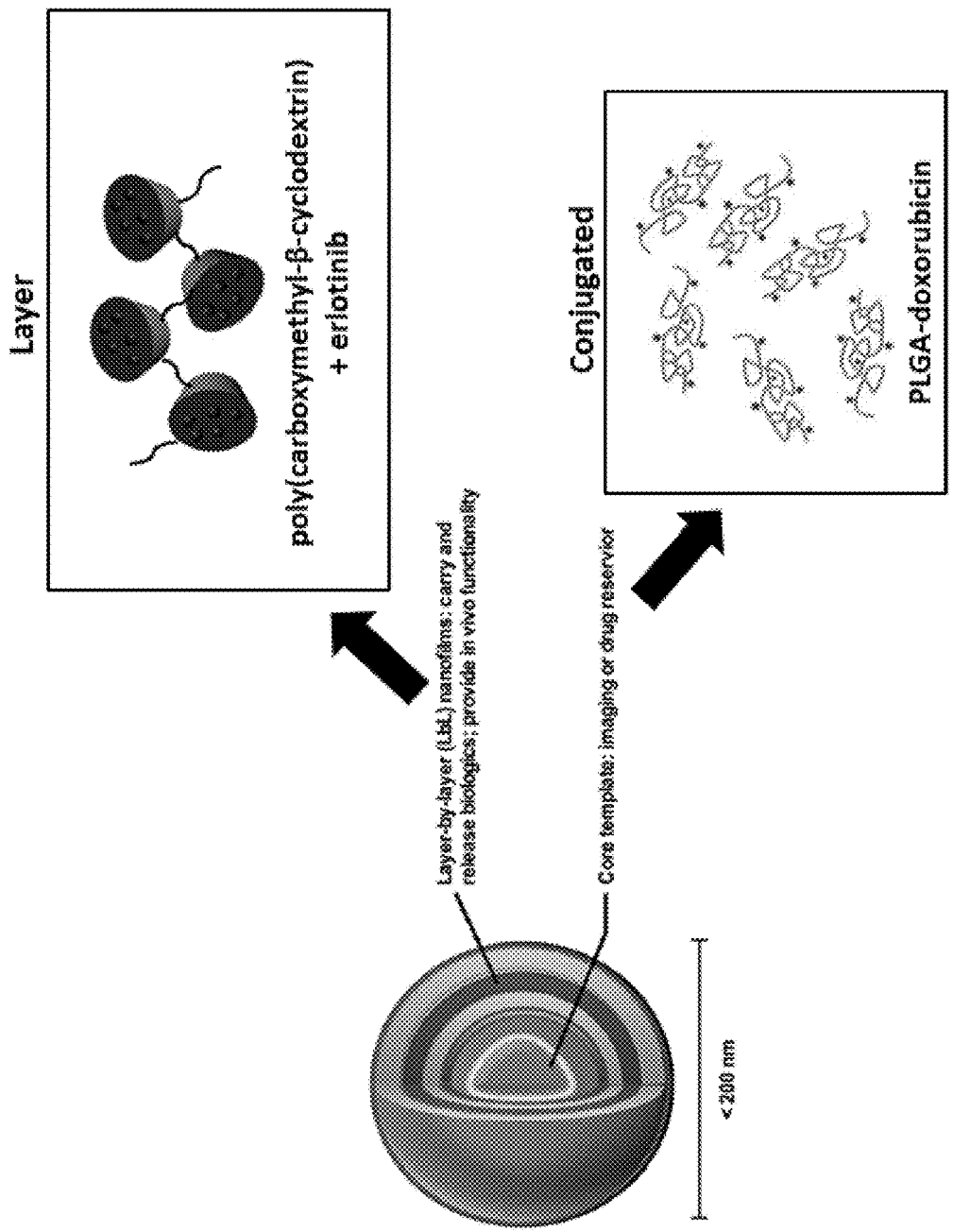
FIG. 28 Schematic of using LbL films for enhanced loadings and staged release of drugs.
Figure 29:
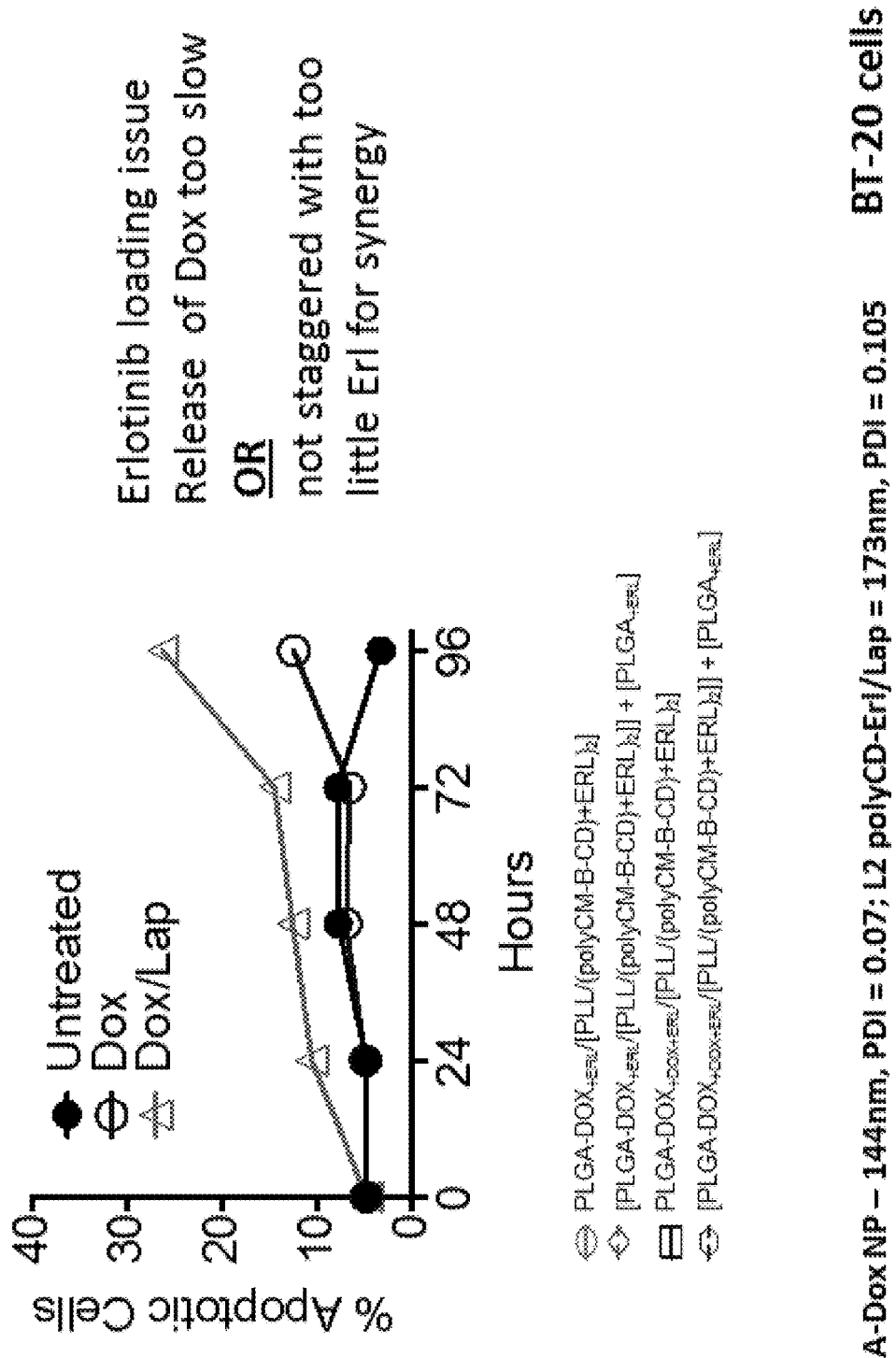
FIG. 29 Cell apoptotic response showing 1) Erlotinib causing issues; 2) use of sister inhibitor (lapatinib).
Figure 30:
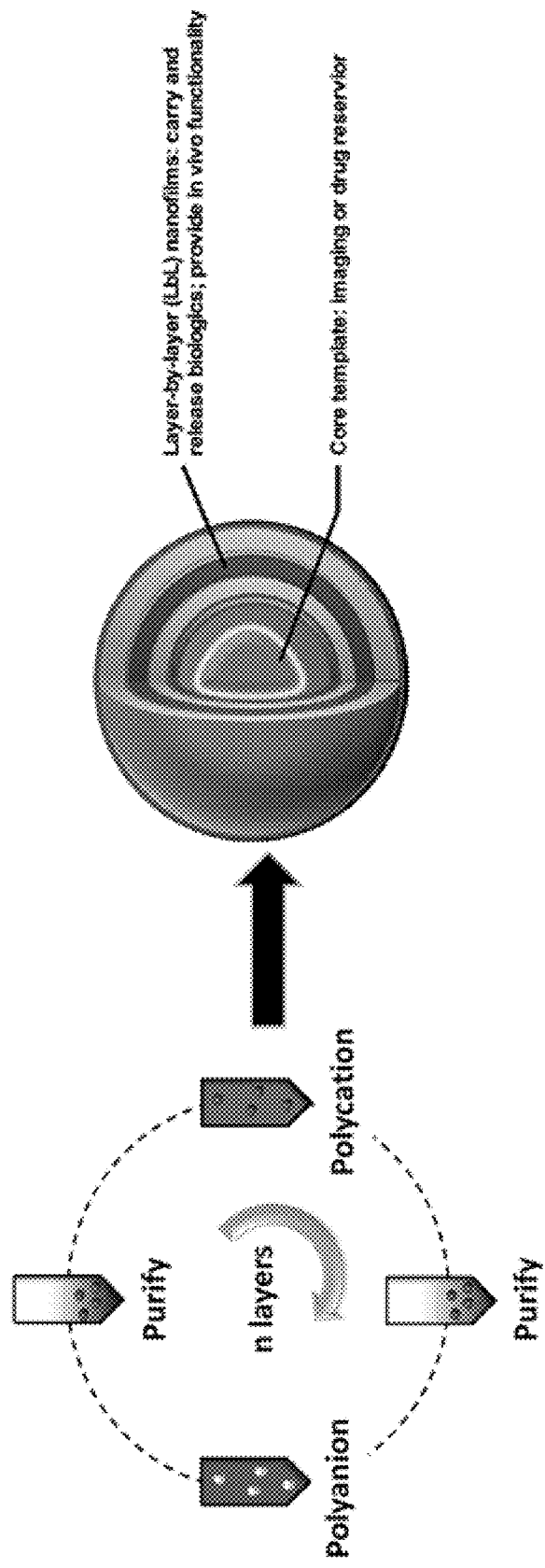
FIG. 30 Schematic for an exemplary LbL films on nanoparticles, which can be used for systemic delivery of RNAi.
Figure 31:
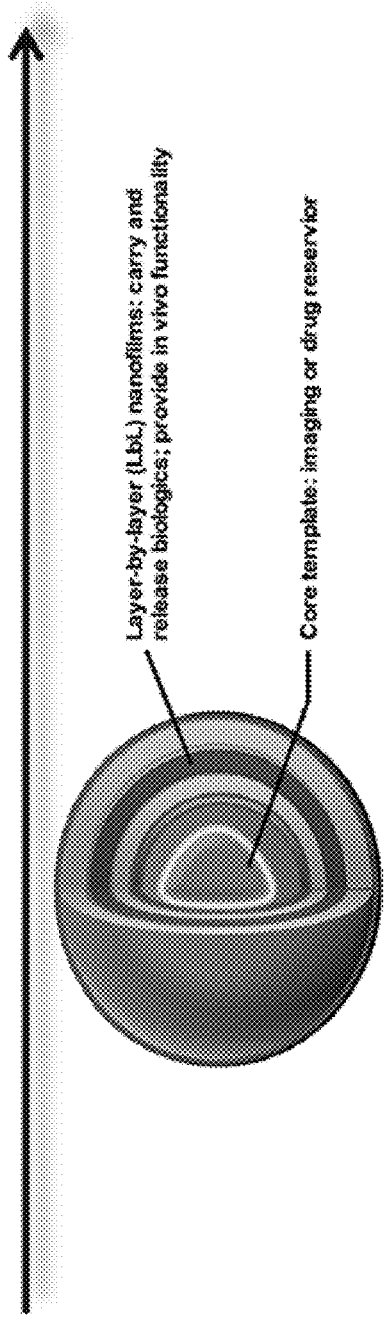
FIG. 31 A modular design of siRNA LbL films on particle cores according to certain embodiments.
Figure 32:
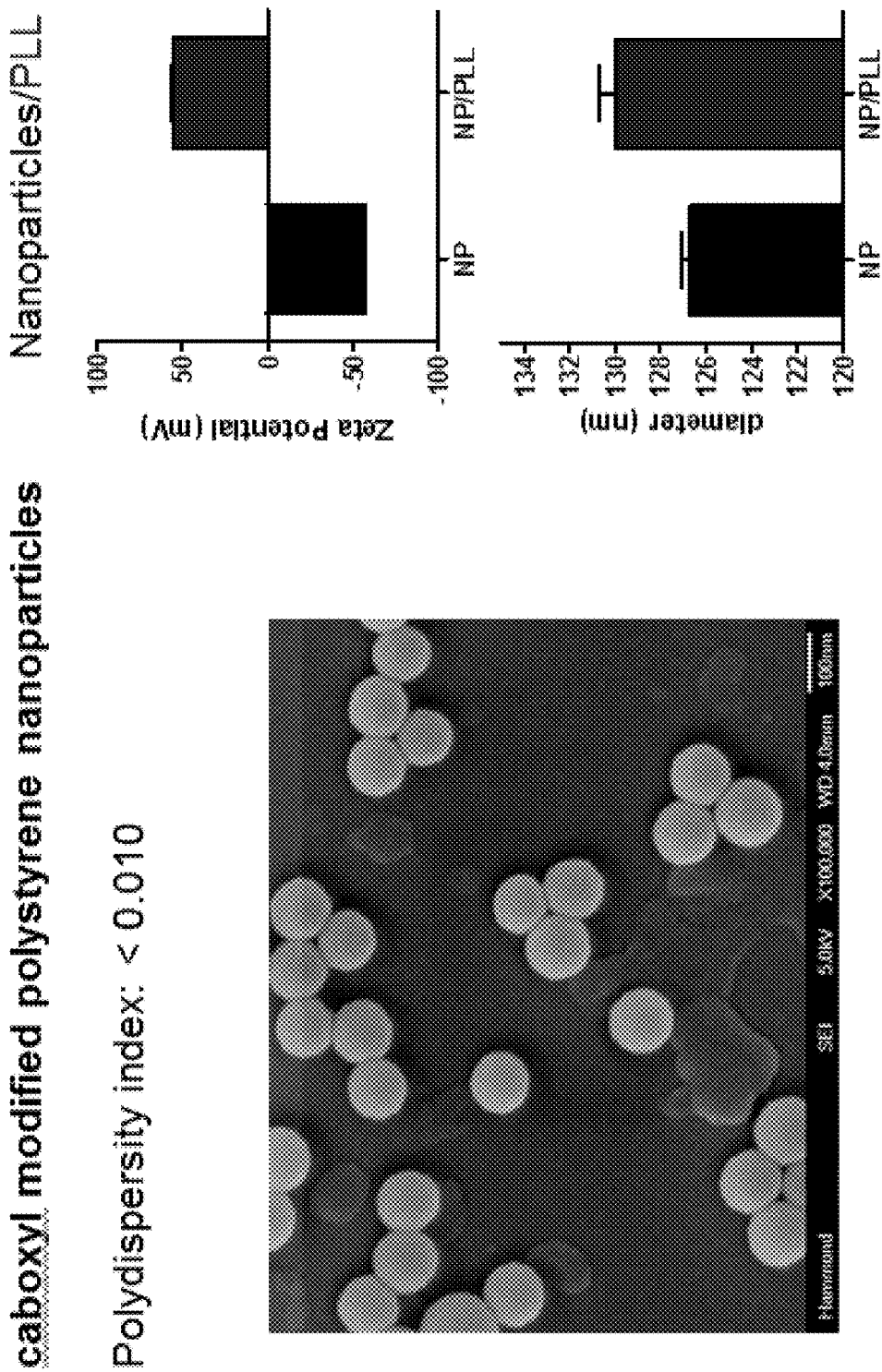
FIG. 32 SEM images of exemplary particle cores.
Figure 33:
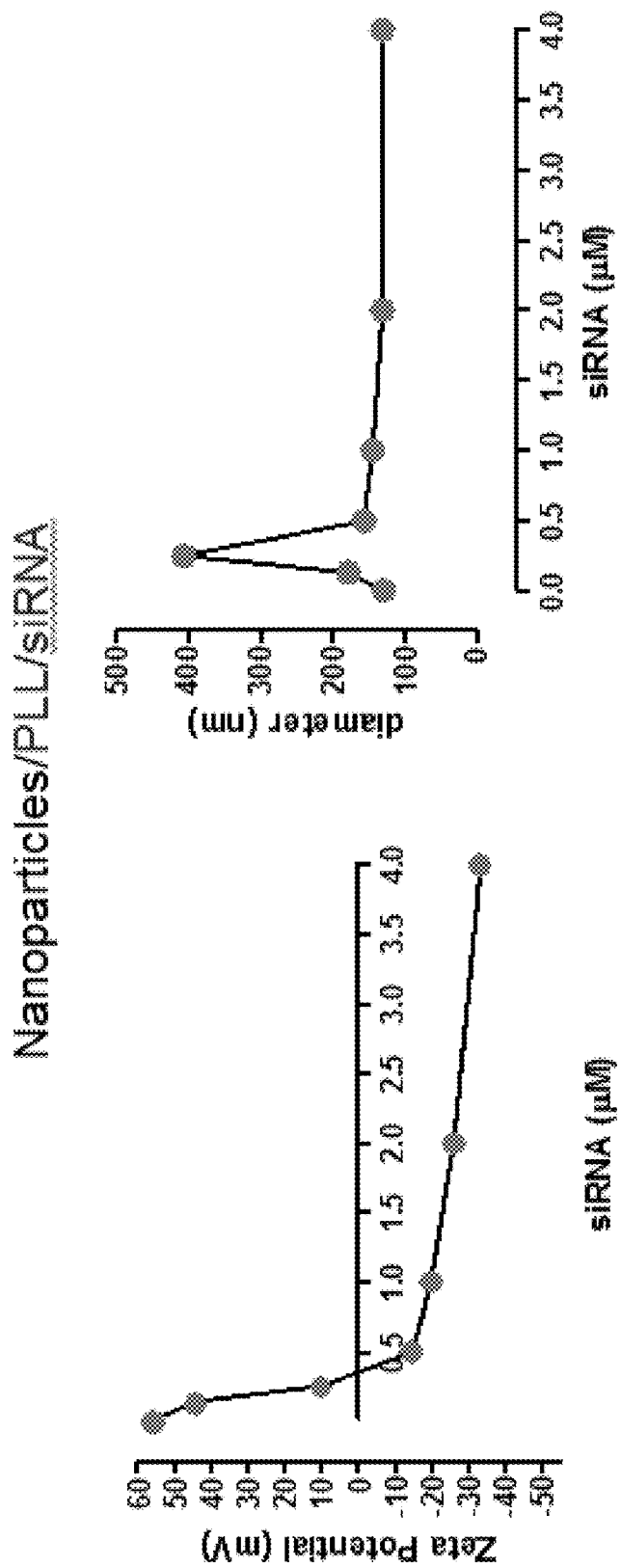
FIG. 33 Characterizations demonstrating colloidal stability of exemplary siRNA LbL films on particle cores.
Figure 34:
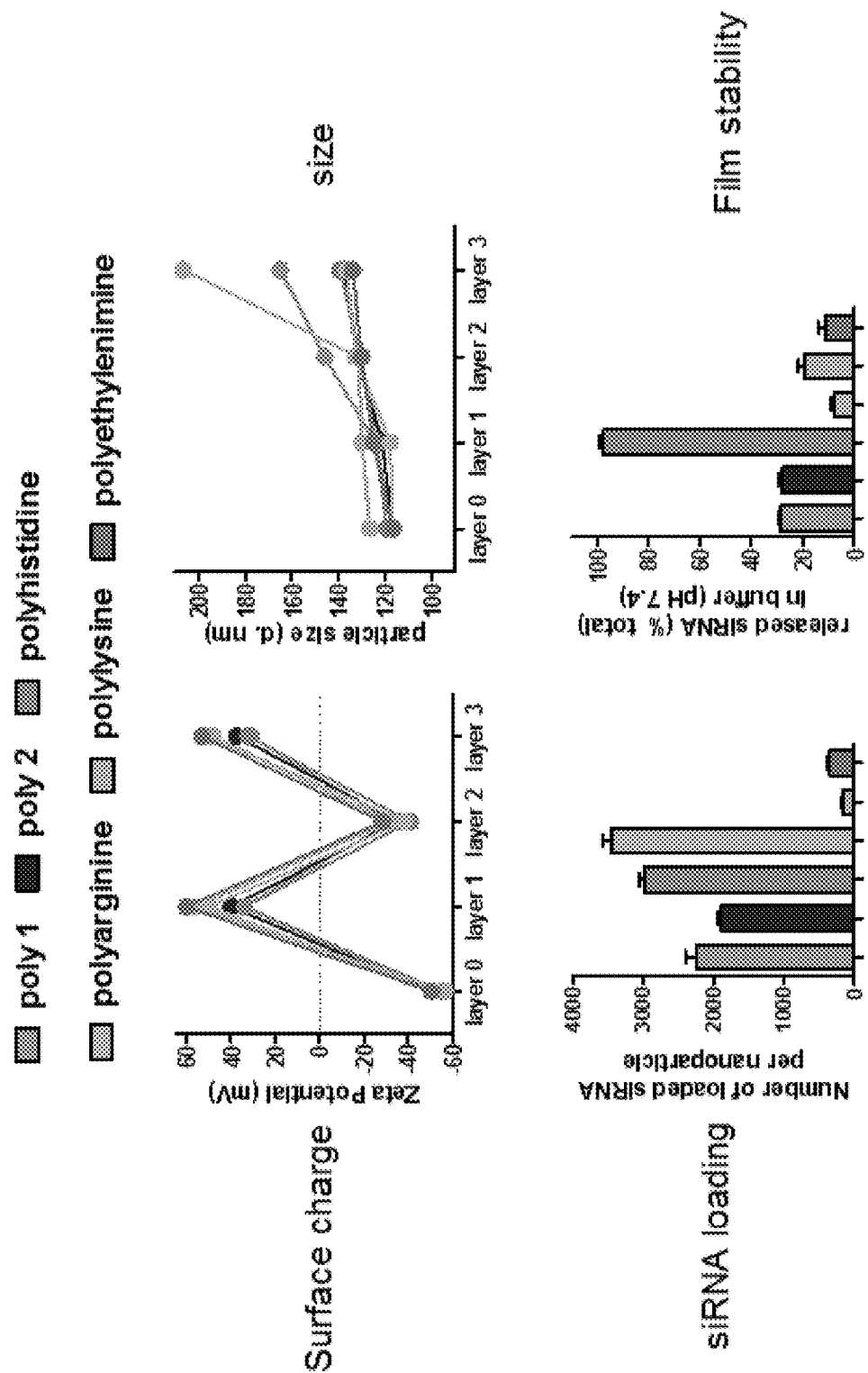
FIG. 34 Screening of exemplary polycation/siRNA LbL films.
Figure 35:
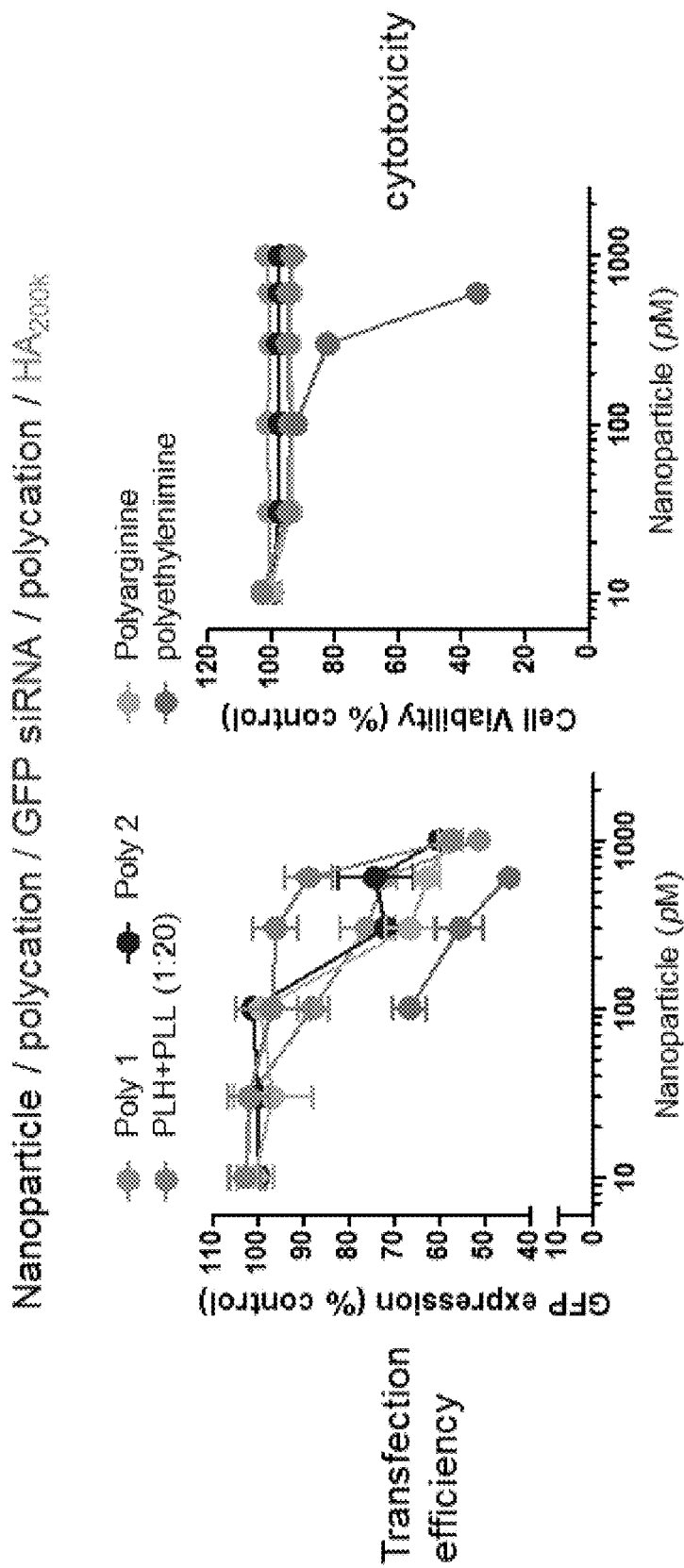
FIG. 35 Transfection efficiency and cytotoxicity of exemplary siRNA LbL films on particles cores.
Figure 36:
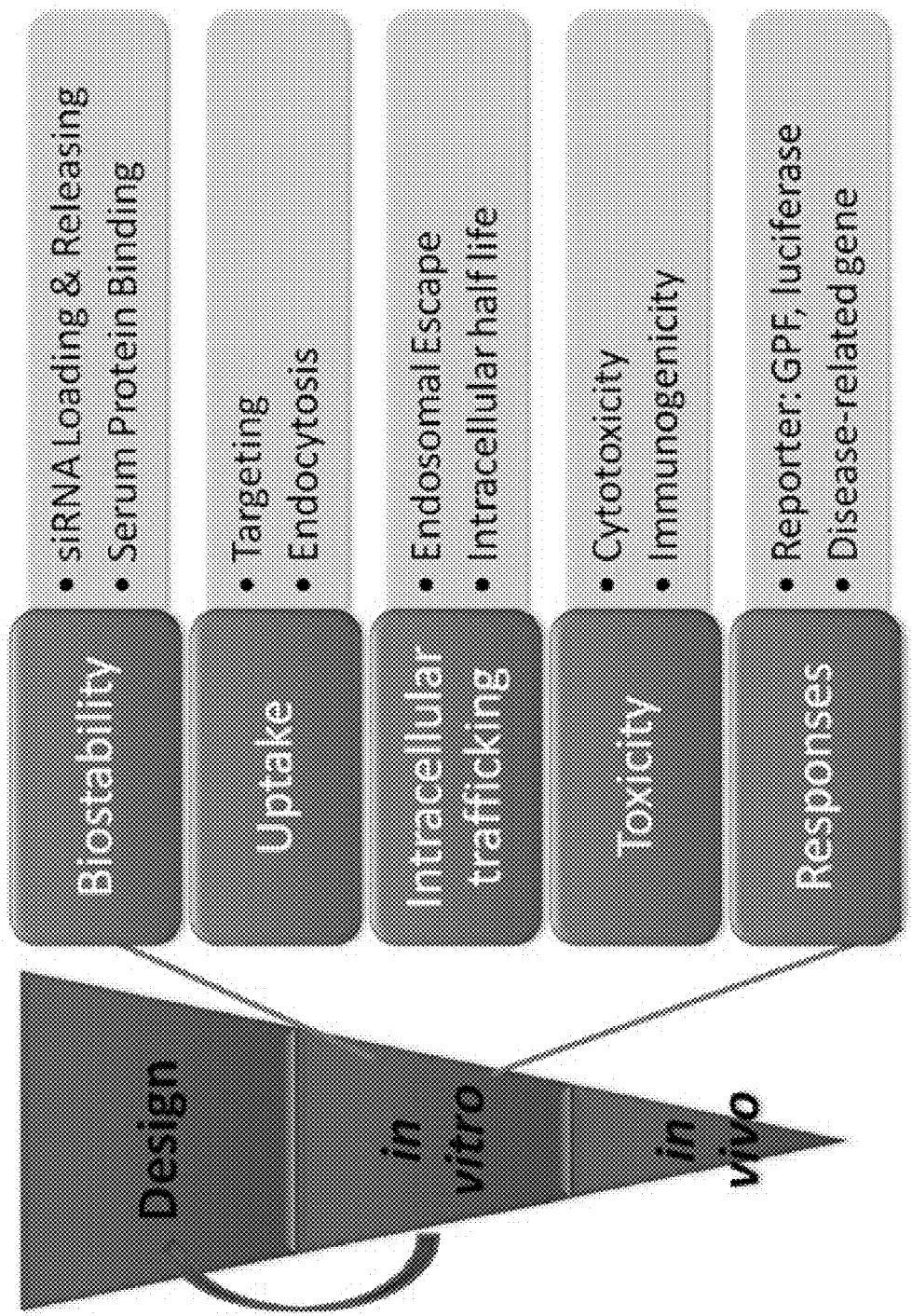
FIG. 36 Characterization tool box for in vitro screening for nanoparticle RNAi delivery.
Figure 37:
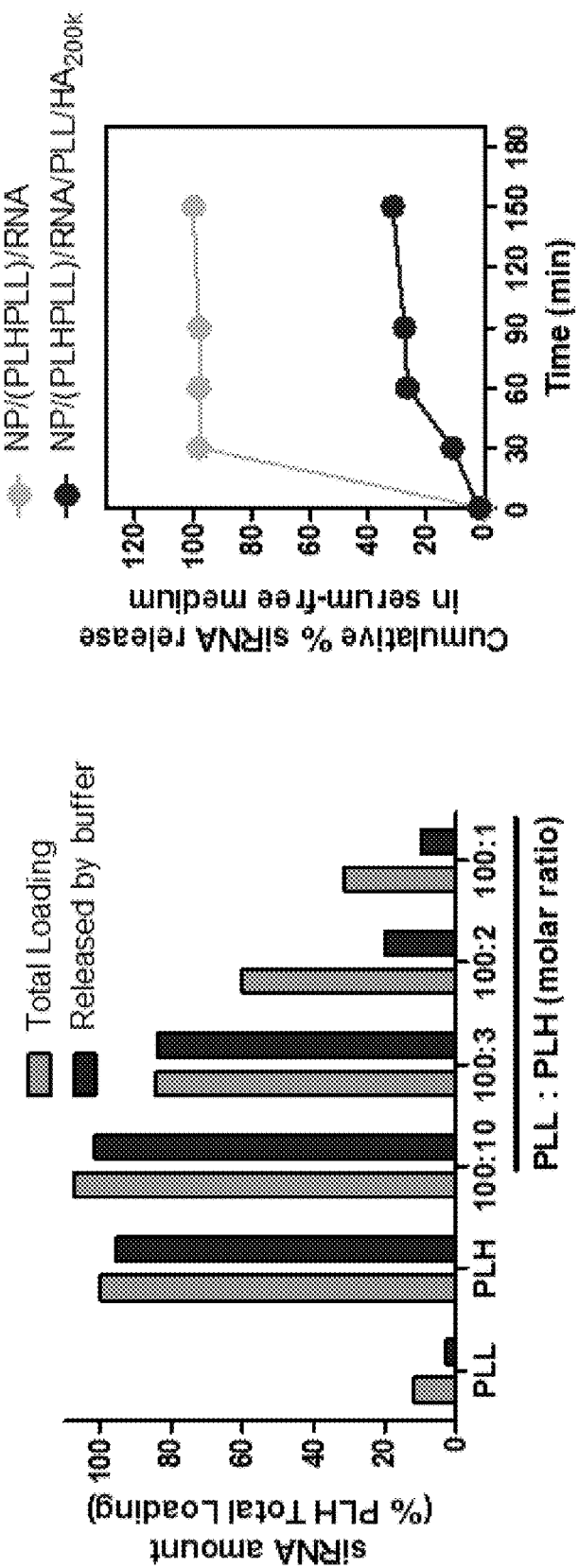
FIG. 37 Fine tuning of loading and film stability of exemplary siRNA LbL films on particles cores.
Figure 38:
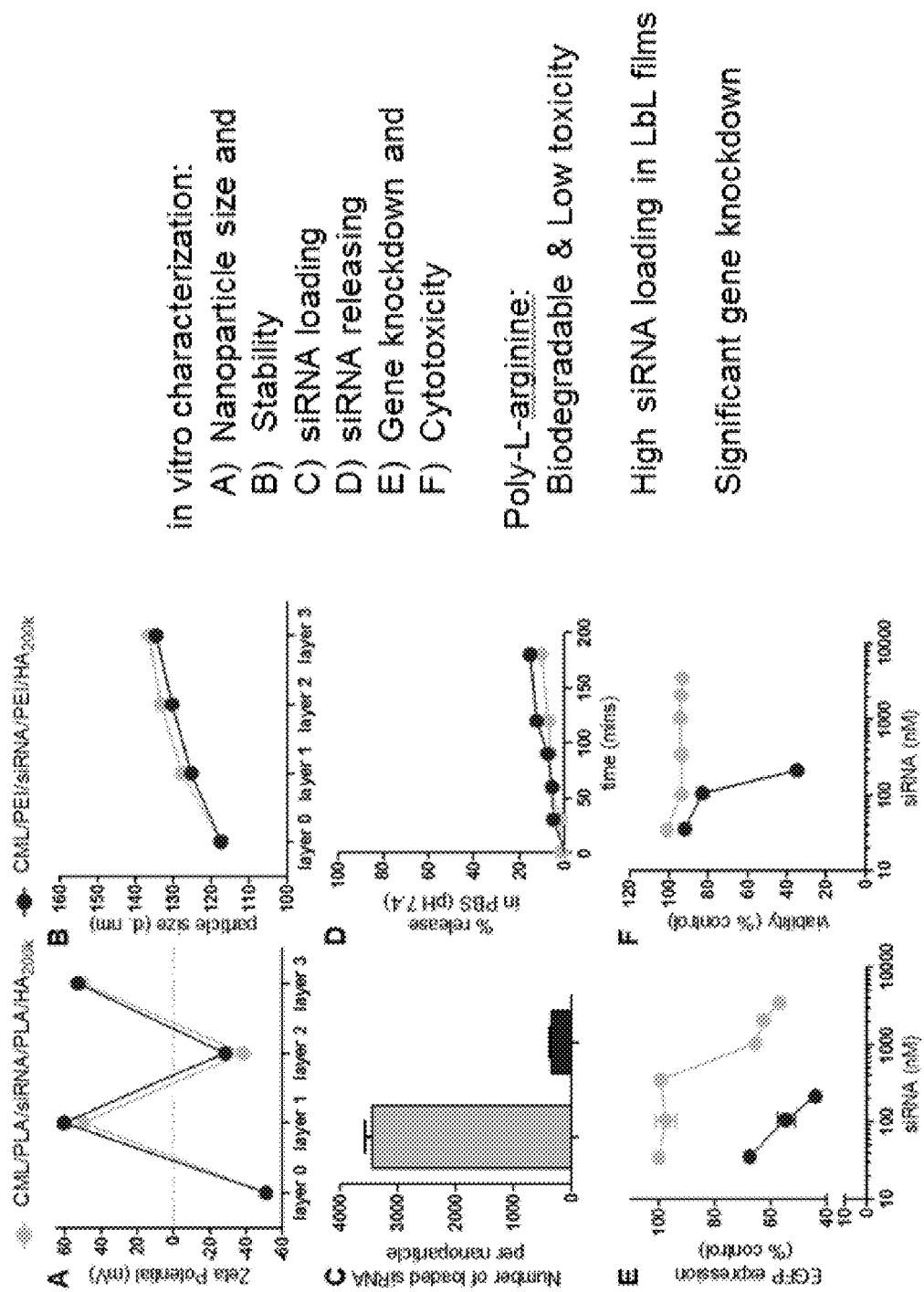
FIG. 38 Comparison of poly-L-arginine vs BPEI.
Figure 39A:
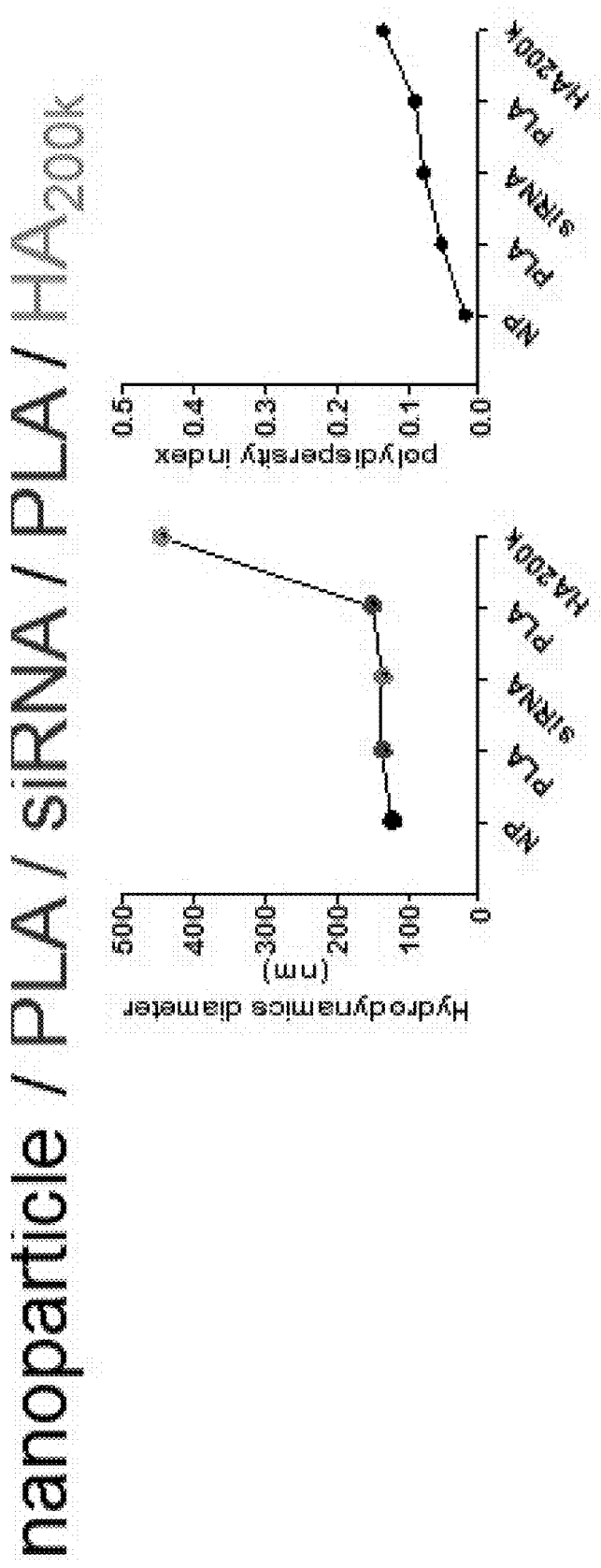
FIG. 39A, FIG. 39B, and FIG. 39C show characterizations of exemplary siRNA LbL films on particles cores.
Figure 39B:
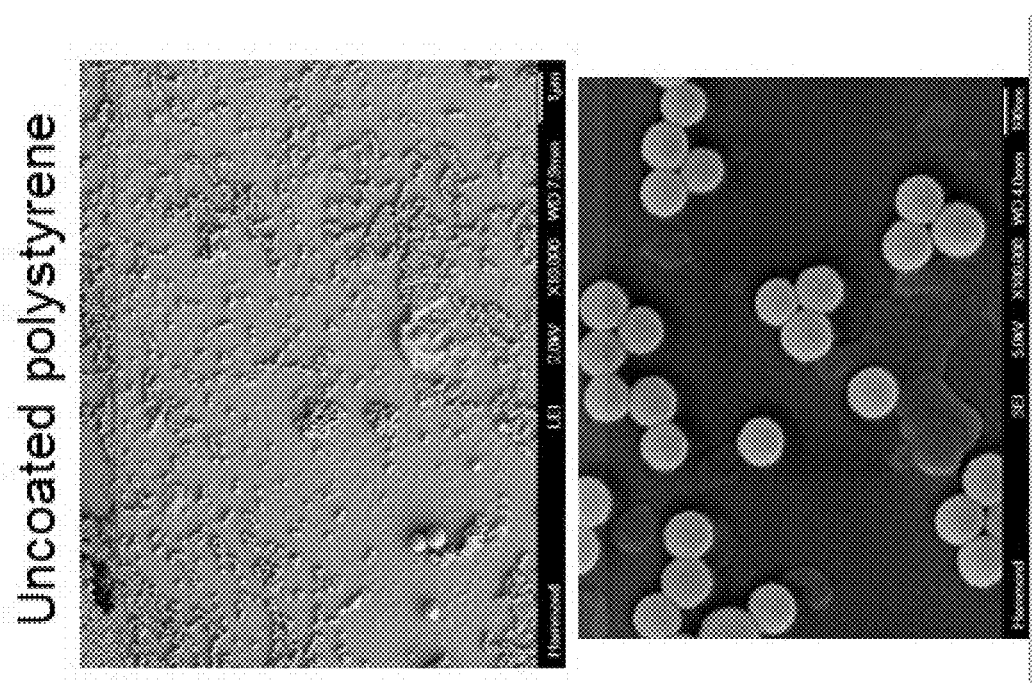
Figure 39C:
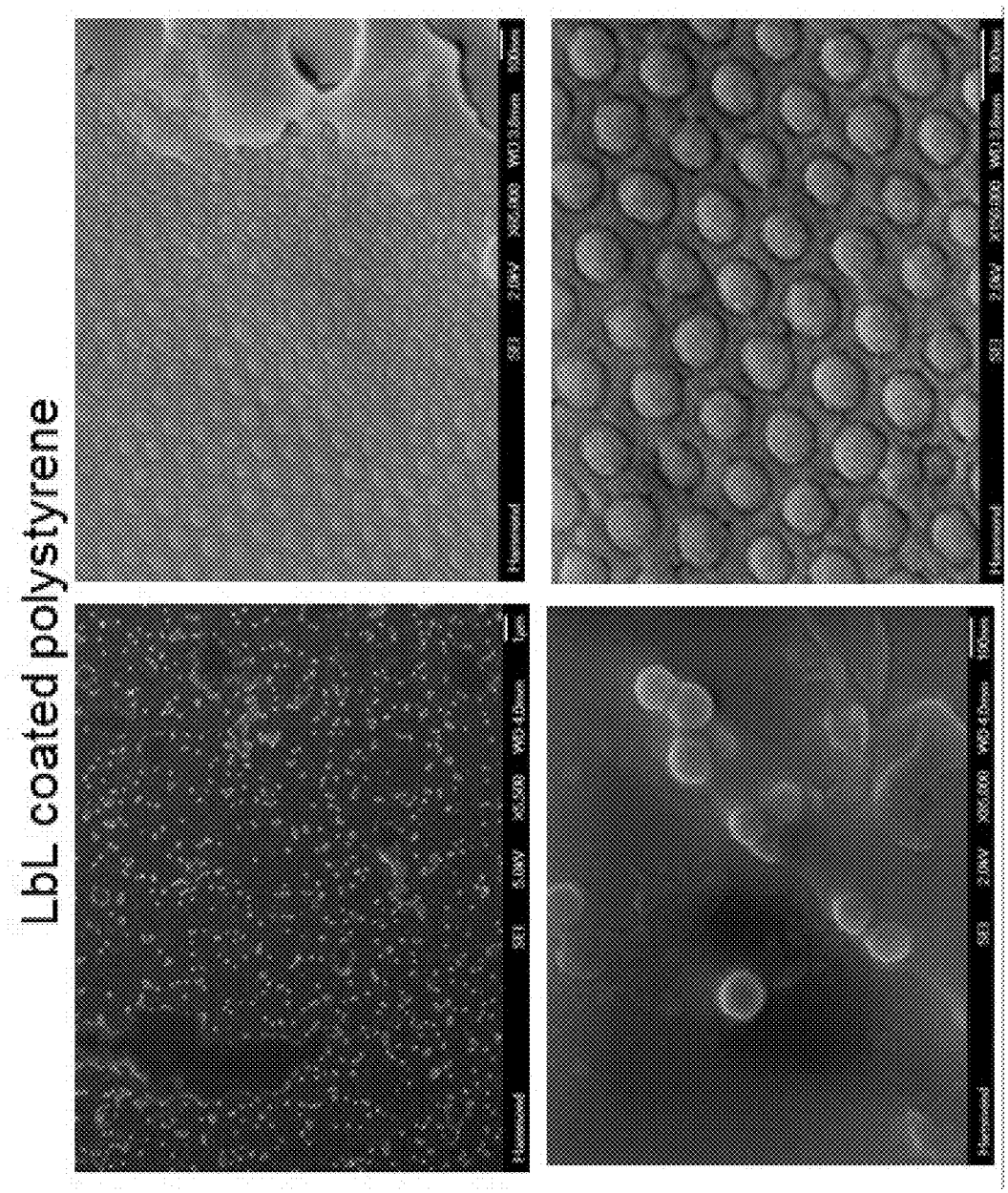
Figure 40:
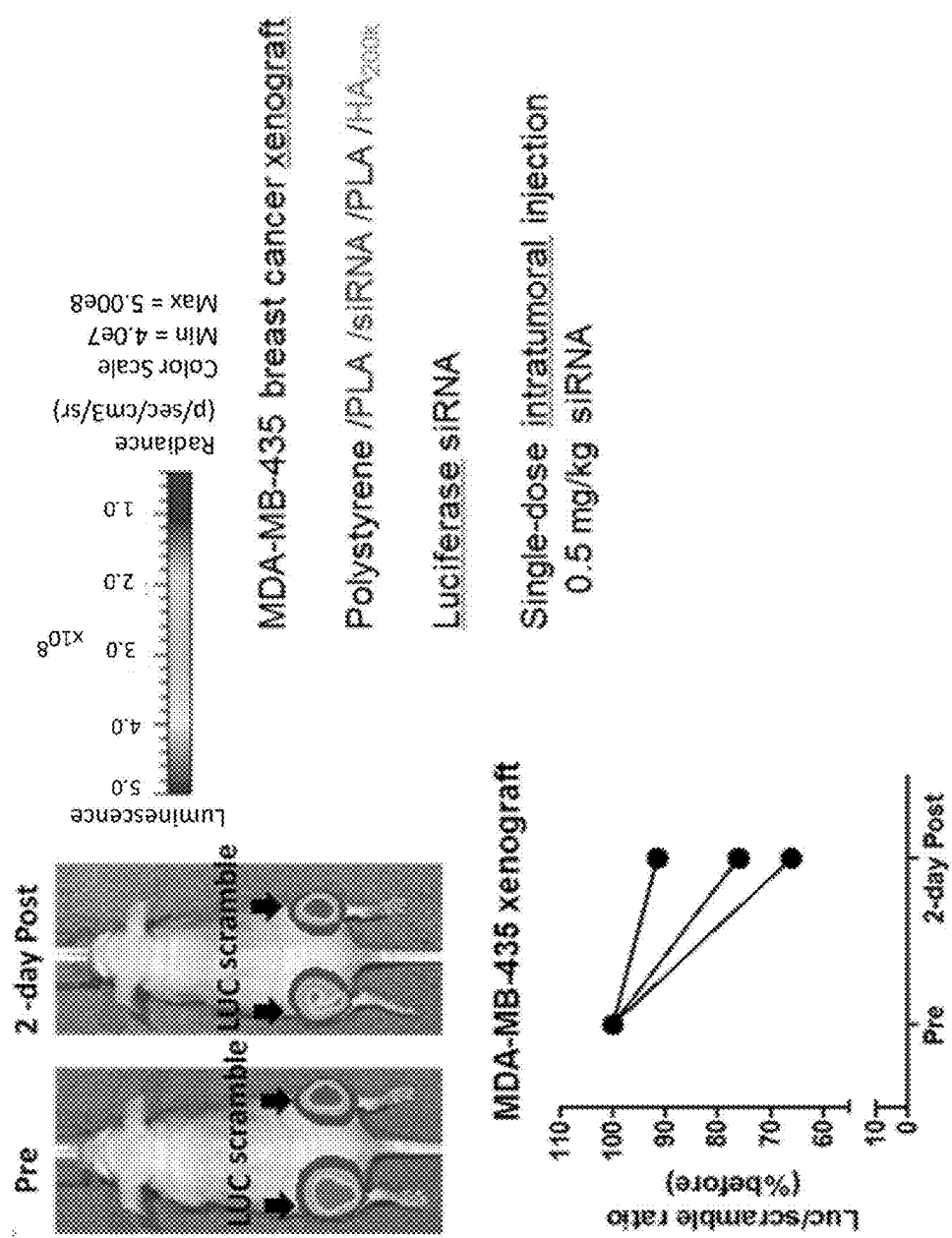
FIG. 40 Local delivery (intratumoral) of siRNA from the exemplary particles shown in FIG. 39.
Figure 41:
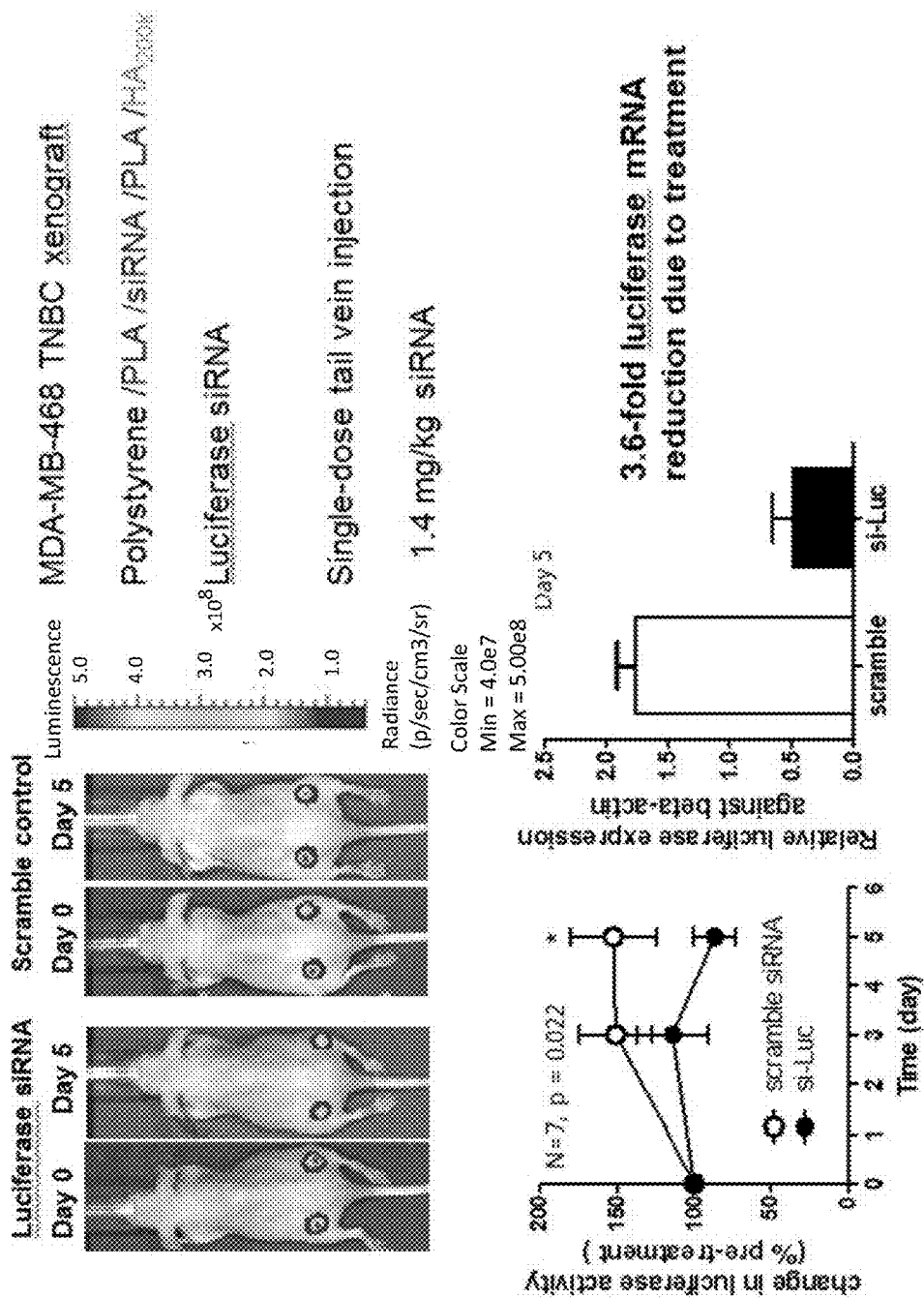
FIG. 41 Systemic delivery (tail vein) of siRNA from the exemplary particles shown in FIG. 39.
Figure 42:
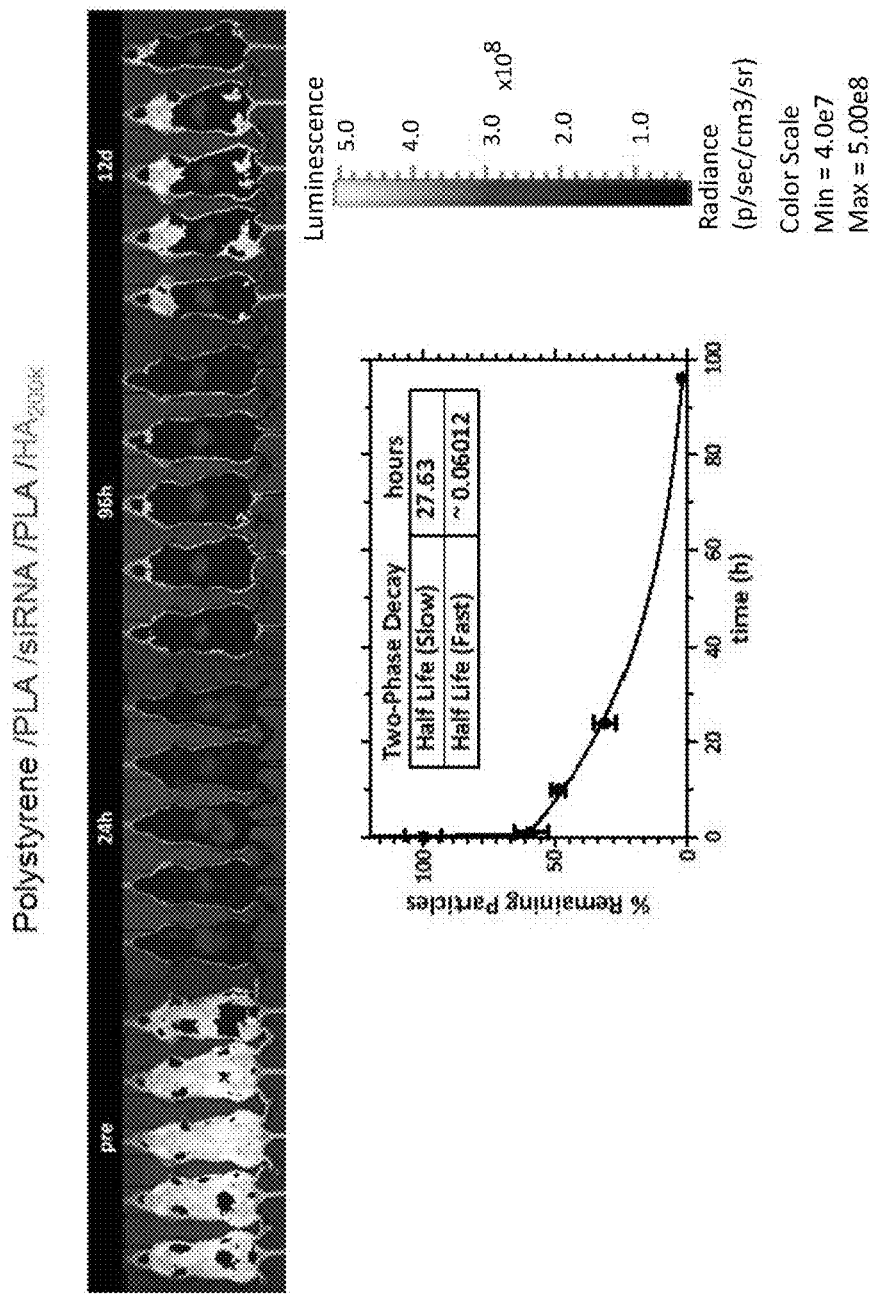
FIG. 42 Blood clearance rate of systemic delivery (tail vein).
Figure 43:
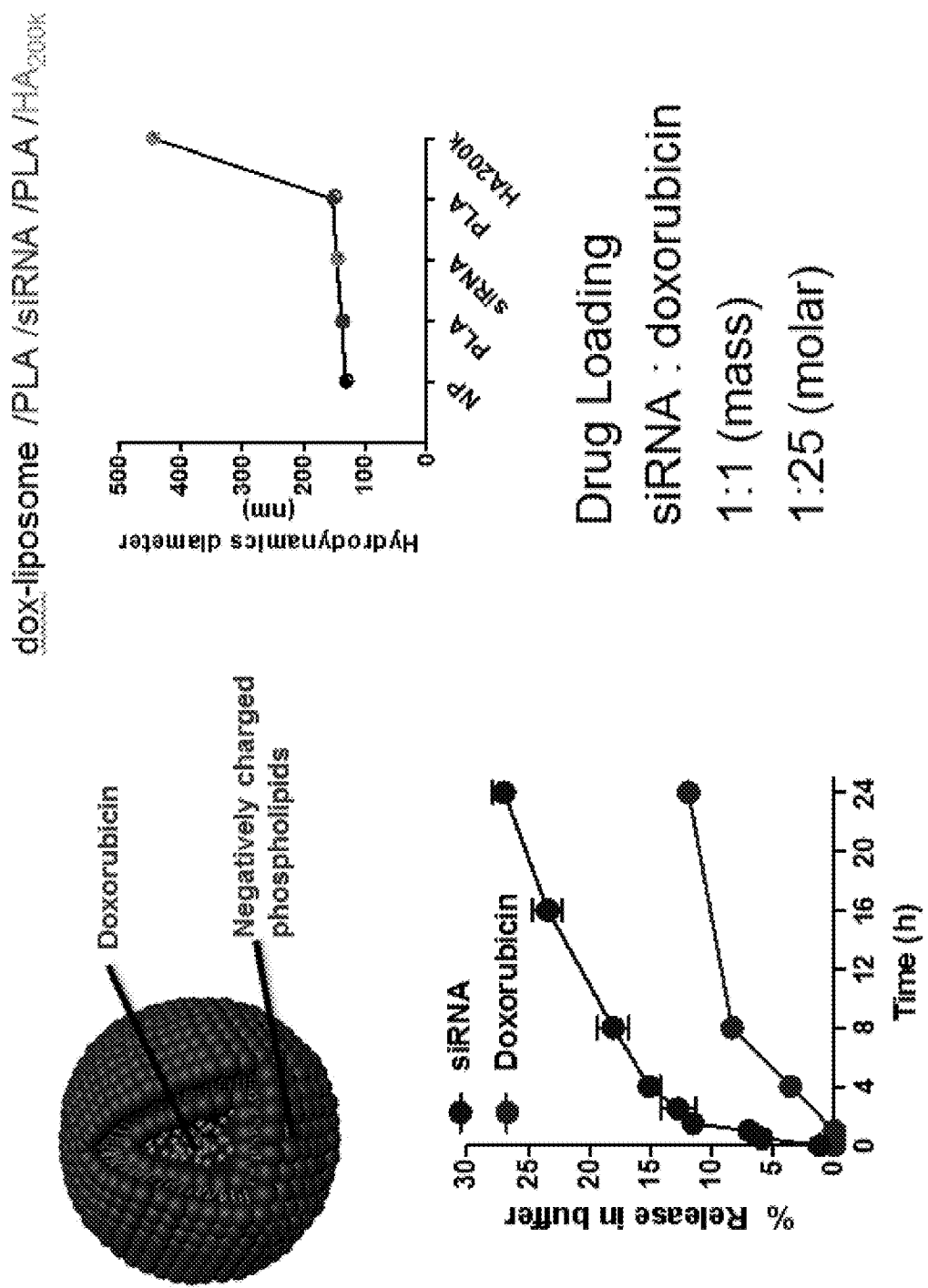
FIG. 43 Combination therapy using liposomal doxorubicin and siRNA.
Figure 44:
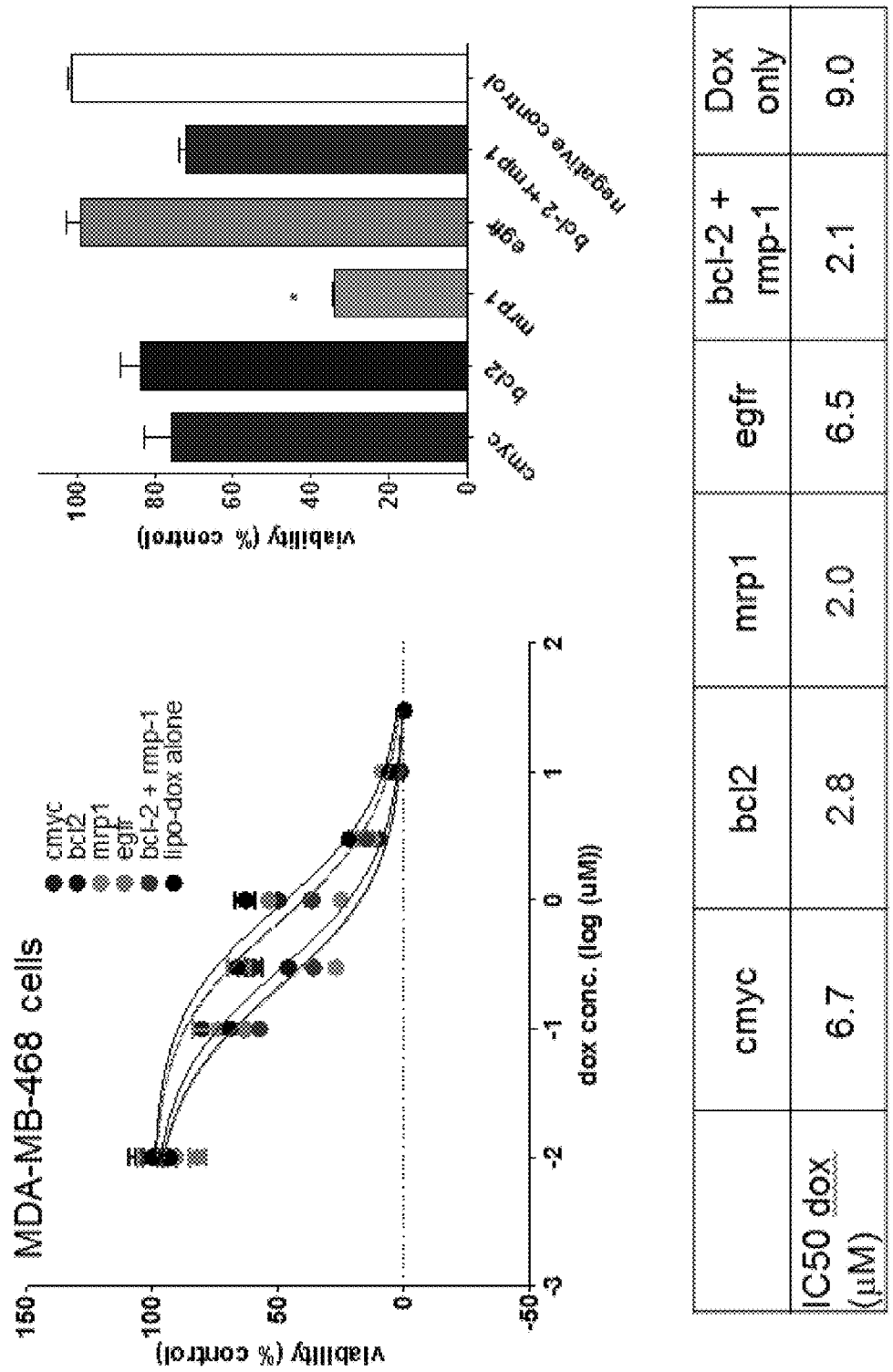
FIG. 44 Synergy of siRNA and doxorubicin (Dox) against triple negative breast cancer.
Figure 45:
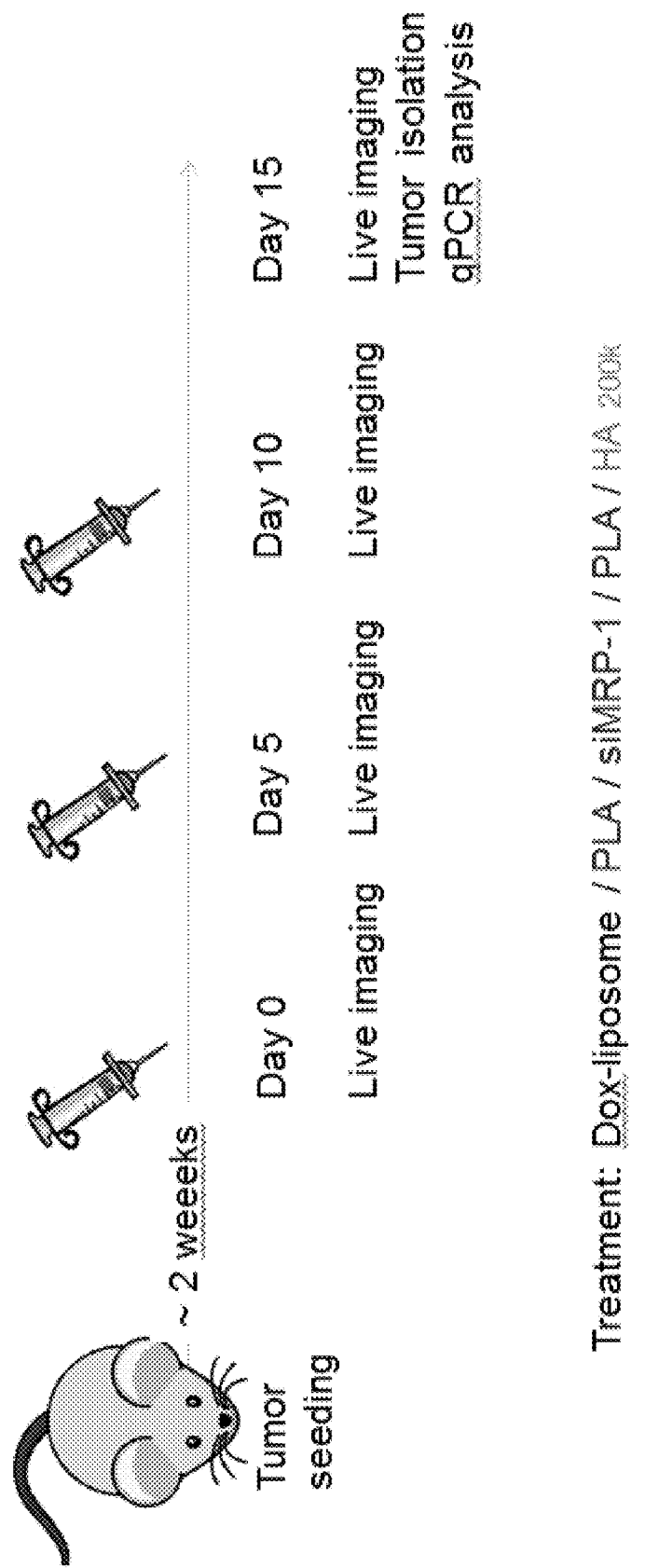
FIG. 45 Procedure for using mrp-1 siRNA and doxorubicin (Dox) in triple negative breast cancer (xenograft model).
Figure 46:
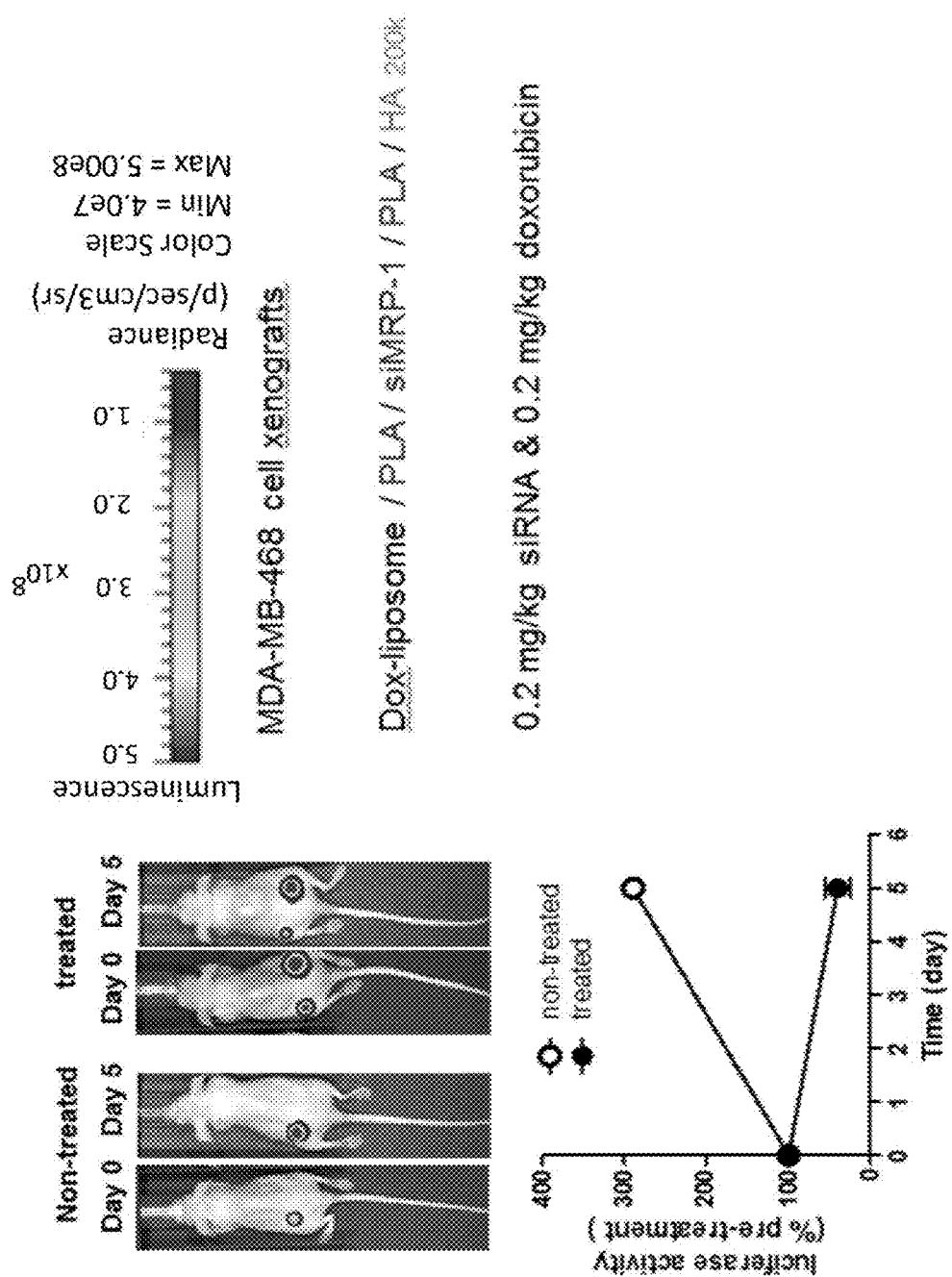
FIG. 46 Combination therapy using mrp-1 siRNA and doxorubicin (Dox).

After passing through vascular borders and accumulating within the tumor interstitials, LbL particles that may be deshielded by acidity do so in hypoxic regions, exposing the PLL layer for cellular uptake; therefore, for the 8 h to 48 h period, the clearance of QD/PLLib/nav/PEG from tumors was much slower compared to QD/PLLb/nav/PEG, which are internalized by cells less readily and are slowly eliminated by the lymphatic system, as observed in the later time points for FIG. 17B. FIG. 17D shows the rate of nanoparticle clearance from both tumor models relative to the 8 h time point (the absolute values are given in FIG. 22B and FIG. 22C, see supplemental information online). The stronger retention of QD/PLLib/nav/PEG demonstrates the deshielding of LbL particles to allow cellular interaction with the underlying PLL layer for improved uptake. Dissociation of the iminobiotin-neutravidin bond in the acidic tumor microenvironment can happen fairly rapidly (~50% dissociation within 3-4 h, FIG. 13B), permitting a significant portion of the accumulated QD/PLLib/PEG particles to be deshielded within the 8 h EPR targeting window. This effect is manifest thereafter, which translates to a greater degree of particle retention observed in the tumors. FIG. 18A shows the left lateral scan of a representative mouse (MDA-MB-435 tumor model) at the 48 h time point and the biodistribution of particles in harvested tissue from these mice; both sets of data clearly indicate stronger and longer retention of QD/PLLib/nav/PEG in tumors. Finally, histological examinations of tumor sections reveal a high level of association between the QD/PLLib/nav/PEG signal and regions stained for hypoxia (FIG. 18B). In contrast, the QD/PLLb/nav/PEG signal is considerably weaker and is not present in hypoxic regions; this data provides further evidence that the deshielding mechanism of the pH sensitive LbL particles is responsible for their persistence in tumors, particularly in regions of hypoxia; this observation provides exciting new opportunities for chemotherapy to solid tumors and delivery of anti-hypoxic cancer therapies using the LbL nanoparticle approach.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

Other Embodiments and Equivalents

While the present disclosures have been described in conjunction with various embodiments and examples, it is not intended that they be limited to such embodiments or examples. On the contrary, the disclosures encompass various alternatives, modifications, and equivalents, as will be appreciated by those of skill in the art. Accordingly, the descriptions, methods and diagrams of should not be read as limited to the described order of elements unless stated to that effect.

Although this disclosure has described and illustrated certain embodiments, it is to be understood that the disclosure is not restricted to those particular embodiments. Rather, the disclosure includes all embodiments that are functional and/or equivalents of the specific embodiments and features that have been described and illustrated.

The invention claimed is:

1. A particle, comprising:
    a liposome core having a negatively charged outer surface and a diameter from about 100 nm to about 200 nm; and
    a film coating the liposome core, the film comprising a first layer, a second layer, a third layer and a fourth layer, wherein:
    the first layer, which coats the liposome core, includes poly-L-arginine (PLA);
    the second layer, which coats the first layer, includes an siRNA therapeutic agent;
    the third layer, which coats the second layer, includes PLA; and
    the fourth layer, which coats the third layer, includes hyaluronic acid (HA),
    and further wherein the liposome core comprises a second therapeutic agent.

2. The particle of claim 1, wherein the second therapeutic agent is doxorubicin.

3. The particle of claim 1, wherein the siRNA therapeutic agent is an siRNA targeting Multidrug Resistant Protein 1 (siRNA MRP1).

4. The particle of claim 1, wherein the particles includes about 3500 copies of siRNA.

5. The particle of claim 1, wherein the siRNA therapeutic agent is an siRNA targeting Multidrug Resistant Protein 1 (siRNA MRP1), the second therapeutic agent is doxorubicin, and the mass ratio of the siRNA therapeutic agent to doxorubicin is from about 1:1 to about 1.25:1.

6. A method of administering a combination of an siRNA therapeutic agent and a second therapeutic agent to a patient in need thereof, the method comprising:
    administering to said patient a therapeutically effective amount of a pharmaceutical composition comprising the particles of claim 1 in a therapeutically acceptable carrier,
    wherein the siRNA therapeutic agent and the second therapeutic agent are delivered to a tumor in a time-staggered manner.

7. The method of claim 6, wherein the particles includes about 3500 copies of siRNA.

8. The method of claim 7, wherein the siRNA therapeutic agent is an siRNA targeting Multidrug Resistant Protein 1 (siRNA MRP1), the second therapeutic agent is doxorubicin, and the mass ratio of the siRNA therapeutic agent to doxorubicin is from about 1:1 to about 1.25:1.

* * * * *

UNITED STATES PATENT AND TRADEMARK OFFICE
CERTIFICATE OF CORRECTION

PATENT NO. : 10,278,927 B2  
APPLICATION NO. : 13/869015  
DATED : May 7, 2019  
INVENTOR(S) : Hammond et al.

Page 1 of 1

It is certified that error appears in the above-identified patent and that said Letters Patent is hereby corrected as shown below:

In the Specification

In Column 1, Line 9, after paragraph "CROSS-REFERENCE TO RELATED APPLICATION" insert heading & paragraph:
--GOVERNMENT SUPPORT
This invention was made with government support under EB008082 awarded by the National Institutes of Health. The government has certain rights in the invention.--

Signed and Sealed this  
Eleventh Day of November, 2025

John A. Squires  
*Director of the United States Patent and Trademark Office*